US007459472B2

(12) United States Patent
Mjalli et al.

(10) Patent No.: US 7,459,472 B2
(45) Date of Patent: Dec. 2, 2008

(54) ARYL AND HETEROARYL COMPOUNDS, COMPOSITIONS, AND METHODS OF USE

(75) Inventors: Adnan M. M. Mjalli, Jamestown, NC (US); Robert C. Andrews, Jamestown, NC (US); Murty N. Arimilli, Oak Ridge, NC (US); Mohan Rao, Greensboro, NC (US); Mustafa Guzel, Jamestown, NC (US); Muralidhar Bondlela, High Point, NC (US); Xiao-Chuan Guo, High Point, NC (US); Guoxiang Huang, Greensboro, NC (US)

(73) Assignee: TransTech Pharma, Inc., High Point, NC (US)

( * ) Notice: Subject to any disclaimer, the term of this patent is extended or adjusted under 35 U.S.C. 154(b) by 281 days.

(21) Appl. No.: 10/913,216

(22) Filed: Aug. 6, 2004

(65) Prior Publication Data

US 2005/0059713 A1 Mar. 17, 2005

Related U.S. Application Data

(60) Provisional application No. 60/493,879, filed on Aug. 8, 2003, provisional application No. 60/493,878, filed on Aug. 8, 2003, provisional application No. 60/493, 903, filed on Aug. 8, 2003.

(51) Int. Cl.
*A61K 31/41* (2006.01)
*C07D 271/06* (2006.01)

(52) U.S. Cl. ........................ 514/364; 548/131; 548/571

(58) Field of Classification Search ................. 562/430, 562/450, 439; 548/571, 131; 514/364, 576, 514/563
See application file for complete search history.

(56) References Cited

U.S. PATENT DOCUMENTS

| | | | |
|---|---|---|---|
| 4,675,439 | A | 6/1987 | Mita et al. |
| 4,717,736 | A | 1/1988 | Rokach et al. |
| 5,273,990 | A | 12/1993 | De Lombaert et al. |
| 5,354,905 | A | 10/1994 | Sato et al. |
| 5,397,798 | A | 3/1995 | Fitch et al. |
| 5,514,719 | A | 5/1996 | LaTorse et al. |
| 5,518,735 | A | 5/1996 | Sturzebecher et al. |
| 5,679,671 | A | 10/1997 | Oinuma et al. |
| 5,703,106 | A | 12/1997 | Fruh et al. |
| 5,750,520 | A | 5/1998 | Danilewicz et al. |
| 5,780,498 | A | 7/1998 | Saika et al. |
| 5,908,843 | A | 6/1999 | Gante et al. |
| 5,977,075 | A | 11/1999 | Ksander et al. |
| 5,977,178 | A | 11/1999 | Hansen et al. |
| 6,001,820 | A | 12/1999 | Hirsh et al. |
| 6,087,380 | A | 7/2000 | Hauel et al. |
| 6,093,731 | A | 7/2000 | Dickinson et al. |
| 6,127,341 | A | 10/2000 | Hansen et al. |
| 6,191,171 | B1 | 2/2001 | DeLaszlo et al. |
| 6,194,448 | B1 | 2/2001 | Bredrget et al. |
| 6,194,458 | B1 | 2/2001 | Baker et al. |
| 6,262,084 | B1 | 7/2001 | Biediger et al. |
| 6,284,871 | B1 | 9/2001 | Mertens et al. |
| 6,291,511 | B1 | 9/2001 | Durette et al. |
| 6,300,330 | B1 | 10/2001 | Stocker et al. |
| 6,306,840 | B1 | 10/2001 | Adams et al. |
| 6,331,564 | B1 | 12/2001 | Brugnara et al. |
| 6,342,504 | B1 | 1/2002 | Brunck et al. |
| 6,358,978 | B1 | 3/2002 | Ritzeler et al. |
| 6,362,204 | B1 | 3/2002 | Head et al. |
| 6,388,138 | B1 | 5/2002 | Lee |
| 6,388,148 | B2 | 5/2002 | Heilmann et al. |
| 6,403,584 | B1 | 6/2002 | De Laszlo et al. |
| 6,420,396 | B1 | 7/2002 | Albers et al. |
| 6,423,727 | B1 | 7/2002 | De Lombaert et al. |
| 6,469,047 | B1 | 10/2002 | Jackson et al. |
| 6,521,666 | B1 | 2/2003 | Sircar et al. |
| 6,528,275 | B1 | 3/2003 | Quibell et al. |
| 6,528,655 | B1 | 3/2003 | N'Zemba et al. |
| 6,559,174 | B2 | 5/2003 | Lin et al. |
| 6,743,790 | B2 | 6/2004 | Klingler et al. |
| 6,855,843 | B2 | 2/2005 | Sircar et al. |
| 6,908,939 | B2 * | 6/2005 | Bernardon et al. .......... 514/369 |
| 2002/0016461 | A1 | 2/2002 | Albers et al. |
| 2002/0095041 | A1 | 7/2002 | Chan et al. |
| 2002/0103195 | A1 | 8/2002 | Curtin et al. |
| 2002/0151595 | A1 | 10/2002 | Ries et al. |
| 2002/0173656 | A1 | 11/2002 | Peyman et al. |

(Continued)

FOREIGN PATENT DOCUMENTS

| | | |
|---|---|---|
| DE | 199 28 424 | 12/2000 |

(Continued)

OTHER PUBLICATIONS

Srivastava et al., 1981, CAS: 95:125911.*

(Continued)

*Primary Examiner*—Rei-tsang Shiao
(74) *Attorney, Agent, or Firm*—Kilpatrick Stockton LLP

(57) ABSTRACT

This invention provides aryl and heteroaryl compounds of Formula (I) as described herein, and methods of their preparation. Also provided are pharmaceutical compositions made with the compounds of Formula (I) and methods for making such compositions. Compounds of Formula (I) may be useful for treating viral infections including orthopox viruses, either alone or in combination with other therapeutic agents.

35 Claims, No Drawings

U.S. PATENT DOCUMENTS

| | | | | |
|---|---|---|---|---|
| 2002/0198195 | A1 | 12/2002 | Nazare et al. | |
| 2003/0045480 | A1 | 3/2003 | Safar et al. | |
| 2003/0149083 | A1 | 8/2003 | Tanaka et al. | |
| 2004/0106626 | A1 | 6/2004 | South et al. | |
| 2004/0126856 | A1 | 7/2004 | Bajal et al. | |
| 2004/0152888 | A1 | 8/2004 | Bourguignon et al. | |
| 2004/0198780 | A1 | 10/2004 | Liu et al. | |
| 2004/0220180 | A1 | 11/2004 | Glick et al. | |
| 2004/0241781 | A1 | 12/2004 | Glick et al. | |
| 2005/0049310 | A1 | 3/2005 | Mjalli et al. | |
| 2005/0053600 | A1 | 3/2005 | Lane | |
| 2005/0059705 | A1 | 3/2005 | Mjalli et al. | |
| 2005/0065346 | A1 | 3/2005 | Ries et al. | |
| 2005/0165107 | A1 | 7/2005 | Inoue et al. | |
| 2005/0187390 | A1 | 8/2005 | Schmitz et al. | |
| 2005/0187409 | A1 | 8/2005 | Powers et al. | |
| 2005/0203135 | A1 | 9/2005 | Burdick et al. | |
| 2005/0256116 | A1* | 11/2005 | Clary et al. .............. | 514/232.5 |

FOREIGN PATENT DOCUMENTS

| | | |
|---|---|---|
| EP | 0150118 | 9/1987 |
| EP | 1213288 | 12/2002 |
| FR | 2 847 251 | 5/2004 |
| GB | 1 501 541 | 2/1978 |
| GB | 2354440 | 7/2000 |
| JP | 61-227555 | 10/1986 |
| JP | 09-124569 | 5/1997 |
| JP | 2001-089368 | 4/2001 |
| JP | 2003-321358 | 11/2003 |
| JP | 2004-323487 | 11/2004 |
| WO | WO 96-33170 | 10/1996 |
| WO | WO 97-23508 | 7/1997 |
| WO | WO 97-40065 | 10/1997 |
| WO | WO 97-42216 | 11/1997 |
| WO | WO 98/37075 | 8/1998 |
| WO | WO 95/12611 | 11/1998 |
| WO | WO 98/53817 | 12/1998 |
| WO | WO 98-58950 | 12/1998 |
| WO | WO 99/26923 | 6/1999 |
| WO | WO 99/36393 | 7/1999 |
| WO | WO 00-35864 | 6/2000 |
| WO | WO 00/37429 | 6/2000 |
| WO | WO 00/67746 | 11/2000 |
| WO | WO 00/68188 | 11/2000 |
| WO | WO 00/76971 | 12/2000 |
| WO | WO 01/10823 | 2/2001 |
| WO | WO 01/21584 | 3/2001 |
| WO | WO 01/38309 | 5/2001 |
| WO | WO 01-056994 | 8/2001 |
| WO | WO 01/68586 | 9/2001 |
| WO | WO 02/18320 | 3/2002 |
| WO | WO 02/26717 | 4/2002 |
| WO | WO 02/062748 | 8/2002 |
| WO | WO 02-083842 | 10/2002 |
| WO | WO 02/085841 | 10/2002 |
| WO | WO 03-002545 | 1/2003 |
| WO | WO 03-006444 | 1/2003 |
| WO | WO 03/007945 | 1/2003 |
| WO | WO 03/033496 | 4/2003 |
| WO | WO 03-072536 | 9/2003 |
| WO | WO 2004/014844 | 2/2004 |
| WO | WO 2004/046091 | 6/2004 |
| WO | WO 2004/080970 | 9/2004 |
| WO | WO 2004/084842 | 10/2004 |
| WO | WO 2004-110983 | 12/2004 |
| WO | WO 2005-012288 | 2/2005 |
| WO | WO 2005-039494 | 5/2005 |

OTHER PUBLICATIONS

St. Hilaire et al. CAS:141:150947.*

Bernardon et al., CAS: 139:101121.*

Burdick et al, "N-Benzoyl Amino Acids as LFA-1/ICAM Inhibitors 1: Amino Acid Structure-Activity Relationship" Bioorganic Medicinal Chemistry Letters, vol. 13, pp. 1015-1018 (2003).

Castanedo et al, "Solid-Phase synthesis of dual alpha4beta1/alpha4beta7 Integrin antagonists: Two Scaffolds with Overlapping Pharmacophores", Bioorganic & Medicinal Chemistry Letters, Oxford, GB vol. 12, pp. 2913-2917 (2002).

Database Caplus Chemical Abstracts Service, Columbus, Ohio, US, XP002319820, rerieed from STN Database accession No. 1973: 504834 abstract; RN 42787-97-3 abstract & I. Hahnemann et al, Journal For Praktische Chemie, vol. 315, No. 4, 1973, pp. 796-800.

Greenspan P.D. et al., "N-aryl Cinnamides: A Novel Class of Rigid and Highly Potent Leukotriene B4 Receptor Antagonists", Bioorganic and Medicinal Chemistry Letters, vol. 7, pp. 949-954 (1997).

International Search Report for related PCT application PCT/US2004/025463 mailed Jan. 26, 2005.

International Search Report for related PCT application PCT/US2004/025478 mailed Jan. 26, 2005.

International Search Report for related PCT application PCT/US2004/025429 mailed Jan. 26, 2005.

International Search Report for PCT application PCT/US03/25045 mailed Mar. 14, 2005.

Knowles, H.S. et al., "A photochemical approach to phenylalanines and related compounds by alkylation of glycine", Tetrahedron, vol. 57, pp. 98115-98124 (2001).

O'Donnell M.J. et al., "Enantioselective Solid-Phase Synthesis of α-Amino Acid Derivatives", Tetrahedron, vol. 55, pp. 6347-6362 (1999).

Sircar et al, "Synthesis and SAR of N-benzoyl-L-Biphenylalanine derivatives: Discovery of TR-14035, A Dual Alpha4Beta7/Alpha4Beta1 Intergrin Antagonist", Bioorganic & Medicinal Chemistry, vol. 10, pp. 2051-2066 (2002).

Bebernitz et al., "Anilides of R-Trifluoro-2-hydroxy-2-methylpropionic Acid as Inhibitors of Pyruvate Dehydrogenase Kinase", Journal of Medicinal Chemistry, vol. 43, pp. 7121-7124, (2000).

Shrader et al., "Neutral Inhibitors of the Serine Protease Factor Xa", Bioorganic & Medicinal Chemistry Letters, vol. 11, pp. 1801-1804, (2001).

Knowles et al., "Photochemical alkylation of glycine leading to phenylalanines", Tetrahedron Letters, vol. 41, pp. 7121-7124, (2000).

International Search Report for related PCT application PCT/US2004/025478 mailed Feb. 23, 2006.

Alves et al., "A Novel 3-step Enantioselective Synthesis of Pyrenrlalanine with Subsequent Incorporation Into Opioid, CCK and Melanotropin Ligands" Biochemical and Biophysical Research Communications, vol. 318, pp. 335-340, (2004).

Amino et al., "Phenylalanine Derivatives Enhancing Intestinal Absorption of Insulin in Mice" Chemical and Pharmaceutical Bulletin, vol. 36, pp. 4426-4434, (1988).

Ankersen et al., "Demonstration of the Strength of Focused Combinatorial Libraries in SAR Optimisation of Growth Hormone Secretagogues" European Journal of Medicinal Chemistry, vol. 34, pp. 783-790, (1999).

Au-Yeung et al., "Unnatural A-Amino Acids Via Asymmetric Hydrogenation of Enamides" Transition Metals for Organic Synthesis and Fine Chemicals, vol. 2, pp. 14-25, (1998).

Balwierczak et al., "Characterization of a Potent and Selective Endothelin-B Receptor Antagonist, IRL 2500" Journal of Cardiovascular Pharmacology, vol. 26, pp. S393-S396, (1995).

Batt et al., "5-Amidinoindoles as Dual Inhibitors of Coagulation Factors IXa and Xa" Bioorganic & Medicinal Chemistry Letters, vol. 14, pp. 5269-5273, (2004).

Bedsted et al., "Heparin and Calcium Ions Dramatically Enhance Antihrombin Reactivity WIth Factor IXa by Generating New Interaction Exosites" Biochemistry, vol. 42, pp. 8143-8152, (2003).
Benincosa et al., "Pharmacokinetics and Pharmacodynamics of a Humanized Monoclonal Antibody to Factor IX in Cynomolgus Monkeys" The Journal of Pharmacology and Experimental Therapeutics, vol. 292, pp. 810-816, (2000).
Blostein et al., "The Gla Domain Factor IXa Binds to Factor VIIIa In the Tenase Complex" The Journal of Biological Chemistry, vol. 278, pp. 31297-31302, (2003).
Boitano et al., "Structure Activity Studies of a Novel Cytotoxic Benzodiazepine" Bioorganic & Medicinal Chemistry Letters, vol. 13, pp. 3327-3330, (2003).
Burger et al., "Ein Neuer Allgemeiner Zugang Zu α-Trifluormethyl-Substituierten Aromatischen und Heteroaromatischen α-Aminosäuren" Synthesis, vol. 11, pp. 850-855, (1989).
Burk et al., "A Versatile Tandem Catalysis Procedure for the Preparation of Novel Amino Acids and Peptides" Journal of the American Chemical Society, vol. 116, pp. 10847-10848, (1994).
Burk et al., "Asymmetric Catalytic Routes to Chiral Building Blocks of Medicinal Interest" Pure and Applied Chemistry, vol. 68, pp. 37-44, (1996).
Chapman et al., "Synthesis of Functionalised Phenylalanines Using Rhodium Catalysis in Water" Advanced Synthesis & Catalysis, vol. 345, pp. 353-355, (2003).
Chisholm et al., "Identification of the Enantioselective Step in the Asymmetric Catalytic Hydrogenation of a Prochiral Olefin" Journal of the American Chemical Society, vol. 102, pp. 5952-5954, (1980).
Cui et al., "An Oxyanion-Hole Selective Serine Protease Inhibitor In Complex With Tryspin" Bioorganic & Medicinal Chemistry Letters, vol. 10, pp. 41-46, (2002).
Das et al., "Molecular Design and Structure—Activity Relationships Leading to the Potent, Selective, and Orally Active Thrombin Active Site Inhibitor BMS—189664" Bioorganic & Medicinal Chemistry Letters, vol. 12, pp. 45-49, (2002).
Delazlo et al., "Identification of Unique VLA-4 Antagonists From a Combinatorial Library" Bioorganc & Medicinal Chemistry Letters, vol. 12, pp. 685-688, (2002).
Dobler et al., "Unusual Amino Acids IV. Asymmetric Synthesis of Thienylalanines" Tetrahedron: Asymmetry, vol. 4, pp. 1833-1842, (1993).
Doherty et al., "N-Aryl 2, 6-Dimethoxybiphenylalanine Analogues as VLA-4 Antagonists" Bioorganic & Medicinal Chemistry Letters, vol. 12, pp. 729-731, (2002).
Egger et al., "A Small Molecule $\alpha^4\beta_1/\alpha_4\beta_7$ Antagonist Differentiates Between the Low-Affinity States of $\alpha4\beta_1$ and $\alpha_4\beta_7$; Characterization of Divalent Cation Dependence" Journal of Pharmacology and Experimental Therapeutics, vol. 306, pp. 903-913, (2003).
Egusa et al., "One-Dimensional Aromatic Crystals in solution. 4. Ground-and Excited-State Interactions of Poly(L-1 Pyrenylalanine) Studied by Chiroptical Spectroscopy Including Circularly Polarized Fluorescence and Fluorescence-Detected Circular Dichroism" Macromolecules, vol. 18, pp. 882-889, (1985).
Feuerstein et al., "Antithrombotic Efficacy of a Novel Murine Antihuman Factor IX Antibody In Rats" Arteriosclerosis, Thrombosis, and Vascular Biology, vol. 19, pp. 2554-2562, (1999).
Firooznia et al., "Synthesis of 4-Substituted Phenylalanines by Cross-Coupling Reactions: Extension of the Methodology to Aryl Chlorides" Tetrahedron Letters, vol. 39, pp. 3985-3988, (1998).
Fruh et al., "IRL 2500: a Potent $ET_8$ Selective Endothelin Antagonist" Bioorganic & Medicinal Chemistry Letters, vol. 6, pp. 2323-2328, (1996).
Gadek et al., "Generation of an LFA-1 Antagonist by the Transfer of the ICAM-1 Immunoregulatory Epitope to a Small Molecule" Science, vol. 295, pp. 1086-1089, (2002).
Hirayama et al., "The Discovery of YM-60828: a Potent, Selective and Orally-Bioavailable Factor Xa Inhibitor" Bioorganic & Medicinal Chemistry Letters, vol. 10, pp. 1509-1523, (2002).
Hoshina et al. "2, 3-Diphenylpropionic Acids as Potent VLA-4 Antagonists" Bioorganic & Medicinal Chemistry Letters, vol. 15, pp. 217-220, (2005).
Hsieh et al., "Topographic Probes of Angiotensin the Receptor: Potent Angiotensin II Agonist Containing Diphenylalanine and Long-Acting Antagonists Containing Biphenylalanine and 2-Indan Amino Acid in Position 8" Journal of Medicinal Chemistry, vol. 32, pp. 898-903, (1989).
Hsu et al., "The Distinct Roles That Gin-192 and Glu-217 of Factor IX Play in Selectivity For Macromolecular Substrates and Inhibitors" Biochemistry, vol. 40, pp. 11261-11269, (2001).
Ikeda, et al., "Diastereoselective Hydrogenation of Dehydrodipeptides with a Polycondensed Aromatic Ring at β-Position of Dehydroamino Acid Residue" Chemistry Express, vol. 5, pp. 29-32, (1990).
Kagan et al., "Asymmetric Catalytic Reduction With Transition Metal Complexes. I. A Catalytic System of Rhodium (I) With (-)-2,3-O-isopropylidene-2,3-dihydroxy-1,4-bis(diphenylphosphino)butane, A New Chiral Diphosphine" Journal of the American Chemical Society, vol. 94, pp. 6429-6433, (1972).
Kannan et al., "Stereochemistry of the Cyclic Tripeptide Antibiotic WS-43708A" Journal of Organic Chemistry, vol. 52, pp. 5435-5437, (1987).
Kato et al., "Novel Benzamides as Selective and Potent Gastrokinetic Agents. III. Synthesis and Structure-Activity Relationships of 4-amino-5-chloro-2-methoxy-and 2-ethoxy-*N*-[(4-substituted 2-morpholinyl) methyl]-benzamides" Chemical and Pharmaceutical Bulletin, vol. 40, pp. 652-660, (1992).
Kolkman et al., "Surface-Loop Residue $Lys^{316}$ In Blood Coagulation Factor IX is a Major Determinant For Factor X But Not Antithrombin Recognition" Biochemistry, vol. 350, pp. 701-707, (2000).
Krause et al., "Unusual Amino Acids VI. Substituted Arylamino Acids by Asymmetric Hydrogenation of *N*-Cbz and *N*-Boc Protected Dehydroamino Acid Derivatives" Chirality, vol. 8, pp. 173-188. (1996).
Kreuzfeld et al., "Unusual Amino Acids v. Asymmetric Hydrogenation of (z)-N-acylaminocinnamic Acid Derivatives Bearing Different Protective Groups" Tetrahedron:Asymmetry, vol. 4, pp. 2047-2051, (1993).
Ksander et al., "Dipeptide Sulfonamides as Endothelin $ET_A/ET_B$ Receptor Antagonists[1]" Canadian Journal of Physiology and Pharmacology, vol. 80, pp. 464-469, (2002).
Kudlacz et al., "Pulmonary Eosinophilia in a Murine Model of Allergic Inflammation is Attenuated By Small Molecule $\alpha4\beta1$ Antagonists" Journal of Pharmacology and Experimental Therapeutics, vol. 301, pp. 747-752, (2002).
Lettre et al., "Chemically Labeled Antigens. III. Introduction of 4-Ring Systems Into Proteins" Hoppe-Seyler's Zeitschrift for Physiologische Chemie, vol. 267, pp. 108-114, (1940).
Leung et al., "Use of A-192621 and IRL-2500 to Unmask the Mesenteric and Renal Vasodilator Role of Endothelin ETb Receptors", Journal of Cardiovascular Pharmacology, vol. 39, pp. 533-543 (2002).
Lopez-Arbeloa et al., "Chiral Discrimination of the Intermolecular Excimer of *N*-acetyl-1-pyrenylalanine Methyl Ester" Journal of the American Chemical Society, vol. 109, pp. 3068-3076, (1987).
Ma et al., "Synthesis of the Biaryl Moiety of the Proteasome Inhibitors TMC-95 Via a Ligandless $Pd(Oac)_2$ -Catalyzed Suzuki-Coupling Reaction" Tetrahedron Letters, vol. 42, pp. 5279-5281, (2001).
Macchia et al., "Toward the Rational Development of Peptidomimetic Analog of the C-Terminal Endothelin Hexapeptide: Development of a Theoretical Model" Farmaco, vol. 53, pp. 545-556, (1998).
Macchiarulo et al., "Insights Into Phenylalanine Derivatives Recognition of VLA-4 Integrin: From a Pharmacophoric Study to 3D-QSAR and Molecular Docking Analyses" Journal of Chemical Information and Computer Sciences, vol. 44, pp. 1829-1839, (2004).
Mazaleyrat et al. "Practical Resolution of an Atropoisomeric α,α-Disubstituted Glycine with L-Phenylalanine Cyclohexylamide as Chiral Auxiliary" Tetrahedron: Asymmetry, vol. 9, pp. 2701-2713, (1998).
Melillo et al., "Practical Enantioselective Synthesis of a Homotyrosine Derivative and (*R*,*R*)-4-propyl-9-Hdroxynaphthoxazine, a Potent Dopamine Agonist" Journal of Organic Chemistry, vol. 52, pp. 5143-5150, (1987).
Mimatsu et al., "Circularly Polarized Luminescence Generated by Intramolecular Excimer of a Chiral Pyrenyl Compound" New Technologies & Medicine, vol. 2, pp. 45-47, (2001).

Mustafa et al., "Reactivity of Unsaturated Centres in Heterocycles and Chalkones Toward Diazoalkanes" Tetrahedron, vol. 21, pp. 2215-2229, (1965).
O'Donnell et al., "An Efficient Homogeneous Catalytic Enantioselective Synthetsis of $\alpha$-Amino Acid Derivatives" Tetrahedron Letters, vol. 39, pp. 8775-8778, (1998).
Ohmomo et al., "Synthesis and Evaluation of Iodinated Benzamide Derivatives as Selective and Reversible Monoamine Oxidase B Inhibitors" Chemical and Pharmaceutical Bulletin, vol. 40, pp. 1789-1792, (1992).
Ojima et al., "Asymmetric Hydrogenation of Prochiral Olefins Catalyzed By Rhodium Complexes With Chiral Pyrrolidinodiphosphines. Crucial Factors for the Effective Asymmetric Induction" Journal of Organic Chemistry, vol. 45, pp. 4728-4739, (1980).
Okamoto et al., "Optical Resolution of Amino Acid Derivatives By High-Performance Liquid Chromatography On Tris(phenylcarbamate)s of Cellulose and Amylose" Journal of Chromatography, vol. 477, pp. 367-376, (1989).
Omote et al., "Dopa Dimer" Chemical Communications, vol. 4, p. 190, (1968).
Omote et al., "Synthesis and Melanogenesis of the DOPA Dimer" Bulletin of the Chemical Society of Japan, vol. 42, pp. 1752-1754, (1969).
Ooi et al., "Design of *N*-spiro $C_2$-Symmetric Chiral Quaternary Ammonium Bromides As Novel Chiral Phase-Transfer Catalysts: Synthesis and Application to Practical Asymmetric Synthesis of $\alpha$-Amino Acids" Journal of the American Chemical Society, vol. 125, pp. 5139-5151, (2003).
Pawlowska et al, "Synthesis of Dextro-and Laevorotatory N-acetyl-$\beta$-(2-dibenzyfuryl)alanines" Polish Journal of Chemistry, vol. 58, pp. 619-620, (1984).
Pierson et al., "Catalytic Asymmetric Oxonium Yide—[2,3] Sigmatropic Rearrangement With Diazocarbonyl Compounds: First Use of $C_2$-Symmetry in Rh(II) Carboxylates" Tetrahedron Letters, vol. 38, pp. 4705-4708, (1997).
Rose et al., "Substrate Recognition Drives the Evolution of Serine Proteases" The Journal of Biological Chemistry, vol. 277, pp. 19243-19246, (2002).
Russell et al., "Characterization of the Binding of Endothelin $ET_B$ Selective Ligands In Human and Rat Heart" British Journal of Pharmacology, vol. 119, pp. 631-636, (1996).
Sakaguchi et al., "Synthesis, Gastrointestinal Prokinetic Activity and Structure-Activity Relationships of Novel *N*-[[2-(dialkylamino)ethoxy]benzyl]benzamide Derivatives" Chemical and Pharmaceutical Bulletin, vol. 40, pp. 202-211, (1992).
Sakaki et al., "Discovery of IRL 3461: a Novel and Potent Endothelin Antagonist With Balanced $ET_A/ET_B$ Affinity" Bioorganic & Medicinal Chemistry Letters, vol. 8, pp. 2241-2246, (1998).
Satoh et al., "Synthesis of 4-Substituted Phenylalanine Derivatives By Cross-Coupling Reaction of *p*-Boronophenylalanines" Tetrahedron Letters, vol. 38, pp. 7645-7648 (1997).
Schmidt et al., "Structure-Function Relationships In Factor IX and Factor IXa" Trends in Cardiovascular Medicine, vol. 13, pp. 39-45, (2003).
Shieh et al., "A Simple Asymmetric Synthesis of 4-arylphenylalanines Via Palladium-Catalyzed Cross-Coupling Reaction of Arylboronic Acids With Tyrosine Triflate" Journal of Organic Chemistry, vol. 57, pp. 379-381, (1992).
Shikamoto et al., "Crystal Structure of $Mg^{2+}$-and $Ca^{2+}$-Bound Gla Domain of Factor IX Complexed with Binding Protein" The Journal of Biological Chemistry, vol. 278, pp. 24090-24094, (2003).
Smallheer et al., "SAR and Factor IXa Crystal Structure of a Dual Inhibitor of Factors IXa and Xa" Bioorganic & Medicinal Chemistry Letters, vol. 14, pp. 5263-5267, (2004).
Stoilova-McPhie et al., "3-Dimensional Structure of Membrane-Bound Coagulation Factor VIII: Modeling of the Factor VIII Heterodimer Within a 3-Dimensional Density Map Derived By Electron Crystallography" Blood, vol. 99, pp. 1215-1223, (2002).
Strauss et al., "Optically Active Cyclic Hexapeptides With Covalently Attached Pyrene Probes: Selective Alkaline Earth Metal Ion Recognition Using Excimer Emission" Organic Letters, vol. 4, pp. 683-686, (2002).
Taudien et al., "Unusual Amino Acids III. Asymmetric Synthesis of 3-arylalanines" Tetrahedron: Asymmetry, vol. 4, pp. 73-84, (1993).
Toomey et al., "Inhibition of Factor IX(a) Is Protective In a Rat Model of Thromboembolic Stroke" Stroke, vol. 33, pp. 578-585, (2002).
Urbahns et al., "Biphenyls as Potent Vitronectin Receptor Antagonists, Part 2: Biphenylalanine Ureas" Bioorganic & Medicinal Chemistry Letters, vol. 13, pp. 1071-1074, (2003).
Webb et al., "Effects of the $ET_8$-Selective Antagonist IRL 2500 In Conscious Spontaneously Hypertensive and Wistar-Kyoto Rats" Journal of Cardiovascular Pharmacology, vol. 26, pp. S389-S392, (1995).
Weltz et al., "New Anticoagulant Drugs" Chest, vol. 119, pp. 95s-107s, (2001).
Yabe et al., "Analogues of Luteinizing Hormone-Releasing Hormone With Modification In Position 3[1]" Chemical & Pharmaceutical Bulletin, vol. 24, pp. 3149-3157, (1976).
Yang et al., "Localization of the Heparin Binding Exosites of Factor IXa" The Journal of Biological Chemistry, vol. 277, pp. 50756-50760, (2002).
Zhang et al., "Acylation of 2,5-Dimethoxycarbonyl[60]fulleropyrrolidine and Synthesis of Its Multifullerene Derivatives" Journal of Organic Chemistry, vol. 67, pp. 883-891, (2002).
Office Action mailed Jul. 9, 2007 for U.S. Appl. No. 10/913,168.
Office Action mailed Mar. 20, 2007 for U.S. Appl. No. 10/913,168.
Response mailed to USPTO on Apr. 16, 2007 for U.S. Appl. No. 10/913,168.
Office Action mailed Apr. 5, 2007 for U.S. Appl. No. 10/913,882.
Office Action mailed Dec. 7, 2006 for U.S. Appl. No. 10/913,882.
Response mailed to USPTO on Jan. 8, 2007 for U.S. Appl. No. 10/913,882.
Patent Cooperation Treaty Notification Concerning Transmittal of International Preliminary Report on Patentability and Written Opinion of the International Searching Authority for Application Serial No. PCT/US2004/025463 dated Jan. 24, 2005.
Patent Cooperation Treaty Notification Concerning Transmittal of International Preliminary Report on Patentability and Written Opinion of the International Searching Authority for Application Serial No. PCT/US2004/025429 dated Jan. 24, 2005.
Patent Cooperation Treaty Notification Concerning Transmittal of International Preliminary Report on Patentability and Written Opinion of the International Searching Authority for Application Serial No. PCT/US2004/025478 dated Jan. 24, 2005.

* cited by examiner

ARYL AND HETEROARYL COMPOUNDS, COMPOSITIONS, AND METHODS OF USE

STATEMENT OF RELATED APPLICATIONS

The present application claims priority under 35 USC 119 from the following U.S. Provisional Patent Applications: Ser. No. 60/493,879, filed Aug. 8, 2003, entitled "Aryl and Heteroaryl Compounds as Antviral agents"; Ser. No. 60/493,878, filed Aug. 8, 2003, entitled "Aryl and Heteroaryl Componds and Methods to Modulate Red Blood Cell Production"; Ser. No. 60/493,903, filed Aug. 8, 2003, entitled "Aryl and Heteroaryl Compounds and Methods to Modulate Coagulation", which are herein incorporated by reference in their entireties.

The invention disclosed herein was made with Government support under Grant Number 1 R43 A1060151-01 from the National Institutes of Health, U.S. Department of Health and Human Services. Accordingly, the U.S. Government has certain rights in this invention.

FIELD OF THE INVENTION

This invention relates to aryl and heteroaryl compounds and compositions that may possess antiviral activity, and methods of use of such compounds and compositions.

BACKGROUND OF THE INVENTION

Viruses may infect cells to take over the host cell machinery and produce new viral particles via transcription and translation processes. Interception of either of these processes, including pre- and post translation events, may cripple virus propagation.

Since the discovery of non-nucleoside reverse transcriptase inhibitors (NNRTI), and protease inhibitors (PI), nonnucleoside organic molecules have been designed to combat viral infections by inhibiting a variety of targets responsible for viral replication. Examples of such targets include reverse transcriptases, DNA polymerases, viral proteases (e.g., serine, cysteine, aspartyl, metalloproteases), integrases, helicases, fusion proteins, chemokines (CCR5, CXCR4), and chemokine receptors. For example, there are drugs which may prevent fusion of the viral envelope with the cell membrane and therefore inhibit the entry of viruses, such as human immunodeficiency virus (HIV), into the cell. Also, other drugs may act at the late stage of the viral replication cycle to prevent propagation of virus that is already in the cell.

Smallpox is a member of the highly homologous orthopox family of viruses. As of the 1990s, it was belileved that smallpox virus was no longer a health concern as the last known case of smallpox had occurred in 1977. Also, universal vaccination programs in the U.S. were discontinued in 1972 because the risk of complications from the vaccine was actually greater than the risk of being infected with the disease. Recently, however, cases of smallpox have been documented. In addition, due to the highly homologous nature of the orthopox family, therapeutics developed against smallpox are also potential candidate therapies for related viruses that continue to plague society such as monkeypox, a virus that recently reemerged in the Africa and spread to the US through exotic animals, and mulluscipox virus, which results in a common cutaneous infection that may be problematic with immunocompromised individuals. Thus, there is a renewed interest in developing antiviral agents to treat orthopox viruses, and more particularly, smallpox.

A wide spectrum of antiviral agents have been investigated using different strains of variola as well as other orthopoxviruses (Baker, et al., Antiviral research, 57, 13, 2003). Among antiviral compounds found to be useful were cidofovir (DNA polymerase), ribavrin and tiazofurin (IMP dehydrogenase), C-ca3-ADO, and C3-Npc-A (SAH hydrolase). Also, HPMPC (Cidofovir), a DNA Polymerase Inhibitor for the treatment of CMV retinitis in AIDS patients, may have therapeutic potential for treatment of various other herpes viruses, as well as polyomavirus, papillomavirus, adenovirus as well as poxvirus. For example, in vitro evidence demonstrates that HPMPC may be active against all poxviruses studied to date as well as vaccinia and cowpox virus infections. However, treatment with HPMPC is only currently available in either topical or intravenous forms. Also, side effects, including significant nephrotoxicity, may result.

While useful anti-viral compounds have been identified, viruses can rapidly acquire resistance to drugs. Thus, new anti-viral agents are needed that can be used alone or in a cocktail of drugs where the cocktail can cripple a virus by hitting a multitude of targets.

SUMMARY OF THE INVENTION

Embodiments of the present invention provide aryl and heteroaryl compounds, compositions, and methods of use of such compounds and compositions. The present invention may be embodied in a variety of ways.

In one embodiment, the present invention provides compounds of Formula (I) as described herein. In another embodiment, the present invention provides methods for the preparation of compounds of Formula (I).

The present invention also provides pharmaceutical compositions comprising compounds of Formula (I). In another embodiment, the present invention also provides methods for the preparation of compositions comprising the compounds of Formula (I). The pharmaceutical compositions may comprise pharmaceutically acceptable carriers, excipients, and/or diluents.

In another embodiment, the present invention provides methods for the use of compounds of Formula (I) and pharmaceutical compositions comprising compounds of Formula (I). In one embodiment, the compounds and pharmaceutical compositions of the present invention may be used for treating human or animal disorders. For example, the compounds and pharmaceutical compositions of the present invention may be used for treating or preventing viral infection in a subject. Compounds of Formula (I) may be useful in a variety of applications including treating or preventing viral infections in a subject such as, but not limited to, orthopox infections including smallpox, vaccinia virus, monkey pox, or cowpox viral infections. Thus, in one embodiment, the compounds and pharmaceutical compositions of the present invention may be used for treating or preventing orthopox viral infection in a subject. In an example embodiment, the the compounds and pharmaceutical compositions of the present invention may be used for treating or preventing smallpox viral infection.

The compounds and pharmaceutical compositions of the present invention may provide a number of advantages when used for treating human or animal disorders. In one embodiment, the compounds and pharmaceutical compositions of the present invention may provide a variety of treatment options. As small molecule therapeutics, example embodiments of the compounds and pharmaceutical compositions of the present invention may be administered orally, topically, or parentally. Also, the compounds and pharmaceutical compositions of the present invention may comprise a primary therapeutic or may be used as an adjunct to other therapeutics. For example, compounds of Formula (I) may also be useful in a combination therapy with an antiviral agent where administration of a the combination of a compound of Formula (I) and an antiviral agent may prevents viruses from bypassing or becoming resistant to an inhibitory effect of a compound of Formula (I) or the antiviral agent.

Additional features of the present invention will be described hereinafter. It is to be understood that the invention is not limited in its application to the details set forth in the foregoing or following description but is capable of other embodiments and of being practiced or carried out in various ways.

DETAILED DESCRIPTION

Embodiments of the present invention provide compounds, compositions and methods of use for such compounds. In certain embodiments, the compounds and compositions of the present invention may be used as antiviral agents for the treatment, preventions, or amelioration of viral infection.

Embodiments of the present invention comprise compounds of Formula (I) as depicted below. Embodiments of the present invention also comprise methods of the preparation of compounds of Formula (I) and/or pharmaceutical compositions comprising compounds of Formula (I).

In other embodiments, the present invention provides methods for the use of compounds of Formula (I) and pharmaceutical compositions comprising compounds of Formula (I) in treating human or animal disorders. Compounds of Formula (I) and pharmaceutical compositions comprising compounds of Formula (I) may be useful in a variety of applications. For example, the present invention provides methods of treating or preventing viral infections in a subject. The present invention also provides methods for the preparation of compounds of Formula (I) and methods of preparation of pharmaceutical compositions comprising compounds of Formula (I).

Compounds of Formula (I) may be useful in a variety of applications including treating or preventing viral infections in a subject such as, but not limited to, orthopox infections such as smallpox, vaccinia virus, monkey pox, or cowpox viral infections. Compounds of Formula (I) may also be useful in a combination therapy with an antiviral agent where administration of a the combination of a compound of Formula (I) and an antiviral agent may prevents viruses from bypassing or becoming resistant to an inhibitory effect of a compound of Formula (I) or antiviral agent.

Thus, in one aspect, the present invention provides compounds of Formula (I):

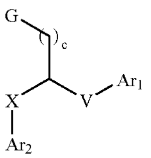

(I)

wherein c is equal to 0, 1, or 2; wherein the values of 0, 1, and 2 comprise a direct bond, $—CH_2—$, and $—CH_2—CH_2—$, optionally substituted 1 to 4 times with a substituent group, wherein said substituent group(s) or the term substituted refers to groups comprising: -alkyl, -aryl, -alkylene-aryl, -arylene-alkyl, -alkylene-arylene-alkyl, —O-alkyl, —O-aryl, or -hydroxyl. In an embodiment, c is equal to 0 or 1. In another embodiment, c is equal to 0.

G comprises: -hydrogen, -alkyl, -heteroaryl, -aryl, -heterocyclcl, $—CH{=}CH—CO_2R_1$, $—CO_2R_1$, $—CH_2OR_1$, $—CH_2SR_1—C(O)—R_1$, $—C(O)NR_1R_2$, $—C(R_1){=}N—O—R_2$, $—C(O)C(O)R_1$, $—C(O)C(O)NR_1R_2$, $—CH{=}CH—NO_2$, $—CH{=}CH—CN$, $—C(O)—C(O)—OR_1$, an acid isostere, or an ester isostere; wherein $R_1$ and $R_2$ independently comprise: -hydrogen, -alkyl, -aryl, -alkenyl, -arylene-alkyl, -alkylene-aryl, -alkylene-arylene-alkyl, -heterocyclyl, or -heteroaryl, or when $R_1$ and $R_2$ are bonded to a nitrogen group in G, $R_1$ and $R_2$ may be taken together to form a ring having the formula $—(CH_2)_m$-$Z_2$-$(CH_2)_n$, wherein m and n are, independently, 1, 2, 3, or 4; $Z_2$ comprises $—CH_2—$, $—C(O)—$, $—O—$, $—N(H)—$, $—S—$, $—S(O)—$, $—S(O_2)—$, $—CON(H)—$, $—NHC(O)—$, $—NHC(O)N(H)—$, $—NH(SO_2)—$, $—S(O_2)N(H)—$, $—(O)CO—$, $—NHS(O_2)NH—$, $—OC(O)—$, $—N(R_{21})—$, $—N(C(O)R_{21})—$, $—N(C(O)NHR_{21})—$, $—N(S(O_2)NHR_{21})—$, $—N(SO_2R_{21})—$, or $—N(C(O)OR_{21})—$; wherein $R_{21}$ comprises hydrogen, aryl, alkyl, or alkylene-aryl; or when when $R_1$ and $R_2$ are bonded to a nitrogen group in G, $R_2$ may be optionally substituted with a substituent of the formula

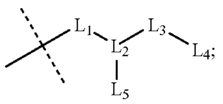

wherein

- $L_1$ comprises a direct bond, alkylene, —O-alkylene-, alkylene-O—, —NH—C(O)—, —C(O)—NH— or —NH—C(O)—NH—;
- $L_2$ comprises alkyline, alkenyline, heteroaryline, aryline, or heterocyclyline;
- $L_3$ comprises —O—, $—N(R_3)—$, $—C(O)—N(R_3)—$, —C(O)—O—, —C(O)—, $—N(R_3)—C(O)—N(R_4)—$, $—CH{=}CH—CO_2R_1$, $—C(O)R_1$, $—C(O)C(O)R_1$, or $—C(O)C(O)NR_1R_2$;
- $L_4$ comprises hydrogen, alkyl, alkenyl, alkynyl, heterocyclyl, heteroaryl, or -alkylene-aryl;
- $L_5$ comprises hydrogen, alkyl, alkenyl, alkynyl, -akylene-aryl, -alkylene-heteroaryl, alkylene-O-alkylene-aryl, -alkylene-S-alkylene-aryl, -alkylene-O-alkyl, -alkylene-S-alkyl, $-alkylene-NH_2$, -alkylene-OH, -alkylene-SH, $-alkylene-C(O)—OR_5$, $-alkylene-C(O)—NR_5R_6$, $-alkylene-NR_5R_6$, $-alkylene-N(R_5)—C(O)—R_6$, $-alkylene-N(R_5)—S(O_2)—R_6$; or

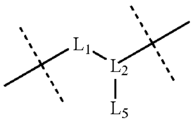

may be taken together to constitute a direct bond; and wherein $R_3$, $R_4$, $R_5$, and $R_6$ independently comprise hydrogen, aryl, heteroaryl, alkyl, -alkylene-aryl, or, -alkylene-heteroaryl.

In an embodiment, G comprises: -hydrogen, $—CO_2R_1$, $—C(O)NR_1R_2$, or $—C(O)R_1$, wherein $R_1$ and $R_2$ independently comprise -hydrogen, -alkyl, -alkenyl, -aryl. In another embodiment, G comprises an ester isostere comprising the substituted oxadiazole:

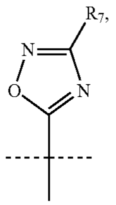

wherein $R_7$ comprises alkyl, aryl, alkylene-sulfonyl-alkyl or alkylene-sulfonyl-aryl. In another embodiment $R_7$ comprises an alkyl group. In another embodiment, G comprises—hydrogen. In another embodiment, G comprises $—CO_2R_1$ wherein $R_1$ comprises alkyl.

V comprises: $—(CH_2)_b—O—(CH_2)_a—$, $—(CH_2)_b—N(R_8)—(CH_2)_a—$, $—(CH_2)_b—O—$, $—(CH_2)_b—N(R_8)$, $—(CH_2)_a—$, $—CH{=}CH—(R_8)—$ or a direct bond; in which a is equal to 0, 1, or 2, b is equal to 1 or 2, and $R_8$ comprises: -hydrogen, -alkyl, -aryl, -arylene-alkyl, -alkylene-aryl, or -alkylene-arylene-alkyl; wherein the $—CH_2—$ groups may be optionally substituted 1 to 4 times with a substituent group comprising: -alkyl, -aryl, -alkylene-aryl, -arylene-alkyl, -alkylene-arylene-alkyl, —O-alkyl, —O-aryl, -hydroxyl, —S-alkyl, or —S-aryl. In an embodiment, V comprises: $—(CH_2)_a—$, $—(CH_2)_b—O—(CH_2)_a—$, or a direct bond, wherein a is equal to 1 or 2, and b is equal to 1. In another embodiment, V comprises: $—(CH_2)_a—$ or a direct bond, wherein a is equal to 1.

X comprises: $—N(R_9)—$, $—CON(R_9)—$, $—N(R_9)CO—$, $—N(R_9)CON(R_{10})—$, $—OC(O)N(R_8)—$, $—SO_2N(R_9)—$, $—N(R_9)\ SO_2—$, or $—N(R_9)SO_2N(R_{10})—$; wherein $R_9$ and $R_{10}$ independently comprise: -hydrogen, -alkyl, -aryl, -arylene-alkyl, -alkylene-aryl, -alkylene-arylene-alkyl, or $—(CH_2)_dY—$, wherein d is equal to 0, 1, or 2, wherein Y comprises: -hydrogen, $—CO_2R_{11}$, $—CH_2OR_{11}$, $—C(O)—R_{11}$, $—C(O)NR_{11}R_{12}$, $—C(R_{11}){=}N—O—R_{12}$, $—NR_{11}R_{12}$, or an acid isostere; wherein $R_{11}$ and $R_{12}$ independently comprise: -hydrogen, -alkyl, -aryl, -arylene-alkyl, -alkylene-aryl, -alkylene-arylene-alkyl, -heterocyclyl, or -heteroaryl. In an embodiment, X comprises: $—N(R_9)—$, $—CON(R_9)—$, $—N(R_9)CO—$, or $—N(R_9)CON(R_{10})—$, wherein $R_9$ and $R_{10}$ independently comprise: -hydrogen, -alkyl, -aryl, -arylene-alkyl, -alkylene-aryl, or -alkylene-arylene-alkyl. In another embodiment, X comprises $—N(R_9)—$, $—CON(R_9)—$, or $—N(R_9)CO—$, wherein $R_9$ comprises -hydrogen, -alkyl, -aryl, -arylene-alkyl, -alkylene-aryl, or -alkylene-arylene-alkyl. In another embodiment, X comprises $—CON(R_9)—$, wherein $R_9$ comprises -hydrogen.

$Ar_1$ comprises an aryl, heteroaryl, fused cycloalkylaryl, fused cycloalkylheteroaryl, fused heterocyclylaryl, or fused heterocyclylheteroaryl group optionally substituted 1 to 7 times. In another embodiment, $Ar_1$ comprises a mono- or bicyclic aryl or heteroaryl group optionally substituted 1 to 7 times. In another embodiment, $Ar_1$ comprises a phenyl group having 1 to 5 substituents. In various embodiments of $Ar_1$, the substituents of $Ar_1$ may independently comprise:

a) -fluoro;
b) -chloro;
c) -bromo;
d) -iodo;
e) -cyano;
f) -nitro;
g) -perfluoroalkyl;
h) -D-$R_{12}$;
i) -alkyl;
j) -aryl;
k) -heteroaryl;
l) -heterocyclyl;
m) -cycloalkyl;
n) -alkylene-aryl;
o) -alkylene-arylene-aryl;
p) -alkylene-arylene-alkyl;
q) -arylene-alkyl;
r) -arylene-arylene-alkyl;
s) -D-alkyl;
t) -D-aryl;
u) -D-alkylene-aryl;
v) -D-arylene-alkyl;
w) -D-alkylene-arylene-aryl;
x) -D-arylene-arylene-aryl;
y) -D-alkylene-arylene-alkyl;
z) -alkylene-D-alkylene-aryl;
aa) -arylene-D-alkyl;
bb) -alkylene-D-aryl;
cc) -alkylene-D-heteroaryl;
dd) -alkylene-D-cycloalkyl;
ee) -alkylene-D-heterocyclyl;
ff) -alkylene-D-arylene-alkyl;
gg) -alkylene-D-alkylene-arylene-alkyl;
hh) -alkylene-D-alkyl;
ii) -alkylene-D-$R_{13}$;
jj) -arylene-D-$R_{13}$;
jj) -arylene-T-$R_{17}$;
kk) -T-alkylene-arylene-heteroaryl;
ll) -T-alkylene-heterocyclyl;
mm) -T-alkylene-heteroaryl;
nn) -T-heteroaryl;
oo) -T-fused heterocyclylaryl;
pp) -T-fused cycloalkylaryl;
qq) -T-fused arylcycloalkyl;
rr) -T-fused fused heterocyclylaryl;
ss) -T-fused fused arylheterocyclyl;
tt) -T-fused fused cycloalkylheteroaryl;
uu) -T-fused fused heteroarylcycloalkyl;
vv) -T-fused heterocyclylheteroaryl;
ww) -T-fused heteroarylheterocyclyl; or
xx) -hydrogen;

wherein T comprises a direct bond, $—CH_2—$, $—O—$, $—N(R_{18})—$, $—C(O)—$, $—CON(R_{18})—$, $—N(R_{18})C(O)—$, $—N(R_{18})CON(R_{19})—$, $—N(R_{18})C(O)O—$, $—OC(O)N(R_{18})—$, $—N(R_{18})SO_2—$, $—SO_2N(R_{18})—$, $—C(O)—O—$, $—O—C(O)—$, $—S—$, $—S(O)—$, $—S(O_2)—$, $—N(R_{18})SO_2N(R_{19})—$,

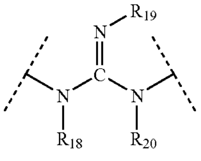

; or

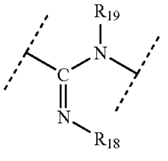

and wherein $R_{17}$, $R_{18}$, $R_{19}$ and $R_{20}$, independently comprise: -hydrogen, -alkyl, -aryl, -arylene-alkyl, -alkylene-aryl, or -alkylene-arylene-alkyl. In another embodiment, $Ar_1$ comprises a mono-substituted phenyl group wherein the substituent comprises: -aryl, -arylene-alkyl, -D-aryl, -D-alkylene-arylene-alkyl, or -arylene-D-alkyl; wherein D comprises —O—, —$N(R_{14})$—, —$CON(R_{14})$—, or —$N(R_{14})C(O)$—, and wherein $R_{14}$ comprises: -hydrogen; -alkyl; or -aryl.

In another embodiment, $Ar_1$ comprises: 2'-(4-tert-butyl-phenoxy -biphenyl-4-yl, 2'-(4-trifluoromethyl-phenoxy)-biphenyl-4-yl, 2'-phenoxy-biphenyl-4-yl, 2'-trifluoromethyl-biphenyl-4-yl, 3',4'-dichloro-biphenyl-4-yl, 3',4'-difluoro-biphenyl-4-yl, 3',5'-bis-trifluoromethyl-biphenyl-4-yl, 3',5'-difluoro-biphenyl-4-yl, 3'-chloro-4'-fluoro-6-methoxy-biphenyl-3-yl, 3'-chloro-4'-fluoro-biphenyl-2-yl, 3'-chloro-4'-fluoro-biphenyl-3-yl, 3'-chloro-4'-fluoro-biphenyl-4-yl, 3'-chloro-biphenyl-4-yl, 3'-nitro-biphenyl-4-yl, 3'-trifluoromethoxy-biphenyl-4-yl, 3'-trifluoromethyl-biphenyl-4-yl, 4'-benzyloxy-3'-fluoro-biphenyl-4-yl, 4-benzyloxy-phenyl, 4'-chloro-biphenyl-4-yl, 4'-fluoro-biphenyl-4-yl, 4'-methanesulfonyl-biphenyl-4-yl, 4-naphthalen-2-yl-phenyl, 4'-nitro-biphenyl-4-yl, 4'-phenoxy-biphenyl-4-yl, 4-pyridin-3-yl-phenyl4'-tert-butyl-biphenyl-4-yl, 4'-trifluoromethyl-biphenyl-4-yl, 6-methoxy-4'-nitro-biphenyl-3-yl, biphenyl, biphenyl-4-yl, chlorofluorophenoxy-phenyl, or (cyano-phenoxy)-phenyl.

In another embodiment, $Ar_1$ comprises: [2-(4-chloro-phenyl)-ethoxy]-phenyl, (4-nitro-phenoxy)-phenyl, (3-phenyl-propylamino)-phenyl, 4-methoxy-4'-nitro-biphenyl-3-yl, (4'-methanesulfonyl-4-methoxy-biphenyl-3-yl), or (4'-methanesulfonyl-4-hydroxy-biphenyl-3-yl).

In another embodiment, $Ar_1$ comprises an unsubstituted biphenyl group.

In yet another embodiment, $Ar_1$ comprises a biphenyl group substituted with at least one of the following groups fluoro, chloro, trifluoroalkyl, trifluoroalkoxy, nitro, benzyloxy, phenoxy, and alkylsulfonyl.

$Ar_2$ comprises an aryl or heteroaryl group optionally substituted 1 to 7 times. In one embodiment, $Ar_2$ comprises a phenyl, naphthyl, pyridyl, isoquinolyl, pyrimidyl or quinazolyl group optionally substituted 1 to 7 times. In another embodiment, $Ar_2$ comprises a substituted phenyl, 2-naphthyl, 2-pyridyl, 3-isoquinolyl, 2-pyrimidyl or 2-quinazolyl group having 1 to 5 substituents. In various embodiments of $Ar_2$, the substituents of $Ar_2$ may independently comprise:

a) -fluoro;
b) -chloro;
c) -bromo;
d) -iodo;
e) -cyano;
f) -nitro;
g) -perfluoroalkyl;
h) -T-$R_{17}$;
i) -alkyl;
j) -aryl;
k) -heteroaryl;
l) -heterocyclyl;
m) -cycloalkyl;
n) -alkylene-aryl;
o) -alkylene-arylene-aryl;
p) -alkylene-arylene-alkyl;
q) -arylene-alkyl;
r) -arylene-arylene-alkyl;
s) -T-alkyl;
t) -T-aryl;
u) -T-alkylene-aryl;
v) -T-arylene-alkyl;
w) -T-alkylene-arylene-aryl;
x) -T-arylene-arylene-aryl;
y) -T-alkylene-arylene-alkyl;

z) -alkylene-T-alkylene-aryl;
aa) -arylene-T-alkyl;
bb) -alkylene-T-aryl;
cc) -alkylene-T-heteroaryl;
dd) -alkylene-T-cycloalkyl;
ee) -alkylene-T-heterocyclyl;
ff) -alkylene-T-arylene-alkyl;
gg) -alkylene-T-alkylene-arylene-alkyl; or
hh) -alkylene-T-alkyl;
ii) -alkylene-T-$R_{17}$;
jj) -arylene-T-$R_{17}$; or
kk) -hydrogen;

wherein T comprises —$CH_2$—, —O—, —$N(R_{18})$—, —C(O)—, —$CON(R_{18})$—, —$N(R_{18})C(O)$—, —$N(R_{18})CON(R_{19})$—, —$N(R_{181})C(O)O$—, —$OC(O)N(R_{18})$—, —$N(R_{18})SO_2$—, —$SO_2N(R_{18})$—, —C(O)—O—, —O—C(O)—, —S—, —S(O)—, —$S(O_2)$—, —$N(R_{18})SO_2N(R_{19})$—,

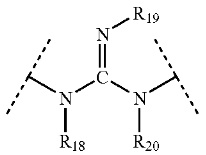
, or
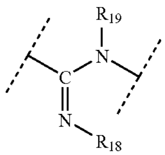
, and wherein $R_{17}$, $R_{18}$, $R_{19}$ and $R_{20}$, independently comprise: -hydrogen, -alkyl, -aryl, -arylene-alkyl, -alkylene-aryl, or -alkylene-arylene-alkyl. In another embodiment, $Ar_2$ comprises a substituted phenyl, 2-naphthyl, 2-pyridyl, 3-isoquinolyl, 2-pyrimidyl or 2-quinazolyl group having 1 to 5 substituents independently comprising:

a) -fluoro;
b) -chloro;
c) -bromo;
d) -iodo;
e) -cyano;
f) -nitro;
g) -perfluoroalkyl;
h) -T-$R_{17}$;
i) -alkyl;
j) -aryl;
k) -arylene-alkyl;
l) -T-alkyl;
m) -T-alkylene-aryl;
n) -T-alkylene-arylene-aryl;
o) -T-alkylene-arylene-alkyl; or
p) -arylene-T-alkyl;

wherein T comprises —$CH_2$—, —O—, —$N(R_{18})$—, —$CON(R_{18})$—, or —$N(R_{18})C(O)$—; wherein $R_{17}$, and $R_{18}$, independently comprise: -hydrogen, -alkyl, or -aryl.

In another embodiment, $Ar_2$ comprises: 3'-chloro-4'-fluoro-4-hydroxy-biphenyl, 2-hydroxy-5-[2-(4'-trifluoromethyl-biphenyl-3-yl)-acetylamino]-phenyl, 2-hydroxy-5-pyridin-3-yl-phenyl, 3',5'-difluoro-4-hydroxy-biphenyl, 3'-chloro-4'-fluoro-4-hydroxy-biphenyl, 3'-fluoro-4-hydroxy-biphenyl, 3'-trifluoromethyl-biphenyl-4-yl, 4-(5-trifluoromethyl-pyridin-2-yloxy)-phenyl, 4'-amino-4-hydroxy-biphenyl, 4'-fluoro-4-hydroxy-biphenyl, 4-hydroxy-2'-trifluoromethyl-biphenyl, 4-hydroxy-3',5'-bis-trifluoromethyl-biphenyl, 4-hydroxy-3'-nitro-biphenyl, 4-hydroxy-4'-trifluoromethoxy-biphenyl, 4-Hydroxy-4'-trifluoromethyl-biphenyl, 4-hydroxy-biphenyl, 5-benzo[1,3]dioxol-5-yl-2-hydroxy-phenyl, 5-bromo-2-hydroxy-phenyl, 5-chloro-4-hydroxy-4'-trifluoromethyl-biphenyl, 5-fluoro-4-hydroxy-4'-trifluoromethyl-biphenyl, or 6-benzyloxy-4-hydroxy-4'-trifluoromethyl-biphenyl.

In another embodiment, $Ar_2$ comprises 3'-chloro-4'-fluoro-4-hydroxy-biphenyl, or 4-Hydroxy-4'-trifluoromethyl-biphenyl.

In another embodiment, $Ar_2$ comprises: [2-(3,4-bis-benzyloxy-benzyloxy) -benzyloxy]-5-bromo-phenyl, 2-(4-tert-butyl-benzyloxy)-5-chlorophenyl, 3-bromo-5-chloro-2,6-dimethoxy-phenyl, 4-(4-tert-butyl-benzyloxy)-4'-trifluoromethyl-biphenyl, 4-acetoxy-2-phneyl-4'-trifluoromethyl-biphenyl, 4-acetoxy-4'-trifluoromethyl-biphenyl, 4-amino-4'-trifluoromethyl-biphenyl, 4-butoxy-3'-chloro-4'-fluoro-biphenyl, 4-methanesulfonylamino-4'-trifluoromethyl-biphenyl, 4-methoxy-4'-trifluoromethyl-biphenyl, 5-bromo-2-(4-[1,2,4]triazol-1-yl-benzyloxy)-phenyl, 5-bromo-2-(4-tert-butyl-benzyloxy)-phenyl, 5-bromo-2-cyclohexyloxy-phenyl, 5-bromo-2-heptyloxy-phenyl, 5-chloro-2,4-dimethoxy-4'-trifluoromethyl-biphenyl, 5-chloro-2-heptyloxy-phenyl.

In another embodiment, $Ar_2$ comprises: 5-bromo-2-(3-pyridin-4-yl-propoxy)-phenyl, 5-bromo-2-[2-(2-oxo-pyrrolidin-1-yl)-ethoxy]-phenyl, 5-bromo-2-(2-morpholin-4-yl-ethoxy)-phenyl, 5-bromo-2-(4,4,4-trifluoro-butoxy)-phneyl, or 5-bromo-2-(2-piperidin-1-yl-ethoxy)-phenyl.

In another embodiment, $Ar_2$ comprises 3-hydroxy-naphthalene.

In another embodiment, $Ar_2$ comprises a phenyl or biphenyl group containing a hydroxy, alkyloxy, or acetoxy group ortho to the $Ar_2$ group's point of attachment to X.

In yet another embodiment, $Ar_2$ comprises a phenyl or biphenyl group containing a hydroxy, alkyloxy, or acetoxy group ortho to the $Ar_2$ group's point of attachment to X and further substituted with at least one of the following groups fluoro, chloro, trifluoroalkyl, trifluoroalkoxy, nitro, benzyloxy, phenoxy, phenyl, and alkylsulfonyl.

The alkyl, aryl, heteroaryl, alkylene, and arylene groups in $Ar_1$, $Ar_2$, G, $R_1$—$R_{21}$, may be optionally substituted 1 to 4 times with a substituent group, wherein said substituent group (s) or the term substituted refers to groups comprising:

a) -hydrogen;
b) -fluoro;
c) -chloro;
d) -bromo;
e) -iodo;
f) -cyano;
g) -nitro;
h) -perfluoroalkyl;
i) -Q-$R_{22}$;
j) -Q-alkyl;
k) -Q-aryl;
l) -Q-alkylene-aryl;
m) -Q-alkylene-$NR_{23}R_{24}$; or
n) -Q-alkyl-W—$R_{25}$;

wherein Q and W independently comprise: —$CH_2$—, —O—, —N($R_{26}$)—, —C(O)—, —CON($R_{26}$)—, —N($R_{26}$)C(O)—, —N($R_{26}$)CON($R_{27}$)—, —N($R_{26}$)C(O)O—, —OC(O)N($R_{26}$)—, —N($R_{26}$)$SO_2$—, —$SO_2$N($R_{26}$)—, —C(O)—O—, —O—C(O)—, or —N($R_{26}$)$SO_2$N($R_{27}$)—, wherein $R_{22}$, $R_{23}$, $R_{24}$, $R_{25}$, $R_{26}$ and $R_{27}$, independently comprise: -hydrogen, -alkyl, -aryl, -arylene-alkyl, -alkylene-aryl, or -alkylene-arylene-alkyl.

Also included within the scope of the invention are the individual enantiomers of the compounds represented by Formula (I) above as well as any wholly or partially racemic mixtures thereof. The present invention also covers the individual enantiomers of the compounds represented by formula above as mixtures with diastereoisomers thereof in which one or more stereocenters are inverted.

Compounds of the present invention are listed in Table 1.

TABLE 1

| Ex. | Structure | Chemical Name |
|---|---|---|
| 1 | 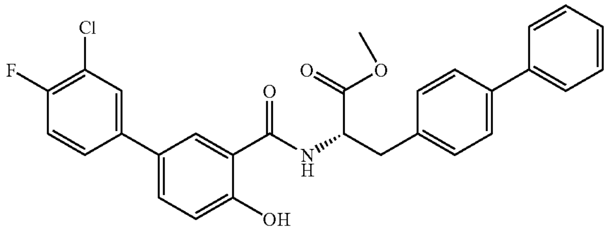 | 3-Biphenyl-4-yl-(2S)-[(3'-chloro-4'-fluoro-4-hydroxy-biphenyl-3-carbonyl)-amino]-propionic acid methyl ester |
| 2 | 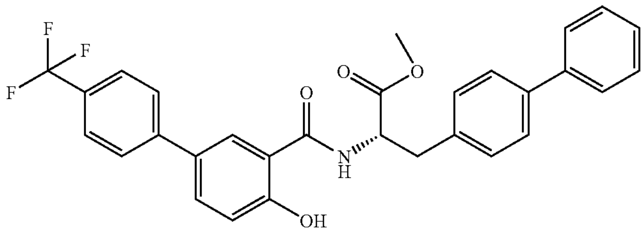 | 4-Hydroxy-4'-trifluoromethyl-biphenyl-3-carboxylic acid biphenyl-4-yl-1(S)-formyl-ethyl)-amide; compound with methoxymethane |

TABLE 1-continued

| Ex. | Structure | Chemical Name |
|---|---|---|
| 3 | 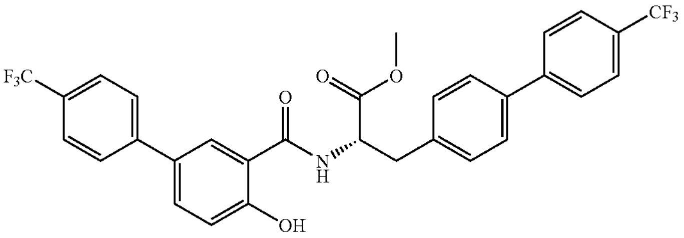 | 2-(S)-[(4-Hydroxy-4'-trifluoromethyl-biphenyl-3-carbonyl)-amino]-3-(4'-trifluoromethyl-biphenyl-4-yl)propionic acid methyl ester |
| 4 | 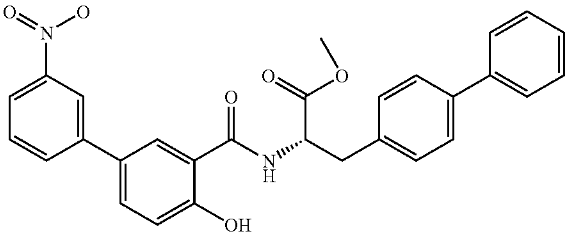 | 3-Biphenyl-4-yl-(2S)-[(4-hydroxy-3'-nitro-biphenyl-3-carbonyl)-amino]-propionic acid methyl ester |
| 5 | 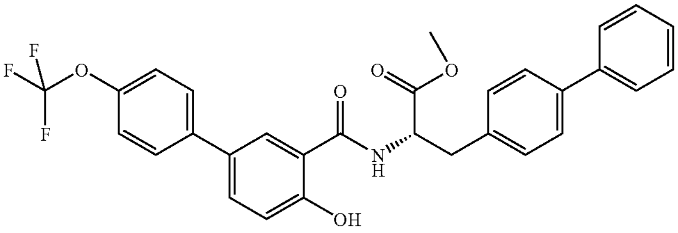 | 3-Biphenyl-4-yl-2-(S)-[(4-hydroxy-4'-trifluoromethoxy-biphenyl-3-carbonyl)-amino]-propionic acid methyl ester |
| 6 | 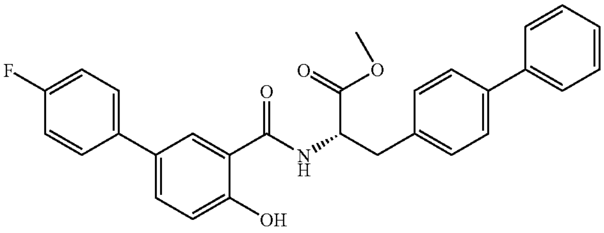 | 3-Biphenyl-4-yl-2-(S)-[(4'-fluoro-4-hydroxy-biphenyl-3-carbonyl)-amino]-propionic acid methyl ester |
| 7 | 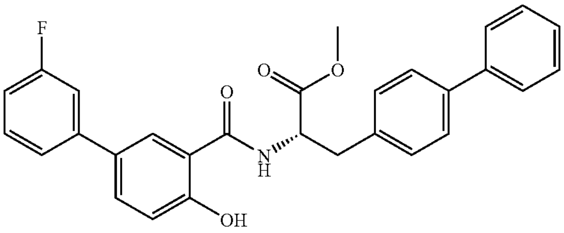 | 3-Biphenyl-4-yl-2-(2S)-[(3'-fluoro-4-hydroxy-biphenyl-3-carbonyl)-amino]-propionic acid methyl ester |
| 8 | 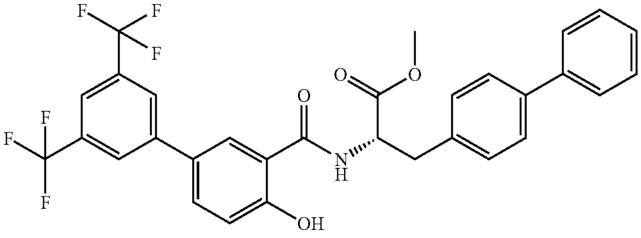 | 3-Biphenyl-4-yl-2-(2S)-[(4-hydroxy-3',5'-bis-trifluoromethyl-biphenyl-3-carbonyl)-amino]-propionic acid methyl ester |

TABLE 1-continued

| Ex. | Structure | Chemical Name |
|---|---|---|
| 9 | 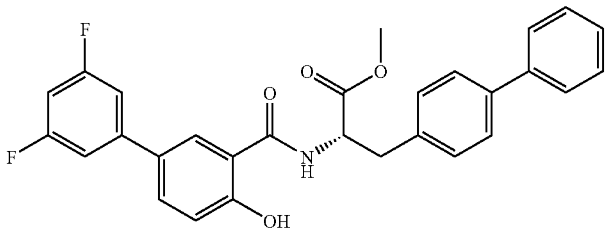 | 3-Biphenyl-4-yl-2-(2S)-[(3',5'-difluoro-4-hydroxy-biphenyl-3-carbonyl)-amino]-propionic acid methyl ester |
| 10 | 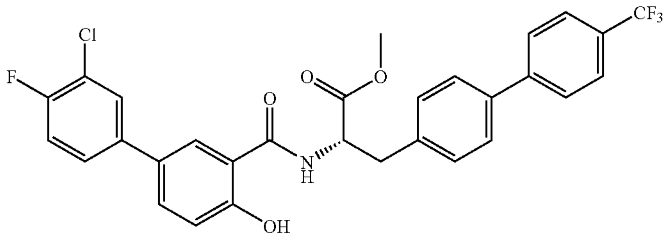 | 2-(2S)-[(3'-Chloro-4'-fluoro-4-hydroxy-biphenyl-3-carbonyl)-amino]-3-(4'-trifluoromethyl-biphenyl-4-yl)-propionic acid methyl ester |
| 11 | 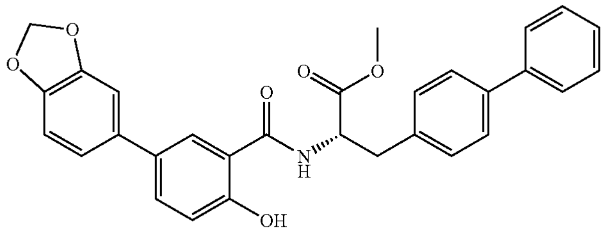 | 2-(2S)-(5-Benzo[1,3]dioxol-5-yl-2-hydroxy-benzoylamino)-3-biphenyl-4-yl-propionic acid methyl ester |
| 12 | 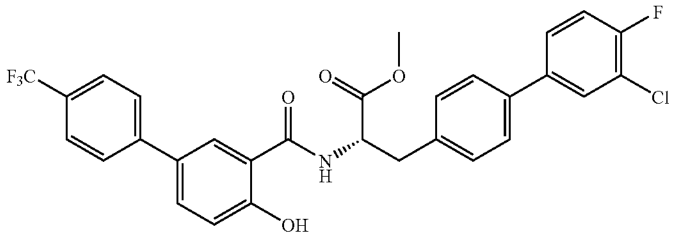 | 3-(3'-Chloro-4'-fluoro-biphenyl-4-yl)-2-(2S)-[(4-hydroxy-4'-trifluoromethyl-biphenyl-3-carbonyl)-amino]-propionic acid methyl ester |
| 13 | 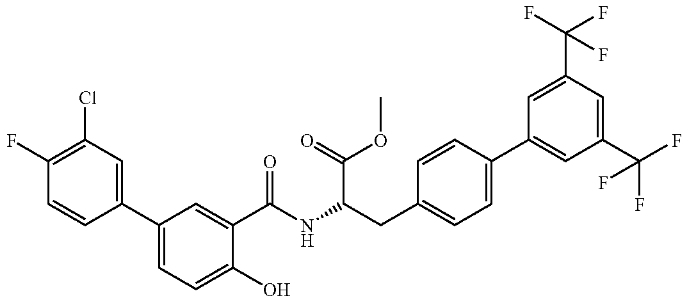 | 3-(3',5'-Bis-trifluoromethyl-biphenyl-4-yl)-2-(2S)-[(3'-chloro-4'-fluoro-4-hydroxy-biphenyl-3-carbonyl)-amino]-propionic acid methyl ester |
| 14 | 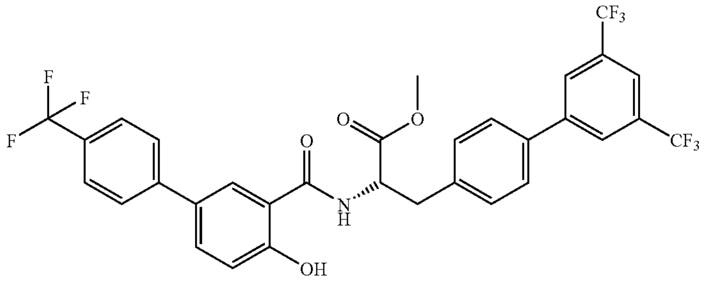 | 3-(3',5'-Bis-trifluoromethyl-biphenyl-4-yl)-2-(2S)-[(3'chloro-4'-fluoro-4-hydroxy-biphenyl-3-carbonyl)amino]-propionic acid methyl ester |

TABLE 1-continued

| Ex. | Structure | Chemical Name |
| --- | --- | --- |
| 15 | 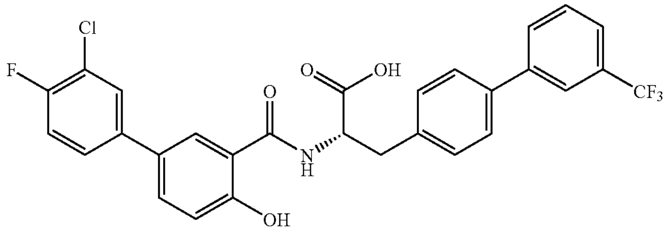 | 2-(2S)-[(3'-Chloro-4'-fluoro-4-hydroxy-biphenyl-3-carbonyl)-amino]-3-(3'-trifluoromethyl-biphenyl-4-yl)-propionic acid |
| 16 | 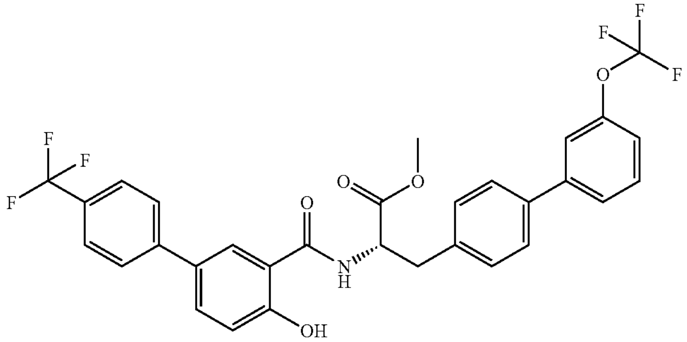 | 2-(2S)-[(4-Hydroxy-4'-trifluoromethyl-biphenyl-3-carbonyl)-amino]-3-(3'-trifluoromethoxy-biphenyl-4-yl)-propionic acid methyl ester |
| 17 | 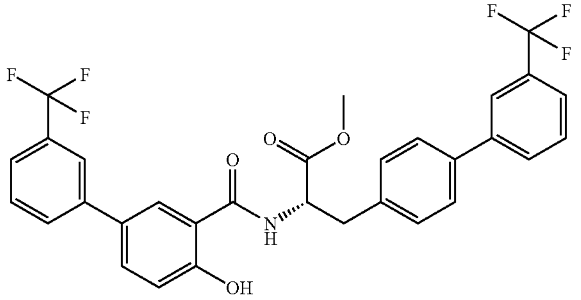 | 2-(2S)-[(4-Hydroxy-3'-trifluoromethyl-biphenyl-3-carbonyl)-amino]-3-(3'-trifluoromethyl-biphenyl-4-yl)-propionic acid methyl ester |
| 18 | 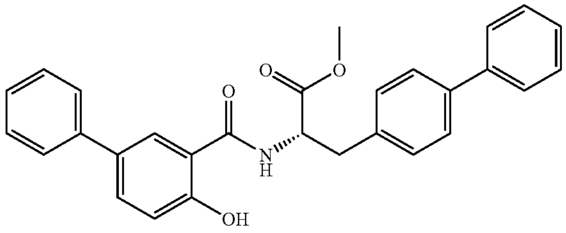 | 3-Biphenyl-4-yl-2-(S)-[(4-hydroxy-biphenyl-3-carbonyl)-amino]-propionic acid methyl ester |
| 19 | 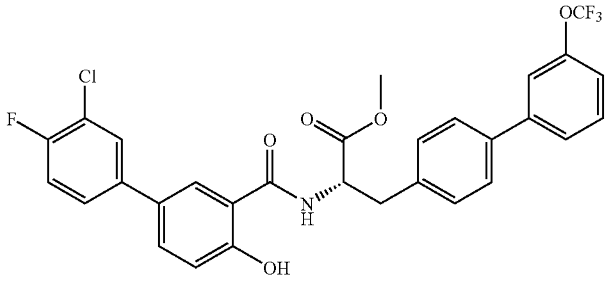 | 2-(S)-[(3'-Chloro-4'-fluoro-4-hydroxy-biphenyl-3-carbonyl)-amino]-3-(3'-trifluoromethoxy-biphenyl-4-yl)-propionic acid methyl ester |

TABLE 1-continued

| Ex. | Structure | Chemical Name |
|---|---|---|
| 20 | 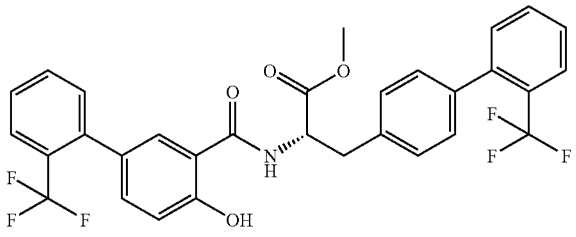 | 2-(S)-[(4-Hydroxy-2'-trifluoromethyl-biphenyl-3-carbonyl)-amino]-3-(2'-trifluoromethyl-biphenyl-4-yl)-propionic acid methyl ester |
| 21 | 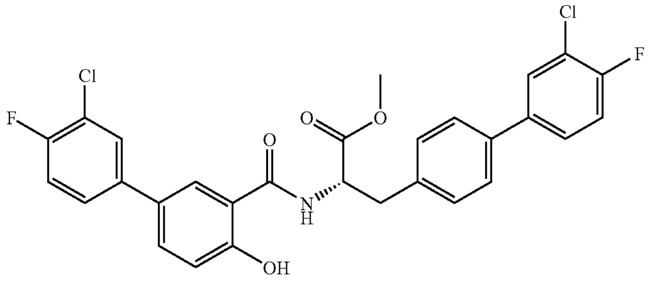 | 3-(3'-Chloro-4'-fluoro-biphenyl-4-yl)-2-(S)-[(3'-chloro-4'-fluoro-4-hydroxy-biphenyl-3-carbonyl)-amino]-propionic acid methyl ester |
| 22 | 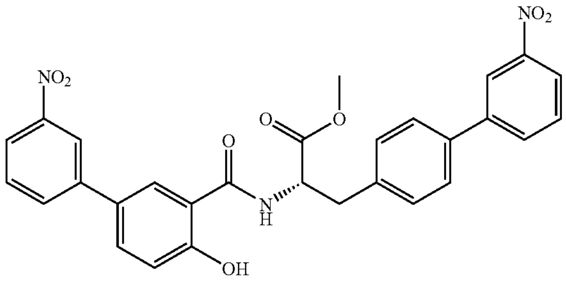 | 2-(S)-[(4-Hydroxy-3'-nitro-biphenyl-3-carbonyl)-amino]-3-(3'-nitro-biphenyl-4-yl)-propionic acid methyl ester |
| 23 | 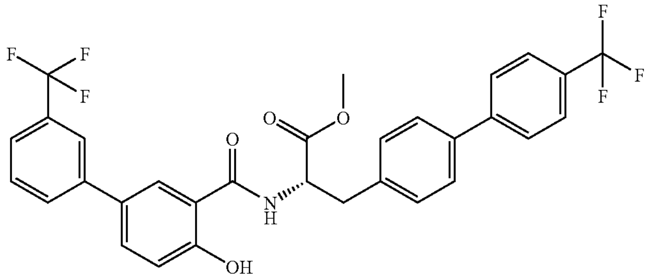 | 2-(S)-[(4-Hydroxy-3'-trifluoromethyl-biphenyl-3-carbonyl)-amino]-3-(4'-trifluoromethyl-biphenyl-4-yl)-propionic acid methyl ester |
| 24 | 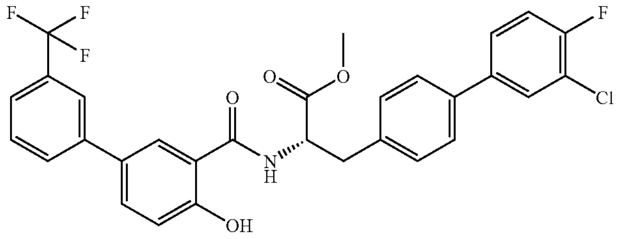 | 3-(3'-Chloro-4'-fluoro-biphenyl-4-yl)-2-(S)-[(4-hydroxy-3'-trifluoromethyl-biphenyl-3-carbonyl)-amino]-propionic acid methyl ester |
| 25 | 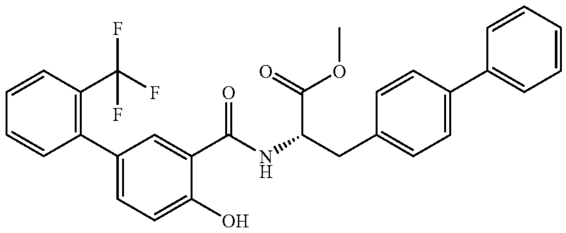 | 3-Biphenyl-4-yl-2-(S)-[(4-hydroxy-2'-trifluoromethyl-biphenyl-3-carbonyl)-amino]-propionic acid methyl ester |

TABLE 1-continued

| Ex. | Structure | Chemical Name |
|---|---|---|
| 26 | 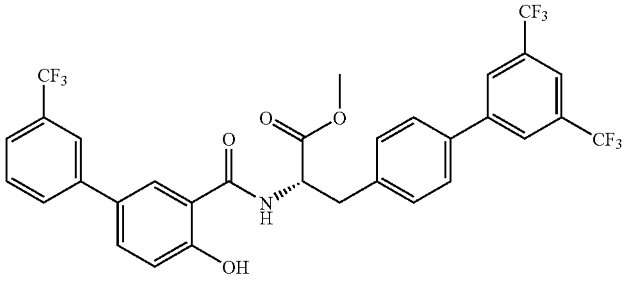 | 3-(3',5'-Bis-trifluoromethyl-biphenyl-4-yl)-2-(S)-[(4-hydroxy-3'-trifluoromethyl-biphenyl-3-carbonyl)-amino]-propionic acid methyl ester |
| 27 | 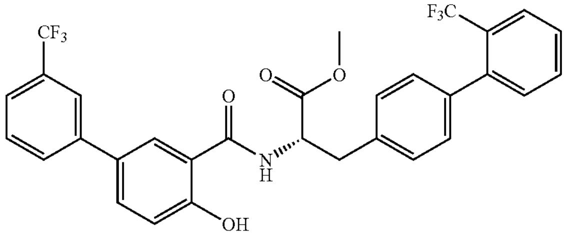 | 2-(S)-[(4-Hydroxy-3'-trifluoromethyl-biphenyl-3-carbonyl)-amino]-3-(2'-trifluoromethyl-biphenyl-4-yl)-propionic acid methyl ester |
| 28 | 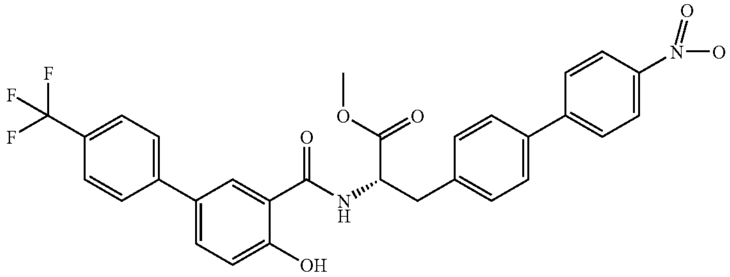 | 2-(2S)-[(4-Hydroxy-4-trifluoromethyl-biphenyl-3-carbonyl)-amino]-3-(4'-nitro-biphenyl-4-yl)-propionic acid methyl ester |
| 29 | 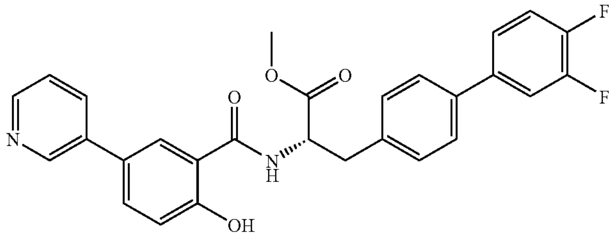 | 3-(3',4'-Difluoro-biphenyl-4-yl)-2-(S)(2-hydroxy-5-pyridin-3-yl-benzoylamino)-propionic acid methyl ester |
| 30 | 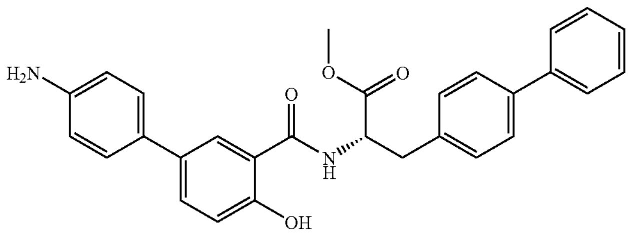 | 2-(S)-[4'-Amino-4-hydroxy-biphenyl-3-carbonyl)-amino]-3-biphenyl-4yl-propionic acid methyl ester |

TABLE 1-continued

| Ex. | Structure | Chemical Name |
| --- | --- | --- |
| 31 | 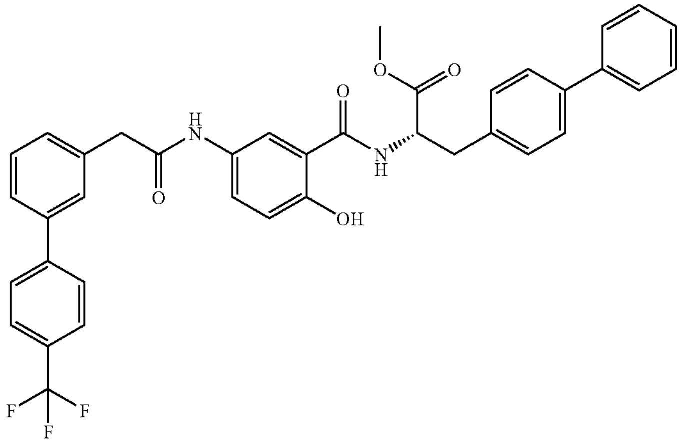 | 3-Biphenyl-4-yl-2-(2S)-{2-hydroxy-5-[2-(4'-trifluoromethyl-biphenyl-3-yl)-acetylamino]-benzoylamino]propionic acid methyl ester |
| 32 | 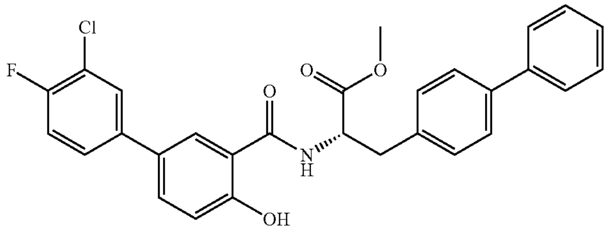 | 3-Biphenyl-4-yl-2-(S)-[(3'-chloro-4'-fluoro-4-hydroxy-biphenyl-3-carbonyl)-amino]-propionic acid methyl ester |
| 33 | 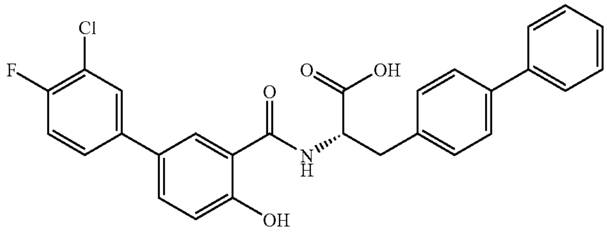 | 3-Biphenyl-4-yl-2-(S)-[(3'-chloro-4'-fluoro-4-hydroxy-biphenyl-3-carbonyl)-amino]-propionic acid |
| 34 | 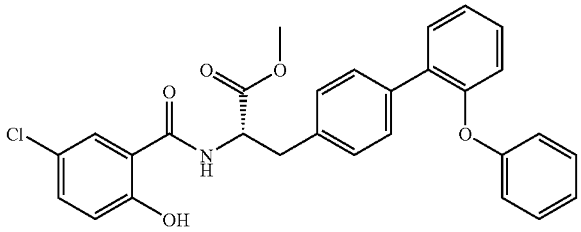 | 2-(S)-(5-Chloro-2-hydroxy-benzoylamino)-3-(2'-phenoxy-biphenyl-4-yl)-propionic acid methyl ester |
| 35 | 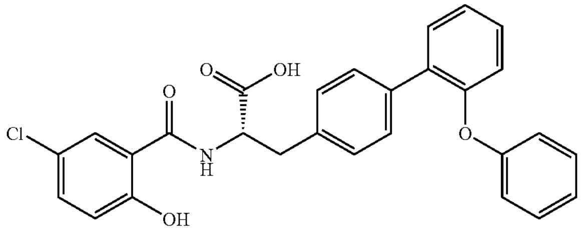 | 2-(S)-(5-Chloro-2-hydroxy-benzoylamino)-3-(2'-phenoxy-biphenyl-4-yl)-propionic acid |

TABLE 1-continued

| Ex. | Structure | Chemical Name |
|---|---|---|
| 36 | 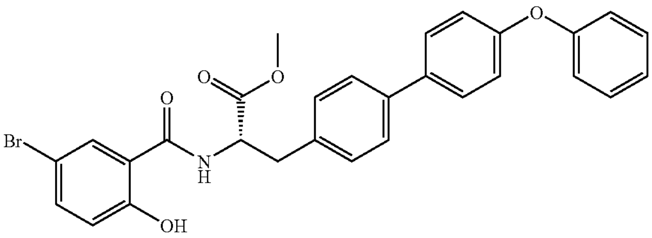 | 2-(S)-(5-Bromo-2-hydroxy-benzoylamino)-3-(4'-phenoxy-biphenyl-4-yl)-propionic acid methyl ester |
| 37 | 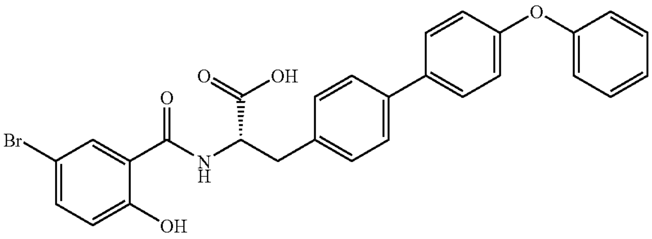 | 2-(S)-(5-Bromo-2-hydroxy-benzoylamino)-3-(4'-phenoxy-biphenyl-4-yl)-propionic acid |
| 38 | 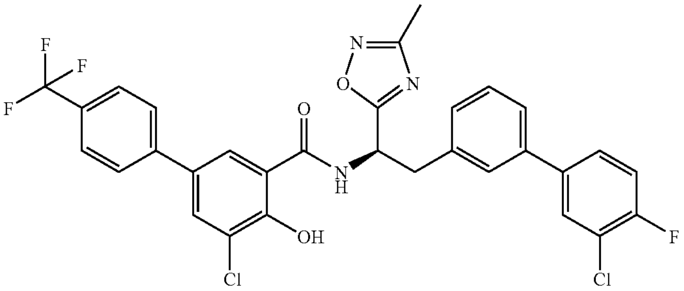 | 5-Chloro-4-hydroxy-4'-trifluoromethyl-biphenyl-3-carboxylic acid [2-(3'-chloro-4'-fluoro-biphenyl-3-yl)-1(R)-(3-methyl-[1,2,4]oxadiazol-5-yl)-ethyl]-amide |
| 39 | 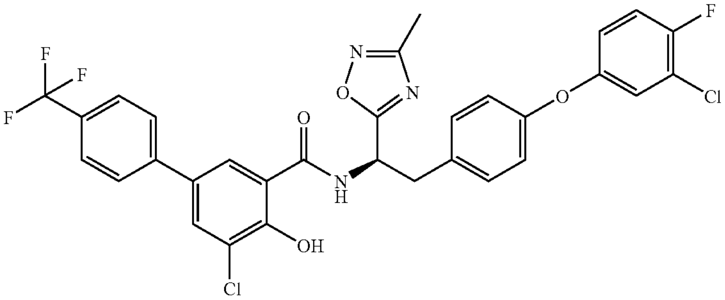 | 5-Chloro-4-hydroxy-4'-trifluoromethyl-biphenyl-3-carboxylic acid [2-[4-(3-chloro-4-fluorophenoxy)-phenyl]-1(R)-(3-methyl-[1,2,4]oxadiazol-5-yl)-ethyl]-amide |
| 40 | 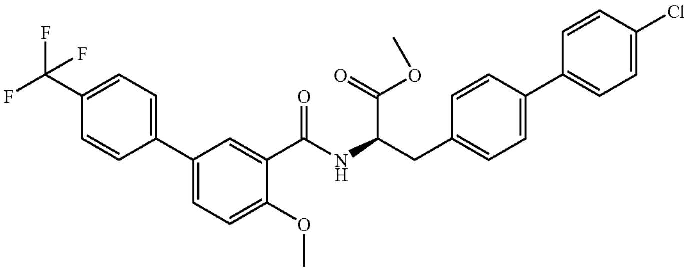 | 3-(4'-Chloro-biphenyl-4-yl)-2-(R)-[(4-methoxy-4'-trifluoromethyl-biphenyl-3-carbonyl)-amino]-propionic acid methyl ester |

TABLE 1-continued

| Ex. | Structure | Chemical Name |
|---|---|---|
| 41 | 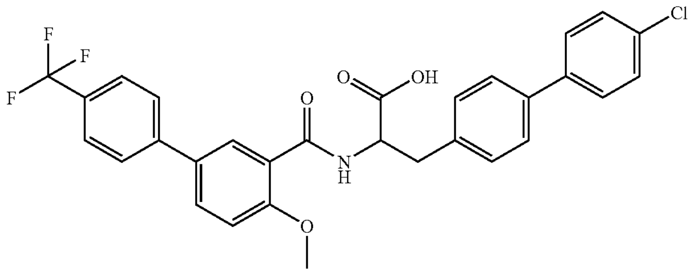 | 3-(4'-Chloro-biphenyl-4-yl)-2-(R)-[(4-methoxy-4'-trifluoromethyl-biphenyl-3-carbonyl)-amino]-propionic acid |
| 42 | 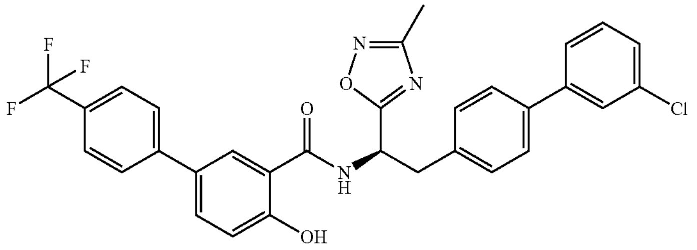 | 4-Hydroxy-4'-trifluoromethyl-biphenyl-3-carboxylic acid [2-(3'-chloro-biphenyl-4-yl)-1(R)-(3-methyl-[1,2,4]oxadiazol-5-yl)-ethyl]-amide |
| 43 | 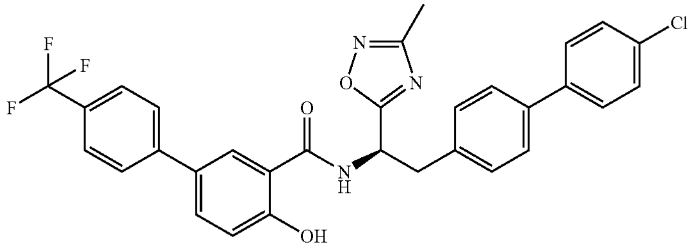 | 4-Hydroxy-4'-trifluoromethyl-biphenyl-3-carboxylic acid [2-(4'-chloro-biphenyl-4-yl)-1(R)-(3-methyl-[1,2,4]oxadiazol-5-yl)-ethyl]-amide |
| 44 | 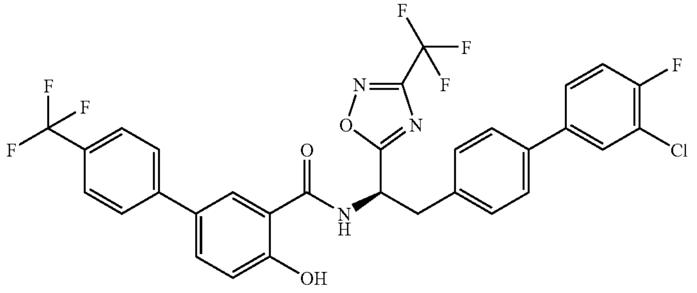 | 4-Hydroxy-4'-trifluoromethyl-biphenyl-3-carboxylic acid [2-(3'-chloro-4'-fluoro-biphenyl-4-yl)-1(R)-(3-trifluoromethyl[1,2,4]oxadiazol-5-yl)-ethyl]-amide |
| 45 | 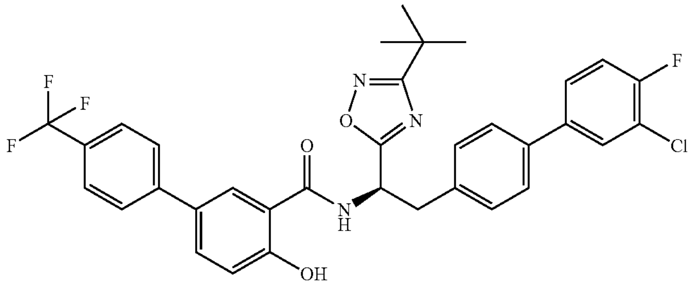 | 4-Hydroxy-4'-trifluoromethyl-biphenyl-3-carboxylic acid [1(R)-(3-tert-butyl-[1,2,4]oxadiazol-5-yl)-2-(3'-chloro-4'-fluoro-biphenyl-4-yl)-ethyl]-amide |

TABLE 1-continued

| Ex. | Structure | Chemical Name |
|---|---|---|
| 46 | 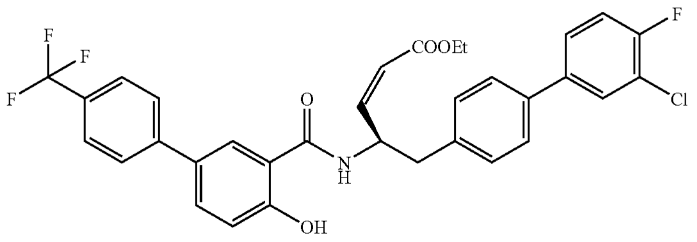 | 5-(3'-Chloro-4'-fluoro-biphenyl-4-yl)-4-[(4-hydroxy-4'-trifluoromethyl-biphenyl-3(R)-carbonyl) amino]-pent-2-enoic acid ethyl ester |
| 47 | 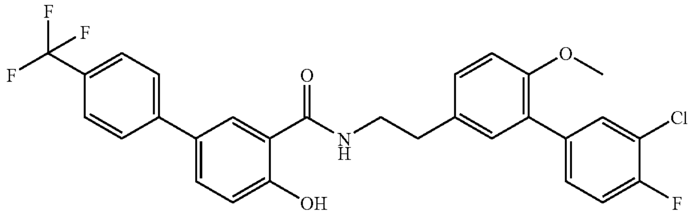 | 4-Hydroxy-4'-trifluoromethyl-biphenyl-3-carboxylic acid [2-(3'-chloro-4'-fluoro-6-methoxy-biphenyl-3-yl)-ethyl]-amide |
| 48 | 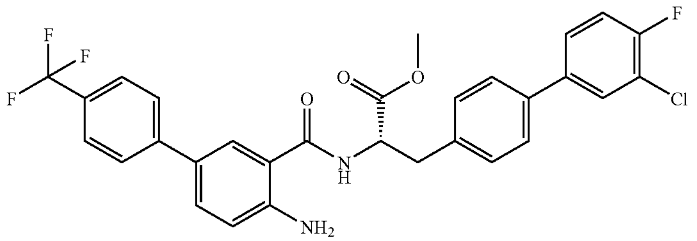 | 2-(S)-[(4-Amino-4'-trifluoromethyl-biphenyl-3-carbonyl)-amino]-3-(3'-chloro-4'-fluoro-biphenyl-4-yl)-propionic acid methyl ester |
| 49 | 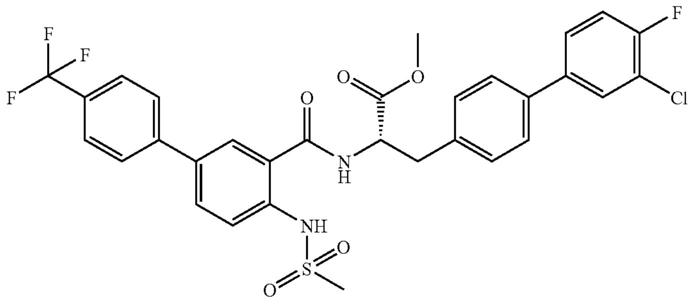 | 3-(3'-Chloro-4'-fluoro-biphenyl-4-yl)-2-(S)-[(4-methanesulfonyl amino-4'-trifluoromethyl-biphenyl-3-carbonyl)-amino]propionic acid methyl ester |
| 50 | 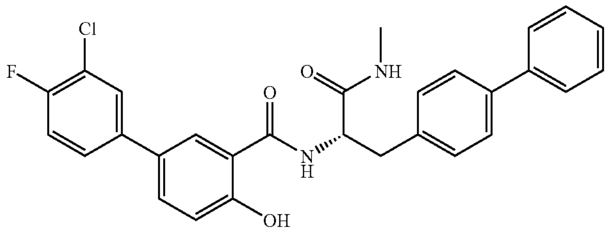 | 3'-Chloro-4'-fluoro-4-hydroxy-biphenyl-3-carboxylic acid (2-biphenyl-4-yl-1(S)-methylcarbamoyl-ethyl)-amide |
| 51 | 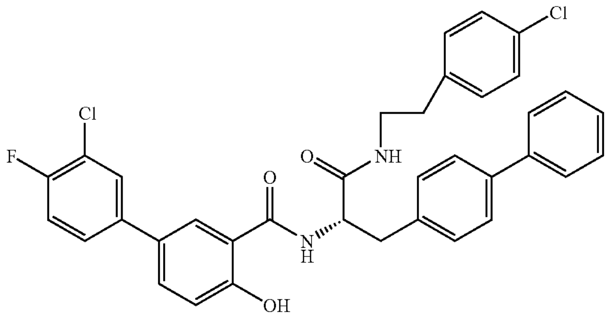 | 3'-Chloro-4'-fluoro-4-hydroxy-biphenyl-3-carboxylic acid {2-biphenyl-4-yl-1-(S)-[2-(4-chloro-phenyl)-ethylcarbamoyl]-ethyl}-amide |

TABLE 1-continued

| Ex. | Structure | Chemical Name |
|---|---|---|
| 52 | 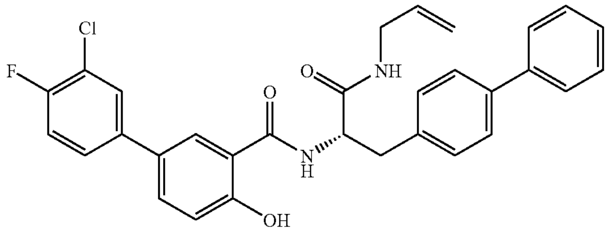 | 3'-Chloro-4'-fluoro-4-hydroxy-biphenyl-3-carboxylic acid (1-(S)-allylcarbamoyl-2-biphenyl-4-yl-ethyl)-amide |
| 53 | 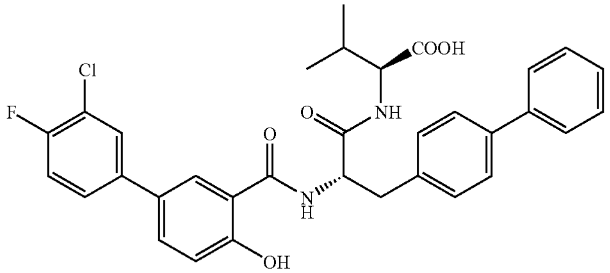 | 2-(S)-{3-Biphenyl-4-yl-2-(S)-[(3'-chloro-4'-fluoro-4-hydroxy-biphenyl-3-carbonyl)amino]propionylamino}-3-methyl-butyricacid |
| 54 | 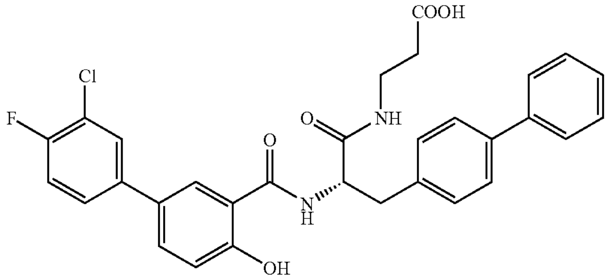 | 3-(S)-{3-Biphenyl-4-yl-2-[(3'-chloro-4'-fluoro-4-hydroxy-biphenyl-3-carbonyl)-amino]propionylamino}-propionic acid |
| 55 | 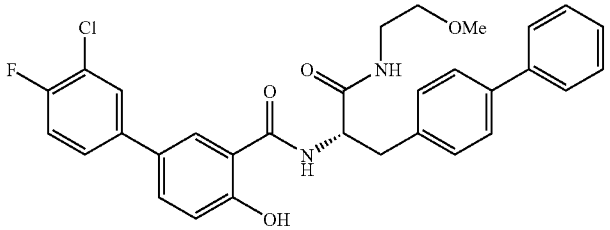 | 3'-Chloro-4'-fluoro-4-hydroxy-biphenyl-3-carboxylic acid [2-biphenyl-4-yl-1-(S)-(2-methoxy-ethylcarbamoyl)-ethyl]-amide |
| 56 | 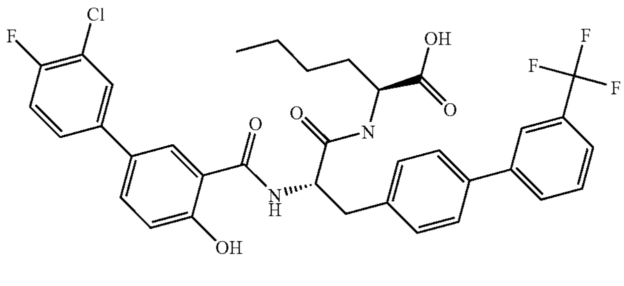 | 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-hexanoic acid |

TABLE 1-continued

| Ex. | Structure | Chemical Name |
|---|---|---|
| 57 | 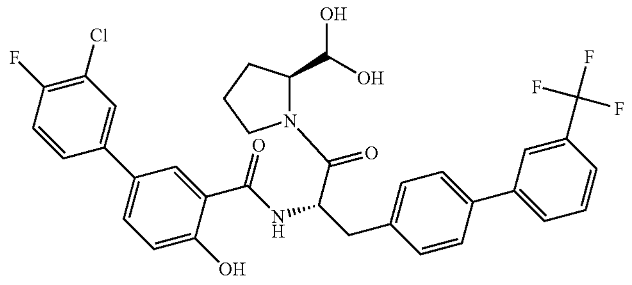 | 1-[2-(S)-[(3'-Chloro-4'-fluoro-4-hydroxy-biphenyl-3-carbonyl)-amino]-3-(3'-trifluoromethyl-biphenyl-4-yl)-propionyl]-pyrrolidine-2-(S)-carboxylic acid |
| 58 | 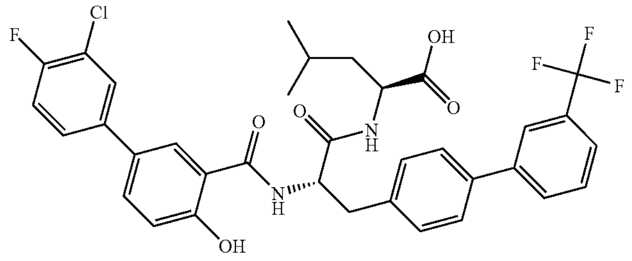 | 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-4-methylpentanoic acid |
| 59 | 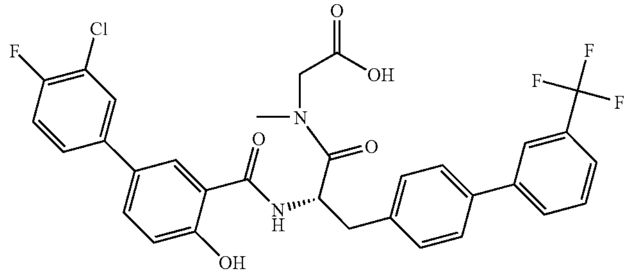 | {[2-(S)-[(3'-Chloro-4'-fluoro-4-hydroxy biphenyl-3-carbonyl)-amino]-3-(3'-trifluoromethyl-biphenyl-4-yl)-propionyl]-methyl-amino}-acetic acid |
| 60 | 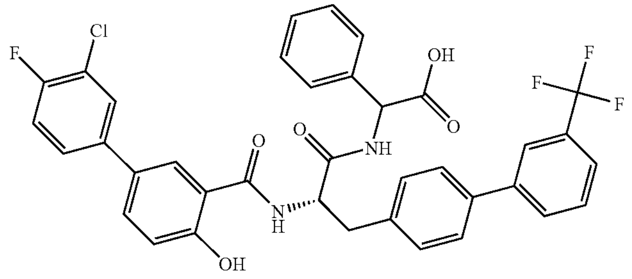 | [2-(S)-[(3'-Chloro-4'-fluoro-4-hydroxy-biphenyl-3-carbonyl)-amino]-3-(3'-trifluoromethyl-biphenyl-4-yl)-propionylamino]-2-(S)-phenyl-acetic acid |
| 61 | 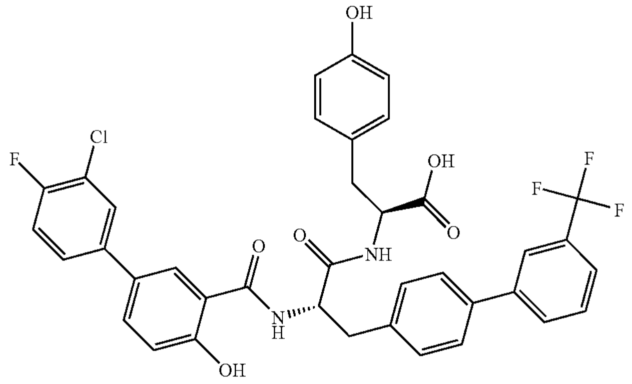 | 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-3-(4-hydroxy-phenyl)-propionic acid |

TABLE 1-continued

| Ex. | Structure | Chemical Name |
|---|---|---|
| 62 | 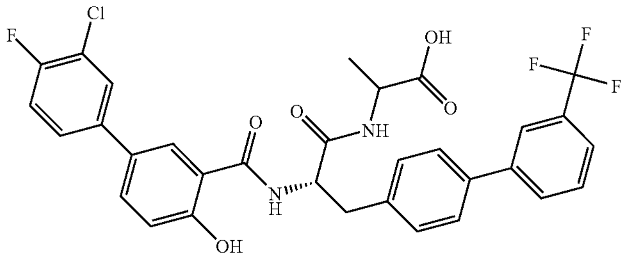 | 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-propionic acid |
| 63 | 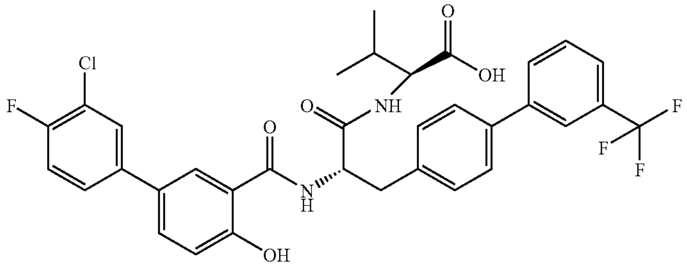 | 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-3-methyl-butyric acid |
| 64 | 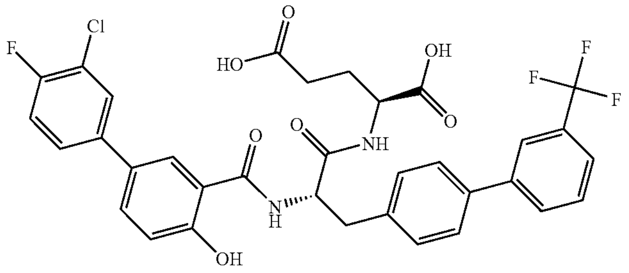 | 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-pentanedioic acid |
| 65 | 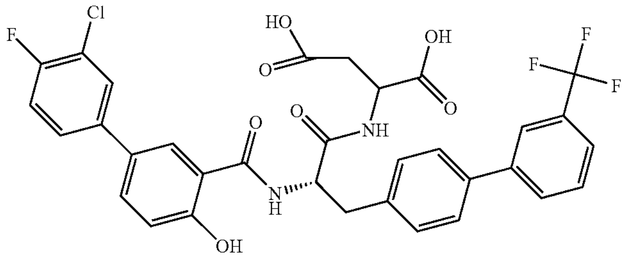 | 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-succinic acid |
| 66 | 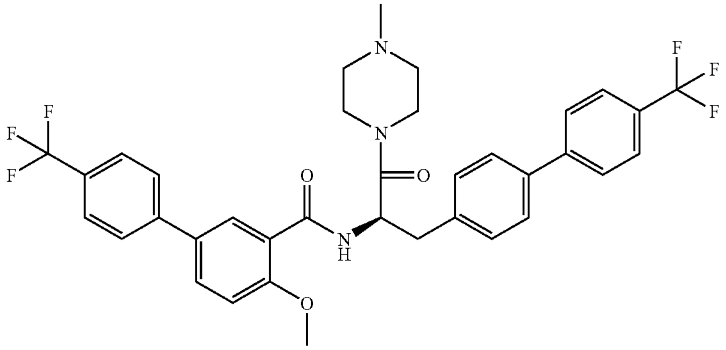 | 4-Methoxy-4'-trifluoromethyl-biphenyl-3-carboxylic acid [2-(R)-(4-methyl-piperazin-1-yl)-2-oxo-1 -(4'-trifluoromethyl-biphenyl-4-ylmethyl)-ethyl]-amide |

TABLE 1-continued

| Ex. | Structure | Chemical Name |
| --- | --- | --- |
| 67 | 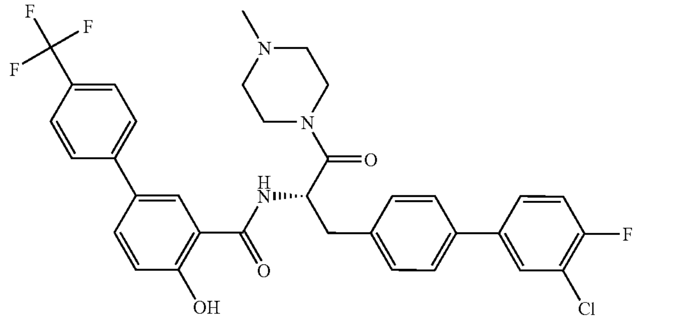 | 4-Hydroxy-4'-trifluoromethyl-biphenyl-3-carboxylic acid [1-(3'-chloro-4'-fluoro-biphenyl-4-ylmethyl)-2-(S)-(4-methyl-piperazin-1-yl)-2-oxo-ethyl]-amide |
| 68 | 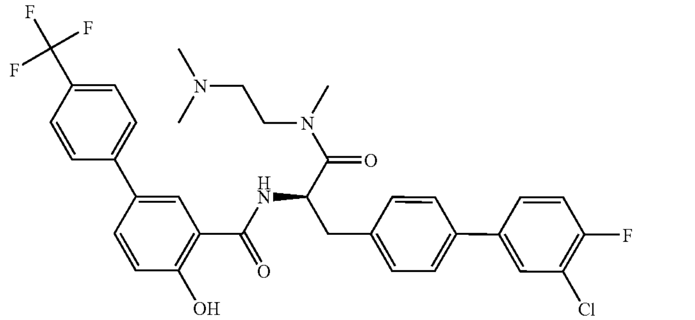 | 4-Hydroxy-4'-trifluoromethyl-biphenyl-3-carboxylic acid {2-(3'-chloro-4'-fluoro-biphenyl-4-yl)-1-(R)-[(2-dimethylamino-ethyl)-methyl-carbamoyl]-ethyl}-amide |
| 69 | 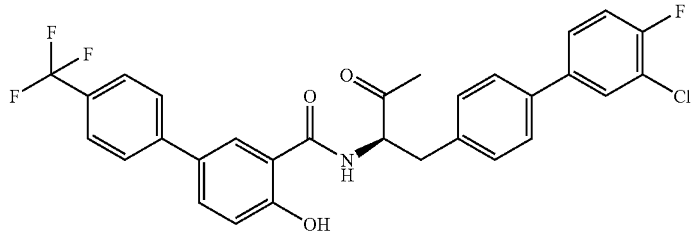 | 4-Hydroxy-4'-trifluoromethyl-biphenyl-3-carboxylic acid [1-(R)-(3'-chloro-4'-fluoro-biphenyl-4-ylmethyl)-2-oxo-propyl]-amide |
| 70 | 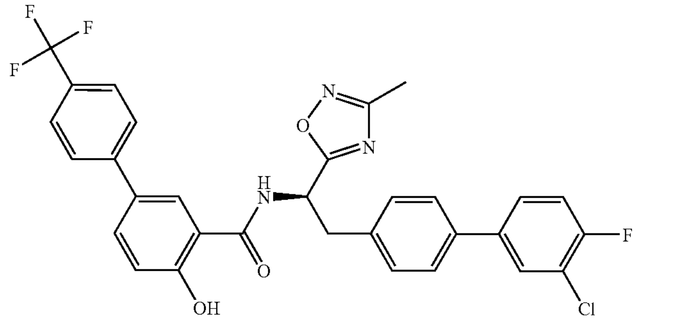 | 4-Hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyI]-amide |
| 71 | 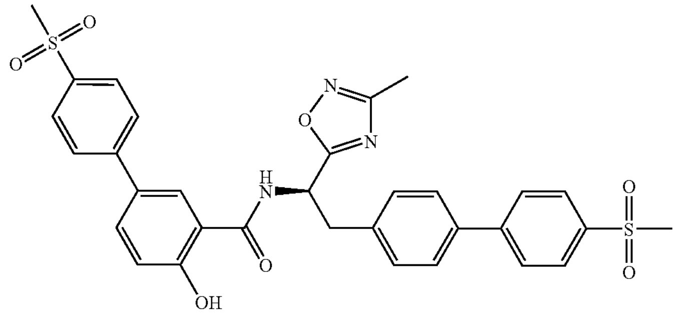 | 4-Hydroxy-4'-methanesulfonyl-biphenyl-3-carboxylic acid[2-(4'-methanesulfonyl-biphenyl-4-yl)-1-(R)-(3-methyl-[1,2,4]oxadiazol-5-yl)-ethyl]-amide |

TABLE 1-continued

| Ex. | Structure | Chemical Name |
| --- | --- | --- |
| 72 | 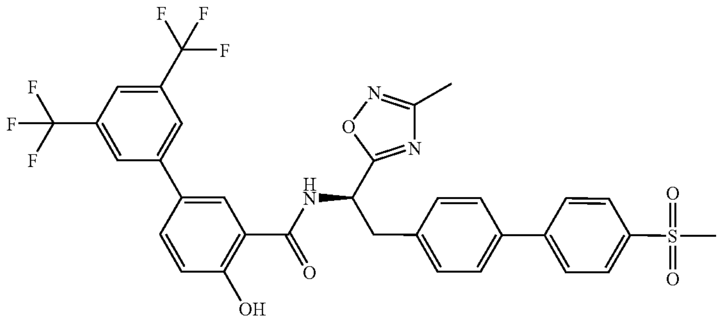 | 4-Hydroxy-3',5'-bis-trifluoromethyl-biphenyl-3-carboxylic acid [2-(4'-methanesulfonyl-biphenyl-4-yl)-1-(R)-(-methyl-[1,2,4]oxadiazol-5-yl)-ethyl]-amide |
| 73 | 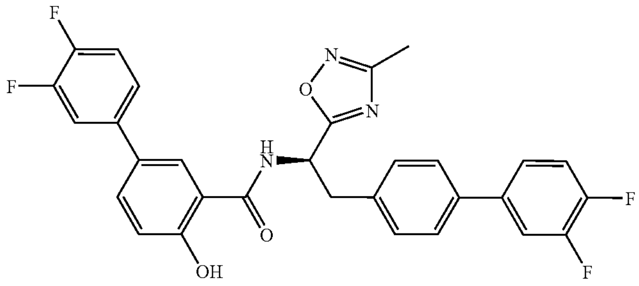 | 3',4-Difluoro-4-hydroxy-biphenyl-3-carboxylic acid [2-(3',4'-difluoro-biphenyl-4-yl)-1-(R)-(3-methyl-[1,2,4]oxadiazol-5-yl)-ethyl]-amide |
| 74 | 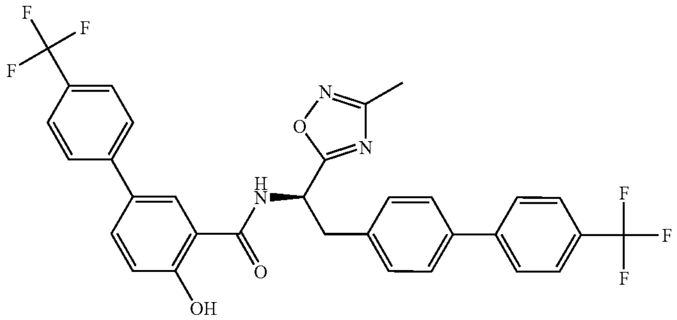 | 4-Hydroxy-4'-trifluoromethyl-biphenyl-3-carboxylic acid [1-(R)-(3-methyl-[1,2,4]oxadiazol-5-yl)-2-(4'-trifluoromethyl-biphenyl-4-yl)-ethyl]-amide |
| 75 | 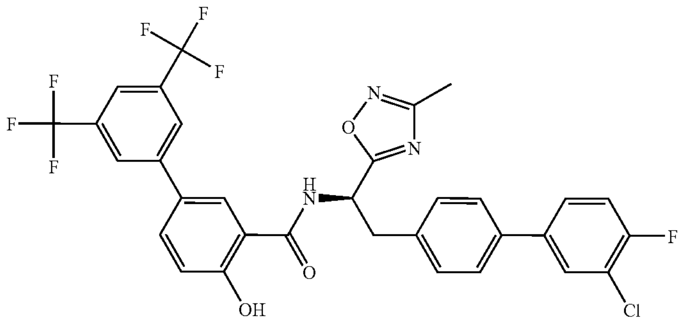 | 4-Hydroxy-3',5'-bis-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide |

TABLE 1-continued

| Ex. | Structure | Chemical Name |
|---|---|---|
| 76 | 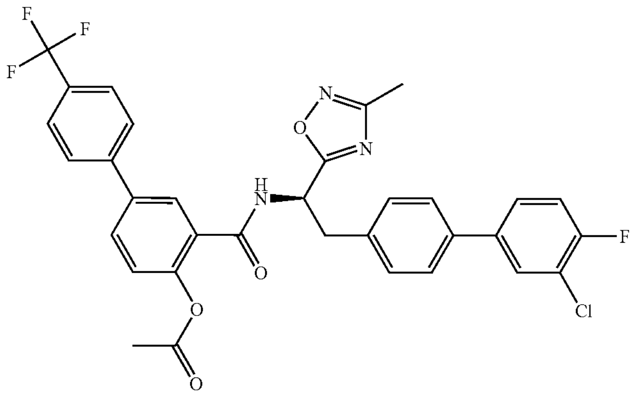 | Acetic acid 3-[2-(3'-chloro-4'-fluoro-biphenyl-4-yl)-1-(R)-(3-methyl-[1,2,4]oxadiazol-5-yl)-ethylcarbamoyl]-4'-trifluoromethyl-biphenyl-4-yl ester |
| 77 | 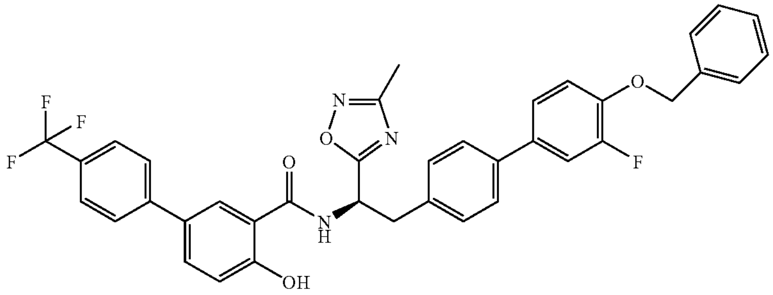 | 4-Hydroxy-4'-trifluoromethyl-biphenyl-3-carboxylic acid [2-(4'-benzyloxy-3'-fluoro-biphenyl-4-yl)-1-(R)-(3-methyl-[1,2,4]oxadiazol-5-yl)-ethyl]-amide |
| 78 | 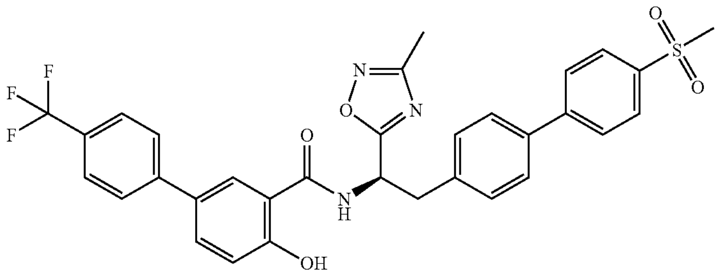 | 4-Hydroxy-4'-trifluoromethyl-biphenyl-3-carboxylic acid [2-(4'-methanesulfonyl-biphenyl-4-yl)-1-(R)(3-methyl-[1,2,4]oxadiazol-5-yl)-ethyl]-amide |
| 79 | 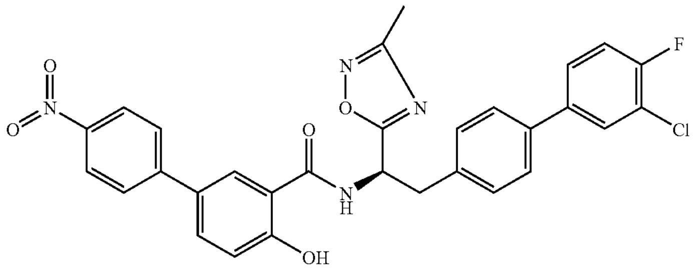 | 4-Hydroxy-4'-nitro-biphenyl-3-carboxylic acid [2-(3'-chloro-4'-fluoro-biphenyl-4-yl)-1-(R)-(3-methyl-[1,2,4]oxadiazol-5-yl)-ethyl]-amide |

TABLE 1-continued

| Ex. | Structure | Chemical Name |
|---|---|---|
| 80 | 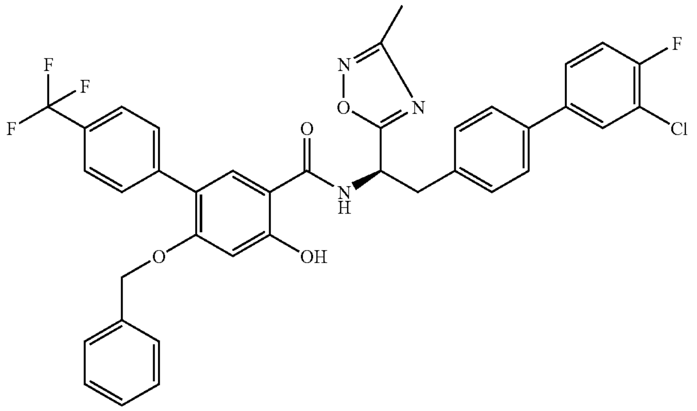 | 6-Benzyloxy-4-hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide |
| 81 | 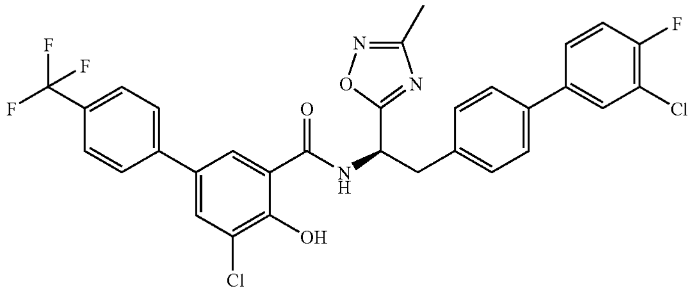 | 5-Chloro-4-hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide |
| 82 | 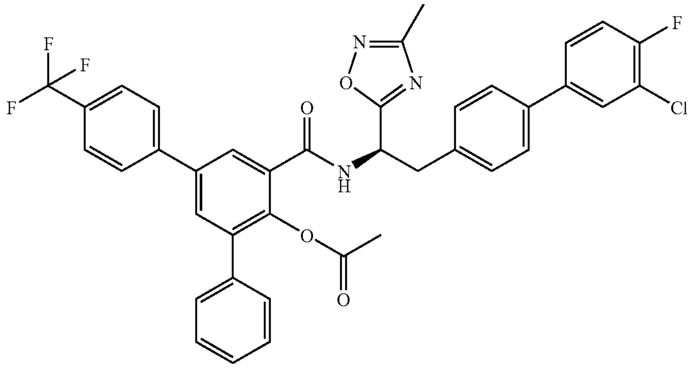 | Acetic acid 5'-[2-(3'-chloro-4-fluoro-biphenyl-4-yl)-1-(R)-(3-methyl-[1,2,4]oxadiazol-5-yl) ethylcarbamoyl]-4-trifluoromethyl[1,1';3',1'']terphenyl-4'-yl ester |
| 83 | 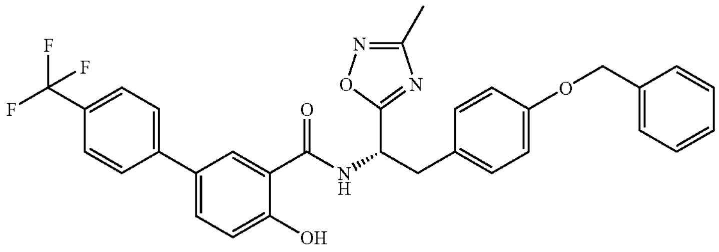 | 4-Hydroxy-4'-trifluoromethyl-biphenyl-3-carboxylic acid [2-(4-benzyloxy-phenyl)-1-(R)-(3-methyl-[1,2,4]oxadiazol-5-yl)-ethyl]-amide |
| 84 | 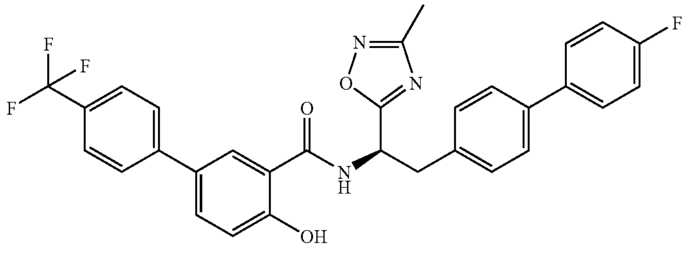 | 4-Hydroxy-4'-trifluoromethyl-biphenyl-3-carboxylic acid [2-(4'-fluoro-biphenyl-4-yl)-1-(R)-(3-methyl-[1,2,4]oxadiazol-5-yl)-ethyl]-amide |

TABLE 1-continued

| Ex. | Structure | Chemical Name |
|---|---|---|
| 85 | 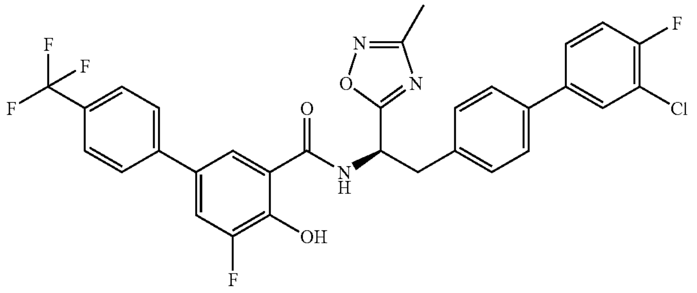 | 5-Fluoro-4-hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide |
| 86 | 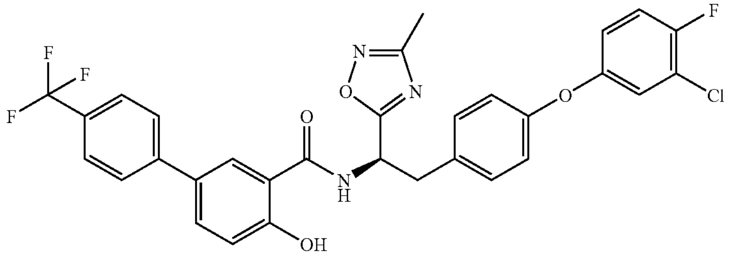 | 4-Hydroxy-4'-trifluoromethyl-biphenyl-3-carboxylic acid [2-[4-(3-chloro-4-fluoro-phenoxy)-phenyl]-1-(R)-(3-methyl 1,2,4]oxadiazol-5-yl)-ethyl]-amide |
| 87 | 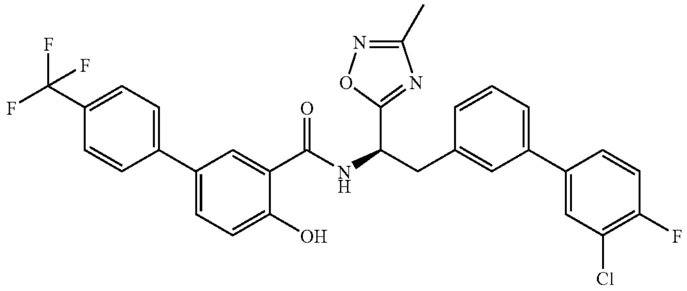 | 4-Hydroxy-4'-trifluoromethyl-biphenyl-3-carboxylic acid [2-(3'-chloro-4'-fluoro-biphenyl-3-yl)-1-(R)-(3-methyl-[1,2,4]oxadiazol-5-yl)-ethyl]-amide |
| 88 | 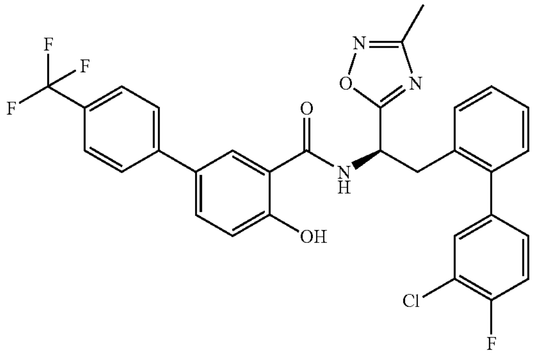 | 4-Hydroxy-4'-trifluoromethyl-biphenyl-3-carboxylic acid [2-(3'-chloro-4'-fluoro-biphenyl-2-yl)-1-(R)-(3-methyl-[1,2,4]oxadiazol-5-yl)-ethyl]-amide |
| 89 | 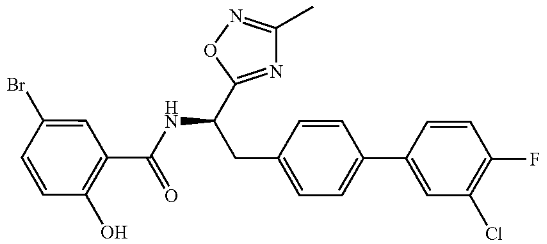 | 5-Bromo-N-[2-(3'-chloro-4'-fluoro-biphenyl-4-yl)-1-(R)-(3-methyl-[1,2,4]oxadiazol-5-yl)-ethyl]-2-hydroxy-benzamide |

TABLE 1-continued

| Ex. | Structure | Chemical Name |
|---|---|---|
| 90 | 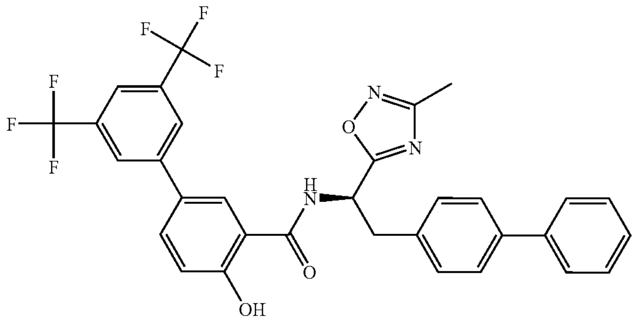 | 4-Hydroxy-3',5'-bis-trifluoromethyl-biphenyl-3-carboxylic acid [2-biphenyl-4-yl-1-(R)-(3-methyl-[1,2,4]oxadiazol-5-yl)-ethyl]-amide |
| 91 | 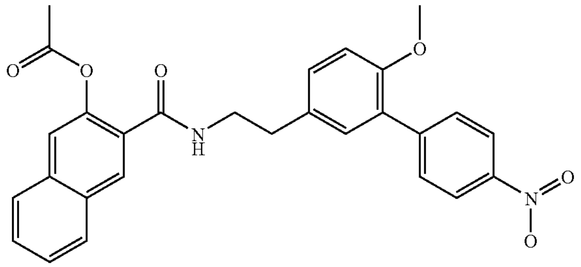 | Acetic acid 3-[2-(6-methoxy-4'-nitro-biphenyl-3-yl)-ethylcarbamoyl]-naphthalen-2-yl ester |
| 92 | 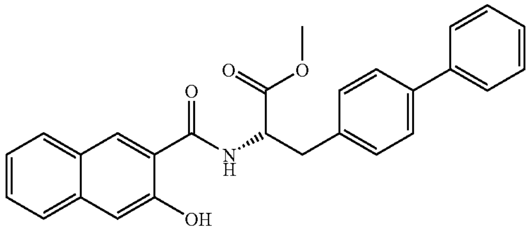 | 3-Biphenyl-4-yl-2-(S)-[(3-hydroxy-naphthalene-2-carbonyl)-amino]-propionic acid methyl ester |
| 93 | 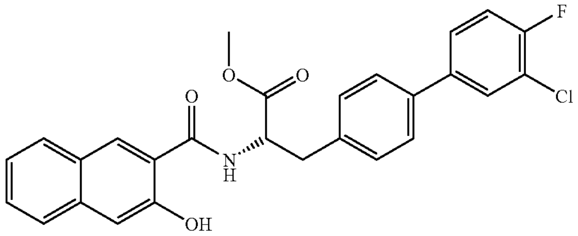 | 3-(3'-Chloro-4'-fluoro-biphenyl-4-yl)-2-(S)-[(3-hydroxy-naphthalene-2-carbonyl)-amino]-propionic acid methyl ester |
| 94 | 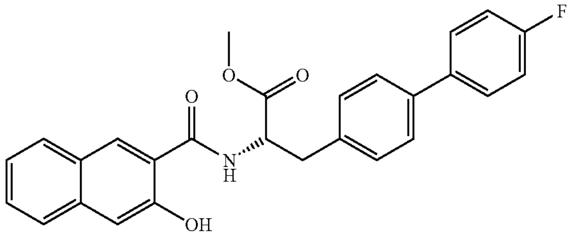 | 3-(4'-Fluoro-biphenyl-4-yl)-2-(S)-[(3-hydroxy-naphthalene-2-carbonyl)-amino]-propionic acid methyl ester |
| 95 | 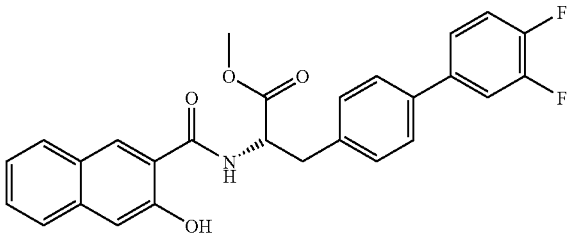 | 3-(3',4'-Difluoro-biphenyl-4-yl)-2-(S)-[(3-hydroxy-naphthalene-2-carbonyl)-amino]-propionic acid methyl ester |

TABLE 1-continued

| Ex. | Structure | Chemical Name |
| --- | --- | --- |
| 96 | 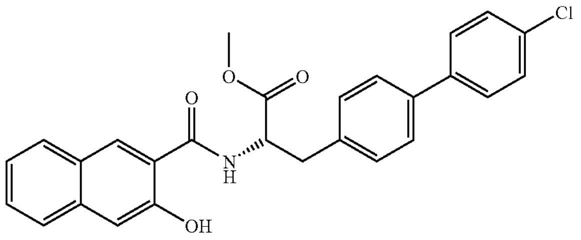 | 3-(4'-Chloro-biphenyl-4-yl)-2-(S)-[(3-hydroxy-naphthalene-2-carbonyl)-amino]-propionic acid methyl ester |
| 97 | 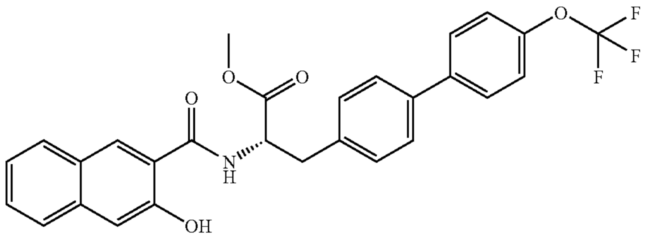 | 2-(S)-[(3-Hydroxy-naphthalene-2-carbonyl)-amino]-3-(4'-trifluoromethoxy-biphenyl-4-yl)-propionic acid methyl ester |
| 98 | 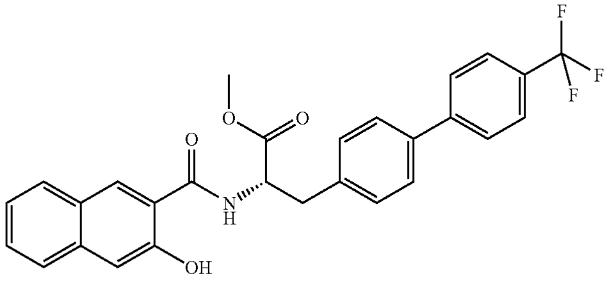 | 2-(S)-[(3-Hydroxy-naphthalene-2-carbonyl)-amino]-3-(4'-trifluoromethyl-biphenyl-4-yl)-propionic acid methyl ester |
| 99 | 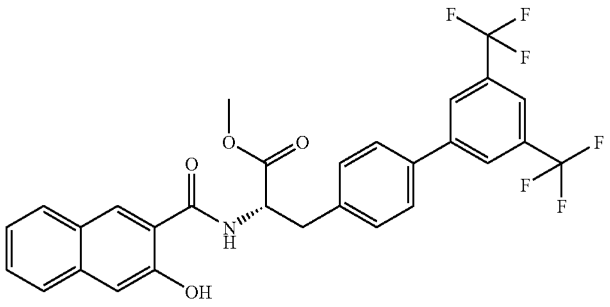 | 3-(3',5'-Bis-trifluoromethyl-biphenyl-4-yl)-2-(S)-[(3-hydroxy-naphthalene-2-carbonyl)-amino]-propionic acid methyl ester |
| 100 | 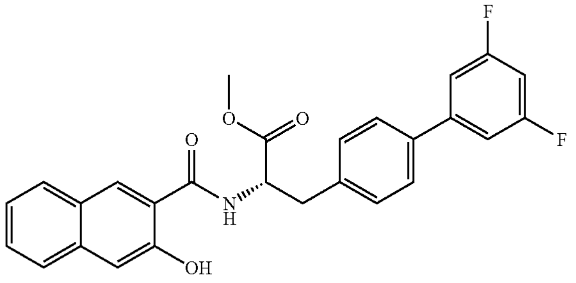 | 3-(3',5'-Difluoro-biphenyl-4-yl)-2-(S)-[(3-hydroxy-naphthalene-2-carbonyl)-amino]-propionic acid methyl ester |

TABLE 1-continued

| Ex. | Structure | Chemical Name |
|---|---|---|
| 101 | 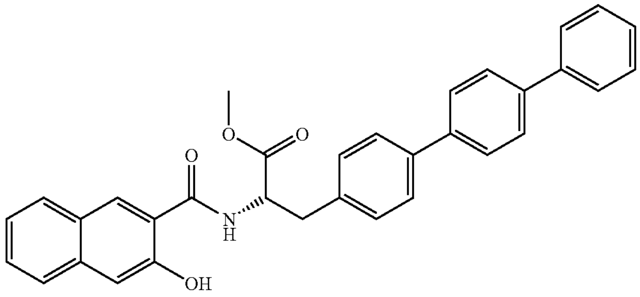 | 2-(S)-[(3-Hydroxy-naphthalene-2-carbonyl)-amino]-3-[1,1';4',1"terphenyl-4-yl-propionic acid methyl ester |
| 102 | 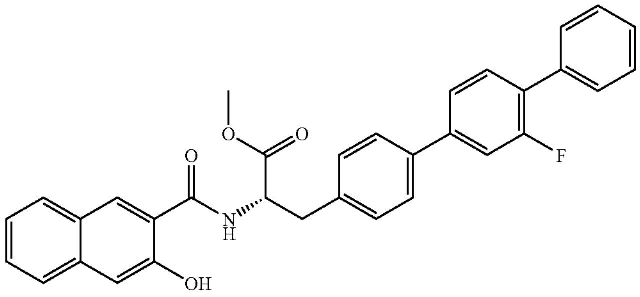 | 3-(2'-Fluoro-[1,1';4',1"]terphenyl-4"-yl)-2-(S)-[(3-hydroxy-naphthalene-2-carbonyl)-amino]-propionic acid methyl ester |
| 103 | 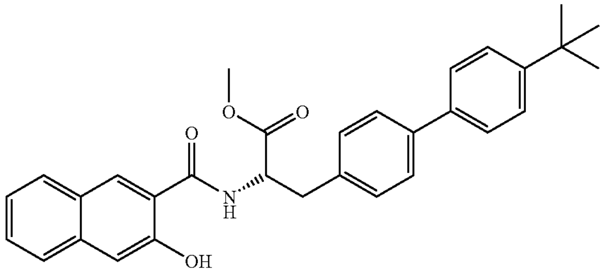 | 3-(4'-tert-Butyl-biphenyl-4-yl)-2-[(3-hydroxy-napthalene-2-(S)-carbonyl)-amino]-propionic acid methyl ester |
| 104 | 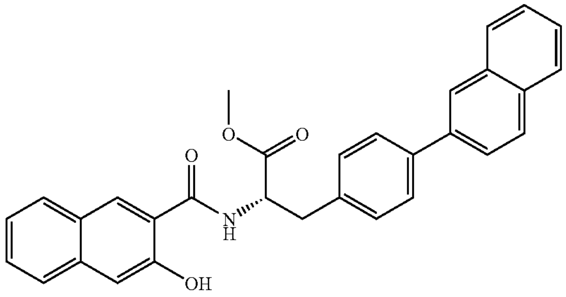 | 2-(S)-[(3-Hydroxy-naphthalene-2-carbonyl)-amino]-3-(4-naphthalen-2-yl-phenyl)-propionic acid methyl ester |
| 105 | 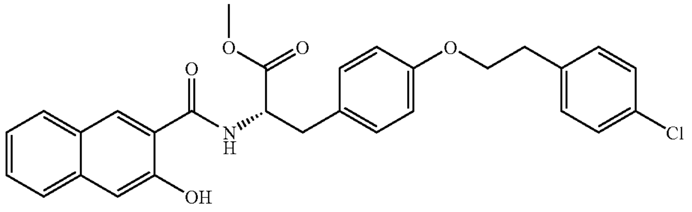 | 3-{4-[2-(4-Chloro-phenyl)-ethoxy]-phenyl}-2-(S)-[(3-hydroxy-naphthalene-2-carbonyl)-amino]-propionic acid methyl ester |
| 106 | 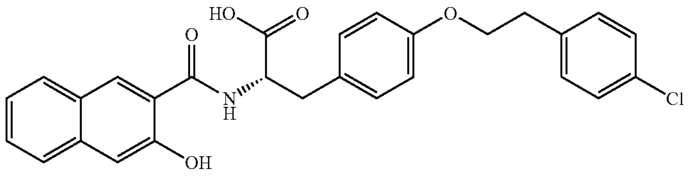 | 2-(S)-[(3-Hydroxy-naphthalene-2-carbonyl)-amino]-3-(4-naphthalen-2-ylphenyl)-propionic acid methyl ester |

TABLE 1-continued

| Ex. | Structure | Chemical Name |
| --- | --- | --- |
| 107 | 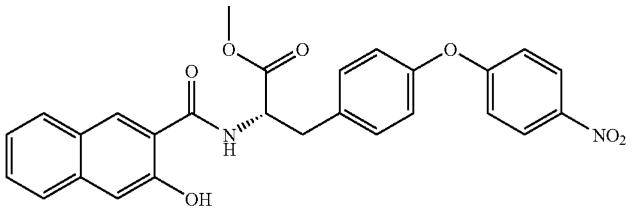 | 2-(S)-[(3-Hydroxy-naphthalene-2-carbonyl)-amino]-3-[4-(4-nitro-phenoxy)-phenyl]propionic acid methyl ester |
| 108 | 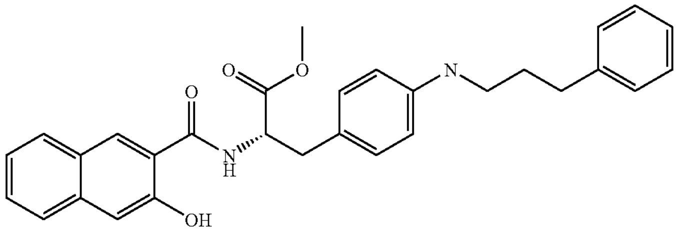 | 2-(S)-[(3-Hydroxy-naphthalene-2-carbonyl)-amino]-3-[4-(3-phenyl-propylamino)-phenyl]-propionic acid methyl ester |
| 109 | 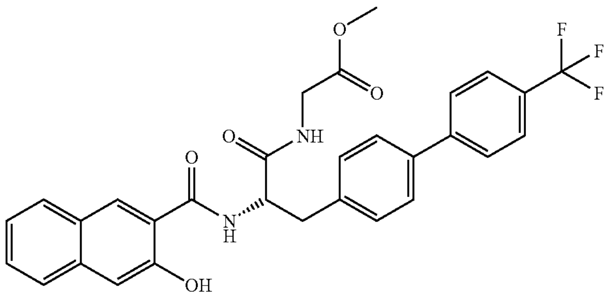 | [2-(S)-[(3-Hydroxy-naphthalene-2-carbonyl)-amino]-3-(4'-trifluoromethyl-biphenyl-4-yl)-propionylamino]-acetic acid methyl ester |
| 110 | 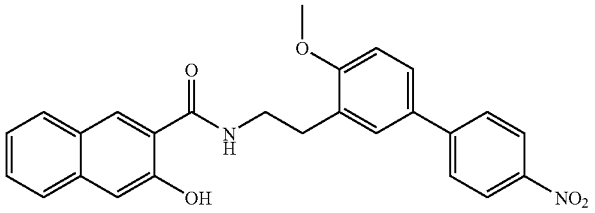 | 3-Hydroxy-naphthalene-2-carboxylic acid [2-(4-methoxy-4'-nitro-biphenyl-3-yl)-ethyl]-amide |
| 111 | 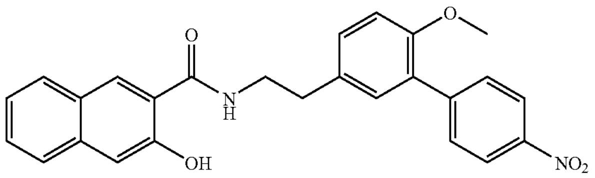 | 3-Hydroxy-naphthalene-2-carboxylic acid [2-(6-methoxy-4'-nitro-biphenyl-3-yl)-ethyl]-amide |
| 112 | 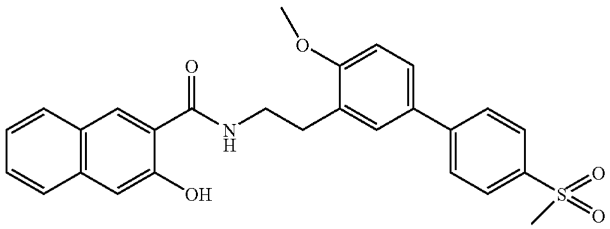 | 3-Hydroxy-naphthalene-2-carboxylic acid [2-(4'-methanesulfonyl-4-methoxy-biphenyl-3-yl)-ethyl]-amide |

TABLE 1-continued

| Ex. | Structure | Chemical Name |
|---|---|---|
| 113 | 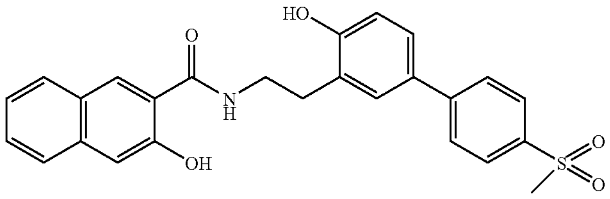 | 3-Hydroxy-naphthalene-2-carboxylic acid [2-(4-hydroxy-4'-methanesulfonyl-biphenyl-3-yl)-ethyl]-amide |
| 114 | 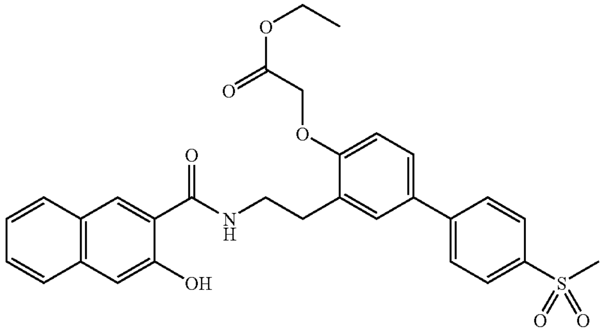 | (3-{2-[(3-Hydroxy-naphthalene-2-carbonyl)-amino]-ethyl}-4'-methanesulfonyl-biphenyl-4-yloxy)-acetic acid ethyl ester |
| 115 | 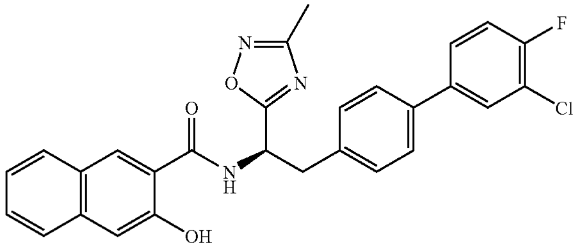 | 3-Hydroxy-naphthalene-2-carboxylic acid [2-(3'-chloro-4'-fluoro-biphenyl-4-yl)-1-(R)-(3-methyl-[1,2,4]oxadiazol-5-yl)-ethyl]-amide |
| 116 | 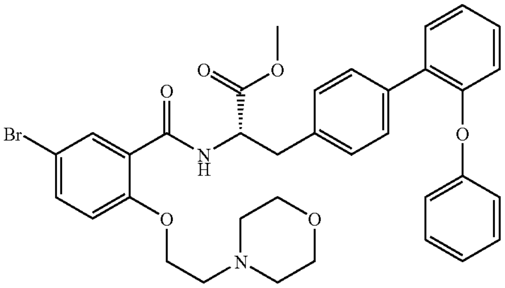 | 2-(S)-[5-Bromo-2-(2-morpholin-4-yl-ethoxy)-benzoylamino]-3-(2'-phenoxy-biphenyl-4-yl)-propionic acid methyl ester |
| 117 | 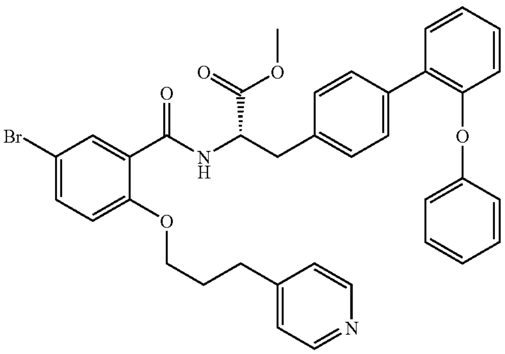 | 2-(S)-[5-Bromo-2-(3-pyridin-4-yl-propoxy)-benzoylamino]-3-(2'-phenoxy-biphenyl-4-yl)-propionic acid methyl ester |

TABLE 1-continued

| Ex. | Structure | Chemical Name |
|---|---|---|
| 118 | 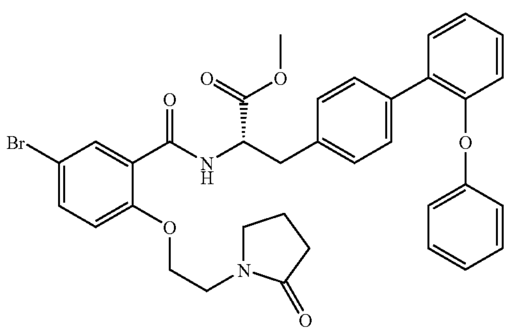 | 2-(S)-{5-Bromo-2-[2-(2-oxo-pyrrolidin-1-yl)-ethoxy]-benzoylamino}-3-(2'-phenoxy-biphenyl-4-yl)-propionic acid methyl ester |
| 119 | 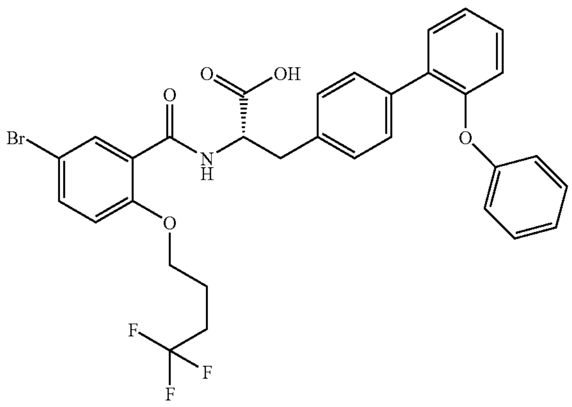 | 2-(S)-[5-Bromo-2-(4,4,4-trifluoro-butoxy)-benzoylamino]-3-(2'-phenoxy-biphenyl-4-yl)-propionic acid |
| 120 | 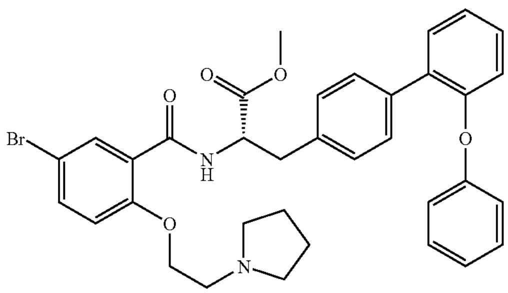 | 2-(S)-[5-Bromo-2-(2-pyrrolidin-1-yl-ethoxy)-benzoylamino]-3-(2'-phenoxy-biphenyl-4-yl)-propionic acid methyl ester |
| 121 | 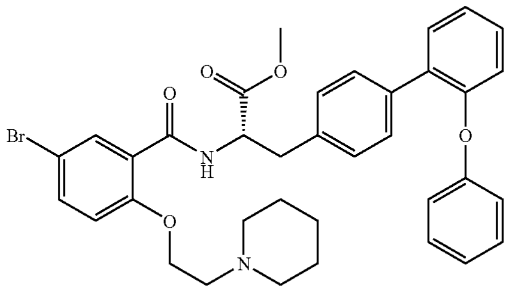 | 2-S)-[5-Bromo-2-(2-piperidin-1-yl-ethoxy)-benzoylamino]-3-(2'-phenoxy-biphenyl-4-yl)-propionic acid methyl ester |
| 122 | 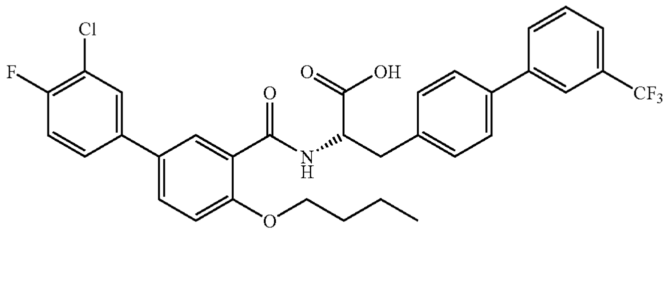 | 2-(S)-[(4-Butoxy-3'-chloro-4'-fluoro-biphenyl-3-carbonyl)-amino]-3-(3'-trifluoromethyl-biphenyl-4-yl)-propionic acid |

TABLE 1-continued
| Ex. | Structure | Chemical Name |
|---|---|---|
| 123 | 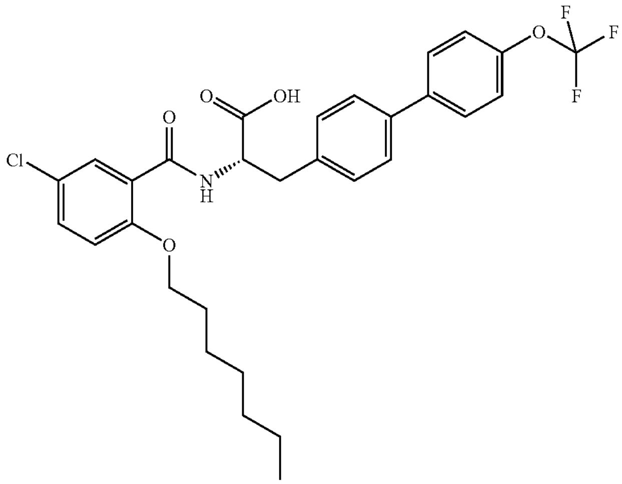 | 2-(S)-(5-Chloro-2-heptyloxy-benzoylamino)-3-(4'-trifluoromethoxy-biphenyl-4-yl)-propionic acid |
| 124 | 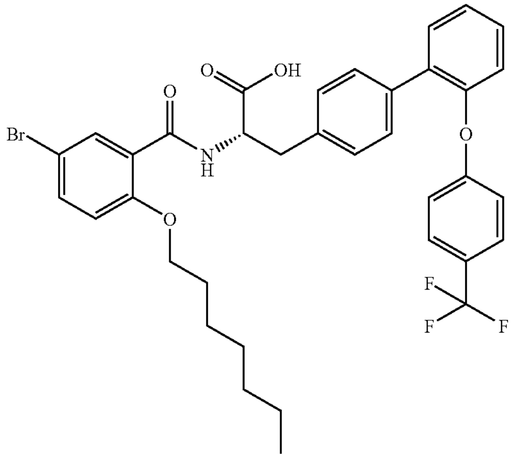 | 2-(S)-(5-Bromo-2-heptyloxy-benzoylamino)-3-[2'-(4-trifluoromethyl-phenoxy)-biphenyl-4-yl]-propionic acid |
| 125 | 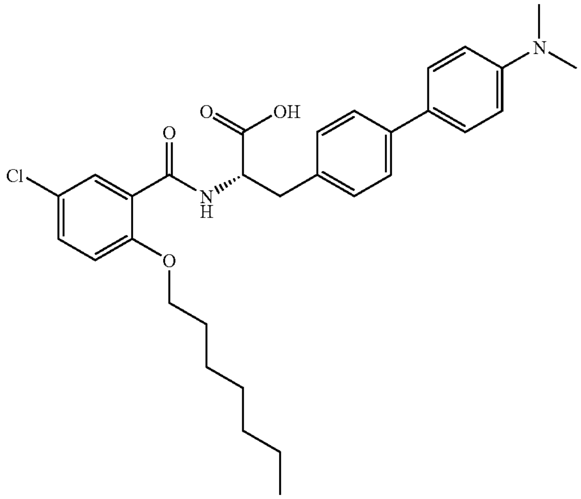 | 2-(S)-(5-Chloro-2-heptyloxy-benzoylamino)-3-(4'-dimethylamino-biphenyl-4-yl)-propionic acid |

TABLE 1-continued
| Ex. | Structure | Chemical Name |
| --- | --- | --- |
| 126 | 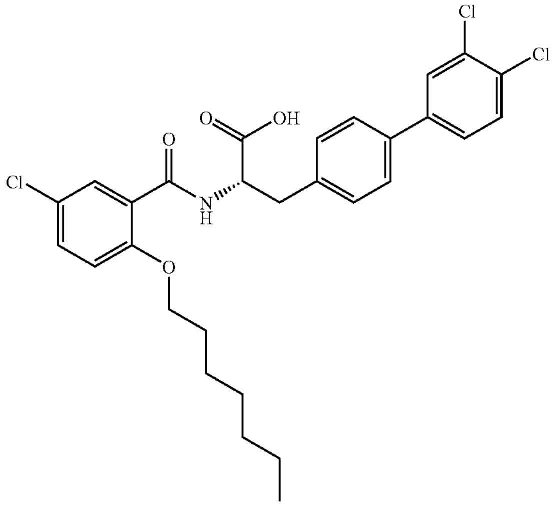 | 2-S)-(5-Chloro-2-heptyloxy-benzoylamino)-3-(3',4'-dichloro-biphenyl-4-yl)-propionic acid |
| 127 | 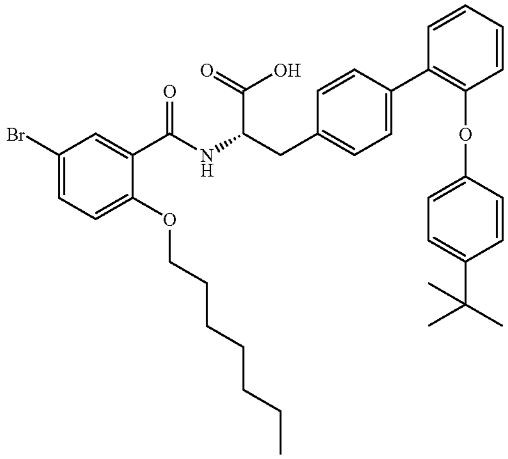 | 2-(S)-(5-Bromo-2-heptyloxy-benzoylamino)-3-[2'-(4-tert-butyl-phenoxy)-biphenyl-4-yl]-propionic acid |
| 128 | 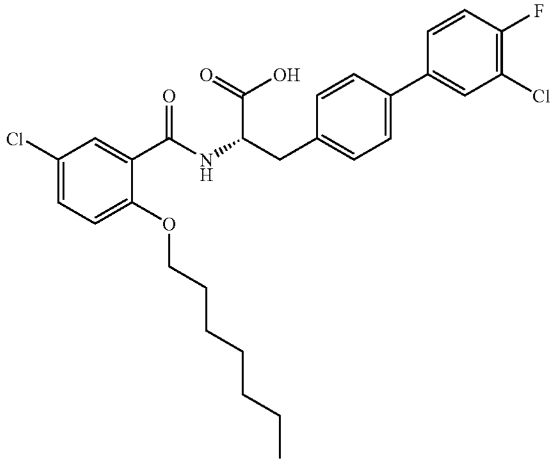 | 3-(3'-Chloro-4'-fluoro-biphenyl-4-yl)-2-(S)-(5-chloro-2-heptyloxy-benzoylamino)-propionic acid |

TABLE 1-continued
| Ex. | Structure | Chemical Name |
| --- | --- | --- |
| 129 | 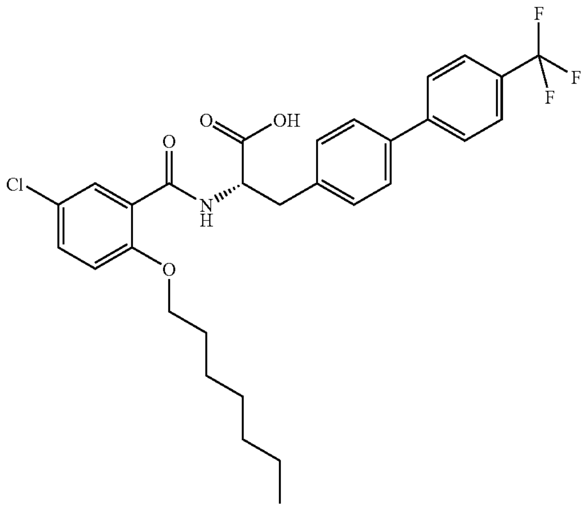 | 2-(S)-(5-Chloro-2-heptyloxy-benzoylamino)-3-(4'-trifluoromethyl-biphenyl-4-yl)-propionic acid |
| 130 | 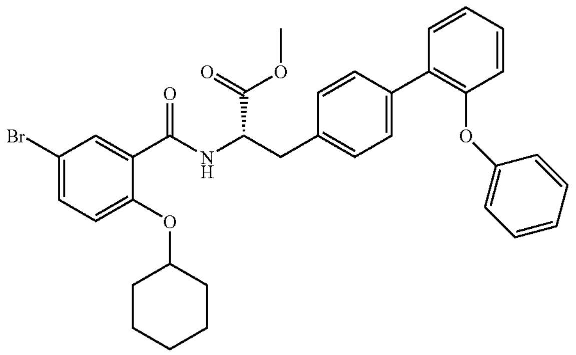 | 2-(S)-(5-Bromo-2-cyclohexyloxy-benzoylamino)-3-(2'-phenoxy-biphenyl-4-yl)-propionic acid methyl ester |
| 131 | 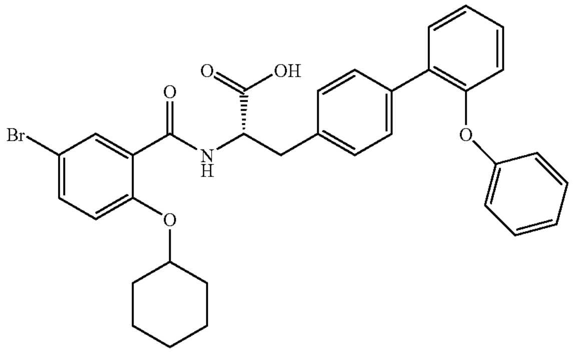 | 2-S)-(5-Bromo-2-cyclohexyloxy-benzoylamino)-3-(2'-phenoxy-biphenyl-4-yl)-propionic acid |

TABLE 1-continued
| Ex. | Structure | Chemical Name |
| --- | --- | --- |
| 132 | 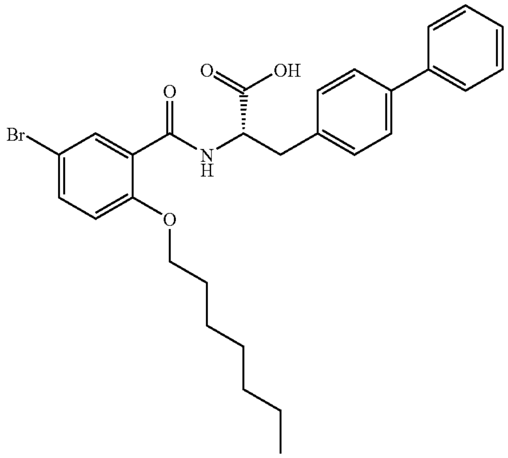 | 3-Biphenyl-4-yl-2-(5-bromo-2-heptyloxy-benzoylamino)-propionic acid |
| 133 | 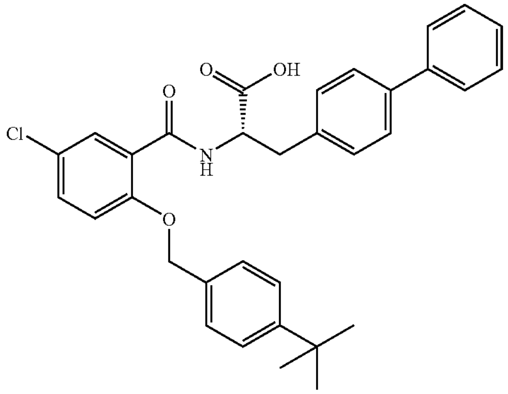 | 3-Biphenyl-4-yl-2-(S)-[2-(4-tert-butyl-benzyloxy)-5-chlorobenzoyl amino]-propionic acid |
| 134 | 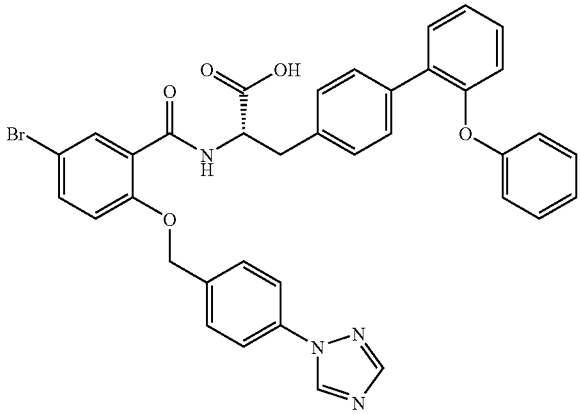 | 2-(S)-[5-Bromo-2-(4-[1,2,4]triazol-1-yl-benzyloxy)-benzoylamino]-3-(2'-phenoxy-biphenyl-4-yl)-propionic acid |

TABLE 1-continued
| Ex. | Structure | Chemical Name |
| --- | --- | --- |
| 135 | 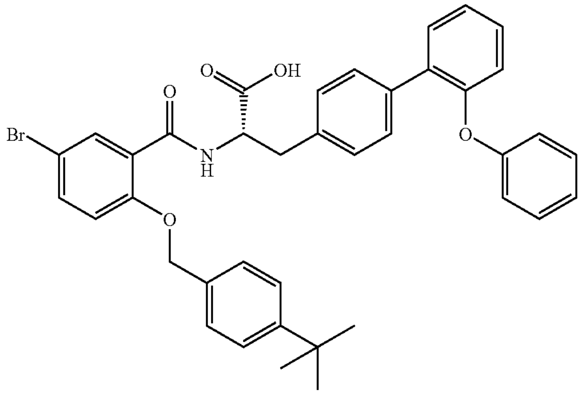 | 2-(S)-[5-Bromo-2-(4-tert-butyl-benzyloxy)-benzoylamino]-3-(2'-phenoxy-biphenyl-4-yl)-propionic acid |
| 136 | 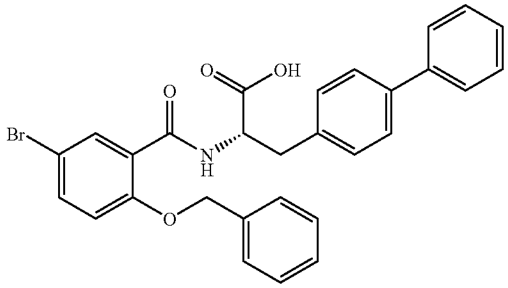 | 2-S)-(2-Benzyloxy-5-bromo-benzoylamino)-3-biphenyl-4-yl-propionic acid |
| 137 | 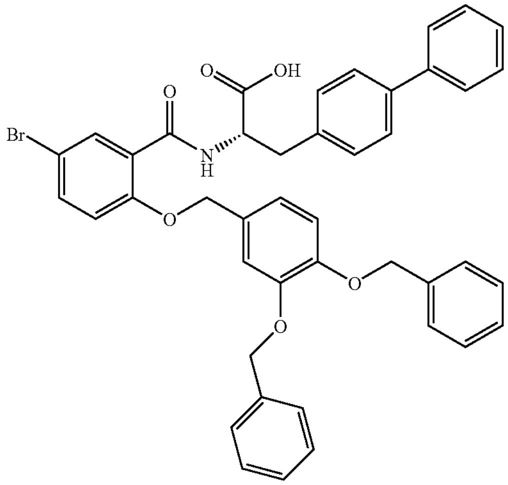 | 3-Biphenyl-4-yl-2-(S)-[2-(3,4-bis-benzyloxy-benzyloxy)-5-bromo-benzoylamino]-propionic acid |
| 138 | 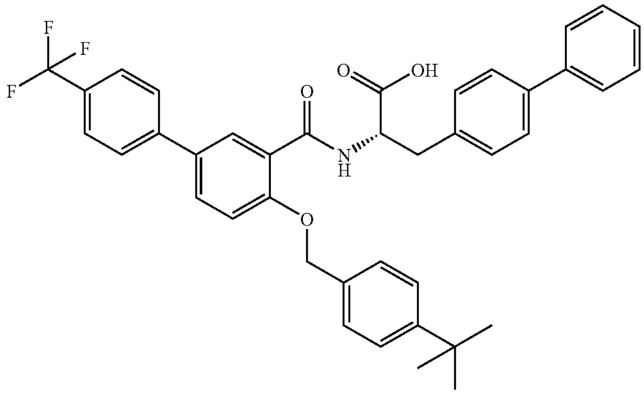 | 3-Biphenyl-4-yl-2-(S)-{[4-(4-tert-butyl-benzyloxy)-4'-trifluoromethyl-biphenyl-3-carbonyl]-amino}-propionic acid |

TABLE 1-continued

| Ex. | Structure | Chemical Name |
|---|---|---|
| 139 | 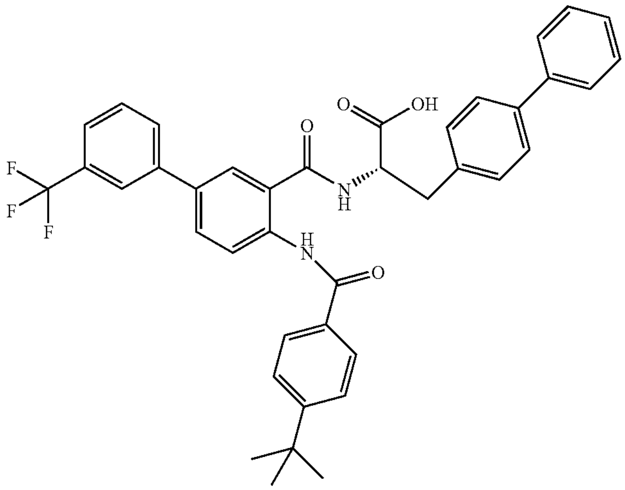 | 3-Biphenyl-4-yl-2-(S)-{[4-(4-tert-butyl-benzoylamino)-3'-trifluoromethyl biphenyl-3-carbonyl]-amino}-propionic acid |
| 140 | 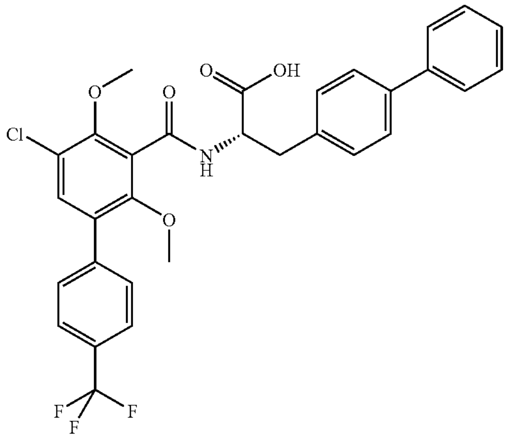 | 3-Biphenyl-4-yl-2-(S)-[(5-chloro-2,4-dimethoxy-4'-trifluoromethyl-biphenyl-3-carbonyl)-amino]-propionic acid |
| 141 | 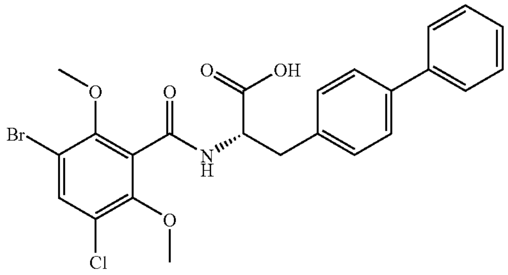 | 3-Biphenyl-4-yl-2-(S)-(3-bromo-5-chloro-2,6-dimethoxy-benzoylamino)-propionic acid |
| 142 | 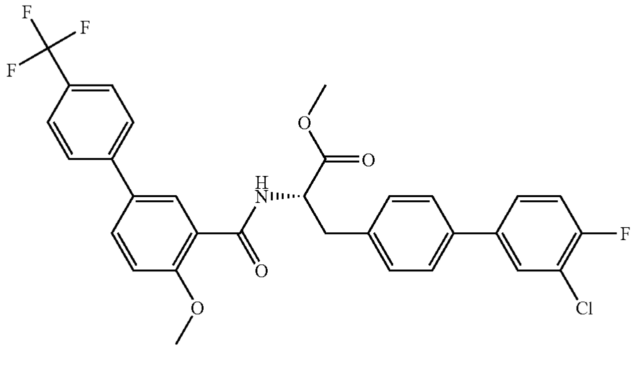 | 3-(3'-Chloro-4'-fluoro-biphenyl-4-yl)-2-(S)-[(4-methoxy-4'-trifluoromethyl-biphenyl-3-carbonyl)-amino]-propionic acid methyl ester |

TABLE 1-continued

| Ex. | Structure | Chemical Name |
|---|---|---|
| 143 | 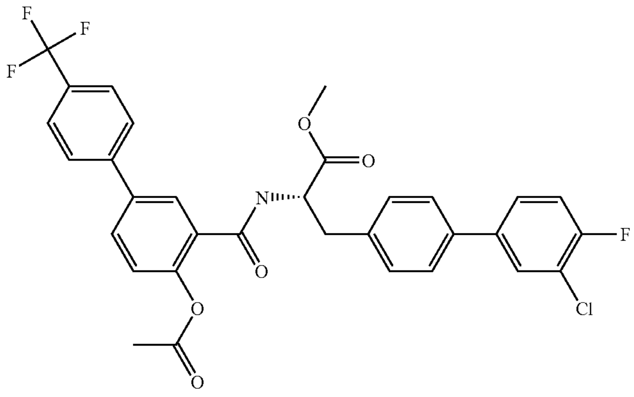 | 2-(S)-[(4-Acetoxy-4'-trifluoromethyl-biphenyl-3-carbonyl)-amino]-3-(3'-chloro-4'-fluoro-biphenyl-4-yl)-propionic acid methyl ester |
| 144 | 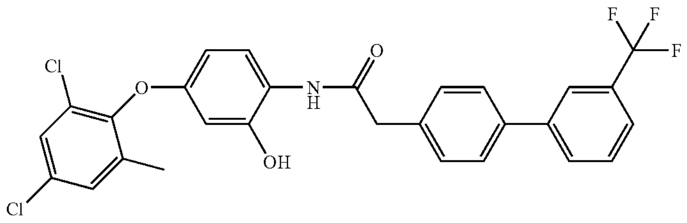 | N-[4-(2,4-Dichloro-6-methyl-phenoxy)-2-hydroxy-phenyl]-2-(3'-trifluoromethyl-biphenyl-4-yl)-acetamide |
| 145 | 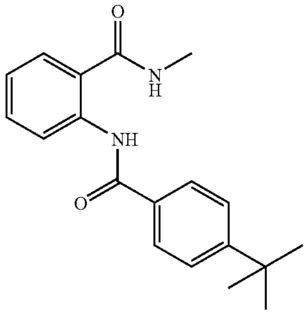 | 2-(4-t-butyl-1-Benzoylamino)-N-methyl-benzamide |
| 146 | 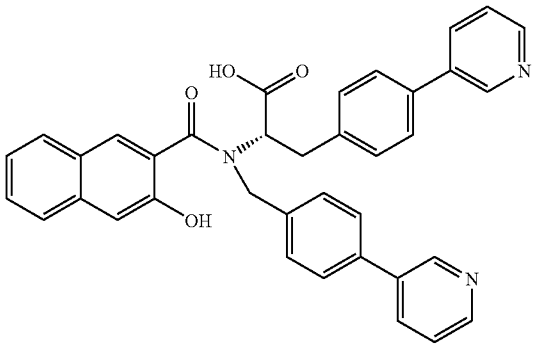 | 2-(S)-[(3-Hydroxy-naphthalene-2-carbonyl)-(4-pyridin-3-yl-benzyl)-amino]-3-(4-pyridin-3-yl-phenyl)-propionic acid |

TABLE 1-continued

| Ex. | Structure | Chemical Name |
| --- | --- | --- |
| 147 | 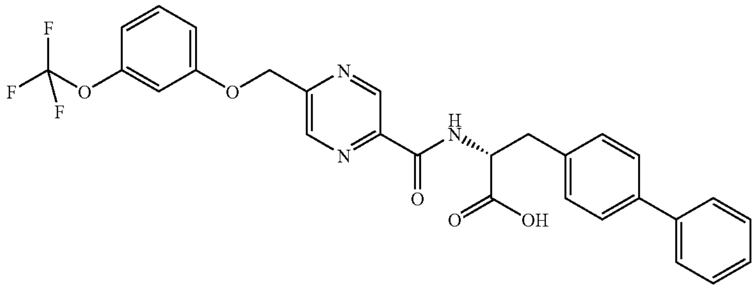 | 3-Biphenyl-4-yl-2-(S)-{[5-(3-trifluoromethoxy-phenoxymethyl)-pyrazine-2-carbonyl]-amino}-propionic acid |
| 148 | 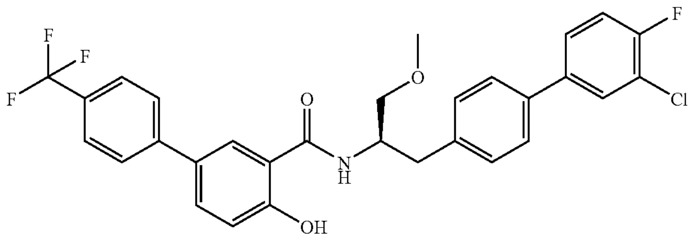 | 4-Hydroxy-4'-trifluoromethyl-biphenyl-3-carboxylic acid [2-(3'-chloro-4'-fluoro-biphenyl-4-yl)-1-(R)-methoxymethyl-ethyl]-amide |
| 149 | 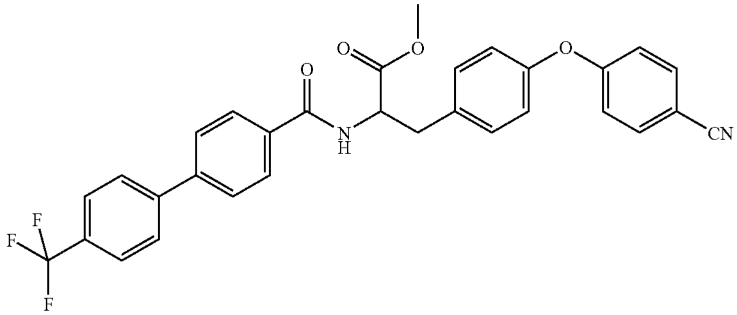 | 3-[4-(4-Cyano-phenoxy)-phenyl]-2-(S)-[(4'-trifluoromethyl-biphenyl-4-carbonyl)-amino]propionic acid methyl ester |
| 150 | 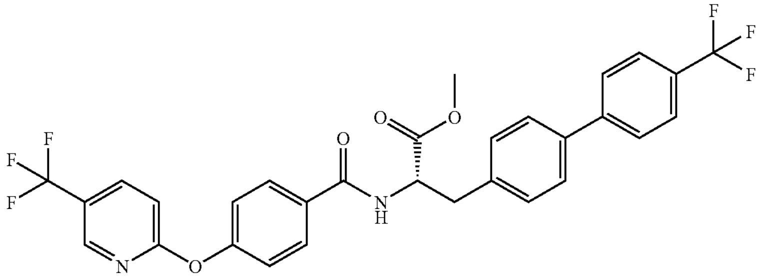 | 3-(4'-Trifluoromethyl-biphenyl-4-yl)-2-(S)-[4-(5-trifluoromethyl-pyridin-2-yloxy)-benzoylamino]-propionic acid methyl ester |
| 151 | 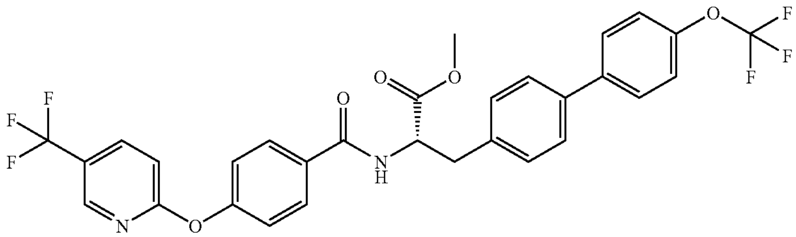 | 3-(4'-Trifluoromethoxy-biphenyl-4-yl)-2-(S)-[4-(5-trifluoromethyl-pyridin-2-yloxy)-benzoylamino]-propionic acid methyl ester |

Unless otherwise indicated, the structures of examples of compounds of Formula (I) having vacant connectivity for heteroatoms, such as oxygen and nitrogen, are assumed to have a hydrogen atom attached thereto.

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may containing one or more O, S, S(O), or $S(O)_2$ atoms. Examples of "alkyl" as used herein include, but are not limited to, methyl, n-butyl, t-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may containing one or more O, S, S(O), or $S(O)_2$ atoms. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may containing one or more O, S, S(O), or $S(O)_2$ atoms.

As used herein, the term "alkenylene" refers to a straight or branched chain divalent hydrocarbon radical having from two to ten carbon atoms and one or more carbon-carbon double bonds, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenylene" group may containing one or more O, S, S(O), or $S(O)_2$ atoms. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may containing one or more O, S, S(O), or $S(O)_2$ atoms.

As used herein, the term "alkynylene" refers to a straight or branched chain divalent hydrocarbon radical having from two to ten carbon atoms and one or more carbon-carbon triple bonds, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynylene" group may containing one or more O, S, S(O), or $S(O)_2$ atoms. Examples of "alkynylene" as used herein include, but are not limited to, ethyne-1,2-diyl, propyne-1,3-diyl, and the like.

As used herein, "cycloalkyl" refers to a alicyclic hydrocarbon group optionally possessing one or more degrees of unsaturation, having from three to twelve carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms and optionally possessing one or more degrees of unsaturation, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered heterocyclic ring optionally possessing one or more degrees of unsaturation, containing one or more heteroatomic substitutions selected from S, SO, $SO_2$, O, or N, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like.

As used herein, the term "heterocyclylene" refers to a three to twelve-membered heterocyclic ring diradical optionally having one or more degrees of unsaturation containing one or more heteroatoms selected from S, SO, $SO_2$, O, or N, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-dyil, and the like.

As used herein, the term "aryl" refers to a benzene ring or to an optionally substituted benzene ring system fused to one or more optionally substituted benzene rings, optionally substituted with substituents selected from the group consisting of halo, lower alkyl, lower alkoxy, lower alkylsulfanyl, lower alkylsulfenyl, lower alkylsulfonyl, oxo, —CH═CH—$CO_2R_1$, —$C(O)R_1$, —$C(O)C(O)R_1$, —$C(O)C(O)OR_1$, —$C(O)C(O)NR_1R_2$, alkyl ketones, ketoesters, keto amides, alkylene keto esters, alkylene ketoamides, carboxy esters, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of halo, lower alkyl, lower alkoxy, lower alkylsulfanyl, lower alkylsulfenyl, lower alkylsulfonyl, oxo, —CH═CH—$CO_2R_1$, —$C(O)R_1$, —$C(O)C(O)R_1$, —$C(O)C(O)OR_1$, —$C(O)C(O)NR_1R_2$, alkyl ketones, ketoesters, keto amides, alkylene keto esters, alkylene ketoamides, carboxy esters, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include 5-indanyl, 5,6,7,8-tetrahydro-2-naphthyl,

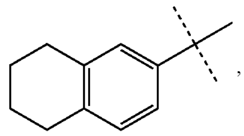

, and the like.

As used herein, the term "fused cycloalkylarylene" refers to a fused cycloalkylaryl, wherein the aryl group is divalent. Examples include

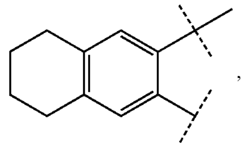

, and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

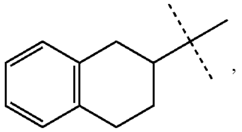

and the like.

As used herein, the term "fused arylcycloalkylene" refers to a fused arylcycloalkyl, wherein the cycloalkyl group is divalent. Examples include

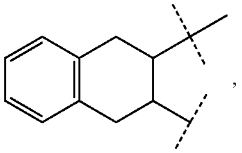

and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include 3,4-methylenedioxy-1-phenyl,

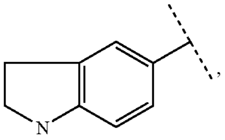

and the like

As used herein, the term "fused heterocyclylarylene" refers to a fused heterocyclylaryl, wherein the aryl group is divalent. Examples include

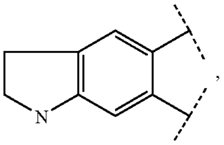

and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include 2-(1,3-benzodioxolyl),

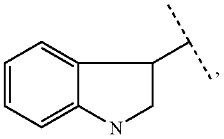

and the like.

As used herein, the term "fused arylheterocyclylene" refers to a fused arylheterocyclyl, wherein the heterocyclyl group is divalent. Examples include

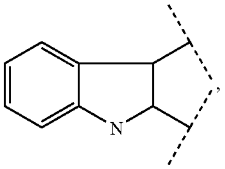

and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include 5-aza-6-indanyl,

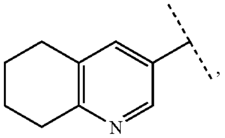

and the like.

As used herein, the term "fused cycloalkylheteroarylene" refers to a fused cycloalkylheteroaryl, wherein the heteroaryl group is divalent. Examples include

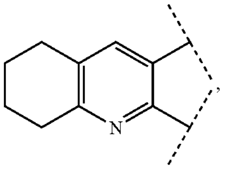

and the like.

As used herein, the term "fused heteroarylcycloalkyl" refers to a heteroaryl group fused to a cycloalkyl group, the two having two atoms in common, and wherein the cycloalkyl group is the point of substitution. Examples of "fused heteroarylcycloalkyl" used herein include 5-aza-1-indanyl,

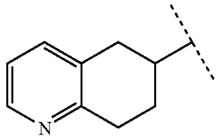

and the like.

As used herein, the term "fused heteroarylcycloalkylene" refers to a fused heteroarylcycloalkyl, wherein the cycloalkyl group is divalent. Examples include

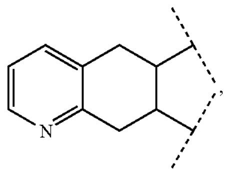

and the like.

As used herein, the term “fused heterocyclylheteroaryl” refers to a heterocyclyl group fused to a heteroaryl group, the two having two atoms in common, and wherein the heteroaryl group is the point of substitution. Examples of “fused heterocyclylheteroaryl” used herein include 1,2,3,4-tetrahydro-beta-carbolin-8-yl,

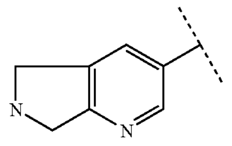

and the like.

As used herein, the term “fused heterocyclylheteroarylene” refers to a fused heterocyclylheteroaryl, wherein the heteroaryl group is divalent. Examples include

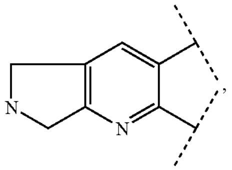

and the like.

As used herein, the term “fused heteroarylheterocyclyl” refers to a heteroaryl group fused to a heterocyclyl group, the two having two atoms in common, and wherein the heterocyclyl group is the point of substitution. Examples of “fused heteroarylheterocyclyl” used herein include -5-aza-2,3-dihydrobenzofuran-2-yl,

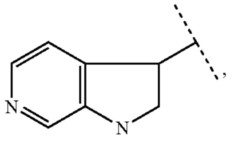

and the like.

As used herein, the term “fused heteroarylheterocyclylene” refers to a fused heteroarylheterocyclyl, wherein the heterocyclyl group is divalent. Examples include

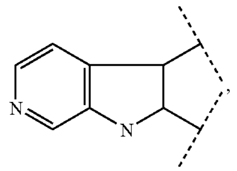

and the like.

As used herein, the term “acid isostere” refers to a substituent group that can ionize at physiological pH to bear a net negative charge. Examples of such “acid isosteres” include but are not limited to heteroaryl groups such as, but not limited to, isoxazol-3-ol-5-yl, 1H-tetrazole-5-yl, or 2H-tetrazole-5-yl. Such acid isosteres include but are not limited to heterocyclyl groups such as, but not limited to, imidazolidine-2,4-dione-5-yl, imidazolidine-2,4-dione-1-yl, 1,3-thiazolidine-2,4-dione-5-yl, or 5-hydroxy-4H-pyran-4-on-2-yl.

As used herein, the term “ester isostere” refers to a substituent group that can be metabolically stable and can retain the selectivity and affinity of a corresponding ester toward a target protein. Examples of such “ester isosteres” include, but are not limited to, heteroaryl groups such as, but not limited to, 1,3-oxazole-5-yl, 1,3-oxazole-2-yl, 1,2,3-oxadiazole-5-yl, 1,2,4-oxadiazole-5-yl, 1,3,4-oxadiazole-5-yl, 1,2,3-thiadiazole-5-yl, 1,2,4-thiadiazole-5-yl, 1,3,4-thiadiazole-5-yl, 5-alkyl-1,3-oxazole-2-yl, 2-alkyl-1,3-oxazole-5-yl, 4-alkyl-1,2,3-oxadiazole-5-yl, 3-alkyl-1,2,4-oxadiazole-5-yl, 2-alkyl-1,3,4-oxadiazole-5-yl, 4-alkyl-1,2,3-thiadiazole-5-yl, 3-alkyl-1,2,4-thiadiazole-5-yl, 2-alkyl-1,3,4-thiadiazole-5-yl, 1,2,4-triazole-1-yl, 3-alkyl-1,2,4-triazole-1-yl, tetrazole-1-yl, and 1-alkyl-tetrazole-5-yl; aryl groups such as, but not limited to, 3,5-difluoro-4-alkoxyphenyl; and heterocyclyl groups such as, but not limited to, 1-alkyl-imidazolidine-2,4-dione-5-yl, imidazolidine-2,4-dione-1-yl, 3-alkyl-1,3-thiazolidine-2,4-dione-5-yl, and 5-alkoxy-4H-pyran-4-on-2-yl. The alkyl groups in the heterocyclyl, aryl, and heteroaryl groups of the ester isosteres may be replaced with a phenyl or alkylphenyl group.

As used herein, the term “direct bond”, where part of a structural variable specification, refers to the direct joining of the substituents flanking (preceding and succeeding) the variable taken as a “direct bond”.

As used herein, the term “alkoxy” refers to the group $R_aO$—, where $R_a$ is alkyl.

As used herein, the term “alkenyloxy” refers to the group $R_aO$—, where $R_a$ is alkenyl.

As used herein, the term “alkynyloxy” refers to the group $R_aO$—, where $R_a$ is alkynyl.

As used herein, the term “alkylsulfanyl” refers to the group $R_aS$—, where $R_a$ is alkyl.

As used herein, the term “alkenylsulfanyl” refers to the group $R_aS$—, where $R_a$ is alkenyl.

As used herein, the term “alkynylsulfanyl” refers to the group $R_aS$—, where $R_a$ is alkynyl.

As used herein, the term “alkylsulfenyl” refers to the group $R_aS(O)$—, where $R_a$ is alkyl.

As used herein, the term “alkenylsulfenyl” refers to the group $R_aS(O)$—, where $R_a$ is alkenyl.

As used herein, the term "alkynylsulfenyl" refers to the group $R_aS(O)$—, where $R_a$ is alkynyl.

As used herein, the term "alkylsulfonyl" refers to the group $R_aSO_2$—, where $R_a$ is alkyl.

As used herein, the term "alkenylsulfonyl" refers to the group $R_aSO_2$—, where $R_a$ is alkenyl.

As used herein, the term "alkynylsulfonyl" refers to the group $R_aSO_2$—, where $R_a$ is alkynyl.

As used herein, the term "acyl" refers to the group $R_aC(O)$—, where $R_a$ is alkyl, alkenyl, alkynyl, cycloalkyl, cycloalkenyl, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is alkyl.

As used herein, the term "acyloxy" refers to the group $R_aC(O)O$—, where $R_a$ is alkyl, alkenyl, alkynyl, cycloalkyl, cycloalkenyl, or heterocyclyl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, $—CH_2—O—CH_2—$, $—CH_2—SO_2—CH_2—$, $—CH_2—NH—CH_3$ and so forth.

Whenever the terms "alkyl" or "aryl" or either of their prefix roots appear in a name of a substituent (e.g. arylalkoxyaryloxy) they shall be interpreted as including those limitations given above for "alkyl" and "aryl". Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent $—SO_2NH_2$.

As used herein, the term "carbamoyl" shall refer to the substituent $—C(O)NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent $—S(O)_2—$.

As used herein, the term "solvate" is a complex of variable stoichiometry formed by a solute (in this invention, a compound of Formula (I)) and a solvent. Such solvents for the purpose of the invention may not sunstantially interfere with the biological activity of the solute. Solvents may be, by way of example, water, ethanol, or acetic acid.

As used herein, the term "biohydrolyzable ester" is an ester of a drug substance (in this invention, a compound of formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to Formula (I) in plasma. Many examples of such are known in the art and include by way of example lower alkyl esters (e.g., $C_1$-$C_4$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to Formula (I) in plasma. Many examples of such are known in the art and include by way of example lower alkyl amides, .alpha-amino acid amides, alkoxyacyl amides, and alkylaminoalkylcarbonyl amides.

As used herein, the term "prodrug" includes biohydrolyzable amides and biohydrolyzable esters and encompasses a) compounds in which the biohydrolyzable functionality in such a prodrug is encompassed in the compound of formula (I) and b) compounds which may be oxidized or reduced biologically at a given functional group to yield drug substances of formula (I). Examples of these functional groups include, but are not limited to, 1,4-dihydropyridine, N-alkylcarbonyl-1,4-dihydropyridine, 1,4-cyclohexadiene, tert-butyl, and the like.

The present invention also provides a method for the synthesis of compounds useful as intermediates in the preparation of compounds of Formula (I) along with methods for the preparation of compounds of Formula (I). The compounds can be prepared according to the following reaction Schemes and procedures in which variables are as defined. In these reactions, it is also possible to make use of variants that are themselves known to those of ordinary skill in this art, but are not mentioned in greater detail.

Scheme I describes the synthesis of an intermediate of structure (4). $Ar_3$ and $Ar_4$ are, independently, groups such as, but not limited to, a heteroaryl or aryl ring system. As shown in Scheme I, in one embodiment, bromo- or iodo-substituted aryl alanine methyl ester (or amino acid esterified in linkage to Wang resin) (1) is treated with a carboxylic acid in the presence of a coupling reagent, such as, but not limited to, diisopropyl carbodiimide (DIC) to form the amide (2). The resulting amide is then subjected to coupling with an arylboronic acid in the presence of a catalyst such as, but not limited to, tetrakis(triphenylphosphine)palladium (0), in the presence of base such as, but not limited to, sodium carbonate to form compound (3). The methyl ester (3) is hydrolyzed using a base such as, but not limited to, LiOH to provide the free carboxylic acid (4), where $Ar_1$ and $Ar_2$ are as defined for Formula (I).

Scheme I

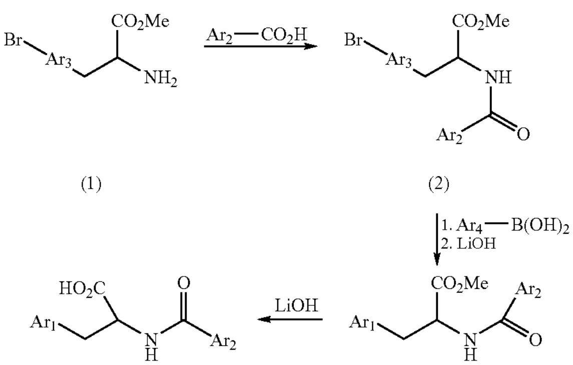

(1) (2) (3) (4)

Scheme II describes the preparation of a compound of structure (4). $Ar_3$ and $Ar_4$ are, independently, groups such as, but not limited to, a heteroaryl or aryl ring system. As shown in Scheme II, in another embodiment, an aryl hydroxy amino acid methyl ester (or amino acid esterified in linkage to Wang resin) (5) is treated with a carboxylic acid $Ar_2$—$CO_2H$ in the presence of a coupling reagent such as, but not limited to, diisopropyl carbodiimide (DIC) to form the amide (6). The resulting amide is then subjected to: 1) nucleophilic substitutions with an optionally substituted electron—deficient fluoroaromatic or fluoroheteroaromatic in the presence of base such as, but not limited to, potassium carbonate; or 2) coupling with an aryl bromide, or heteroaryl bromide, and copper iodide in the presence of a base including, but not limited to, cesium carbonate to form compound (7). The methyl ester in (7) is hydrolyzed using a base such as LiOH to provide the free carboxylic acid (4), where $Ar_1$ and $Ar_2$ are as defined for Formula (I)

Scheme II

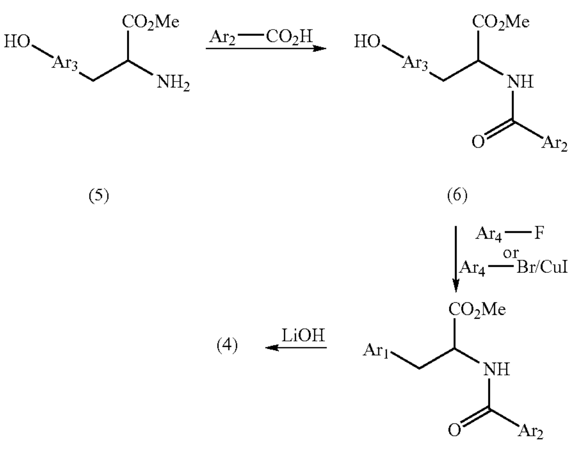

(5) (6) (7) (4)

Scheme III describes the preparation of a compouind of formula (4). $Ar_5$ and $Ar_6$ are, independently, groups such as, but not limited to, a heteroaryl or aryl ring system. As shown in Scheme 111, in another embodiment, an amino acid methyl ester (or, alternately, an amino acid esterified in linkage to Wang resin) (8) is treated with a bromo-substituted aryl carboxylic acid in the presence of a coupling reagent such as, but not limited to, diisopropyl carbodiimide (DIC) to form the amide (9). The resulting amide then is subjected to coupling with an arylboronic acid or heteroarylboronic acid in the presence of a catalyst such as, but not limited to, tetrakis (triphenylphosphine)palladium(0), in the presence of base such as, but not limited to, sodium carbonate to form compound (10). The methyl ester (10) is hydrolyzed using a base such as, but not limited to, LiOH to provide the free carboxylic acid (4), where $Ar_1$ and $Ar_2$ are as defined for Formula (I).

Scheme III

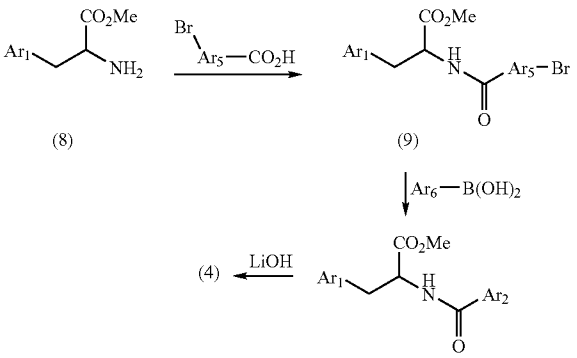

(8) (9) (10) (4)

Scheme IV describes the synthesis of a compound of formula (4). $Ar_3$, $Ar_7$, $Ar_5$ and $Ar_6$ are, independently, groups such as, but not limited to, a heteroaryl or aryl ring system. As shown in Scheme IV, in another embodiment, a bromo or iodo aryl alanine methyl ester (or amino acid esterified in linkage to Wang resin) (11) is subjected to coupling with an arylboronic acid in the presence of a catalyst such as, but not limited to, tetrakis(triphenylphosphine)palladium(0), in the presence of base such as, but not limited to, sodium carbonate to form compound (12). The resulting compound is treated with a bromo- or iodo-substituted aryl carboxylic acid in the presence of a coupling reagent such as, but not limited to, diisopropyl carbodiimide (DIC) to form the amide (13). The resulting amide is then subjected to coupling with a arylboronic acid or heteroarylboronic acid in the presence of a catalyst such as, but not limited to, tetrakis(triphenylphosphine)palladium(0), in the presence of base such as, but not limited to, sodium carbonate, and the product methyl ester is hydrolyzed using a base such as LiOH to provide the free carboxylic acid (4), where $Ar_1$ and $Ar_2$ are as defined for Formula (I).

Scheme IV

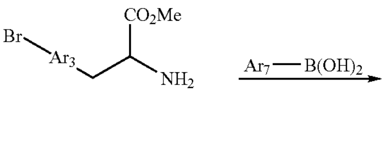

(11)

-continued

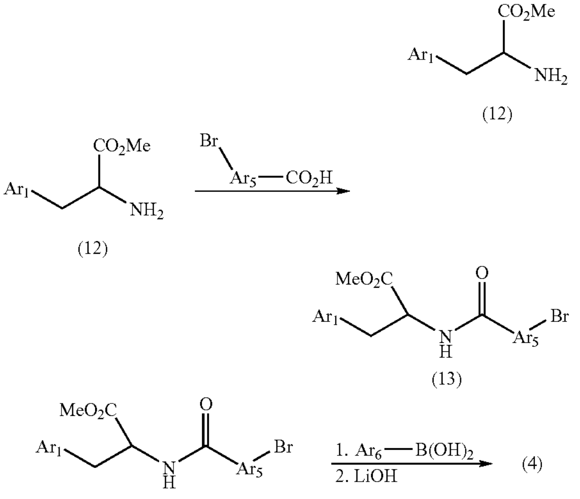

(12)

(12)

(13)

(13)

(4)

Scheme V describes the preparation of a compound of formula (16). $Ar_3$ and $Ar_7$ are, independently, groups such as, but not limited to, a heteroaryl or aryl ring system. Pol is a functionalized polymeric support, such as, but not limited to, Wang Resin. As shown in Scheme V, in another embodiment, a hydroxy aryl ester loaded onto the Wang Bromo resin or Merrifield resin using base such as, but not limited to, sodium methoxide in DMA, and hydrolyzed to give (14), is coupled with a bromo- or iodo-subsituted aryl amino acid methyl ester (11) in the presence of a coupling reagent such as, but not limited to, diisopropyl carbodiimide (DIC) to give the amide (15). The resulting amide (15) is then subjected to a coupling with an arylboronic acid or heteroarylboronic acid in the presence of a catalyst such as, but not limited to, tetrakis (triphenylphosphine)palladium(0), in the presence of base such as, but not limited to, sodium carbonate followed by cleavage from the resin with TMSBr/TFA/DCM (1:1:1) or a similar suitable cleavage cocktail to yield the desired product (16), where $Ar_1$ and $Ar_2$ are as defined for Formula (I).

Scheme V

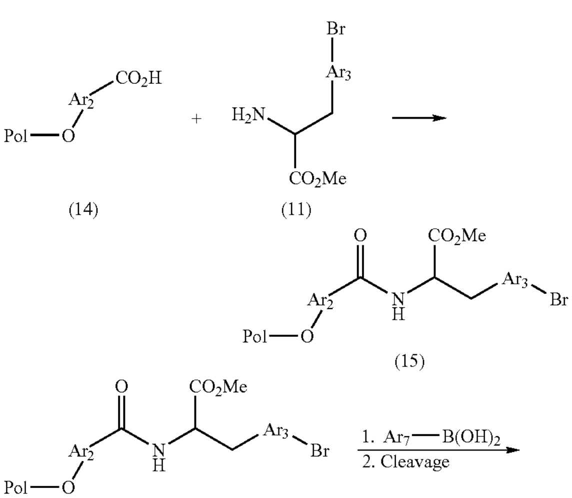

(14)

(11)

(15)

(15)

-continued

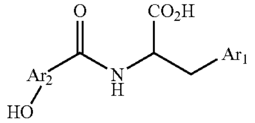

(16)

Scheme VI describes the preparation of a compound of formula (19). $Ar_6$ and $Ar_8$ are, independently, groups such as, but not limited to, a heteroaryl or aryl ring system. Pol is a functionalized polymeric support, such as, but not limited to, Wang Resin. As shown in Scheme VI, in another embodiment, a hydroxy aryl ester loaded onto the Wang Bromo resin, Merrifiend resin, or other suitable support using base such as, but not limited to, sodium methoxide in DMA, is hydrolyzed to give (17), and is coupled with an amino acid methyl ester (8) in the presence of a coupling reagent such as, but not limited to, diisopropyl carbodiimide (DIC) to give the amide (18). The resulting amide (18) is then subjected to a coupling with an arylboronic acid or heteroarylboronic acid in the presence of a catalyst such as, but not limited to, tetrakis (triphenylphosphine)palladium(0), in the presence of base such as, but not limited to, sodium carbonate, and is then cleaved from the resin with TMSBr/TFA/DCM (1:1:1) or a similar suitable cleavage cocktail to yield the desired product (19), where $Ar_1$ and $Ar_2$ are as defined for Formula (I).

Scheme VI

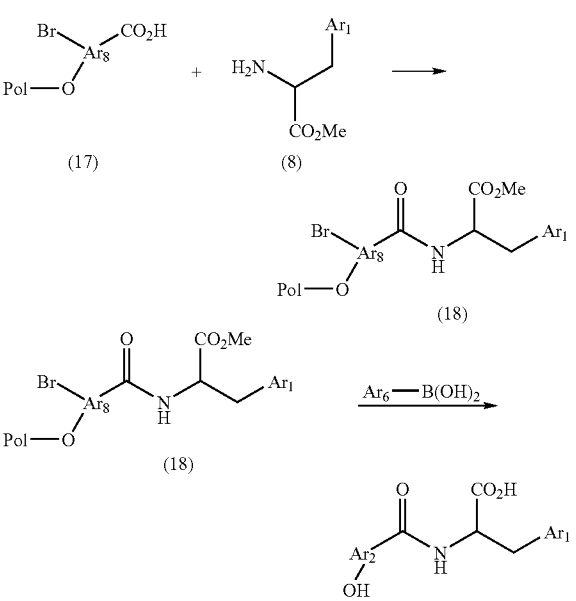

(17)

(8)

(18)

(18)

(19)

Scheme VII describes the synthesis of a compound of formula (23). $Ar_6$, $Ar_7$, and $Ar_8$ are, independently, groups such as, but not limited to, a heteroaryl or aryl ring system. Pol is a functionalized polymeric support, such as, but not limited to, Wang Resin. As shown in Scheme VII, in another embodiment, a bromo hydroxy aryl ester (20) loaded onto Wang Bromo resin, Merrifield resin, or other suitable support using base such as, but not limited to, sodium methoxide in DMF, is then subjected to a coupling with an arylboronic acid or heteroarylboronic acid in the presence of a catalyst such as, but not limited to, tetrakis(triphenylphosphine)plladium(0), in the presence of base such as, but not limited to, sodium carbonate, followed by hydrolysis of the product ester to yield the acid (21). The resulting carboxylic acid (21) is then subjected to coupling with a bromo- or iodo-substituted aryl amino acid methyl ester (11) in the presence of a coupling reagent such as, but not limited to, diisopropyl carbodiimide (DIC) to give the amide (22). The resulting amide (22) is then subjected to a coupling with an arylboronic acid or heteroaryl boronic acid in the presence of a catalyst such as, but not limited to, tetrakis(triphenylphosphine)palladium(0), in the presence of base such as, but not limited to, sodium carbonate followed by cleavage from the resin with TMSBr/TFA/DCM (1:1:1) or a similar cleavage cocktail to yield the desired product (23), where $Ar_1$ and $Ar_2$ are as defined for Formula (I).

Scheme VII

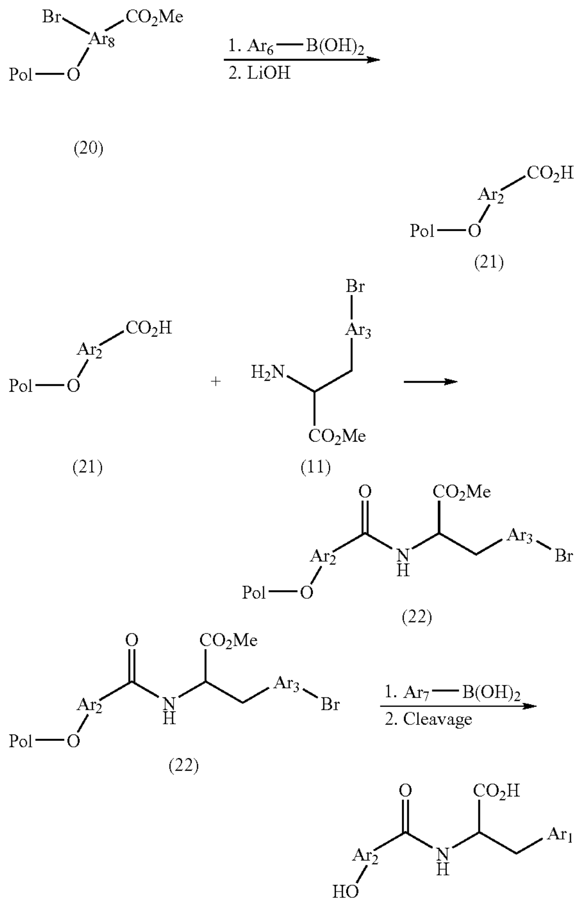

(20) (21) (21) (11) (22) (22) (23)

Scheme VIII describes the preparation of a compound of formula (29). $Ar_7$, $Ar_9$, $Ar_{10}$, and $Ar_{11}$ are, independently, groups such as, but not limited to, a heteroaryl or aryl ring system. As shown in Scheme VIII, in another embodiment, a fluoro nitro phenol (24) loaded onto a polymer such as Wang Bromo resin using base such as, but not limited to, sodium methoxide in DMA, is then treated with a hydroxy aryl compound (25) in the presence of base, followed by reduction of the nitro group to give the free amine (26). The resulting amine (26) is then subjected to coupling with a bromo- or iodo-substituted aryl acid (27) in the presence of a coupling reagent such as, but not limited to, diisopropyl carbodiimide (DIC) to give the amide (28). The resulting amide (28) is then subjected to a coupling with an arylboronic acid or heteroarylboronic acid in the presence of a catalyst such as, but not limited to, tetrakis(triphenylphosphine)palladium(0), in the presence of base such as, but not limited to, sodium carbonate followed by cleavage from the resin with TMSBr/TFA/DCM (1:1:1) or a similar suitable cleavage cocktail to yield the desired product (29), where $Ar_1$ and $Ar_2$ are as defined for Formula (I).

Scheme VIII

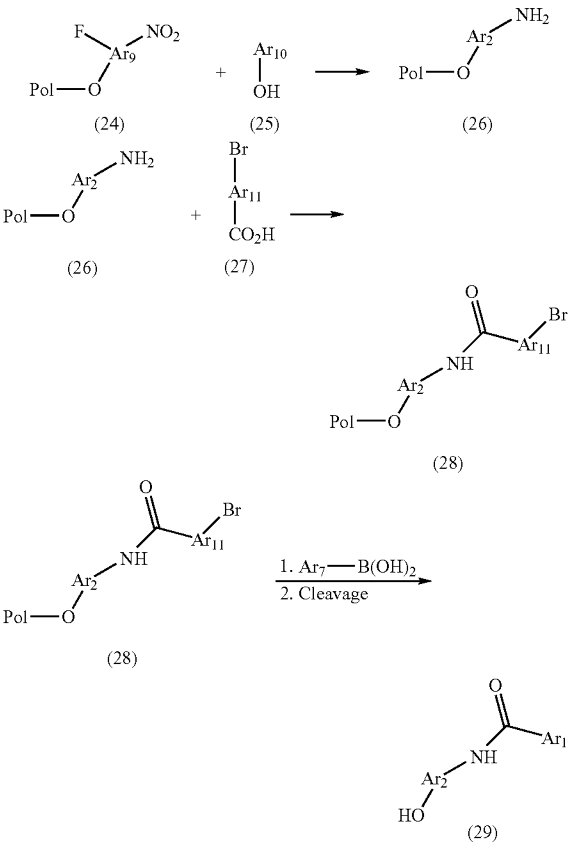

(24) (25) (26) (26) (27) (28) (28) (29)

Scheme IX describes the preparation of a compound of formula (32). $Ar_6$, $Ar_{12}$, and $Ar_{13}$ are, independently, groups such as, but not limited to, a heteroaryl or aryl ring system. $PG_1$ is an amino protecting group such as allyloxycarbonyl or tert-butoxycarbonyl. As shown in Scheme IX, in another embodiment, an aryl amino acid methyl ester (8) is reacted with an iodo-subsituted aryl amino carboxylic acid (the amino group of which may be protected with an amino protecting group $PG_1$ in the presence of a coupling reagent such as, but not limited to, diisopropyl carbodiimide (DIC) giving the amide (30). The amino group of the amide (30) may be then deprotected, if desired, by treatment with, in the case of $PG_1$ as tert-butoxycarbonyl, TFA, and is then treated with an aroyl chloride in the presence of a base such as pyridine or TEA to give the iodo amide (31). The amide (31) is subjected to coupling with an arylboronic acid or heteroaryl boronic acid in the presence of a catalyst such as, but not limited to, tetrakis(triphenylphosphine)palladium(0), in the presence of base such as, but not limited to, sodium carbonate. Hydrolysis of the product methyl ester with an alkaline reagent such as LiOH provides compound (32), where $Ar_1$ and $Ar_2$ are as defined for Formula (I).

Scheme IX

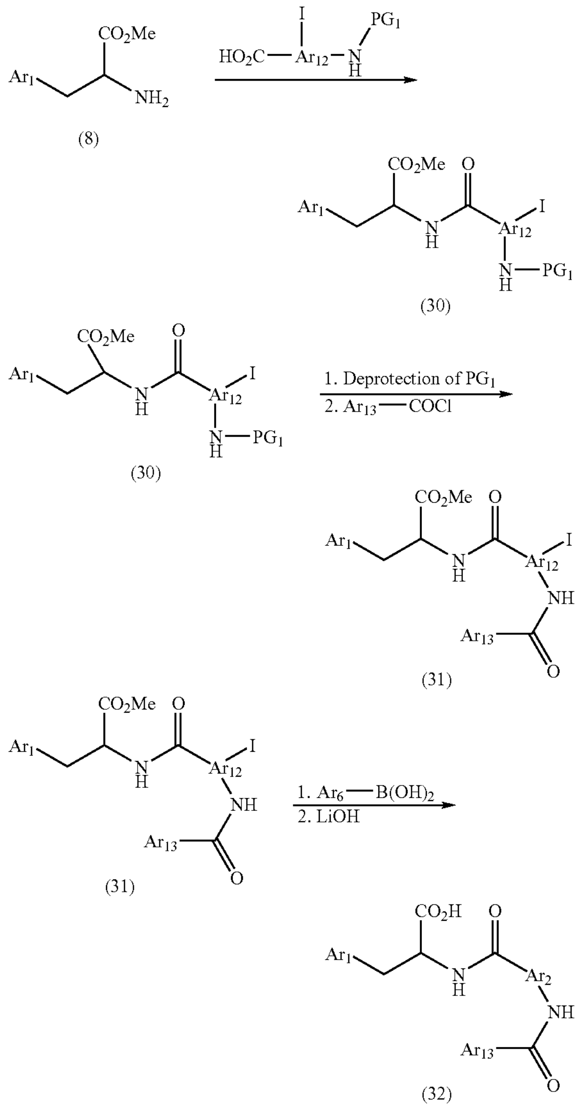

(8) (30) (30) (31) (31) (32)

Scheme X describes the preparation of a compound of formula (37). $Ar_{14}$ and $Ar_7$ are, independently, groups such as, but not limited to, a heteroaryl or aryl ring system. R is a group such as methyl, trifluromethyl, t-butyl, alkylene-sulfonyl alkyl or alkylene sulfonyl aryl, aryl, heterocyclyl. As shown in Scheme X, in another embodiment, a bromo or iodo aryl alanine t-butylcarbamate (or amino acid esterified in linkage to Wang resin) (33) is subjected to coupling with an arylboronic acid in the presence of a catalyst such as, but not limited to, tetrakis(triphenylphosphine)palladium(0), in the presence of base such as, but not limited to, sodium carbonate to form compound (34). The resulting acid is subjected to esterification with pentafluorophenol in the presence of a coupling reagent such as, but not limited to, DCC to form the ester, which is then treated with hydroxyamidine to yield oxadiazole. The resulting BOC oxadiazole is deprotected using HCl to provide the free amino oxadiazole (35). The amine is then coupled with the methoxy substituted aryl carboxylic acid (36) in the presence of a coupling reagent such as, but not limited to, HBTU, to form the amide. The resulting amide-methyl ether is hydrolyzed using agent such as, but not limited to, $BBr_3$ to provide free phenol (37), where $Ar_1$ and $Ar_2$ are as defined for formula(I).

Scheme X

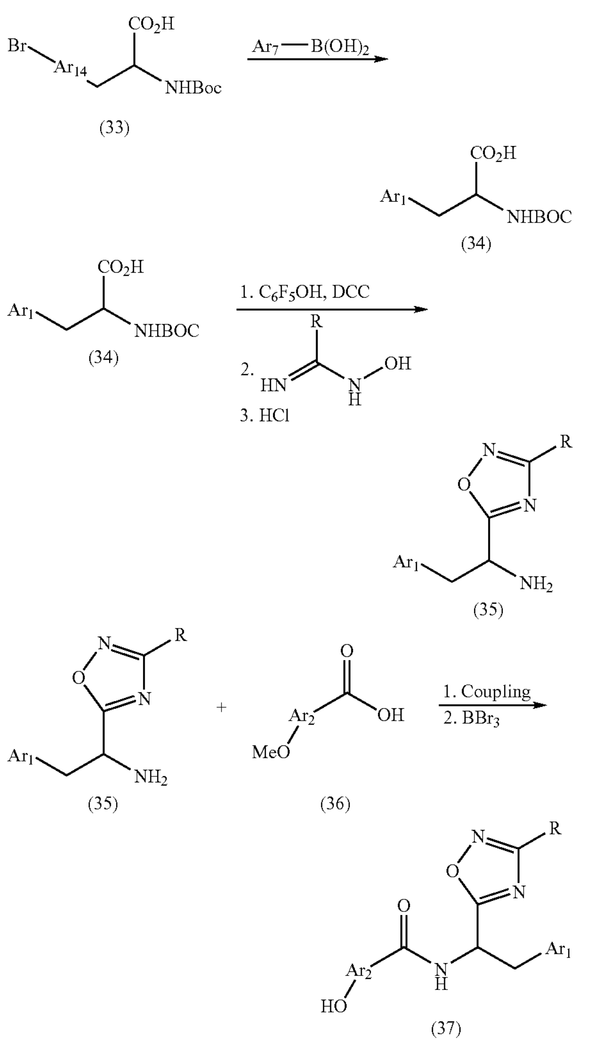

(33) (34) (34) (35) (35) (36) (37)

Scheme XI describes the preparation of a compound of formula (37). $Ar_3$ and $Ar_7$ are, independently, groups such as, but not limited to, a heteroaryl or aryl ring system. R is a group such as methyl, trifluromethyl, t-butyl, alkylene-sulfonyl alkyl or alkylene sulfonyl aryl, aryl, heterocyclyl. As shown in Scheme XI, in another embodiment, a bromo or lodo methoxy ester (38) (as shown in Scheme VII, but starting from bromomethoxy arylcarboxy ester) is subjected to coupling with an arylboronic acid in the presence of a catalyst such as, but not limited to, tetrakis(triphenylphosphine)palladium(0), in the presence of base such as, but not limited to, sodium carbonate to form the bisaryl ester which is hydrolyzed to the corresponding acid with LiOH. The resulting acid is then esterified using pentaflurophenol and in the presence of coupling reagent such as, but not limited to, DCC to provide methoxyester (39). The ester (39) is converted to oxadiazole using hydroxylamidine and the resulting methoxy oxadiazole is hydrolyzed with $BBr_3$ to obtain the free phenol (37), where $Ar_1$ and $Ar_2$ are as defined for formula (I).

Scheme XI

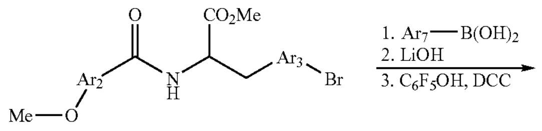

(38)

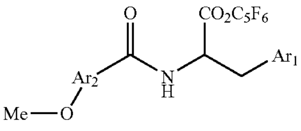

(39)

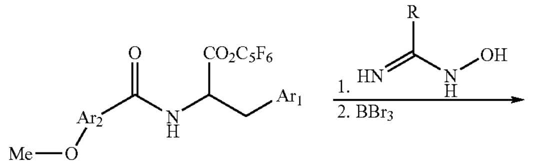

(39)

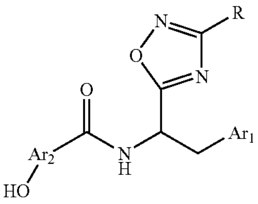

(37)

Scheme XII describes the preparation of a compound of formula (4). $Ar_{15}$, $Ar_{16}$, and $Ar_{17}$ are, independently, groups such as, but not limited to, a heteroaryl or aryl ring system. As shown in Scheme XII, in another embodiment, a fluoro aryl aldehyde (40) is treated with a hydroxy aryl compound in the presence of base, such as, but not limited to, sodium methoxide in DMA, to afford aryloxyaryl aldehyde (41) which is then oxidized with oxidation agent such as, but not limited to, silver nitrate to provide aryl carboxylic acid (42). The acid (42) is subjected to a coupling reaction with amine (8) using coupling reagent diisopropyl carbodimide (DIC) to give the amide (10). The resulting ester-amide (10) is hydrolyzed with LiOH to yield free carboxylic acid (4), where $Ar_1$ and $Ar_2$ are as defined for formula (I).

Scheme XII

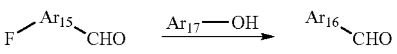

(40) (41)

-continued

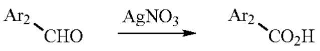

(41) (42)

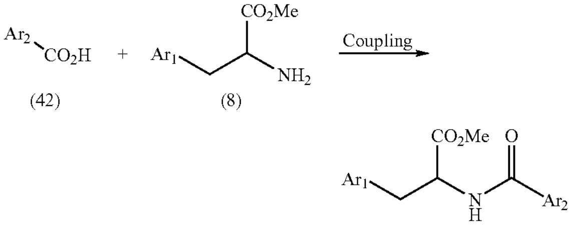

(42) (8)

(10)

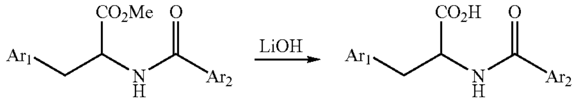

(10) (4)

Scheme XIIa describes the preparation of a compound of formula (44). As shown in scheme XIIa, the acid (42) is coupled with an amine (43), wherein G is an acid isostere such as, but not limited to, tetrazole, or an ester isostere, such as, but not limited to, oxadiazole or oxazole, using a coupling reagent such as, but not limited to, DCC to give the amide (44), where $Ar_1$ and $Ar_2$ are as defined for formula (I).

Scheme XIIa

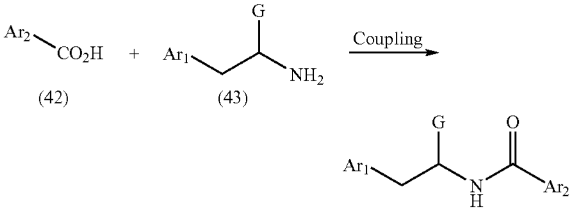

(42) (43)

(44)

Scheme XII describes the preparation of a compound of formula (23). $Ar_6$ and $Ar_{18}$ are, independently, groups such as, but not limited to, a heteroaryl or aryl ring system. As shown in Scheme XIII, in another embodiment, a bromo or iododihydroxyaryl ester (45) is converted to monohydroxyaryl ester (46) using alkylation method with alkyl halide (RBr) in the presence of base such as but not limited to, $Cs_2CO_3$ or Mitsunobu method using alkyl alcohol in the presence of diethylazadicarboxylate (DEAD). The resulting bromohydroxy ester (46) is subjected to coupling with an arylboronic acid in the presence of a catalyst such as, but not limited to, tetrakis (triphenylphosphine)palladium(0), in the presence of base such as, but not limited to, sodium carbonate to form the bisaryl ester which is hydrolysed to the corresponding acid (47) with LiOH. The hydroxyl acid (47) is then subjected to acetylation followed by acid chloride formation using acetic anhydride and oxalyl chloride, respectively, to provide the acid choride (48). Treatment of the acid chloride with the amine (8) in the presence of a base such as but not limited to, diisopropylethylamine, yields the amide (49), which then hydrolyzed using LiOH to provide the free acid (23), where $Ar_1$ and $Ar_2$ are as defined for formula (I).

Scheme XIII

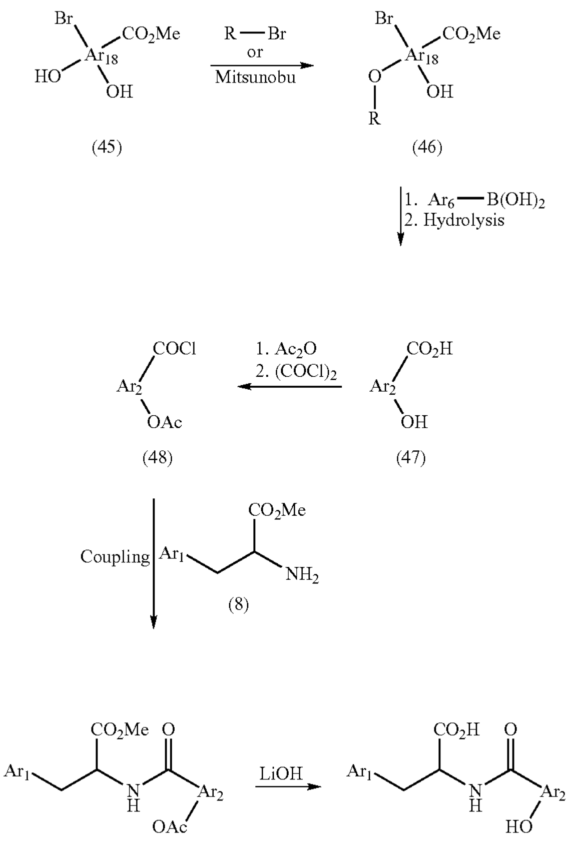

(45) (46) (47) (48) (8) (49) (23)

Scheme XIIIa describes the preparation of a compound of formula (50). As shown in Scheme XIIIa, the acid chloride (48) is coupled with the amine (43), wherein G is an acid isostere such as, but not limited to, tetrazole, or an ester isostere such as, but not limited to, oxadiazole and oxazole in the presence of base such as, but not limited to DIEA to give the acetate-amide, which is then hydrolyzed using base such as but not limited to, LiOH to provide the free phenol (50), where $Ar_1$ and $Ar_2$ are as defined for formula (I).

Scheme XIIIa

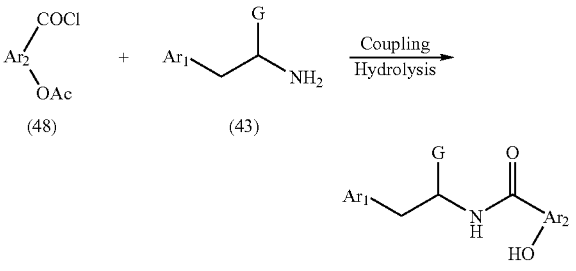

(48) (43) (50)

Scheme XIV describes the preparation of a compound of formula (23). $Ar_6$ and $Ar_{19}$ are, independently, groups such as, but not limited to, a heteroaryl or aryl ring system. As shown in Scheme XIV, in another embodiment, hydroxylaryl ester (51) is brominated using brominating agent such as bromine but not limited to, to provide bromo ester (52). The bromo-hydroxy ester (52) is subjected to either Suzuki coupling with an arylboronic acid in the presence of a catalyst such as, but not limited to, tetrakis(triphenylphosphine)palladium(0), in the presence of base such as, but not limited to, sodium carbonate or Stille coupling with alkyl or aryl stananes in the presence of a catalyst such as but not limited to, tetrakis (triphenylphosphine)palladium(0) to form the hydroxy ester which is hydrolyzed to the corresponding acid (47) with LiOH. The hydroxyl acid (47) is then subjected to acetylation followed by acid chloride formation using acetic anhydride and oxalyl chloride, respectively, to provide the acid choride (48). Treatment of the acid chloride (48) with the amine (8) in the presence of a base such as but not limited to, diisopropylethylamine, to yield the amide (49), which then hydrolyzed using LiOH to provide the free acid (23), where $Ar_1$ and $Ar_2$ are as defined for formula (I).

Scheme XIV

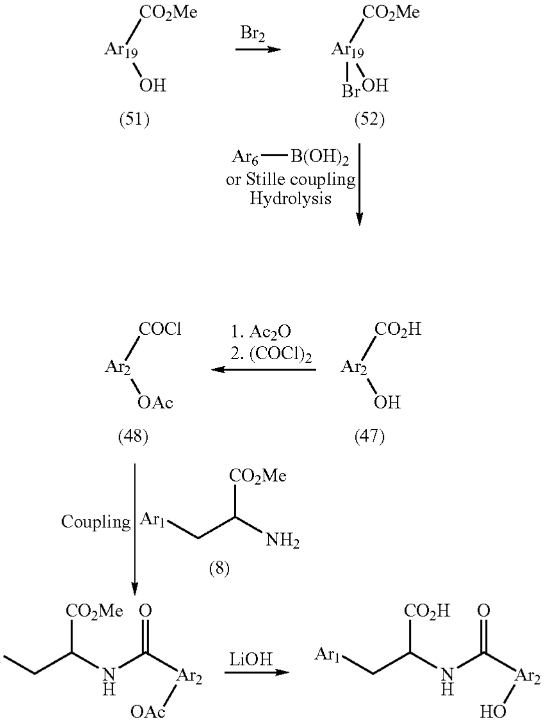

(51) (52) (48) (47) (8) (49) (23)

Scheme XIVa describes the preparation of a compound of formula (53). As shown in scheme XIVa, the acid chloride (48) is coupled with the amine (43), wherein G is an acid isostere such as, but not limited to, tetrazole, and an ester isostere, (such as, but not limited to, oxadiazole and oxazole) in the presence of a base such as, but not limited to, DIEA to give the acetate-amide, which is then hydrolyzed using base such as, but not limited to, LiOH to provide the free phenol (53), where $Ar_1$ and $Ar_2$ are as defined for formula (I).

Scheme XIVa

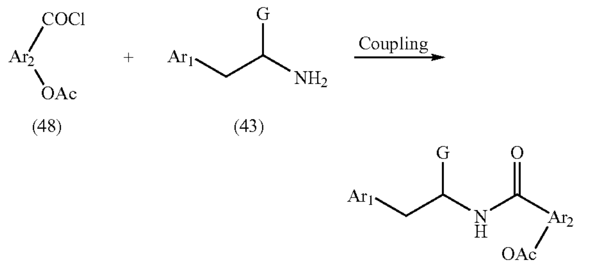

(48) (43)

(53)

Scheme XV describes the preparation of a compound of formula (23). $Ar_6$ and $Ar_{20}$ are, independently, groups such as, but not limited to, a heteroaryl or aryl ring system. As shown in Scheme XV, in another embodiment, chlorohydroxylaryl ester (54) is brominated using brominating agent such as bromine but not limited to, to provide bromo ester which was then alkylated with MeI in the presence of base such as but not limited to, potassium carbonate to provide dihalomethoxy ester (55). The bromomethoxy ester (55) is subjected to Suzuki coupling with an arylboronic acid in the presence of a catalyst such as but not limited to, tetrakis(triphenylphosphine)palladium(0), in the presence of base such as, but not limited to, sodium carbonate to form the methoxy ester which is hydrolyzed to the corresponding acid (56) with LiOH. The methoxy acid (56) is then coupled with the amine (8) using a coupling agent such as, but not limited to, HBTU to form the amide (57). The methyl ether (57) is then hydrolyzed using $BBr_3$ to yield the hydroxy acid (23), where $Ar_1$ and $Ar_2$ are as defined for formula (I).

Scheme XV

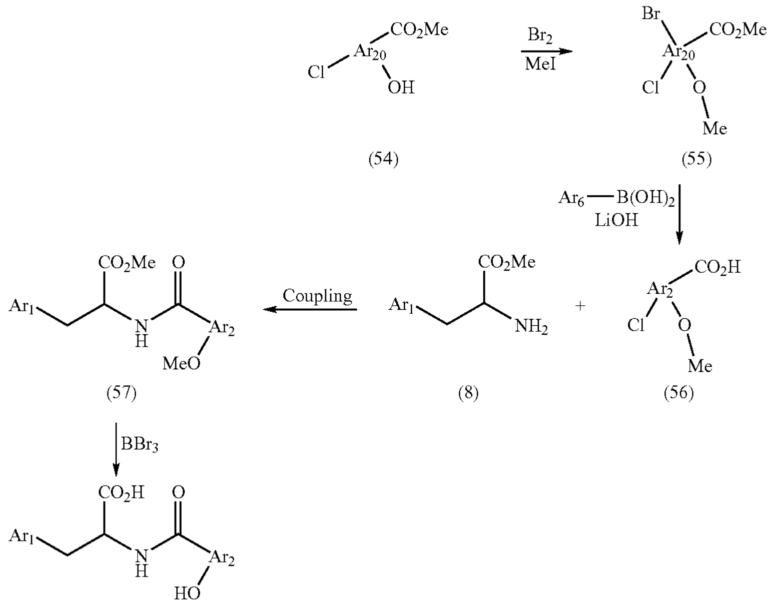

(54) (55) (57) (8) (56) (23)

Scheme XVa describes the preparation of a compound of formula (58). As shown in scheme XVa, the methoxy acid

(56) is coupled with a amine (43), wherein G is an acid isostere such as, but not limited to, tetrazole, and an ester isostere, (such as, but not limited to, oxadiazole and oxazole) using a coupling reagent such as, but not limited to HBTU to give the methoxyamide, which is then hydrolyzed using an agent such as but not limited to, $BBr_3$ to provide the free phenol (58), where $Ar_1$ and $Ar_2$ are as defined for formula(I).

Scheme XVa

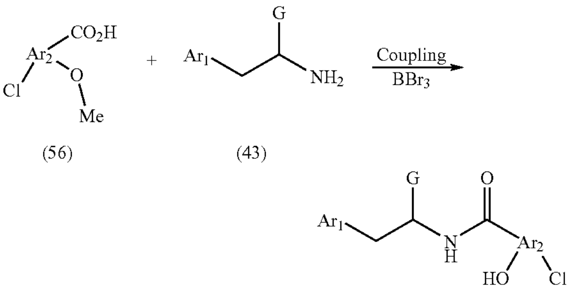

(56) (43)

(58)

Scheme XVI describes the preparation of a compound of formula (63). $Ar_6$ and $Ar_{21}$ are, independently, groups such as, but not limited to, a heteroaryl or aryl ring system. As shown in Scheme XVI, in another embodiment, fluorobromoarylaldehyde (59) is subjected to alkylation with MeI using a base such as but not limited to, potassium carbonate followed by oxidation using reagent such, as but not limited to, pyridinium dichromate (PDC) to provide methoxy acid which is then coverted to the ester using esterification methods such as, but not limited to, methanolic HCl to obtain methoxyester (60). The dihalomethoxy ester (60) is subjected to Suzuki coupling with an arylboronic acid in the presence of a catalyst such as but not limited to, tetrakis(triphenylphosphine)palladium(0), in the presence of base such as, but not limited to, sodium carbonate to form the methoxy ester which is hydrolyzed to the corresponding acid (61) with LiOH. The methoxy acid (61) is then coupled with the amine (8) using coupling agent such as, but not limited, to HBTU to form the amide (62). The methyl ether (62) is then hydrolyzed using $BBr_3$ to yield the hydroxyl ester (63), which is hydrolyzed with LiOH to provide hydroxy acid (63), where $Ar_1$ and $Ar_2$ are as defined for formula (I).

Scheme XVI

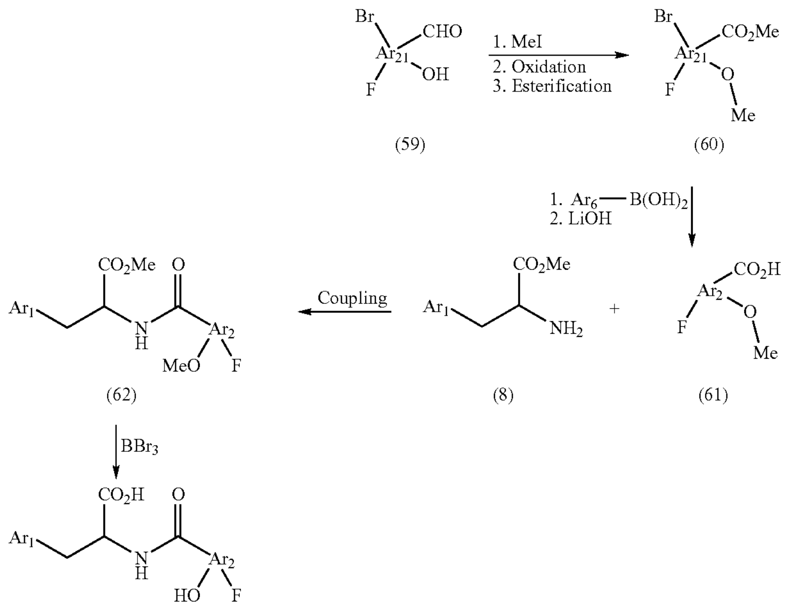

(59) (60) (62) (8) (61) (63)

Scheme XVIa describes the preparation of a compound of formula (64). As shown in scheme XVIa, the methoxy acid (61) is coupled with a amine (43), wherein G is an acid isostere such as, but not limited to, tetrazole, and an ester isostere, (such as, but not limited to, oxadiazole and oxazole) using a coupling reagent such as, but not limited to, DCC to give the methoxyamide, which is then hydrolyzed using an agent such as, but not limited to, $BBr_3$ to provide the free phenol (64), where $Ar_1$ and $Ar_2$ are as defined for formula (I).

Scheme XVIa

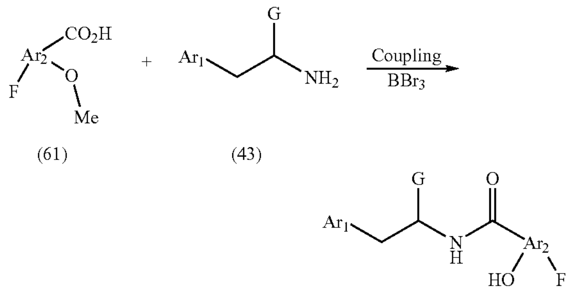

(61) (43) (64)

Scheme XVII describes the preparation of a compound of formula (23). $Ar_6$ and $Ar_{18}$ are, independently, groups such as, but not limited to, a heteroaryl or aryl ring system. As shown in Scheme XVII, in another embodiment, a bromo or iododihydroxyaryl ester (45) is converted to monohydroxyaryl ester (65) using alkylation method with benzyl bromide in the presence of base such as but not limited to, $Cs_2CO_3$. The bromoester (65) is then subjected to Suzuki coupling with an arylboronic acid in the presence of a catalyst such as but not limited to, tetrakis(triphenylphosphine)palladium(0), in the presence of base such as, but not limited to, sodium carbonate to form the hydroxy ester which is alkylated using MeI. The methoxy ester is reduced using Pd/C in the presence of hydrogen gas to obtain the hydroxyl ester (66). The hydroxyl ester is then subjected to oxidative coupling using aryl boronic acid in the presence of copper acetate to obtain aryloxy arylester which is then hydrolyzed with LiOH to provide methoxy acid (36). The methoxy acid (36) is then coupled with the amine (8) using coupling agent such as, but not limited to, HBTU to form the amide (57). The methyl ether (57) is then subjected to hydrolysis using $BBr_3$ and subsequent ester hydrolysis with LiOH to yield the hydroxyl acid (23), where $Ar_1$ and $Ar_2$ are as defined for formula (I).

Scheme XVII

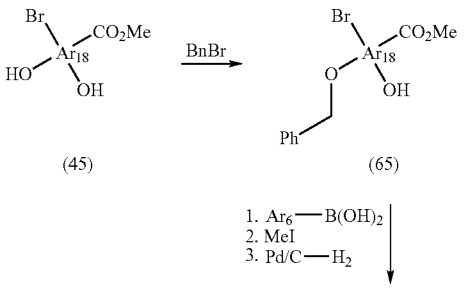

(45) (65)

-continued

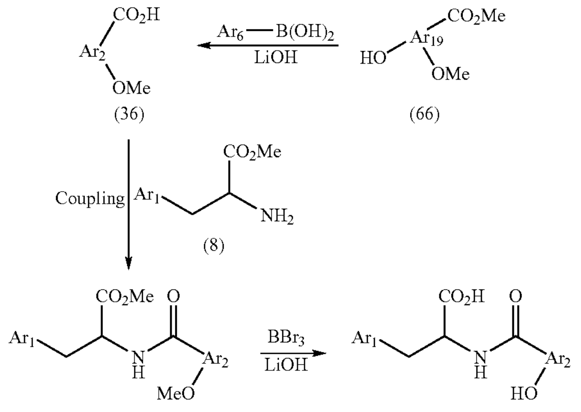

(36) (66) (8) (57) (23)

Scheme XVIIa describes the preparation of a compound of formula (64). As shown in scheme XVIIa, the methoxy acid (36) is coupled with a amine (43), wherein G is an acid isostere such as, but not limited to, tetrazole, and an ester isostere, (such as, but not limited to, oxadiazole and oxazole) using a coupling reagent such as, but not limited to, HBTU to give the methoxyamide, which is then hydrolyzed using an agent such as, but not limited to, $BBr_3$ to provide the free phenol (67), where $Ar_1$ and $Ar_2$ are as defined for formula (I).

Scheme XVIIa

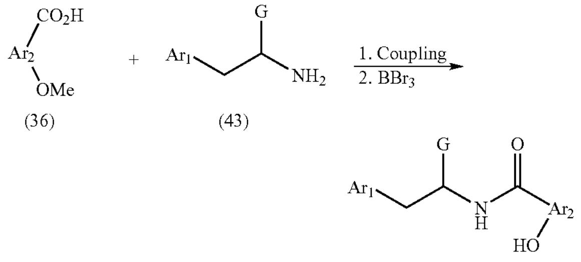

(36) (43) (67)

Scheme XVIII describes the preparation of a compound of formula (23). $Ar_6$ and $Ar_{22}$ are, independently, groups such as, but not limited to, a heteroaryl or aryl ring system. As shown in Scheme XVIII, in another embodiment, a bromo or dihydroxyaryl ester (68) is treated with triflic anhydride to obtain the hydroxy triflate which is then alkylated with benzyl bromide to get benzyloxy ester (69). The benzyloxyester (69) is then subjected to Suzuki coupling with an arylboronic acid in the presence of a catalyst such as but not limited to, tetrakis (triphenylphosphine)palladium(0), in the presence of base such as, but not limited to, sodium carbonate to form the hydroxy ester which is hydrolyzed to the corresponding acid (70) with LiOH. The benzyloxy acid (70) is then coupled with the amine (8) using coupling agent such as, but not limited to, HBTU to form the amide (71). The benzyl ether (71) is then subjected to hydrogenolysis and hydrolysis using Pd/C catalyst in the presence of hydrogen and LiOH, respectively, to obtain the free acid (23), where $Ar_1$ and $Ar_2$ are as defined for formula (I).

Scheme XVIII

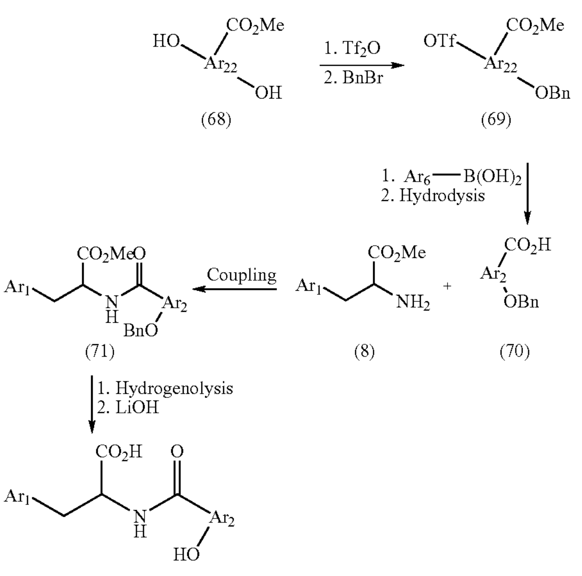

(68) (69) (71) (8) (70) (23)

Scheme XVIIa describes the preparation of a compound of formula (72). As shown in scheme XVIIIa, the benzyloxy acid (70) is coupled with a amine (43), wherein G is an acid isostere such as, but not limited to, tetrazole, and an ester isostere, (such as, but not limited to, oxadiazole and oxazole) using a coupling reagent such as, but not limited to, HBTU to give the methoxyamide, which is then subjected to hydrogenolysis using Pd/C in the presence of hydrogen to provide the free phenol (72), where $Ar_1$ and $Ar_2$ are as defined for formula (I).

Scheme XVIIIa

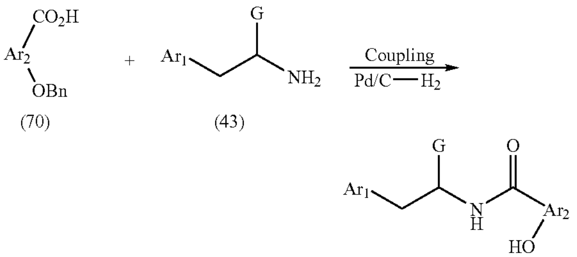

(70) (43) (72)

Scheme XIX describes the preparation of a compound of formula (78). $Ar_{23}$ is a group such as, but not limited to, a heteroaryl, aryl, alkylene-aryl, or alkyl group. As shown in Scheme XIX, in another embodiment, an arylaldehyde (73) is subjected to Wittig reaction to obtain the dehydroaminoester (74). The dehydroaminoester is then treated with $Ar_{23}SH$, followed by the hydrolysis using HCl to obtain the aminoester (75). The amino ester is then coupled with methoxy acid (36) using a coupling agent such as, but not limited to, HBTU, to provide the amide (76). The amide is subjected to oxidation with metachloroperbenzoic acid and the resulting sulfone is treated with DBU to obtain methoxy ester and the methyl ether is hydrolyzed with $BBr_3$ to provide the free phenol (77). The hydroxyester is hydrolyzed to free carboxylic acid (78) using LiOH, where $Ar_1$ and $Ar_2$ are as defined for formula (I).

Scheme XIX

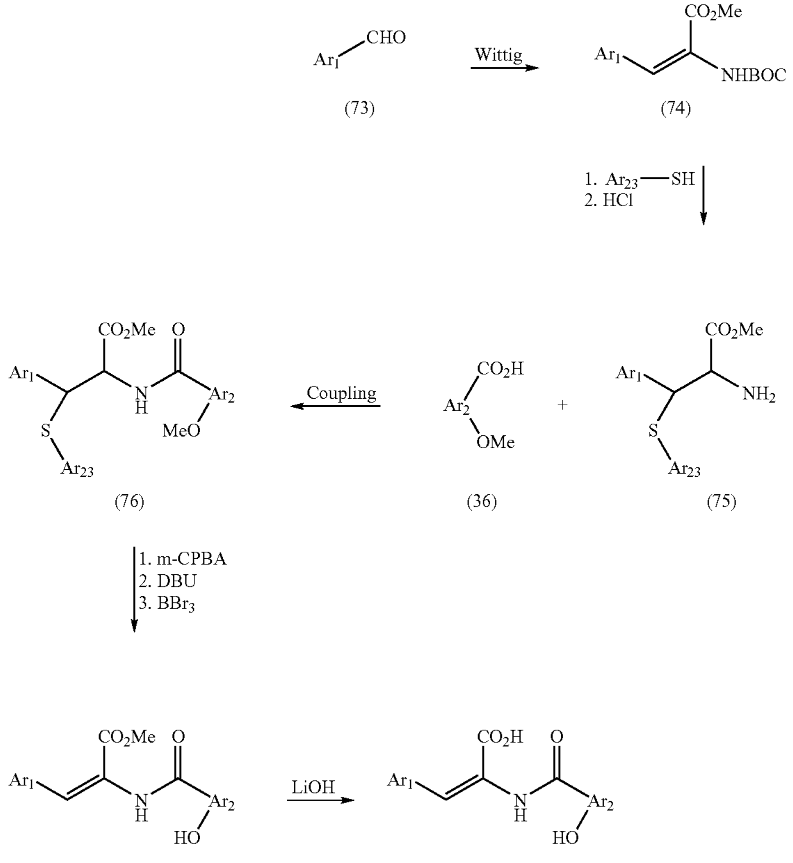

(73) (74) (76) (36) (75) (77) (78)

Scheme XX describes the preparation of a compound of formula (82). As shown in Scheme XX, in another embodiment, the methoxy methyl ester (57) is hydrolyzed with LiOH and then coupled with N,O-dimethylhydroxylamine using HBTU to obtain the Weinreb amide (79). The amide (79) is then reduced with DIBAL to get the aldehyde (80). The aldehyde (80) is then subjected to Wittig reaction to provide the alpha,beta-unsaturated ester (81). The methyl ether (81) is then hydrolyzed with $BBr_3$ to obtain the free phenol (82).

Scheme XX

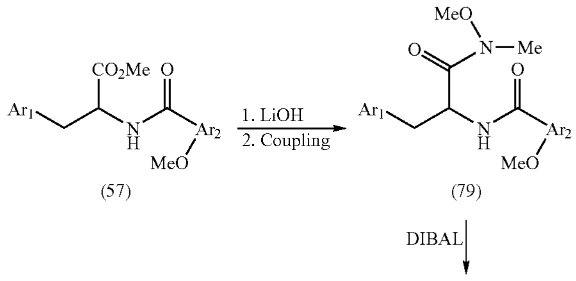

(57) (79)

-continued

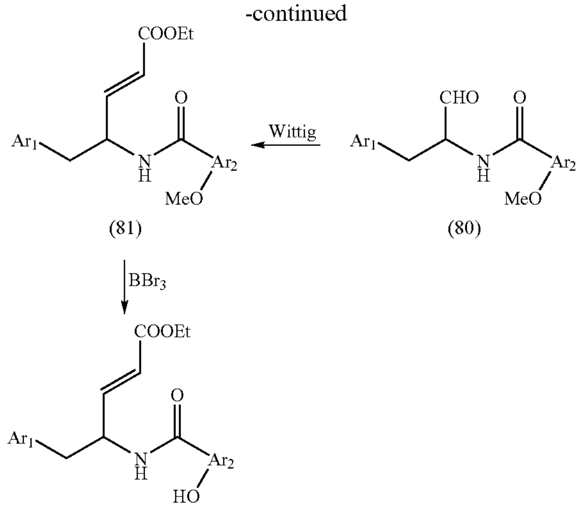

(81) (80) (82)

Scheme XXI describes the preparation of a compound of formula (84). As shown in Scheme XXI, in another embodiment, the Weinreb amide (79) is treated with Grignard reagent (RMgX, where R is alkyl, aryl, heteroaryl and X is a halogen) to obtain the ketone (83). The methyl ether (83) is hydrolyzed with $BBr_3$ to get the free phenol (84).

Scheme XXI

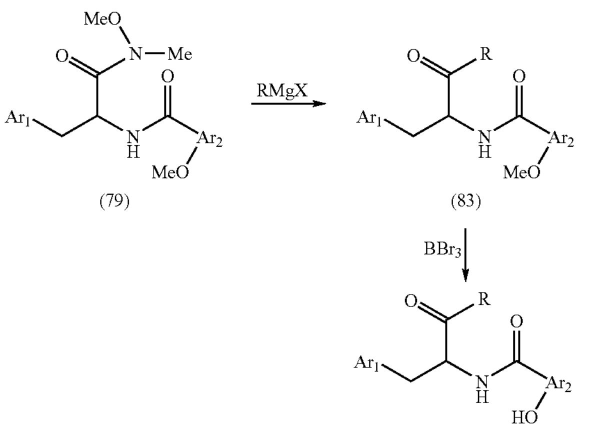

(79) (83) (84)

The term "amino protecting group" as used herein refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino)ethoxycarbonyl, 9-fluorenylmethoxycarbonyl ("FMOC"), t-butoxycarbonyl ("BOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the compound of Formula (I) and can be removed at the desired point without disrupting the remainder of the molecule. Examples of commonly used amino-protecting groups are the allyloxycarbonyl, the t-butoxycarbonyl, 9-fluorenylmethoxycarbonyl, and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected amino" or "protected amino group" defines an amino group substituted with an amino-protecting group discussed above.

The term "hydroxyl protecting group" as used herein refers to substituents of the alcohol group commonly employed to block or protect the alcohol functionality while reacting other functional groups on the compound. Examples of such alcohol-protecting groups include the 2-tetrahydropyranyl group, 2-ethoxyethyl group, the trityl group, the trichloroacetyl group, urethane-type blocking groups such as benzyloxycarbonyl, and the trialkylsilyl group, examples of such being trimethylsilyl, tert-butyldimethylsilyl, phenyldimethylsilyl, triiospropylsilyl and thexyldimethylsilyl. The choice of of alcohol-protecting group employed is not critical so long as the derivatized alcohol group is stable to the condition of subsequent reaction(s) on other positions of the compound of the formulae and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected hydroxyl" or "protected alcohol" defines a hydroxyl group substituted with a hydroxyl-protecting group as discussed above.

The term "carboxyl protecting group" as used herein refers to substituents of the carboxyl group commonly employed to block or protect the —OH functionality while reacting other functional groups on the compound. Examples of such alcohol-protecting groups include the 2-tetrahydropyranyl group, 2-ethoxyethyl group, the trityl group, the allyl group, the trimethylsilylethoxymethyl group, the 2,2,2-trichloroethyl group, the benzyl group, and the trialkylsilyl group, examples of such being trimethylsilyl, tert-butyldimethylsilyl, phenyldimethylsilyl, triiospropylsilyl and thexyldimethylsilyl. The choice of carboxyl protecting group employed is not critical so long as the derivatized alcohol group is stable to the condition of subsequent reaction(s) on other positions of the compound of the formulae and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected carboxyl" defines a carboxyl group substituted with a carboxyl-protecting group as discussed above.

The invention also provides pharmaceutical compositions comprising the antiviral active compounds of the invention. Thus, in another embodiment, the present invention comprises a pharmaceutical composition comprising the compound of Formula (I) and one or more pharmaceutically acceptable carriers, excipients, or diluents. The term "pharmaceutical composition" is used herein to denote a composition that may be administered to a mammalian host, e.g., orally, topically, parenterally, by inhalation spray, or rectally, in unit dosage formulations containing conventional nontoxic carriers, diluents, adjuvants, vehicles and the like. The term "parenteral" as used herein, includes subcutaneous injections, intravenous, intramuscular, intracisternal injection, or by infusion techniques.

The compounds and compositions of the present invention may be administered to a subject in a therapeutically effective amount. The term "therapeutically effective amount" is used herein to denote that amount of a drug or pharmaceutical agent that will elicit the therapeutic response of an animal or human that is being sought.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; or dispersing or wetting agents, such as a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alchol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient that is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include eyedrops, mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Also provided by the present invention are prodrugs of the invention.

Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Methanesulfonate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1-19.

Other salts which are not pharmaceutically acceptable may be useful in the preparation of compounds of the invention and these form a further aspect of the invention.

In addition, some of the compounds of Formula (I) may form solvates with water or common organic solvents. Such solvates are also encompassed within the scope of the invention.

Thus, in another embodiment of the present invention, there is provided a pharmaceutical composition comprising a therapeutically effective amount of a compound of Formula (I), or a pharmaceutically acceptable salt, solvate, or prodrug therof, and one or more pharmaceutically acceptable carriers, excipients, or diluents. In an embodiment of the pharmaceutical composition, the compound of Formula (I) is an inhibitor of smallpox virus. Thus, in one embodiment, a therapeutically effective amount of the compounds of Formula (I) is an amount sufficient to reduce viral load in a subject. In an embodiment, the virus is an orthopox virus. For example, the compounds of the present invention may be used to inhibit smallpox infection.

In yet another embodiment, the present invention also provides a pharmaceutical composition comprising a therapeutically effective amount of the compound of Formula (I), and one or more pharmaceutically acceptable carriers, excipients, or diluents, further comprising one or more additional therapeutic agents. Additional therapeutic agents may be those as described below, or may include other therapeutic agents as may be known in the art.

The present invention also comprises a method of administering a compound of Formula (I) to a subject. In one embodiment of the method, the compound of Formula (I) is administered in an amount sufficient to substantially reduce the viral load in a subject. In another embodiment, the compound of Formula (I) is administered in an amount sufficient to partially reduce the viral load in said subject.

The compounds of the present invention may be effective antiviral agents preventing, ameliorating or treating a virus infection. Embodiments of the present invention may therefore comprise methods for the inhibition of a virus comprising administering to a subject in need thereof a compound of Formula (I), wherein said compound of Formula (I) is administered to said subject as a pharmaceutical composition comprising a therapeutically effective amount of said compound of Formula (I) and one or more pharmaceutically acceptable carriers, excipients, or diluents. In one embodiment, a therapeutically effective amount of the compound of Formula (I) may inhibit an orthopox virus such as smallpox virus. Thus, in one example embodiment, the present invention provides a method for the inhibition of the smallpox virus comprising administering to a subject in need thereof a compound of Formula (I), wherein the compound of Formula (I) is administered to said subject as a pharmaceutical composition comprising a therapeutically effective amount of the compound of Formula (I) and one or more pharmaceutically acceptable carriers, excipients, or diluents, wherein a therapeutically effective amount of the compound of Formula (I) comprises an amount for treatment or prevention of orthopox-mediated diseases or prevention of opportunistic infections. In alternate embodiments, other types of viral infectons may be targeted by the compounds of the present invention.

The dosage at which the compounds of Formula (I) are used may be varied depending upon the condition being treated, the size of the individual, pharmacokinetic parameters, and the individual compound. In one embodiment, the compound of Formula (I) may comprise a dosage such that the concentration of the compound of Formula (I) at the surface of a virus infected cell is about 100 micromolar (μM) or less. In another embodiment, the compound of Formula (I) may comprise a dosage such that the concentration of compound at the surface of a virus infected cell is about 50 micromolar (μM) or less. In yet another embodiment, the compound of Formula (I) may comprise a dosage such that the concentration of compound at the surface of a virus infected cell is about 10 micromolar (μM) or less.

In another embodiment, a therapeutically effective amount of the compound of Formula (I) comprises an amount sufficient to achieve and maintain a sustained blood level that at least partially inhibit the virus growth. In alternate embodiments, the sustained blood level comprises a concentration ranging from about 0.01 μM to 200 μM, more preferably from about 1 μM to 50 μM, and even more preferably from about 10 μM to about 25 μM. In another embodiment of the method, the pharmaceutical composition further comprises one or more therapeutic agents.

The pharmaceutical compositions of the present invention may be administered in the form of an oral dosage, a parenteral dosage unit, or by other routes. For example, in various embodiments, the compound of Formula (I) may be administered as a dose in a range from about 0.01 to 1,000 mg/kg of body weight per day, or as a dose in a range from about 0.1 to 100 mg/kg of body weight per day, or as a dose in a range from about 0.5 to 10 mg/kg of body weight per day.

The amount of active ingredient that may be combined with the carrier materials to produce a single dosage will vary depending upon the host treated and the particular mode of administration. For example, a formulation intended for oral administration to humans may contain 1 mg to 2 grams of a compound of Formula (I) with an appropriate and convenient amount of carrier material that may vary from about 5 to 95 percent of the total composition. Dosage unit forms will generally contain between from about 5 mg to about 500 mg of active ingredient. The dosage may be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

As used herein, the term "subject" includes mammalian subjects such as, but not limited not, humans, cows, horses, and other agricultural live stock, and birds. In an embodiment, a subject may include one that either suffers from one or more aforesaid diseases, disease states, or viral infections, or one that is at risk for contracting one or more aforesaid diseases, disease states, or viral infections. Accordingly, in the context of the method of treatment comprising administration of a compound of Formula (I) or a pharmaceutical composition comprising a compound of Formula (I) to a subject prophylactically, or prior to the onset of or diagnosis of such diseases, disease states, or viral infections.

The term "treatment" as used herein, refers to the full spectrum of treatments for a given disorder from which the patient is suffering, including alleviation of one, most of all symptoms resulting from that disorder, to an outright cure for the particular disorder or prevention of the onset of the disorder.

As used herein, the terms "virus", "viral", or "viral infection" includes DNA and RNA viruses As described above, the compound of Formula (I) may be used alone, or to replace or supplement compounds that inhibit viruses. Additionally, the compound of Formula I may be used in conjuction with other therapeutic agents. The following is a non-exhaustive listing of adjuvants and additional therapeutic agents that may be used in combination with the viral inhibitor of the present invention:

1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab
5. Glucocorticoids
6. Immunosuppresants and immunomodulators Pharmacologic classifications of treatment for bacterial or viral infection 1. gyrase inhibitors; ciprofloxacin
2. beta lactam antibiotics; cefuroxime, amoxicillin, cephalexin, ceclor, meropenem, aztreonam
3. miscellaneous antibiotics; linezolid, erythromycin, streptomycin, vancomycin, doxycycline, rifampin, isoniazid
4. antifungal agents; terbinafine, fluconazole, ketoconazole, amphotericin B, griseofulvin
5. antiviral agents
   a. Antiviral agents for AIDS treatment; AZT, abacavir, ddC, ddI, d4T, 3TC, ZDV, tenofovir, nevirapine, pentafuside, amprenavir, fosamprenavir, indinavir, nelfinavir, ritonavir, saquanivir
   b. Antiviral agents (general); lamivudine, foscarnet, acyclovir, cidofovir, ganciclovir, valaciclovir The present invention therefore provides a method of treating or preventing viral mediated diseases including comprising administering to a subject in need thereof, a therapeutically effective amount of a compound of Formula (I) alone or in combination with therapeutic agents selected from the group consisting of antibiotics, hormones, biologic response modifiers, analgesics, NSAIDs, DMARDs, glucocorticoids, immunosuppressants, immunomodulators, thrombolytic agents, antidepressants, gyrase inhibitors, beta lactam antibiotics, antifungal agents, and antiviral agents (as described above). In one embodiment, the virus targeted using the compositions of the present invention (comprising compounds of Formula (I) alone or in combination with other agents) may comprise a pox virus. In another embodiment, the virus may comprise smallpox.

EXAMPLES

The present invention may be further understood by reference to the following non-limiting examples. Examples of compounds of the present invention and procedures that may be used in to prepare and identify useful compounds of the present invention are described below.

General Experimental:

LC-MS data was obtained using gradient elution on a Waters 600 controller equipped with a 2487 dual wavelength detector and a Leap Technologies HTS PAL Autosampler using an YMC Combiscreen ODS-A 50×4.6 mm column. A three minute gradient was run from 25% B (97.5% acetonitrile, 2.5% water, 0.05% TFA) and 75% A (97.5% water, 2.5% acetonitrile, 0.05% TFA) to 100% B. The mass spectrometer used was a Micromass ZMD instrument. All data was obtained in the positive mode unless otherwise noted. $^1$H NMR data was obtained on a Varian 400 MHz spectrometer. Common names and definitions for resin reagents used in the disclosure are;

| | |
|---|---|
| Merrifield | p-Chloromethyl polystyrene |
| Hydroxy-Merrifield | p-Hydroxymethyl polystyrene |
| Wang | (4-Hydroxymethyl)phenoxymethyl polystyrene |
| Wang carbonate | 4-(p-nitrophenyl carbonate) phenoxymethyl polystyrene |
| Rink Resin | 4-(2',4'-Dimethoxyphenyl-Fmco-aminomethyl)-phenoxy polystyrene resin |
| Wang Bromo Resin | (4-Bromomethyl)phenoxymethyl polystyrene |
| THP Resin | 3,4-Dihydro-2H-pyran-2-ylmethoxymethyl polystyrene |

Aldehyde resin can refer to the following:

4-Benzyloxybenzaldehyde polystyrene
3-Benzyloxybenzaldehyde polystyrene
4-(4-Formyl-3-methoxyphenoxy)butyryl-aminomethyl polystyrene
2-(4-Formyl-3-methoxyphenoxy)ethyl polystyrene
2-(3,5-dimethoxy-4-formylphenoxy)ethoxy-methyl polystyrene
2-(3,5-dimethoxy-4-formylphenoxy)ethoxy polystyrene
(3-Formylindolyl)acetamidomethyl polystyrene
(4-Formyl-3-methoxyphenoxy) grafted (polyethyleneglycol)-polystyrene; or
(4-Formyl-3-methoxyphenoxy)methylpolystyrene.

Abbreviations used in the Examples are as follows:

APCI=atmospheric pressure chemical ionization
BOC=tert-butoxycarbonyl
BOP=(1-benzotriazolyloxy)tris(dimethylamino)phosphonium hexafluorophosphate
d=day
DIAD=diisopropyl azodicarboxylate
DCC=dicyclohexylcarbodiimide
DCM=dichloromethane
DCE=dichloroethane
DIC=diisopropylcarbodiimide
DIEA=diisopropylethylamine DMA=N,N-dimethylacetamide
DMAP=dimethylaminopyridine
DME=1,2 dimethoxyethane
DMF=N,N-dimethylformamide
DMPU=1,3-dimethypropylene urea
DMSO=dimethylsulfoxide
EDC=1-ethyl-3-(3-dimethylaminopropyl)-carbodiimide hydrochloride
EDTA=ethylenediamine tetraacetic acid
ELISA=enzyme-linked immunosorbent assay
ESI=electrospray ionization
ether=diethyl ether
EtOAc=ethyl acetate
FBS=fetal bovine serum
g=gram
h=hour
HBTU=O-benzotriazol-1-yl-N,N,N', N'-tetramethyluronium hexafluorophosphate
HMPA=hexamethylphosphoric triamide
HOBt=1-hydroxybenzotriazole
Hz=hertz
i.v.=intravenous
kD=kiloDalton
L=liter
LAH=lithium aluminum hydride
LDA=lithium diisopropylamide
LPS=lipopolysaccharide
M=molar
m/z=mass to charge ratio
mbar=millibar
MeOH=methanol
mg=milligram
min=minute
mL=milliliter
mM=millimolar
mmol=millimole
mol=mole
mp=melting point
MS=mass spectrometry
N=normal
NMM=N-methylmorpholine, 4-methylmorpholine
NMR=nuclear magnetic resonance spectroscopy
p.o.=per oral
PBS=phosphate buffered saline solution
PMA=phorbol myristate acetate
ppm=parts per million
psi=pounds per square inch
$R_f$=relative TLC mobility
rt=room temperature
s.c.=subcutaneous
SPA=scintillation proximity assay
TEA=triethylamine
TFA=trifluoroacetic acid
THF=tetrahydrofuran
THP=tetrahydropyranyl
TLC=thin layer chromatography
TMSBr=bromotrimethylsilane, trimethylsilylbromide
$T_r$=retention time Thus, in an embodiment, the following compounds were synthesized according to the Schemes described herein.

General Procedure A:

To a solution of a carboxylic acid (1.0-1.5 mmol) in DMF (6 mL) was added an amino acid methyl ester (1.0-1.5 mmol), HBTU (1.0-1.5 mmol), and DIEA (2.0-3.0 mmol) and the mixture was stirred overnight. After completion of the reaction, sufficient amount of water was added and the mixture was extracted with ethyl acetate (3×15 ml). The combined organic layer was washed with water and brine, and then dried over sodium sulfate. The solvent was removed in vacuum to afford the amide, which was used for further usage without further purification or purified by flash chromatography.

General Procedure B:

To a mixture of phenol and the aryl fluoride (2 eq) in DMF was added solid potassium carbonate or sodium methoxide (10 eq), and the mixture was heated at 80° C. for 12 h. After completion of the reaction, sufficient amount of water was added, and the mixture was extracted with ethyl acetate. The combined organic layer was washed with water and brine, dried over sodium sulfate. The solvent was removed in vacuum and the crude material obtained was purified by flash chromatography to afford the desired aryl ethers.

General Procedure C:

To a solution of ester in THF, $CH_3OH$ (4:1), 2N-lithium hydroxide solution (5 eq) was added, and the resulting reaction mixture was stirred at 0° C. for 30 minutes and then warmed to room temperature. After completion of the reaction, 2N HCl was used to neutralize the base, extracted with ethyl acetate, the organic layer was washed with brine, dried over sodium sulfate, and the solvent was removed in vacuum to afford the product in pure form.

General Procedure D:

To a solution of phenyl bromide in DME were added corresponding boronic acid (5 eq), Pd $(PPh_3)_4$ (0.5% eq), 2N $Na_2CO_3$ solution (5 eq). The mixture was heated at 75° C. for 12 h. After completion of the reaction, solvent was evaporated in vacuo. During the reaction, most of the ester was hydrolyzed to the corresponding acid. The crude product so obtained was re-esterfied by dissolving it in $CH_3OH$ containing 1% of HCl. The mixture was refluxed for 6 h and after the completion of the reaction, the reaction mixture was concentrated under reduced pressure. The residue was purified by column chromatography (silica, $CH_2Cl_2$) to provide the desired ester. The resulting ester was hydrolyzed as described in procedure C yielding the pure acid.

General Procedure E:

To a solution of an aniline (1.0 mmol) in DCM (10 mL) was added a sulfonyl chloride (1.0 mmol), and pyridine (10.0 mmol) and the mixture was stirred overnight. After completion of the reaction, 50 mL of DCM was added and the organic layer was washed with 1N HCl, saturated sodium bicarbonate solution and brine, and then dried over sodium sulfate. The solvent was removed in vacuum to afford the sulfonamide, which was purified by flash chromatography.

General Procedure F:

A flask was charged with phenol or aniline (1.0 equiv), Cu $(OAc)_2$ (1.0 equiv), arylboronic acid (1.0-3.0), and powdered 4 $A^0$ molecular sieves. The reaction mixture was diluted with $CH_2Cl_2$ to yield a solution approximately 0.1M in phenol or aniline, and the $Et_3N$ (5.0 equiv) was added. After stirring the colored heterogeneous reaction mixture for 24 h at 25° C. under ambient atmosphere, the resulting slurry was filtered and the diaryl ether or diaryl amine is isolated from the organic filtrate by flash chromatography.

General Procedure G:

To a solution of a phenol (1.0 mmol) in DMF (5 mL) was added an alkyl halide (1.2 mmol) (a catalytic amount of NaI is added for alkyl chloirdes), and potassium carbonate (2.5 mmol) and the mixture heated at 70° C. overnight. After completion of the reaction, 5 mL of ethyl acetate and 5 mL of water was added. The organic layer was washed with water, and then dried over sodium sulfate. The solvent was removed in vacuum to afford the ether, which was purified by flash chromatography.

General Procedure H:

Approximately, 10 ml of DMF per gram of resin was suspended in a round bottomed flask. In a separate flask, 2.5 eqivalents (relative to the resin) of the carboxylic acid was dissolved in a minimum amount of DMF. Next, the same equivalent of HOBT and 0.1 equivalent of DMAP(relative to the acid) was added. The mixture was stirred until the acid and HOBT dissolved, and then the solution was added to the resin. Next, 1.0 equivalent (relative to the acid) of DIC was added to the resin mixture. The flask was equipped with a drying tube and the mixture agitated on shaker overnight. The resin was filtered in a sintered glass funnel and washed 3 times with DMF, 3 times with methanol, and finally 3 times with DCM. The resin was in vacuo to a constant weight.

General Procedure I:

DIAD or DEAD was added dropwise to a mixture of a phenol, a primary or secondary alcohol (1.5 eq.), and triphenylphosphine (1.5 eq.) dissolved in anhydrous THF, at −20° C. under a nitrogen atmosphere. The mixture was stirred for 1-2 hours while allowing to gradually warm to r.t. The solvent was removed and the residue purified by flash column chromatography to afford the desired alkyl aryl ether.

General Procedure J:

To 1.0 g (2.5 mmol) of resin-bound naphthoic acid was added a mixture of 1.5 g (7.5 mmol) of 4-Bromophenethylamine, 7.5 mL (7.5 mmol) of 1.0 M DIC in DMF, 7.5 mL (7.5 mmol) of 1.0 M HOBt in DMF, and a catalytic amount of DMAP. The resulting mixture was left on a shaker overnight. The resin was washed with DMF, MeOH, DCM three times of each to give resin-bound N-2-(4-Bromophenyl)ethyl-3-hydroxyl-2-naphthamide.

General Procedure K:

To the aryl acid (5.0 mmol) solution in DCM (20 ml) and pyridine (20.0 mmol) was added acetyl chloride (20.0 mmol) at −10° C. and the reaction mixture was stirred and allowed to warm up to r.t. The reaction mixture was then poured in to icy water (50 ml) and extracted with DCM (3×50 mL), organic extracts were combined, dried ($Na_2SO_4$), and concentrated in vacuo to furnish the desired acid.

General Procedure L:

To a solution of 2-acetoxyaryl acid (10.0 mmol) solution in DCM (50 ml) was added oxalyl chloride (25.0 mmol) at −10° C. and the reaction mixture was allowed to warm up to r.t. and stirred for 2 hours. Then the reaction mixture concentrated in vacuo to furnish the desired acid chloride.

General Procedure M:

To a solution of 2-acetoxyaryl acid chloride (5.0 mmol) solution in DCE (20 ml) was added desired amine (5.0 mmol) and 4-methyl morpholine (10.0 mmol). The reaction mixture was stirred at r.t. for 2 hours. The reaction mixture was then concentrated in vacuo and poured into water (20 mL), and extracted with ethyl acetate (3×25 mL). Organic extracts were combined and concentrated in vacuo. The crude product was then purified with silica gel column chromatography by using ethyl acetate:hexanes (5:95 to 20:80) as eluent system to afford desired amides.

General Procedure N:

To a solution of N-Boc-protected amino acids (5.0 mmol) in methanol (20 mL) was added hydrochloric acid (5 mL, 4.0 solution in dioxane) and refluxed for 1 h. The reaction mixture was concentrated in vacuo to give the desired amino ester. Deprotection of Boc groups and esterification of non-amino acids are also performed using this method.

General Procedure O:

To a solution of N-Boc-amino acid (1.0 mmol) in THF (10 mL) was added polymer-supported DCC (2.4 g, 2.0 mmol, as a suspension in chloroform (30 mL)). This mixture was placed to a shaker and was shaken for 10 min. Then pentafluorophenol (300 mg, 1.5 mmol, 5 mL solution in THF) was added to the reaction mixture and placed to the shaker for 16 hours at r.t. The reaction mixture was then filtered through with celite and concentrated in vacuo to give the pentafluoroohenyl ester. This ester was then subjected to further manipulations without purification.

To a solution of above pentafluorophenyl ester (300 mg, 0.5 mmol) was added desired alkylamideoxime (1.0 mmol) and molecular sieves (100 mg) in dry chlorobenzene (20 mL). The reaction mixture was then heated at 120° C. for 4-5 hours and concentrated in vacuo to remove most of chlorobenzene. To this slurry was added DCM (50 mL) and filtered through with a plug of silica gel, again concentrated in vacuo. This crude product was then purified with ethyl acetate:hexanes 5:95 to 10:90 to give the desired oxadiazoles.

The intermediate alkyloxyaryl oxadiazole was then deprotected using hydrochloric acid (1 mL, 4.0 M solution in dioxane) following by general procedure N to give free amine. This free amine was then subjected to general procedure A to give the desired amides in a quantitative yield.

General Procedure P:

To a solution of alkylphenyl ether (0.2 mmol) in anhydrous DCM (10 mL) was added boron tribromide (0.5 mmol, 1.0 M solution in DCM or neat) at −78° C. and the reaction mixture stirred at −78° C. for 3 hours and allowed to warm up to the ambient temperature. After the reaction was completed, the reaction mixture was slowly quenched with saturated aqueous sodium bicarbonate solution (5 mL) and extracted with DCM (3×20 mL). The reaction mixture was concentrated in vacuo to give the crude product. This crude product was then purified by silica gel chromatography with hexanes:ethyl acetate (from 95:5 to 80-20) as an eluent system to obtain desired phenols.

General Procedure Q:

To the phosphonate ester (1.0 mmol) in DCM was added DBU (1.0 mmol) and the mixture was stirred for 10 min, then the aldehyde (0.9 mmol) was added to the mixture and stirred for another 2 h. Aqueous citric acid was then added and the mixture was extracted with ethyl acetate (3×25 mL). Organic extracts were combined and concentrated in vacuo. The crude product was then purified on a silica gel column chromatography by using ethyl acetate:hexanes as eluent system to afford desired alkenes.

General Procedure R:

To a solution of an aniline (1.0 mmol) in DCE (10 mL) was added an aldehyde (2.0-2.2 mmol), acetic acid (3.0 mmol), and sodium triacetoxyborohydride (2.5 mmol) and the mixture was stirred overnight. After completion of the reaction, 50 mL of DCM was added and the organic layer was washed with 1N HCl, saturated sodium bicarbonate solution and brine, and then dried over sodium sulfate. The solvent was removed in vacuum to afford the amine, which was purified by flash chromatography.

The above general methods are for illustration only. Alternative conditions that may optionally be used include: use of alternative solvents, alternative stoichiometries of reagents, alternative reagents, alternative reaction conditions, including temperatures and alternative methods of purification.

Synthesis of Amino Acids

Synthesis of 4'-Trifluoromethyl-biphenyl-4-carboxylic acid

The title compound was prepared following procedure D using 4-bromo benzoic acid (10 g, 50 mmol), 4-trifluoromethyl boronic acid (14.1g, 75 mmol), palladium tetrakis-triphenylphosphine (6.0, 10 mol %) and 2N $Na_2CO_3$ aq.solution (150 ml, 140 mmol) in 500 ml of toluene. 9.9 g of title compound was isolated after usual work up.

(2S)-Amino-3-(2'-phenoxy-biphenyl-4-yl)-propionic acid methyl ester

The title compound was prepared following procedure D using (L)-4-bromophenylalanine (8.55 g, 35.0 mmol), 2-phenoxyphenyl boronic acid (10.00 g, 46.73 mmol), palladium tetrakis-triphenylphosphine (4.0 9, 10% mmol) ) and 2N $Na_2CO_3$ aq. solution (70 mL, 140 mmol) in 140 ml of DME. After removal of solvents, the solid was washed with ether to afford the tile compound in HCl salt form (10.0 g, 26.20 mmol).

Example 1

3-Biphenyl-4-yl-(2S)-[(3'-chloro-4'-fluoro-4-hydroxy- biphenyl-3-carbonyl)-amino]-propionic acid methyl ester To 40 g (200 mmol) of 5-bromo-2-hydroxy-benzoic acid methyl ester, 11.0 g (220 mmol) of sodium methoxide in 500 mL of anhydrous DMA was added 13.30 g (71 mmol) of Merrifield resin. The mixture was heated at 110° C. overnight. The resin was washed with $H_2O$, DMF, MeOH, DCM three times of each, and dried.

To 1.0 g (2.5 mmol) of resin-bound 5-bromo-2-hydroxy-benzoic acid was added 1.92 g (7.5 mmol) of (2S)-amino-3-biphenyl-4-yl-propionic acid methyl ester following general procedure A to give resin-bound 3-(biphenyl-4-yl)-(2S)-(5-bromo-4-hydroxy-benzoylamino)-propionic acid methyl ester.

The resin-bound 3-(biphenyl-4-yl)-(2S)-(5-bromo-4-hydroxy-benzoylamino)-propionic acid methyl ester (50 mg, 0.3 mmol) was reacted with 3-chloro-4-fluorophenylboronic acid (240 mg, 1.5 mmol) following general procedure D, cleaved with TMSBr/TFA/DCM (1:1:5) at rt for 4 h. The residue obtained after removing the solvent was purified by chromatography to give 35 mg of title compound.

$^1$H-NMR(400 MHz, $CDCl_3$): 3.33 (t, 2H), 3.83 (s, 3H), 5.10 (m, 1H), 6.83 (d, 1H), 7.35 (m, 2H), 7.22 (d, 2H), 7.29 (m, 1H), 7.35 (m, 2H), 7.43 (m, 2H), 7.48 (dd, 1H), 7.55 (m, 5H); LC/MS (m/z): 504 $(M+1)^+$.

Example 2

4-Hydroxy-4'-trifluoromethyl-biphenyl-3-carboxylic acid biphenyl-4-yl-1(S)-formyl-ethyl)-amide; compound with methoxymethane The resin-bound 3-(biphenyl-4-yl)-(2S)-(5-bromo-4-hydroxy-benzoyl-amino)-propionic acid methyl ester (30 mg, 0.09 mmol) obtained as in Example 1 was reacted with 4-trifluoromethyl-phenyl boronic acid (86 mg, 0.45 mmol) as described in the general procedure D to provide the title compound (25 mg).

$^1$H-NMR(400 MHz, $CDCl_3$): 3.35 (m, 2H), 3.84 (s, 3H), 5.10 (m, 1H), 6.79 (d, 1H), 7.09 (d, 1H), 7.21 (d, 2H), 7.37 (m, 1H), 7.43 (m, 3H), 7.56 (m, 8H), 7.64 (dd, 1H); LC/MS (m/z): 520 $(M+1)^+$.

Example 3

2-(S)-[(4-Hydroxy-4'-trifluoromethyl-biphenyl-3-carbonyl)-amino]-3-(4'-trifluoromethyl-biphenyl-4-yl)propionic acid methyl ester The resin-bound 3-(4-bromo-phenyl)-(2S)-[(4'-trifluoromethyl-4-hydroxy-biphenyl-3-carbonyl)-amino]-propionic acid methyl ester (30 mg, 0.09 mmol) prepared as described in Example 1 was reacted with 4-trifluoromethyl-phenyl boronic acid (86 mg, 0.45 mmol) by following procedure D to give the title compound (24 mg).

$^1$H NMR (400 MHz, $CDCl_3$): 3.30-3.42 (m, 2H), 3.84 (s, 3H), 5.11 (dd, 1H, J=12.8, 5.2 Hz), 6.82 (d, 1H, J=7.2 Hz), 7.10 (d, 1H, J=8.8 Hz), 7.43-7.45 (m, 2H), 7.53-7.57 (m, 5H), 7.60-7.70 (m, 7H); LC/MS (m/z): 588 $(M+1)^+$.

By analogous methods to those described above, the following compounds were synthesized.

| EX. | NAME | LC/MS (m/z) |
|---|---|---|
| 4 | 3-Biphenyl-4-yl-(2S)-[(4-hydroxy-3'-nitro-biphenyl-3-carbonyl)-amino]-propionic acid methyl ester | 499 |
| 5 | 3-Biphenyl-4-yl-2-(S)-[(4-hydroxy-4'-trifluoromethoxy-biphenyl-3-carbonyl)-amino]-propionic acid methyl ester | 536 |
| 6 | 3-Biphenyl-4-yl-2-(S)-[(4'-fluoro-4-hydroxy-biphenyl-3-carbonyl)-amino]-propionic acid methyl ester | 470 |
| 7 | 3-Biphenyl-4-yl-2-(2S)-[(3'-fluoro-4-hydroxy-biphenyl-3-carbonyl)-amino]-propionic acid methyl ester | 470 |
| 8 | 3-Biphenyl-4-yl-2-(2S)-[(4-hydroxy-3',5'-bis-trifluoromethyl-biphenyl-3-carbonyl)-amino]-propionic acid methyl ester | 588 |
| 9 | 3-Biphenyl-4-yl-2-(2S)-[(3',5'-difluoro-4-hydroxy-biphenyl-3-carbonyl)-amino]-propionic acid methyl ester | 488 |
| 10 | 2-(2S)-[(3'-Chloro-4'-fluoro-4-hydroxy-biphenyl-3-carbonyl)-amino]-3-(4'-trifluoromethyl-biphenyl-4-yl)-propionic acid methyl ester | 572 |

-continued

| EX. | NAME | LC/MS (m/z) |
|---|---|---|
| 11 | 2-(2S)-(5-Benzo[1,3]dioxol-5-yl-2-hydroxy-benzoylamino)-3-biphenyl-4-yl-propionic acid methyl ester | 496 |
| 12 | 3-(3'-Chloro-4'-fluoro-biphenyl-4-yl)-2-(2S)-[(4-hydroxy-4'-trifluoromethyl-biphenyl-3-carbonyl)-amino]-propionic acid methyl ester | 572 |
| 13 | 3-(3',5'-Bis-trifluoromethyl-biphenyl-4-yl)-2-(2S)-[(3'-chloro-4'-fluoro-4-hydroxy-biphenyl-3-carbonyl)-amino]-propionic acid methyl ester | 640 |
| 14 | 3-(3',5'-Bis-trifluoromethyl-biphenyl-4-yl)-2-(2S)-[(3'chloro-4'-fluoro-4-hydroxy-biphenyl-3-carbonyl)amino]-propionic acid methyl ester | 656 |
| 15 | 2-(2S)-[(3'-Chloro-4'-fluoro-4-hydroxy-biphenyl-3-carbonyl)-amino]-3-(3'-trifluoromethyl-biphenyl-4-yl)-propionic acid | 558 |
| 16 | 2-(2S)-[(4-Hydroxy-4'-trifluoromethyl-biphenyl-3-carbonyl)-amino]-3-(3'-trifluoromethoxy-biphenyl-4-yl)-propionic acid methyl ester | 604 |
| 17 | 2-(2S)-[(4-Hydroxy-3'-trifluoromethyl-biphenyl-3-carbonyl)-amino]-3-(3'-trifluoromethyl-biphenyl-4-yl)-propionic acid methyl ester | 588 |
| 18 | 3-Biphenyl-4-yl-2-(S)-[(4-hydroxy-biphenyl-3-carbonyl)-amino]-propionic acid methyl ester | 452 |
| 19 | 2-(S)-[(3'-Chloro-4'-fluoro-4-hydroxy-biphenyl-3-carbonyl)-amino]-3-(3'-trifluoromethoxy-biphenyl-4-yl)-propionic acid methyl ester | 588 |
| 20 | 2-(S)-[(4-Hydroxy-2'-trifluoromethyl-biphenyl-3-carbonyl)-amino]-3-(2'-trifluoromethyl-biphenyl-4-yl)-propionic acid methyl ester | 588 |
| 21 | 3-(3'-Chloro-4'-fluoro-biphenyl-4-yl)-2-(S)-[(3'-chloro-4'-fluoro-4-hydroxy-biphenyl-3-carbonyl)-amino]-propionic acid methyl ester | 556 |
| 22 | 2-(S)-[(4-Hydroxy-3'-nitro-biphenyl-3-carbonyl)-amino]-3-(3'-nitro-biphenyl-4-yl)-propionic acid methyl ester | 542 |
| 23 | 2-(S)-[(4-Hydroxy-3'-trifluoromethyl-biphenyl-3-carbonyl)-amino]-3-(4'-trifluoromethyl-biphenyl-4-yl)-propionic acid methyl ester | 588 |
| 24 | 3-(3'-Chloro-4'-fluoro-biphenyl-4-yl)-2-(S)-[(4-hydroxy-3'-trifluoromethyl-biphenyl-3-carbonyl)-amino]-propionic acid methyl ester | 572 |
| 25 | 3-Biphenyl-4-yl-2-(S)-[(4-hydroxy-2'-trifluoromethyl-biphenyl-3-carbonyl)-amino]-propionic acid methyl ester | 520 |
| 26 | 3-(3',5'-Bis-trifluoromethyl-biphenyl-4-yl)-2-(S)-[(4-hydroxy-3'-trifluoromethyl-biphenyl-3-carbonyl)-amino]-propionic acid methyl ester | 656 |
| 27 | 2-(S)-[(4-Hydroxy-3'-trifluoromethyl-biphenyl-3-carbonyl)-amino]-3-(2'-trifluoromethyl-biphenyl-4-yl)-propionic acid methyl ester | 588 |

Example 28

2-(2S)-[(4-Hydroxy-4'-trifluoromethyl-biphenyl-3-carbonyl)-amino]-3-(4'-nitro-biphenyl-4-yl)-propionic acid methyl ester To 2.50 g (5.0 mmol) of resin-bound methyl 5-bromo-2-hydroxy-benzoate obtained by a similiar procedure as in Example 1 in 30 mL of DME was added 2.90 g (15 mmol of 4-(trifluoromethyl)phenylboronic acid, 1.12 g (1.10 mmol) of $Pd(PPh_3)_4$, and 15 mL (30.0 mmol) of 2N $Na_2CO_3$ solution. The mixture was heated to 80° C. for 12 h. The resin was washed with $H_2O$, DMF, MeOH, and DCM (three times of each), and was hydrolyzed by $LiOH/H_2O$/THF/ethanol at rt for 3 days to give the resin-bound 4'-trifluoromethyl-4-hydroxy-biphenyl-3-carboxylic acid.

To 1.5 g (2.5 mmol) of above resin-bound 4'-trifluoromethyl-4-hydroxy-biphenyl-3-carboxylic acid was added 1.95 g (7.5 mmol) of 4-(S)-bromophenylalanine methyl ester, 7.5 mL (7.5 mmol) of 1.0 M DIC in DMF, 7.5 mL (7.5 mmol) of 1.0 M HOBt in DMF, and catalytic amount of DMAP. The resulting mixture was left on a shaker overnight. The resin was washed with DMF, MeOH, and DCM (three times of each) to give resin-bound 3-(4-bromo-phenyl)-2-(S)-[(4'-trifluoromethyl-4-hydroxy-biphenyl-3-carbonyl)-amino]-propionic acid methyl ester.

To 0.05 g (0.1 mmol) of above resin-bound 3-(4-bromo-phenyl)-2-(S)-[(4'-trifluoromethyl-4-hydroxy-biphenyl-3-carbonyl)-amino]-propionic acid methyl ester in 2.0 mL of DME was added 50.1 mg (0.3 mmol) of 4-nitrophenylboronic acid, 30 mg (0.03 mmol) of $Pd(PPh_3)_4$, and 0.3 mL (0.6 mmol) of 2N $Na_2CO_3$ solution. The mixture was heated at 80° C. for 12 h. The resin was washed with $H_2O$, DMF, MeOH, DCM three times of each and cleaved with TMSBr/TFA/DCM (1:1:5) at rt for 4 h. The residue obtained after removing the solvent was purified by chromatography (100% DCM) to give 28.2 mg of the title compound. LC/MS (m/z): 565 $(M+1)^+$.

By analogous methods to those described above the following compounds were synthesized

| EX. | NAME | LC/MS (m/z) |
|---|---|---|
| 29 | 3-(3',4'-Difluoro-biphenyl-4-yl)-2-(S)(2-hydroxy-5-pyridin-3-yl-benzoylamino)-propionic acid methyl ester | 489 |
| 30 | 2-(S)-[(4'-Amino-4-hydroxy-biphenyl-3-carbonyl)-amino]-3-biphenyl-4yl-propionic acid methyl ester | 467 |

Example 31

3-Biphenyl-4-yl-2-(2S)-{2-hydroxy-5-[2-(4'-trifluoromethyl-biphenyl-3-yl)-acetylamino]-benzoylamino] propionic acid methyl ester The resin-bound 2-hydroxy-5-nitro-benzoic acid (500 mg, 0.5 mmol) obtained by a similar procedure as in Example 1 was reacted with 2-S-amino-3-biphenyl-4-yl-propionic acid methyl ester (385mg, 1.5 mmol) as described in general procedure A. The resulting resin was reduced by $SnCl_2$ hydrate in NMP at rt for 4 h to give the resin-bound 3-biphenyl-4-yl-2-(S)-(5-amino-2-hydroxy-phenyl) carbonylamino-propionic acid methyl ester. The above resin (120 mg, 0.1 mmol) was reacted with 110 mg (0.5 mmol) of 4-bromophenylacetyl chloride, followed by 58 mg (0.3 mmol) of 4-trifluormethyl-phenyl boronic acid, 30 mg (0.03 mmol) of $Pd(PPh_3)_4$, and 0.3 mL (0.6 mmol) of 2N $Na_2CO_3$ solution. The mixture was heated to 80° C. for 12 h. The resin was washed with $H_2O$, DMF, MeOH, and DCM (three times of each) and cleaved with TMSBr/TFA/DCM (1:1:5) at rt for 4 h. The residue obtained after removing the solvent was purified by chromatography (100% methylene chloride) to afford 25 mg of title compound. LC/MS (m/z) 653 $(M+1)^+$.

Example 32

3-Biphenyl-4-yl-2-S)-[(3'-chloro-4'-fluoro-4-hydroxy-biphenyl-3-carbonyl)-amino]-propionic acid methyl ester 3-Chloro-4-fluoro-phenylboronic acid (3.2 g, 18.4 mmol), 5-bromo-2-hydroxy-benzoic acid (4.0 g, 18.4 mmol), and Pd $(PPh_3)_4$ (1.67 g, 1.84 mmol) were dissolved in 250 mL of DME, a 1 M $Na_2CO_3$ solution (46 mL, 46.0 mmol) added and the mixture heated to 80° C. for 20 h. The reaction mixture was filtered, partially evaporated and EtOAc (200 mL) and 1 N HCl (100 mL) added. The organic layer washed with 1N HCl and saturated sodium bicarbonate, dried over sodium sulfate, and evaporated. The crude material was filtered through a silica plug (THF) to give 3'-chloro-4'-fluoro-4-hydroxy-biphenyl-3-carboxylic acid (2.15 g).

3-Biphenyl-4-yl-2-(S)-[(3'-chloro-4'-fluoro-4-hydroxy-biphenyl-3-carbonyl)-amino]-propionic acid methyl ester (51 mg) was prepared from 3'-chloro-4'-fluoro4-hydroxy-biphenyl-3-carboxylic acid (300 mg, 1.1 mmol) and 2-(S)-amino-3-biphenyl-4-yl-propionic acid methyl ester-hydrochloride (330 mg, 1.1 mmol) as described in general procedure A, except for an adapted work-up. After reaction completion, the reaction mixture was poured onto 100 mL of 1N HCl and 100 mL of EtOAc. The organic layer was washed with 1N HCl, saturated sodium bicarbonate, dried over sodium sulfate and evaporated. The crude material was purified over silica gel (8:2, DCM-hexanes). LC/MS (m/z): 504 $(M+1)^+$.

Example 33

3-biphenyl-4-yl-2-(S)-[(3'-chloro-4'-fluoro-4-hydroxy-biphenyl-3-carbonyl)-amino]-propionic acid 3-Biphenyl-4-yl-2-(S)-[(3'-chloro-4'-fluoro-4-hydroxy-biphenyl-3-carbonyl)-amino]-propionic acid methyl ester, example 32 (20 mg, 0.040 mmol) was dissolved in 5 mL of THF-MeOH (4-1), cooled to 0° C. and 1.1 equiv of 2 N LiOH added. After 45 minutes, 2.2 additional equiv of 2N LiOH was added and the reaction stirred for 60 minutes. The reaction was worked up according to general procedure C to give 3-(S)-biphenyl-4-yl-2-(S)-[(3'-chloro-4'-fluoro-4-hydroxy-biphenyl-3-carbonyl)-amino]-propionic acid (10 mg). LC/MS (m/z): 490 $(M+1)^+$.

Example 34

2-(S)-(5-Chloro-2-hydroxy-benzoylamino)-3-(2'-phenoxy-biphenyl-4-yl)-propionic acid methyl ester 5-Chloro-salicylic acid (2.16 g, 10 mmol) was first transformed into 2-acetyl-5-chloro-salicylic acid (252 g) with acetyl chloride (2.34 g, 30 mmol) and pyridine (3.95 g, 50 mmol) in DCM. The above acid (1.29 g, 5.0 mmol) was converted into acid chloride by using oxayl chloride (1.97 g, 15 mmol) and catalytic amount of DMF in DCM, then (2S)-Amino-3-(2'-phenoxy-biphenyl-4-yl)-propionic acid methyl ester (1.45 g, 5.0 mmol) and DIEA (0.77 g, 6.0 mmol) were added to the acid chloride to form (2S)-[5-Chloro-2-hydroxy-benzoylamine]-3-(2'-phenoxybiphenyl-4-yl)-propionic acid methyl ester (1.92 g). LC/MS: 502

Example 35

2-(S)-(5-Chloro-2-hydroxy-benzoylamino)-3-(2'-phenoxy-biphenyl-4-yl)-propionic acid To a solution of the preceeding compound, 2-(S)-(5-Chloro-2-hydroxy-benzoylamino)-3-(2'-phenoxy-biphenyl-4-yl)-propionic acid (10 mg, 18 μmol) in THF/MeOH was added aqueous LiOH, as described in General procedure C which, after work-up afforded the title compound (10 mg) LCMS for $C_{28}H_{22}BrNO_5$: 531, 533.

Example 36

2-(S)-(5-Bromo-2-hydroxy-benzoylamino)-3-(4'-phenoxy-biphenyl-4-yl)-propionic acid methyl ester The preparation of the title compound proceeds via the same protocol as in the synthesis of (2S)-(5-Chloro-2-hydroxy-benzoylamino)-3-(2'-phenoxy-biphenyl-4-yl)-propionic acid methyl ester (vide supra) with the one exception that the Suzuki coupling (General procedure D) uses 4-phenoxy-phenylboronic acid instead of 2-phenoxy phenylboronic acid. LCMS for $C_{29}H_{24}BrNO_5$: 546, 548. $^1$H NMR (400 MHz, $CDCl_3$) 11.98 (s, 1H), 7.30-7.65 (m, 8H), 7.03-7.25 (m, 7H), 6.87 (d, 1H), 6.83 (d, 1H), 5.07 (dt, 1H), 3.83 (s,3H), 3.29 (qd,2H).

Example 37

2-(S)-(5-Bromo-2-hydroxy-benzoylamino)-3-(4'-phenoxy-biphenyl-4-yl)-propionic acid To a solution of the preceding compound, (2S)-(5-Bromo-2-hydroxy-benzoylamino)-3-(4'-phenoxy-biphenyl-4-yl)-propionic acid methyl ester (10 mg, 18 μmol) in THF/MeOH was added aqueous LiOH, as described in General procedure C which, after work-up afforded the title compound, (2S)-(5-Bromo-2-hydroxy-benzoylamino)-3-(4'-phenoxy-biphenyl-4-yl)-propionic acid (10 mg ) LCMS for $C_{28}H_{22}BrNO_5$: 531, 533.

Example 38

5-Chloro-4-hydroxy-4'-trifluoromethyl-biphenyl-3-carboxylic acid [2-(3'-chloro-4'-fluoro-biphenyl-3-yl)-1(R)-(3-methyl-[1,2,4]oxadiazol-5-yl)-ethyl]-amide N-Bromosuccinimide (2.38 g, 13.38 mmol) was added to a solution of 3-chlorosalicylic acid (2.1 g, 12.16 mmol) in $CH_3CN$ (10 mL) solution and stirred for 1 h. The reaction mixture was diluted with water (25 mL), solids were filtered and washed with water and dried to get 5-bromo-3-chloro-2-hydroxy-benzoic acid (2.87 g).

Methyl Iodide (3.83 g, 27.04 mmol) was added to a solution of 5-Bromo-3-chloro-2-hydroxy-benzoic acid (1.7 g, 6.76 mmol) and $Cs_2CO_3$ (4.83 g, 14.86 mmol) in DMF (10 mL) and heated at 50° C. for 12 h. The reaction mixture was diluted with EtOAc (30 mL) and filtered over celite pad. Filtrate was washed with water, brine and dried over $Na_2SO_4$. Solvent was removed and the residue was purified by silicagel column chromagography to get pure 5-Bromo-3-chloro-2-methoxy-benzoic acid methyl ester (1.56 g)

4-Trifluorophenylboronic acid (0.815 g, 4.29 mmol) was added to a solution of 5-Bromo-3-chloro-2-methoxy-benzoic acid methyl ester (1.0 g, 3.57 mmol), $Pd(PPh_3)_4$ (0.2 g, 0.178 mmol) and CsF (1.08 g, 7.15 mmol) in DME (10 mL) and heated at 85° C. for 10 h. The reaction was diluted with EtOAc (20 mL) and filtered, filtrate was washed water, brine and dried over $Na_2SO_4$. The solvent was removed under reduced pressure and the silica gel column chromatography gave pure 5-Chloro-4-methoxy-4'-trifluoromethyl-biphenyl-3-carboxylic acid methyl ester (0.94 g).

5-Chloro-4-methoxy-4'-trifluoromethyl-biphenyl-3-carboxylic acid (0.62 g) was prepared from 5-Chloro-4-methoxy-4'-trifluoromethyl-biphenyl-3-carboxylic acid methyl ester (0.7 g, 2.03 mmol) following the procedure C.

2-(R)-tert-Butoxycarbonylamino-3-(3'-chloro-4'-fluoro-biphenyl-3-yl)-propionic acid (0.93 g ) was prepared from (R)—N-Boc-3-bromophenylalanine (1.0 g, 2.9 mmol) and 3-chloro-4-fluorophenylboronic acid (1.0 g, 5.8 mmol) following general procedure D.

[2-(3'-Chloro-4'-fluoro-biphenyl-3-yl)-1-(3-methyl-[1,2,4]oxadiazol-5-yl)-ethyl]-carbamic acid tert-butylester (0.7 g )was prepared from 2-tert-Butoxycarbonylamino-3-(3'-chloro-4'-fluoro-biphenyl-3-yl)-propionic acid (0.9 g, 2.2 mmol) following general procedure O.

5-Chloro-4-methoxy-4'-trifluoromethyl-biphenyl-3-carboxylic acid [2-(3'-chloro-4'-fluoro-biphenyl-3-yl)-1-(R)-(3-methyl-[1,2,4]oxadiazol-5-yl)-ethyl]-amide (0.087) was prepared using the general procedure A, from 2-(3'-Chloro-4'-fluoro-biphenyl-3-yl)-1-(3-methyl-[1,2,4]oxadiazol-5-yl)-ethylamine hydrochloride salt (0.077 g, 0.21 mmol, prepared from [2-(3'-Chloro-4'-fluoro-biphenyl-3-yl)-1-(3-methyl-[1,2,4]oxadiazol-5-yl)-ethyl]-carbamic acid tert-butylester following general procedure N) and 5-Chloro-4-methoxy-4'-trifluoromethyl-biphenyl-3-carboxylic acid (0.07 g, 0.21 mmol).

The title compound (0.022 g) was prepared from 5-Chloro-4-methoxy-4'-trifluoromethyl-biphenyl-3-carboxylic acid [2-(3'-chloro-4'-fluoro-biphenyl-3-yl)-1-(R)-(3-methyl-[1,2,4]oxadiazol-5-yl)-ethyl]-amide (0.04 g, 0.062 mmol), using the general procedure P. $^1$HNMR (400 MHz, $CDCl_3$): 2.40 (s, 3H), 3.40 (m, 2H), 5.87 (m, 1H), 7.05-7.21 (m, 4H), 7.29 (m, 1H), 7.37 (t, 1H), 7.41-7.48 (m, 3H), 7.53 (d, 2H), 7.67 (d, 2H), 7.76 (d, 1H), 12.04 (br s, 1H).

Example 39

5-Chloro-4-hydroxy-4'-trifluoromethyl-biphenyl-3-carboxylic acid [2-[4-(3-chloro-4-fluorophenoxy)-phenyl]-1(R)-(3-methyl-[1,2,4]oxadiazol-5-yl)-ethyl]-amide 2-tert-Butoxycarbonylamino-3-[4-(3-chloro-4-fluoro-phenoxy)-phenyl]-propionic acid (0.87 g) was prepared from Boc-D-tyrosine methyl ester (1.0 g, 3.38 mmol) 3-chloro-4-fluorophenylboronic acid (1.76 g, 10.15 mmol) as described in general procedure F.

[2-[4-(3-Chloro-4-fluoro-phenoxy)-phenyl]-1-(3-methyl-[1,2,4]oxadiazol-5-yl)-ethyl]-carbamic acid tert-butyl ester (0.57 g ) was prepared from 2-tert-Butoxycarbonylamino-3-[4-(3-chloro-4-fluoro-phenoxy)-phenyl]-propionic acid [0.73 g, 1.78 mmol, [which was prepared from 2-tert-Butoxycarbonylamino-3-[4-(3-chloro-4-fluoro-phenoxy)-phenyl]-propionic acid methyl ester following general procedure C] by following general procedure O.

5-Chloro-4-methoxy-4'-trifluoromethyl-biphenyl-3-carboxylic acid [2-[4-(3-chloro-4-fluoro-phenoxy)-phenyl]-1-(3-methyl-[1,2,4]oxadiazol-5-yl)-ethyl]-amide (0.07 g) was prepared from 2-[4-(3-Chloro-4-fluoro-phenoxy)-phenyl]-1-(3-methyl-[1,2,4]oxadiazol-5-yl)-ethylamine hydrochloride [0.07 g, 0.182 mmol, which was prepared from [2-[4-(3-Chloro-4-fluoro-phenoxy)-phenyl]-1-(3-methyl-[1,2,4]oxadiazol-5-yl)-ethyl]-carbamic acid tert-butyl ester by the hydrolysis of BOC group using the general procedure N] and 5-Chloro 4-methoxy-4'-trifluoromethyl-biphenyl-3-carboxylic acid (as in example 42) (0.053 g, 0.18 mmol) following general procedure A. 5-Chloro-4-hydroxy-4'-trifluoromethyl-biphenyl-3-carboxylic acid [2-[4-(3-chloro-4-fluoro-phenoxy)-phenyl]-1-(3-methyl-[1,2,4]oxadiazol-5-yl)-ethyl]-amide (20 mg) was obtained upon methyl ether hydrolysis using the general procedure P. $^1$HNMR (400 MHz, $CDCl_3$): 2.40 (s, 3H), 3.39 (m, 2H), 5.79 (dd, 1H), 6.84 (m, 1H), 6.90 (d, 2H), 7.02 (1 H), 7.04-7.17 (m, 4H), 7.50 (d, 1H), 7.61 (d, 2H), 7.71 (d, 2H), 7.78 (d, 1H), 12.03 (s, 1H).

Example 40

3-(4'-Chloro-biphenyl-4-yl)-2-(R)-[(4-methoxy-4'-trifluoromethyl-biphenyl-3-carbonyl)-amino]-propionic acid methyl ester 3-(4'-Chloro-biphenyl-4-yl)-2-(R)-[(4-methoxy-4'-trifluoromethyl-biphenyl-3-carbonyl)-amino]-propionic acid methyl ester was synthesized from 3-(4-bromo-phenyl)-2-(S)-[(4-methoxy-4'-trifluoromethyl-biphenyl-3-carbonyl)-amino]-propionic acid methyl ester (300 mg, 0.56 mmol, obtained from the coupling of 4-bromophenylalanine and 4-methoxy-4'-trifluoromethyl-biphenyl-3-carboxylic acid using general procedure A) and 4-chlorophenyl boronic acid (156 mg, 1.0 mmol) following general procedure D. (250 mg). LC/MS (m/z): 568 $(M+1)^+$.

Example 41

3-(4'-Chloro-biphenyl-4-yl)-2-(R)-[(4-methoxy-4'-trifluoromethyl-biphenyl-3-carbonyl) -amino]-propionic acid The title compound was prepared from 3-(4'-chloro-biphenyl-4-yl)-2-[(4-methoxy-4'-trifluoromethyl-biphenyl-3-carbonyl)-amino]-propionic acid methyl ester (250 mg, 0.44 mmol) following general procedure C. (190 mg). LC/MS (m/z): 554 $(M+1)^+$.

Example 42

4-Hydroxy-4'-trifluoromethyl-biphenyl-3-carboxylic acid [2-(3'-chloro-biphenyl-4-yl)-1(R) -(3-methyl-[1, 2,4]oxadiazol-5-yl)-ethyl]-amide The title compound was prepared from 4-methoxy-4'-trifluoromethyl-biphenyl-3-carboxylic acid [2-(3'-chloro-biphenyl-4-yl)-1-(R)-(3-methyl-[1,2,4]oxadiazol-5-yl)-ethyl]-amide (160 mg, 0.27 mmol obtained using protocol similar to example 44) following general procedure O. (78 mg).

$^1$H-NMR(400 MHz, $CDCl_3$): 2.41 (s, 3H), 3.47 (d, 2H), 5.83 (m, 1H), 6.86 (d, 1H), 7.14 (m, 3H), 7.38 (m, 4H), 7.55 (m, 5H), 7.65 (m, 3H); LC/MS (m/z): 578 $(M+1)^+$.

By analogous methods to those described above the following compounds were synthesized

| EX. | NAME | LC/MS (m/z) |
|---|---|---|
| 43 | 4-Hydroxy-4'-trifluoromethyl-biphenyl-3-carboxylic acid [2-(4'-chloro-biphenyl-4-yl)-1(R)-(3-methyl-[1,2,4]oxadiazol-5-yl)-ethyl]-amide | 578 |
| 44 | 4-Hydroxy-4'-trifluoromethyl-biphenyl-3-carboxylic acid [2-(3'-chloro-4'-fluoro-biphenyl-4-yl)-1(R)-(3-trifluoromethyl[1,2,4]oxadiazol-5-yl)-ethyl]-amide | 650 |
| 45 | 4-Hydroxy-4'-trifluoromethyl-biphenyl-3-carboxylic acid [1(R)-(3-tert-butyl-[1,2,4]oxadiazol-5-yl)-2-(3'-chloro-4'-fluoro-biphenyl-4-yl)-ethyl]-amide | 638 |

Example 46

5-(3'-Chloro-4'-fluoro-biphenyl-4-yl)-4-[(4-hydroxy-4'-trifluoromethyl-biphenyl-3(R) -carbonyl) amino]-pent-2-enoic acid ethyl ester 3-(3'-Chloro-4'-fluoro-biphenyl-4-yl)-2-(R)-[(4-methoxy-4'-trifluoromethyl-biphenyl-3-carbonyl)-amino]-propionic acid methyl ester (223 mg) was prepared from 4-Methoxy-4'-trifluoromethyl-biphenyl-3-carboxylic acid (141 mg, 0.5 mmol) and-2-(R)-amino-3-(3'-chloro-4'-fluoro-biphenyl-4-yl)-propionic acid methyl ester (155 mg, 0.5 mmol) following the general procedure A.

LC-MS (m/z): 586 $(M+1)^+$; $^1$H NMR (400 MHz, $CDCl_3$): δ 3.24-3.38 (m, 2H), 3.76 (m, 1H), 3.80 (s, 3H), 3.90 (s, 3H), 5.14 (q, 1H), 6.68 (d, 1H), 7.06 (q, 1H), 7.18 (q, 1H), 7.24 (m, 3H), 7.44 (m, 2H), 7.52-7.60 (m, 2H), 7.68-7.72 (m, 3H) and 8.16 (dd, 1H).

3-(3'-Chloro-4'-fluoro-biphenyl-4-yl)-2-(R)-[(4-methoxy-4'-trifluoromethyl-biphenyl-3-carbonyl)-amino]-propionic acid was obtained from the hydrolysis of the above ester using the general procedure C.

4-Methoxy-4'-trifluoromethyl-biphenyl-3-carboxylic acid [2-(3'-chloro-4'-fluoro-biphenyl-4-yl)-1-(R)-(methoxy-methyl-carbamoyl)-ethyl]-amide (0.078 g ) was prepared from 3-(3'-Chloro-4'-fluoro-biphenyl-4-yl)-2-(R)-[(4-methoxy-4'-trifluoromethyl-biphenyl-3-carbonyl)-amino]-propionic acid (0.1 g, 0.179 mmol) and N,O-dimethylhydroxylamine hydrochloride (0.017 g, 0.179 mmol) following general procedure A 4-Methoxy-4'-trifluoromethyl-biphenyl-3-carboxylic acid [2-(3'-chloro-4'-fluoro-biphenyl-4-yl)-1-(R)-formyl-ethyl]-amide was synthesized by the following procedure: To 4-methoxy-4'-trifluoromethyl-biphenyl-3-carboxylic acid [2-(3'-chloro-4'-fluoro-biphenyl-4-yl)-1-(R)-(methoxy-methyl-carbamoyl)-ethyl]-amide (85 mg, 0.14 mmol) in THF (2 mL) was added DIBAL-H (0.64 mL, 0.64 mmol, 1.0 M in DCM) at −78° C. and the mixture was stirred at −78° C. for 2 h. After that potassium sodium tartrate was added and the mixture was stirred overnight, then the mixture was extracted with ethyl acetate (3×25 mL). Organic extracts were combined and concentrated in *vacuo*. The crude product was then purified with silica gel column chromatography by using ethyl acetate:hexanes (2:1) to afford the aldehyde intermediate(45 mg).

$^1$H-NMR(300 MHz, $CDCl_3$): 3.30 (m, 2H), 3.98 (s, 3H), 4.95 (m, 1H), 7.15 (m, 2H), 7.50 (m, 12H), 8.50 (s, 1H), 9.75 (s, 1H); LC/MS (m/z): 556 $(M+1)^+$.

5-(3'-Chloro-4'-fluoro-biphenyl-4-yl)-4-[(4-methoxy-4'-trifluoromethyl-biphenyl-3-(R)-carbonyl)-amino]-pent-2-enoic acid ethyl ester (Isomer 128 mg) and its geometrical isomer (Isomer II, 15 mg) were prepared from the above, 4-methoxy-4'-trifluoromethyl-biphenyl-3-carboxylic acid [2-(3'-chloro-4'-fluoro-biphenyl-4-yl)-1-(R)-formyl-ethyl]-amide (40 mg, 0.072 mmol) and (diethoxy-phosphoryl)-acetic acid ethyl ester (32 mg, 0.14 mmol) following general procedure Q.

Isomer I: $^1$H-NMR(300 MHz, $CDCl_3$): 1.27 (t, 3H), 3.18 (d, 2H), 3.83 (s, 3H), 4.18 (m, 2H), 5.50 (t, 1H), 1.27 (t, 3H), 3.18 (d, 2H), 3.83 (s, 3H), 4.18 (m, 2H), 5.50 (t, 1H), 7.03 (d, 1H), 7.18 (m, 1H), 7.40 (m, 6H), 7.60 (m, 1H), 7.69 (m, 5H), 8.46 (d, 1H), 9.08 (s, 1H); LC/MS (m/z): 626 (M+1)

Isomer II: $^1$H-NMR(300 MHz, $CDCl_3$): 1.27 (s, 3H), 3,11 (d, 2H), 3.91 (s, 3H), 4.20 (m, 2H), 5.30 (m, 1H), 5.94 (dd, 1H), 7.07 (m, 2H), 7.20 (m, 1H), 7.32 (m, 3H), 7.46 (m, 2H), 7.60 (m, 1H), 7.69 (m, 4H), 8.00 (d, 1H), 8.48 (d, 1H); LC/MS (m/z): 626 $(M+1)^+$.

The title compound (example 50) was prepared from 5-(3'-chloro-4'-fluoro-biphenyl-4-yl)-4-[(4-methoxy-4'-trifluoromethyl-biphenyl-3-(R)-carbonyl)-amino]-pent-2-enoic acid ethyl ester (Isomer II, 15 mg, 0.024 mmol) following general procedure P (2.5 mg).

Example 47

4-Hydroxy-4'-trifluoromethyl-biphenyl-3-carboxylic acid [2-(3'-chloro-4'-fluoro-6-methoxy-biphenyl-3-yl)-ethyl]-amide The resin-bound 4-hydroxy-4'-trifluoromethyl-biphenyl-3-carboxylic acid (20 mg, 0.06 mmol) obtained as in Example 1 was reacted with 3-bromo-4-methoxy-phenethyl amine (57 mg, 0.25 mmol) following general procedure A to give resin bound 4-Hydroxy-4'-trifluoromethyl-biphenyl-3-carboxylic acid [2-3-bromo-4-methoxy-phenyl)-ethyl]-amide(18 mg, 0.05 mmol). The above resin bound amide was treated with 3-chloro-4-fluoro-phenyl boronic acid (43 mg, 0.25 mmol) as described in the general procedure D to provide the title compound (8.0 mg,).

$^1$H-NMR(400 MHz, $CDCl_3$): 2.95 (t, 2H), 3.73 (dd, 2H), 3.80 (s, 3H), 6.94 (d, 1H), 7.11 (m, 3H), 7.21 (dd, 1H), 7.31 (m, 1H), 7.37 (d, 1H), 7.52 (m, 4H), 7.64 (m, 3H); LC/MS (m/z): 544 $(M+1)^+$.

Example 48

2-(S)-[(4-Amino-4'-trifluoromethyl-biphenyl-3-carbonyl)-amino]-3-(3'-chloro-4'-fluoro-biphenyl-4-yl)-propionic acid methyl ester 4-Amino-4'-trifluoromethyl-biphenyl-3-carboxylic acid methyl ester (3.0 g) was prepared from 2-amino-5-bromobenzoic acid methyl ester (4.58 g, 20 mmol) and 4-trifluoromethylphenyl boronic acid (4.75 g, 25 mmol) following general procedure D, then hydrolyzed following general procedure C. The above acid (281 mg, 1.0 mmol) was reacted with 2(S)-amino-3-(3'chloro-4'-fluoro-biphenyl-4-yl)-propionic acid methyl ester (343 mg, 1.0 mmol) as described in general procedure A to give the title compound. (300 mg)

$^1$H NMR (400 MHz, $CDCl_3$): 3.34 (m, 2H), 3.83 (s, 3H), 5.06 (m, 1H), 6.77 (d, 1H), 7.42-7.80 (m, 11H), 7.84 (d, 2H), 8.32 (m, 1H); LC/MS (m/z): 571 $(M+1)^+$.

Example 49

3-(3'-Chloro-4'-fluoro-biphenyl-4-yl)-2-(S)-[(4-methanesulfonyl amino-4'-trifluoromethyl-biphenyl-3-carbonyl)-amino]propionic acid methyl ester 2(S)-[(4-Amino-4'trifluoromethyl-biphenyl-3-carbonyl)-amino]-3-(3'-chloro-4'-fluoro-biphenyl-4-yl)-propionic acid methyl ester (30 mg, 0.053 mmol) was reacted with methanesulfonyl chloride (12 mg, 0.11 mmol) following general procedure E to give the title compound. (21 mg)

$^1$H NMR (400 MHz, $CDCl_3$): 3.05 (s, 3H), 3.28, 3.36 (ABX, 2H), 3.85 (s, 3H), 5.07 (dd, 1H), 6.72 (d, 1H), 7.21 (m, 3H), 7.38 (m, 1H), 7.46-7.62 (m, 8H), 7.71 (dd, 1H), 7.82 (d, 1H); LC/MS (m/z): 649 $(M+1)^+$.

Example 50

3'-Chloro-4'-fluoro-4-hydroxy-biphenyl-3-carboxylic acid (2-biphenyl-4-yl-1(S)-methylcarbamoyl-ethyl)-amide Resin bound 3-(Biphenyl-4-yl)-(2S)-[(3'-chloro-4'-fluoro-4-hydroxy-biphenyl-3-carbonyl)-amino]-propionic acid (30 mg, 0.09 mmol) prepared from resin bound 3-(Biphenyl-4-yl)-(2S)-[(3'-chloro-4'-fluoro-4-hydroxy-biphenyl3-carbonyl)-amino]-propionic acid methyl ester following general procedure C, was reacted with methyl amine in THF(0.45 mmol) as described in general procedure A, then cleaved with TMSBr/TFA/DCM (1:1:5) at rt for 4 h. The residue obtained after removing the solvent was purified by chromatography to give the title compound. (36 mg). LC/MS (m/z): 503 $(M+1)^+$.

By analogous methods to those described above the following compounds were synthesized.

| EX. | NAME | LC/MS (M + 1) |
|---|---|---|
| 51 | 3'-Chloro-4'-fluoro-4-hydroxy-biphenyl-3-carboxylic acid {2-biphenyl-4-yl-1-(S)-[2-(4-chloro-phenyl)-ethylcarbamoyl]-ethyl}-amide | 627 |
| 52 | 3'-Chloro-4'-fluoro-4-hydroxy-biphenyl-3-carboxylic acid (1-(S)-allylcarbamoyl-2-biphenyl-4-yl-ethyl)-amide | 529 |
| 53 | 2-(S)-{3-Biphenyl-4-yl-2-(S)-[(3'-chloro-4'-fluoro-4-hydroxy-biphenyl-3-carbonyl)amino]propionylamino}-3-methyl-butyric acid | 589 |

-continued

| EX. | NAME | LC/MS (M + 1) |
|---|---|---|
| 54 | 3-(S)-{3-Biphenyl-4-yl-2-[(3'-chloro-4'-fluoro-4-hydroxy-biphenyl-3-carbonyl)-amino]propionylamino}-propionic acid | 561 |
| 55 | 3'-Chloro-4'-fluoro-4-hydroxy-biphenyl-3-carboxylic acid [2-biphenyl-4-yl-1-(S)-(2-methoxy-ethylcarbamoyl)-ethyl]-amide | 547 |

Example 56

2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-hexanoic acid 5-Bromomsalicylic acid (12.4 g, 57.3 mmol), 3-chloro-4-fluorophenylboronic acid (10.0 g, 57.3 mmol), and palladium tetrakistriphenylphosphine (5.2 g, 5.73 mmol) were dissolved in 200 mL DME and a 2N sodium carbonate (143.4 mL, 143.4 mmol) solution added. The reaction mixture was stirred overnight at 75° C. The solvent was removed and 10 mL concentrated HCl was added, followed by 100 mL THF. Additional HCl was added until the solution was neutralized and the mixture was filtered through a silica gel plug to remove the catalyst. DCM was added to the solution until the layers separated and the organic layer was dried over magnesium sulfate and evaporated. The solid was stirred with DCM for 2 hours, filtered, washed 2× with hexanes and dried (9.1 g).

The 3'-chloro-4'-fluoro-4-hydroxy-biphenyl-3-carboxylic acid (4.56 g, 17.1 mmol), 2-(S)-amino-3-(4-bromo-phenyl)-propionic acid methyl ester (5.0 g, 17.1 mmol) and HBTU (6.48 g, 17.1 mmol) were dissolved in 100 mL DMF. DIEA (5.96 mL, 34.2 mmol) was added and the mixture was stirred overnight. Ethyl acetate (200 mL) and 1N HCl (200 mL) were added to the mixture and the organic layer was washed with 10% sodium carbonate, dried over sodium sulfate and evaporated. The product was purified over silica (hexanes/ethyl acetate) (5.6 g). LC/MS (m/z): 508 $[(M+1)^+]$.

3-(4-bromo-phenyl)-2-(S)-[(3'-chloro-4'-fluoro-4-hydroxy-biphenyl-3-carbonyl)-amino]-propionic acid methyl ester (4.3 g, 8.49 mmol), 3-trifluoromethylphenylboronic acid (3.22 g, 16.98 mmol), and palladium tetrakistriphenylphosphine (1.54 g, 1.70 mmol) were dissolved in 200 mL DME and a 2N sodium carbonate (21.23 mL, 21.23 mmol) solution added. The reaction mixture was stirred overnight at 75° C. The solvent was removed and 5 mL concentrated HCl was added, followed by 100 mL THF. Additional HCl was added until solution was neutralized and the mixture was filtered through a silica gel plug to remove the catalyst. DCM was added to the solution until the layers separated and the organic layer was dried over magnesium sulfate and evaporated. The solid was stirred with DCM for 2 hours, filtered, washed 2× with hexanes and dried (3.0 g). LC/MS (m/z): 572 $[(M+1)^+]$.

2-(S)-[(3'-Chloro-4'-fluoro-4-hydroxy-biphenyl-3-carbonyl)-amino]-3-(3'-trifluoromethyl-biphenyl-4-yl)-propionic acid methyl ester (3.0 g, 5.2 mmol) was dissolved in 100 mL of THF-methanol (4-1), cooled to 0° C. and 20 mL 2N LiOH added. The reaction was stirred at 0° C. for 1 hour. Ethyl acetate (100 mL) and 1N HCl (100 mL) were added to the mixture and the organic washed with brine, dried and evaporated to give 2-(S)-[(3'-chloro-4'-fluoro-4-hydroxy-biphenyl- 3-carbonyl)-amino]-3-(3'-trifluoromethyl-biphenyl-4-yl)-propionic acid (2.8 g). LC/MS (m/z): 558 [$(M+1)^+$].

Resin-bound fmoc-norleucine (0.08 mmol) was deprotected with 20% piperidine in DMF (25 mL) for 2 hours. The reaction mixture was drained and washed 3× with DMF, methanol and DCM (3×15 mL each solvent).

To the resin-bound norleucine (0.08 mmol), a solution of 2-(S)-[(3'-chloro-4'-fluoro-4-hydroxy-biphenyl-3-carbonyl)-amino]-3-(3'-trifluoromethyl-biphenyl-4-yl)-propionic acid (0.118 g, 0.20 mmol) in DMF (0.2 mL), HOBt (0.027 g, 0.20 mmol) in DMF (0.2 mL) and DIC (0.025 g, 0.2 mmol) in DMF (0.2 mL) were added and the mixture was shaken overnight. The reaction mixture was drained and washed with DMF, methanol and DCM (3×150 mL each solvent).

Resin-bound 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-3-phenyl-propionic acid was treated with 20% TFA in DCM (2 mL) for 1 hour. The filtrate was collected and evaporated to give 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-3-phenyl-propionic acid. The product was purified via prep TLC (ethyl acetate/methanol/acetic acid). LC/MS (m/z): 671 [$(M+1)^+$].

By analogous methods to those described above the following compounds were synthesized.

| EX. | NAME | LC/MS (M + 1) |
|---|---|---|
| 57 | 1-[2-(S)-[(3'-Chloro-4'-fluoro-4-hydroxy-biphenyl-3-carbonyl)-amino]-3-(3'-trifluoromethyl-biphenyl-4-yl)-propionyl]-pyrrolidine-2-(S)-carboxylic acid | 655 |
| 58 | 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-4-methylpentanoic acid | 504 |
| 59 | {[2-(S)-[(3'-Chloro-4'-fluoro-4-hydroxy-biphenyl-3-carbonyl)-amino]-3-(3'-trifluoromethyl-biphenyl-4-yl)-propionyl]-methyl-amino}-acetic acid | 504 |
| 60 | [2-(S)-[(3'-Chloro-4'-fluoro-4-hydroxy-biphenyl-3-carbonyl)-amino]-3-(3'-trifluoromethyl-biphenyl-4-yl)-propionylamino]-2-(S)-phenyl-acetic acid | 490 |
| 61 | 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-3-(4-hydroxy-phenyl)-propionic acid | 721 |
| 62 | 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-propionic acid | 629 |
| 63 | 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-3-methyl-butyric acid | 657 |
| 64 | 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-pentanedioic acid | 687 |
| 65 | 2-(S)-[2-(S)-[(3'-Chloro-4'-fluoro-4-hydroxy-biphenyl-3-carbonyl)-amino]-3-(3'-trifluoromethyl-biphenyl-4-yl)-propionylamino]-succinic acid | 673 |

Example 66

4-Methoxy-4'-trifluoromethyl-biphenyl-3-carboxylic acid [2-(R)-(4-methyl-piperazin-1-yl)-2-oxo-1-(4'-trifluoromethyl-biphenyl-4-ylmethyl)-ethyl]-amide 4-Methoxy-4'-trifluoromethyl-biphenyl-3-carboxylic acid [2-(R)-(4-methyl-piperazin-1-yl)-2-oxo-1-(4'-trifluoromethyl-biphenyl-4-ylmethyl)-ethyl]-amide (83 mg) was prepared from 2-(R)-[(4-methoxy-4'-trifluoromethyl-biphenyl-3-carbonyl)-amino]-3-(4'-trifluoromethyl-biphenyl-4-yl)-propionic acid (96 mg, 0.0.16 mmol), N-methyl piperazine (22 μL, 0.19 mmol), HBTU (68 mg, 0.18 mmol) and DIEA (43 μL, 0.24 mmol) similar to general procedure A. Silica gel chromatography using 25% EtOAc in hexanes afforded the title compound.

LC-MS (m/z): 670 $(M+1)^+$; $^1$H NMR (400 MHz, $CDCl_3$): δ 2.22 (s, 3H), 2.30-2.36 (m, 4H), 3.13-3.21 (m, 2H), 3.42 (m, 2H), 3.62 (m, 2H), 3.82 (s, 3H), 5.36 (q, 1H), 7.09 (d, 1H), 7.20 (t, 1H), 7.28 (d, 2H), 7.39-7.42 (m, 1H), 7.46 (d, 3H), 7.57 (d, 1H), 7.59 (m, 2H), 7.63 (m, 2H), 7.66 (m, 2H), and 12.14 (s, 1H).

Example 67

4-Hydroxy-4'-trifluoromethyl-biphenyl-3-carboxylic acid [1-(3'-chloro-4'-fluoro-biphenyl-4-ylmethyl)-2-(S)-(4-methyl-piperazin-1-yl)-2-oxo-ethyl]-amide 4-Hydroxy-4'-trifluoromethyl-biphenyl-3-carboxylic acid [1-(3'-chloro-4'-fluoro-biphenyl-4-ylmethyl)-2-(S)-(4-methyl-piperazin-1-yl)-2-oxo-ethyl]-amide (46 mg) was prepared from 3-(3'-Chloro-4'-fluoro-biphenyl-4-yl)-2-(S)-[(4-hydroxy-4'-trifluoromethyl-biphenyl-3-carbonyl)-amino]-propionic acid (55 mg, 0.1 mmol) and N-methyl piperazine following the general procedure A.

LC-MS (m/z): 640 $(M+1)^+$; $^1$H NMR (400 MHz, $CDCl_3$): δ 2.22 (s, 3H), 2.30-2.36 (m, 4H), 3.13-3.21 (m, 2H), 3.42 (m, 2H), 3.62 (m, 2H), 5.36 (q, 1H), 7.09 (d, 1H), 7.20 (t, 1H), 7.28 (d, 2H), 7.39-7.42 (m, 1H), 7.46 (d, 3H), 7.57 (d, 1H), 7.59 (m, 2H), 7.63 (m, 2H), 7.66 (m, 2H), and 12.14 (br, 1H).

Example 68

4-Hydroxy-4'-trifluoromethyl-biphenyl-3-carboxylic acid {2-(3'-chloro-4'-fluoro-biphenyl-4-yl)-1-(R)-[(2-dimethylamino-ethyl)-methyl-carbamoyl]-ethyl}-amide 4-Hydroxy-4'-trifluoromethyl-biphenyl-3-carboxylic acid {2-(3'-chloro-4'-fluoro-biphenyl-4-yl)-1-(R)-[(2-dimethylamino-ethyl)-methyl-carbamoyl]-ethyl}-amide (49 mg, 76%) was prepared from 3-(3'-Chloro-4'-fluoro-biphenyl-4-yl)-2-(R)-[(4-hydroxy-4'-trifluoromethyl-biphenyl-3-carbonyl)-amino]-propionic acid (55 mg, 0.1 mmol) following the general procedure A.

LC-MS (m/z): 643 $(M+3)^+$; $^1$H NMR (400 MHz, $CDCl_3$): δ 2.02 (s, 3H), 2.12 (s, 6H), 2.28 (m, 1H), 2.42 (m, 1H), 3.24 (t, 2H), 3.38 (m, 2H), 4.74 (q, 1H), 7.10 (dd, 1H), 7.18 (t, 2H), 7.36 (m, 2H), 7.44 (dd, 2H), 7.49 (d, 2H), 7.56 (m, 1H), 7.68 (d, 2H), 7.72 (d, 2H), 7.78 (t, 1H), and 12.12 (br, 1H).

Example 69

4-Hydroxy-4'-trifluoromethyl-biphenyl-3-carboxylic acid [1-(R)-(3'-chloro-4'-fluoro-biphenyl-4-ylmethyl)-2-oxo-propyl]-amide 4-Methoxy-4'-trifluoromethyl-biphenyl-3-carboxylic acid [2-(3'-chloro-4'-fluoro-biphenyl-4-yl)-1-(R)-(methoxy-methyl-carbamoyl)-ethyl]-amide (0.13 g) was prepared from the 3-(3'-Chloro-4'-fluoro-biphenyl-4-yl)-2-(R)-[(4-methoxy-4'-trifluoromethyl-biphenyl-3-carbonyl)-amino]-propionic acid (0.16 g, 0.28 mmol) and N,O-dimethylhydroxylamine hydrochloride (0.027, 0.28 mmol) according to the general procedure A.

To a solution of 4-Methoxy-4'-trifluoromethyl-biphenyl-3-carboxylic acid [2-(3'-chloro-4'-fluoro-biphenyl-4-yl)-1-

(R)-(methoxy-methyl-carbamoyl)-ethyl]-amide (0.1 g, 0.162 mmol) in anhydrous THF (2 mL) was added methyl magnesium bromide [0.35 ml, 1.4M solution in Toluene/THF (75:25)] at 0° C. and allowed to come to room temperature and stirred for 6 h. Reaction was quenched with aq $NH_4Cl$ and extracted with EtOAc. Organic layer was washed with water, brine and dried over $Na_2SO_4$. Solvent was removed under reduced pressure and the residue was purified by silicagel column chromatography to get pure 4-Methoxy-4'-trifluoromethyl-biphenyl-3-carboxylic acid [1-(R)-(3'-chloro-4'-fluoro-biphenyl-4-ylmethyl)-2-oxo-propyl]-amide (0.055 g)

LC/MS (m/z): 570.2 $(M+1)^+$.

4-Hydroxy-4'-trifluoromethyl-biphenyl-3-carboxylic acid [1-(R)-(3'-chloro4'-fluoro-biphenyl-4-ylmethyl)-2-oxo-propyl]-amide, example 73 (0.028 g) was prepared from 4-Methoxy-4'-trifluoromethyl-biphenyl-3-carboxylic acid [1-(R)-(3'-chloro-4'-fluoro-biphenyl-4-ylmethyl)-2-oxo-propyl]-amide (0.05 g, 0.087 mmol) following general procedure P. $^1$HNMR (400 MHz, $CDCl_3$): 2.30 (s, 3H), 3.27 (dd, 1H), 3.37 (dd, 1H), 5.10 (s, 1H) 7.08-7.30 (m, 5H) 7.38 (m, 1H), 7.44-7.52 (m, 3H), 7.54-7.70 (m, 6H), 12.15 (s, 1H)

LC/MS (m/z): 556.9 $(M+1)^+$.

Example 70

4-Hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide

[2-(3'-Chloro-4'-fluoro-biphenyl-4-yl)-1-(R)-(3-methyl-[1,2,4]oxadiazol-5-yl)-ethyl]-carbamic acid tert-butyl ester (96 mg,) was prepared from 2-(R)-tert-butoxycarbonylamino-3-(3'-chloro-4'-fluoro-biphenyl-4-yl)-propionic acid pentafluorophenyl ester (140 mg, 0.25 mmol) and N-hydroxy-acetamidine (37 mg, 0.5 mmol) following the general procedure O.

2-(3'-Chloro-4'-fluoro-biphenyl-4-yl)-1-(3-methyl-[1,2,4]oxadiazol-5-yl)-ethylamine (33 mg) was prepared from [2-(3'-Chloro-4'-fluoro-biphenyl-4-yl)-1-(R)-(3-methyl-[1,2,4]oxadiazol-5-yl)-ethyl]-carbamic acid tert-butyl ester (43 mg, 0.1 mmol) and hydrochloric acid (0.5 mL, 4.0 M. solution in dioxane) following the typical Boc deprotection procedure N.

4-Methoxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide (55 mg) was prepared from 4-Methoxy-4'-trifluoromethyl-biphenyl-3-carbonyl chloride (31 mg, 0.1 mmol) and 2-(3'-Chloro-4'-fluoro-biphenyl-4-yl)-1-(R)-(3-methyl-[1,2,4]oxadiazol-5-yl)-ethylamine (40 mg, 0.12 mmol) following the general procedure M.

LC-MS (m/z): 610 $(M+1)^+$; $^1$H NMR (400 MHz, $CDCl_3$): δ 2.41 (s, 3H), 3.59 (t, 2H), 3.91 (s, 3H), 5.87 (q, 1H), 7.08 (d, 1H), 7.20 (dd, 2H), 7.38 (m, 1H), 7.46 (d, 3H), 7.58 (dd, 1H), 7.64-7.72 (m, 4H), 7.74 (d, 1H), 7.82 (dd, 1H), and 12.16 (br, 1H).

4-Hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide (94 mg) was prepared from 4-methoxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide (122 mg, 0.20 mmol) and boron tribromide (0.5 mL, 0.5 mmol, 1.0 M solution in DCM) following the general procedure P.

LC-MS (m/z): 596 $(M+1)^+$; $^1$H NMR (400 MHz, $CDCl_3$): δ 2.41 (s, 3H), 3.45 (d, 2H), 3.98 (m, 1H), 5.84 (q, 1H), 6.98 (d, 1H), 7.10 (d, 1H), 7.16-7.20 (m, 2H), 7.36 (m, 1H), 7.44 (d, 2H), 7.48 (d, 1H), 7.58 (m, 2H), 7.62-7.68 (m, 4H), and 11.85 (br, 1H).

By analogous methods to those described above the following compounds were synthesized.

| EX. | NAME | LC/MS (M + 1) |
|---|---|---|
| 71 | 4-Hydroxy-4'-methanesulfonyl-biphenyl-3-carboxylic acid [2-(4'-methanesulfonyl-biphenyl-4-yl)-1-(R)-(3-methyl-[1,2,4]oxadiazol-5-yl)-ethyl]-amide | 631.7 |
| 72 | 4-Hydroxy-3',5'-bis-trifluoromethyl-biphenyl-3-carboxylic acid [2-(4'-methanesulfonyl-biphenyl-4-yl)-1-(R)-(-methyl-[1,2,4]oxadiazol-5-yl)-ethyl]-amide | 689.6 |
| 73 | 3',4'-Difluoro-4-hydroxy-biphenyl-3-carboxylic acid [2-(3',4'-difluoro-biphenyl-4-yl)-1-(R)-(3-methyl-[1,2,4]oxadiazol-5-yl)-ethyl]-amide | 547.5 |
| 74 | 4-Hydroxy-4'-trifluoromethyl-biphenyl-3-carboxylic acid [1-(R)-(3-methyl-[1,2,4]oxadiazol-5-yl)-2-(4'-trifluoromethyl-biphenyl-4-yl)-ethyl]-amide | 611.5 |

Example 75

4-Hydroxy-3',5'-bis-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide 4-Ethoxy-3',5'-bis-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide (57 mg) was prepared from 2-(3'-chloro-4'-fluoro-biphenyl-4-yl)-1-(R)-(3-methyl-[1,2,4]oxadiazol-5-yl)-ethylamine (33 mg, 0.10 mmol) and 4-Ethoxy-3',5'-bis-trifluoromethyl-biphenyl-3-carboxylic acid (37 mg, 0.1 mmol) following the general procedure A.

LC-MS (m/z): 693 $(M+2)^+$; $^1$H NMR (400 MHz, $CDCl_3$): δ 1.49 (t, 3H), 2.41 (s, 3H), 3.47 (d, 2H), 4.09 (q, 2H), 5.85 (q, 1H), 7.03 (d, 1H), 7.19 (m, 2H), 7.38 (m, 1H), 7.42 (d, 4H), 7.52 (dd, 1H), 7.58 (d, 1H), 7.64 (dd, 1H), 7.81 (s, 2H), and 7.88 (s, 1H).

4-Hydroxy-3',5'-bis-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide (48 mg) was prepared from 4-Ethoxy-3',5'-bis-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide (69 mg, 0.10 mmol) and boron tribromide (0.25 mL, 0.25 mmol, 1.0 M solution in DCM) following the general procedure P.

LC-MS (m/z): 665 $(M+2)^+$; $^1$H NMR (400 MHz, $CDCl_3$): δ 2.39 (s, 3H), 3.45 (d, 2H), 5.84 (q, 1H), 7.08 (d, 1H), 7.18 (m, 2H), 7.38 (m, 1H), 7.44 (d, 4H), 7.54 (dd, 1H). 7.60 (d, 1H), 7.66 (dd, 1H), 7.83 (s, 2H), 7.90 (s, 1 H), and 11.91 (br, 1H).

Example 76

Acetic acid 3-[2-(3'-chloro-4'-fluoro-biphenyl-4-yl)-1-(R)-(3-methyl-[1,2,4]oxadiazol-5-yl)-ethylcarbamoyl]-4'-trifluoromethyl-biphenyl-4-yl ester Acetic acid 3-[2-(3'-chloro-4'-fluoro-biphenyl-4-yl)-1-(R)-(3-methyl-[1,2,4]oxadiazol-5-yl)-ethylcarbamoyl]-4'-trifluoromethyl-biphenyl-4-yl ester (45 mg) was prepared from 2-(3'-Chloro-4'-fluoro-biphenyl-4-yl)-1-(R)-(3-methyl-[1,2,4]oxadiazol-5-yl)-ethylamine (33 mg, 0.1 mmol) and acetic acid 3-chlorocarbonyl-4'-trifluoromethyl-biphenyl-4-yl ester (34 mg, 0.1 mmol) following the general procedure M.

LC-MS (m/z): 582 $(M+2)^+$; $^1$H NMR (400 MHz, $CDCl_3$): δ 2.10 (s, 3H), 2.39 (s, 3H), 3.42 (dd, 1 H), 3.50 (dd, 1H), 5.85

(q, 1H), 7.06 (d, 1H), 7.24 (dd, 2H), 7.38 (m, 1H), 7.42 (d, 2H), 7.48 (d, 1H), 7.58 (dd, 1H), 7.69 (m, 4H), 7.74 (d, 2H), and 8.18 (d, 1H).

Example 77

4-Hydroxy-4'-trifluoromethyl-biphenyl-3-carboxylic acid [2-(4'-benzyloxy-3'-fluoro-biphenyl-4-yl)-1-(R)-(3-methyl-[1,2,4]oxadiazol-5-yl)-ethyl]-amide 4-Hydroxy-4'-trifluoromethyl-biphenyl-3-carboxylic acid [(4'-benzyloxy-3'-fluoro-biphenyl-4-yl)-1-(R)-(3-methyl-[1,2,4]oxadiazol-5-yl)-ethyl]-amide (58 mg) was prepared from acetic acid 3-chlorocarbonyl-4'-trifluoromethyl-biphenyl-4-yl ester (1.96 mL, 0.1 M $CH_2Cl_2$), 2-(4'-benzyloxy-3'-fluoro-biphenyl-4-yl)-1-(R)-(3-methyl-[1,2,4]oxadiazol-5-yl)-ethylamine hydrochloride (90 mg, 0.178 mmol) and DIEA (95 μL, 0.55 mmol) analogous to procedure M. The crude reaction mixture was concentrated and redissolved in THF (3 mL) and MeOH (1 mL). 1N $NaHCO_3$ (200 μL) and 1 N $Na_2CO_3$ (50 μL) were added and the hydrolysis was followed by TLC and LCMS. Once complete, the reaction was diluted with EtOAc and the layers were separated. After extraction and drying the combined organics over $MgSO_4$, the crude mixture was concentrated onto silica gel and purified by chromatography using 15% EtOAc in hexanes.

LC-MS (m/z): 668 $(M+1)^+$; $^1H$ NMR (400 MHz, $CDCl_3$): δ 2.40 (s, 3H), 3.43 (d, 2H), 5.20 (s, 2H), 5.82 (q, 1H), 7.02-7.22 (m, 5H), 7.27-7.41(m, 2H), 7.42-7.44 (m, 6H), 7.50-7.68 (m, 6H), 11.83 (s, 1 H).

Example 78

4-Hydroxy-4'-trifluoromethyl-biphenyl-3-carboxylic acid [2-(4'-methanesulfonyl-biphenyl-4-yl)-1-(R)-(3-methyl-[1,2,4]oxadiazol-5-yl)-ethyl]-amide 4-Hydroxy-4'-trifluoromethyl-biphenyl-3-carboxylic acid [2(4'-methanesulfonyl-biphenyl-4-yl)-1-(R)-(3-methyl-[1,2,4]oxadiazol-5-yl)-ethyl]-amide (49 mg) was prepared from acetic acid 3-chlorocarbonyl-4'-trifluoromethyl-biphenyl-4-yl ester (1.93 mL, 0.1 M $CH_2Cl_2$) and 2-(4'-methanesulfonyl-biphenyl-4-yl)-1-(R)-(3-methyl-[1,2,4]oxadiazol-5-yl)-ethylamine hydrochloride (80 mg, 0.175 mmol) and DIEA (92 μL, 0.525 mmol) using standard procedure M. The crude reaction mixture was concentrated and redissolved in THF (3 mL) and MeOH (1 mL). 1 N $NaHCO_3$ (200 μL) and 1N $Na_2CO_3$ (50 μL) were added and the hydrolysis was followed by TLC and LCMS. Once complete, the reaction was diluted with EtOAc and the layers were separated. After extraction and drying the combined organics over $MgSO_4$, the crude mixture was concentrated onto silica gel and purified by chromatography using 15% EtOAc in hexanes.

LC-MS (m/z): 622 $(M+1)^+$; $^1H$ NMR (400 MHz, $CDCl_3$): δ 2.42 (s, 3H), 3.09 (s, 3H), 3.46 (d, 2H), 5.86 (q, 1H), 7.09-7.19 (m, 3H), 7.23 (d, 2H), 7.52-7.73 (m, 8H), 7.99 (d, 2H), 11.80(s, 1H).

Example 79

4-Hydroxy-4'-nitro-biphenyl-3-carboxylic acid [2-(3'-chloro-4'-fluoro-biphenyl-4-yl)-1-(R)-(3-methyl-[1,2,4]oxadiazol-5-yl)-ethyl]-amide 4-Hydroxy-4'-nitro-biphenyl-3-carboxylic acid (1.98) was prepared from 5-bromosalicylic acid (2.6 g, 11.9 mmol ) and 4-nitrophenylboronic acid (3.0 g, 17.9) following general procedure D To a solution of 4-Hydroxy-4'-nitro-biphenyl-3-carboxylic acid (2.0 g, 7.71 mmol) in acetone was added $K_2CO_3$(2.34 g, 16.9 mmol) and MeI (4.3 g, 30.8 mmol) and refluxed for 12 h. Reaction mixture was diluted with EtOAc and filtered, filtrate was washed with water brine and dried over $Na_2SO_4$. Solvent was removed under reduced pressure and silicagel column chromatography gave pure 4-Methoxy-4'-nitro-biphenyl-3-carboxylic acid methyl ester (1.9 g).

To a solution of 4-Methoxy-4'-nitro-biphenyl-3-carboxylic acid methyl ester (0.15 g, 0.52 mmol) in THF-MeOH (3:1) was added LiOH (1.04 mL of 1N solution) and heated at 65° C. for 12 h. Reaction mixture was acidified with HCl (1N, 1.04 mL) and diluted with EtOAc, and washed with water, brine and dried over $Na_2SO_4$. Solvent was removed under reduced pressure and the product 4-Methoxy-4'-nitro-biphenyl-3-carboxylic acid (0.12 g) was used in the next reaction without further purification.

4-Methoxy-4'-nitro-biphenyl-3-carboxylic acid [2-(3'-chloro-4'-fluoro-biphenyl-4-yl)-1-(R)-(3-methyl-[1,2,4]oxadiazol-5-yl)-ethyl]-amide (0.045 g) was prepared from 4-Methoxy-4'-nitro-biphenyl-3-carboxylic acid (0.03 g, 0.11 mmol) and 2-(3'-Chloro-4'-fluoro-biphenyl-4-yl)-1-(R)-(3-methyl-[1,2,4]oxadiazol-5-yl)-ethylamine hydrochloride salt (0.04 g, 0.11 mmol) following general procedure A LC/MS (m/z): 587.9 $(M+1)^+$.

4-Hydroxy-4'-nitro-biphenyl-3-carboxylic acid [2-(3'-chloro-4'-fluoro-biphenyl-4-yl)-1-(R)-(3-methyl-[1,2,4]oxadiazol-5-yl)-ethyl]-amide (0.017 g) was prepared from 4-Methoxy-4'-nitro-biphenyl-3-carboxylic acid [2-(3'-chloro-4'-fluoro-biphenyl-4-yl)-1-(R)-(3-methyl-[1,2,4]oxadiazol-5-yl)-ethyl]-amide (0.03 g, 0.05 mmol) following general procedure P.

$^1$HNMR (400 MHz, $CDCl_3$): 2.42 (s, 3H), 3.46 (dd, 2H), 5.84 (m, 1H), 6.94 (d, 1H), 7.10-7.24 (m, 4H), 7.38 (m, 1H), 7.45 (d, 2H), 7.51 (d, 1H), 7.56 (dd, 1H), 7.64 (m 2H), 7.70 (m, 1H) 8.26 (d, 2H), 11.90 (s, 1H).

LC/MS (m/z): 573.8 $(M+1)^+$.

Example 80

6-Benzyloxy-4-hydroxy4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide To a solution of 5-Bromo-2,4-dihydroxy-benzoic acid methyl ester (1.0 g, 4.04 mmol) in DMF (7 mL) was added $Cs_2CO_3$ (1.58 g, 4.85 mmol) and benzylbromide (0.69 g, 4.04 mmol) and heated at 70° C. for 6 h. Reaction mixture was diluted with EtOAc (10 mL) and filtered, filtrate was washed with water, brine and dried over $Na_2SO_4$. Solvent was removed under reduced pressure and silicagel column chromatography (EtOAc:Hex, 1:3) gave pure 4-benzyloxy-5-bromo-2-hydroxy-benzoic acid methyl ester (0.62 g).

To a solution of 4-benzyloxy-5-bromo-2-hydroxy-benzoic acid methyl ester (0.5 g, 1.48 mmol) in toluene (5 mL) was added 4-trifluorophenylboronic acid (0.56 g, 2.96 mmol), tetrakistriphenylphosphine (0.17 g, 0.14 mmol), $Na_2CO_3$ (2.96 ml, 1N solution) and stirred the reaction mixture at 80° C. for 12 h. Reaction mixture was diluted with EtOAc (10 mL) and washed with water, brine and dried over $Na_2SO_4$. Solvent was removed under reduced pressure and silicagel column chromatography (20:80 EtOAc:hexane) gave pure 6-Benzyloxy-4-hydroxy-4'-trifluoromethyl-biphenyl-3-carboxylic acid methyl ester (0.39 g).

6-Benzyloxy-4-hydroxy-4'-trifluoromethyl-biphenyl-3-carboxylic acid (0.13 g,) was prepared from 6-Benzyloxy-4- hydroxy-4'-trifluoromethyl-biphenyl-3-carboxylic acid methyl ester (0.16 g, 0.39 mmol) following general procedure C.

To a solution of 6-Benzyloxy-4-hydroxy-4'-trifluoromethyl-biphenyl-3-carboxylic acid (52 mg, 0.13 mmol) in THF:DCE (1:1, 2 mL) was added PS-Carbodiimide resin (0.14 g, 1.3 mmol/g) and 2-(3'-Chloro-4'-fluoro-biphenyl-4-yl)-1-(R)-(3-methyl-[1,2,4]oxadiazol-5-yl)-ethylamine (0.03 g, 0.09 mmol) and stirred for 12 h, resin was filtered and washed with EtOAc (5 mL), filtrate was concentrated and silicagel chromatography of the residue gave pure 6-Benzyloxy-4-hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide (0.013 g).

$^1$HNMR (400 MHz, $CDCl_3$): 2.39 (s, 3H), 3.42 (dd, 2H), 5.13 (s, 2H), 5.80 (m 1H), 6.63 (s, 1H), 6.68 (d, 1H), 7.10-7.24 (m, 4H), 7.27-7.40 (m, 6H), 7.42 (d, 2H), 7.54-7.64 (m, 5H), 12.2 (s, 1H); LC/MS (m/z): 703.0 $(M+1)^+$.

Example 81

5-Chloro-4-hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide N-Bromosuccinimide (2.38 g, 13.38 mmol) was added to a solution of 3-chlorosalicylic acid (2.1 g, 12.16 mmol) in $CH_3CN$ (10 mL) solution and stirred for 1 h, reaction mixture was diluted with water (25 mL), solids were filtered and washed with water and dried to get 5-Bromo-3-chloro-2-hydroxy-benzoic acid (2.87 g).

Methyl Iodide (3.83 g, 27.04 mmol) was added to a solution of 5-Bromo-3-chloro-2-hydroxy-benzoic acid (1.7 g, 6.76 mmol) and $Cs_2CO_3$ (4.83 g, 14.86 mmol) in DMF (10 mL) and heated at 50° C. for 12 h. The reaction mixture was diluted with EtOAc (30 mL) and filtered over celite pad. Filtrate was washed with water, brine and dried over $Na_2SO_4$. Solvent was removed and the residue was purified by silicagel column chromagography to get pure 5-Bromo-3-chloro-2-methoxy-benzoic acid methyl ester (1.56 g).

4-Trifluoromethylphenylboronic acid (0.815 g, 4.29 mmol) was added to a solution of 5-Bromo-3-chloro-2-methoxy-benzoic acid methyl ester (1.0 g, 3.57 mmol), $Pd(PPh_3)_4$ (0.2 g, 0.178 mmol) and CsF (1.08 g, 7.15 mmol) in DME (10 mL ) and heated at 85° C. for 10 h. The reaction was diluted with EtOAc (20 mL) and filtered, filtrate was washed water, brine and dried over $Na_2SO_4$. Solvent was removed under reduced pressure and the silicagel column chromatography gave pure 5-Chloro-4-methoxy-4'-trifluoromethyl-biphenyl-3-carboxylic acid methyl ester (0.94 g).

5-Chloro-4-methoxy-4'-trifluoromethyl-biphenyl-3-carboxylic acid (0.62 g) was prepared from 5-Chloro-4-methoxy-4'-trifluoromethyl-biphenyl-3-carboxylic acid methyl ester (0.7 g, 2.03 mmol) following the procedure C.

5-Chloro-4-methoxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide (0.5 g) was prepared from 5-Chloro-4-methoxy-4'-trifluoromethyl-biphenyl-3-carboxylic acid (0.4 g, 1.2 mmol) and 2-(3'-chloro-4'-fluoro-biphenyl-4-yl)-1-(R)-(3-methyl-[1,2,4] oxadiazol-5-yl)-ethylamine (0.4 g, 1.2 mmol) according to the general procedure A.

LC/MS (m/z): 644.0 $(M+1)^+$.

5-Chloro-4-hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide (0.22 g) was prepared from 5-Chloro-4-methoxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide (0.4 g, 0.62 mmol) following general procedure P.

$^1$HNMR (400MHz, $CDCl_3$): 2.41 (s, 3H), 3.46 (m, 2H), 5.83 (dd, 1H), 7.06-7.23 (m, 4H), 7.35-7.70 (m, 10H), 7.77 (d, 1H)

LC/MS (m/z): 630.5 $(M+1)^+$.

Example 82

Acetic acid 5'-[2-(3'-chloro-4'-fluoro-biphenyl-4-yl)-1-(R)-(3-methyl-[1,2,4]oxadiazol-5-yl) ethylcarbamoyl]-4-trifluoromethyl[1,1';3',1"]terphenyl-4'-yl ester To a solution of 5-Bromo-4-hydroxy-4'-trifluoromethyl-biphenyl-3-carboxylic acid methylester (0.3 g, 0.8 mmol) in toluene (5 mL) was added phenylboronic acid (0.19 g, 1.6 mmol), tetrakistriphenylphosphine (0.0.09 g, 0.08 mmol), $Na_2CO_3$(2.4 ml, 1N solution) and stirred the reaction mixture at 80° C. for 10 h. The reaction mixture was diluted with EtOAc (10 mL) and washed with water, brine and dried over $Na_2SO_4$. Solvent was removed under reduced pressure and silicagel column chromatography (20:80 EtOAc:hexane) gave pure 4'-Hydroxy-4-trifluoromethyl-[1,1';3',1"]terphenyl-5'-carboxylic acid methyl ester (0.21 g).

4'-Hydroxy-4-trifluoromethyl-[1,1';3',1"]terphenyl-5'-carboxylic acid (0.17 g) was prepared from 4'-Hydroxy-4-trifluoromethyl-[1, 1';3',1"]terphenyl-5'-carboxylic acid methyl ester (0.2 g, 0.53 mmol ) following general procedure C.

Acetic acid 5'-[2-(3'-chloro-4'-fluoro-biphenyl-4-yl)-1-(R)-(3-methyl-[1,2,4]oxadiazol-5-yl)-ethylcarbamoyl]-4-trifluoromethyl-[1,1 ';3',1"]terphenyl-4'-yl ester (0.04 g ) was prepared from Acetic acid 5'-chlorocarbonyl-4-trifluoromethyl-[1,1';3',1"]terphenyl-4'-yl ester (0.06 g, 0.14 mmol) [prepared from 4'-Hydroxy-4-trifluoromethyl-[1,1';3',1"]terphenyl-5'-carboxylic acid following general procedures K & L.] and 2-(3'-Chloro-4'-fluoro-biphenyl-4-yl)-1-(R)-(3-methyl-[1,2,4]oxadiazol-5-yl)-ethylamine (0.047 g,0.14 mmol) following general procedure M.

$^1$HNMR (400 MHz, $CDCl_3$): 1.85 (s, 3H), 2.39 (s, 3H), 3.37 (dd, 1H), 3.53 (dd, 1H), 5.84 (m, 1H), 7.09-7.24 (m, 4H), 7.33-7.50 (m, 8H), 7.55 (dd, 1H), 7.64-7.73 (m, 5H), 7.99 (d, 1H), LC/MS (m/z): 744.9 $(M+1)^+$.

Example 83

4-Hydroxy-4'-trifluoromethyl-biphenyl-3-carboxylic acid [2-(4-benzyloxy-phenyl)-1-(R)-(3-methyl-[1,2,4]oxadiazol-5-yl)-ethyl]-amide

[2-(4-Benzyloxy-phenyl)-1-(R)-(3-methyl-[1,2,4]oxadiazol-5-yl)-ethyl]-carbamic acid tert-butyl ester (2.75 g) was prepared from N-boc-O-benzyl tyrosine (2.6 g, 7.00 mmol) following general procedure G.

2-(4-Benzyloxy-phenyl)-1-(R)-(3-methyl-[1,2,4]oxadiazol-5-yl)-ethylamine hydrochloride salt (1.27 g) was prepared from the [2-(4-Benzyloxy-phenyl)-1-(R)-(3-methyl-[1,2,4]oxadiazol-5-yl)-ethyl]-carbamic acid tert-butyl ester (1.5 g, 3.67 mmol) following general procedure N.

4-Hydroxy-4'-trifluoromethyl-biphenyl-3-carboxylic acid [2-(4-benzyloxy-phenyl)-1-(R)-(3-methyl-[1,2,4]oxadiazol-5-yl)-ethyl]-amide was prepared from Acetic acid 3-chlorocarbonyl-4'-trifluoromethyl-biphenyl-4-yl ester (0.32 g, 0.93 mmol) and 2-(4-Benzyloxy-phenyl)-1-(R)-(3-methyl-[1,2,4] oxadiazol-5-yl)-ethylamine hydrochloride salt (0.32 g, 0.93 mmol) following the general procedure M. followed by the hydrolysis of the resulting acetate using $K_2CO_3$.

$^1$HNMR (400 MHz, $CDCl_3$): 2.39 (s, 3H), 3.35 (d, 2H), 5.01 (s, 2H), 5.75 (, 1H), 6.85-6.93 (m, 3H), 6.97-7.21(m, 2H), 7.10 (d, 1H), 7.29-7.43 (m, 5H), 7.46 (d, 1H), 7.59 (d, 2H), 7.65 (dd, 1H), 7.70 (d, 2H).11.90 (s, 1H)

Example 84

4-Hydroxy-4'-trifluoromethyl-biphenyl-3-carboxylic acid [2-(4'-fluoro-biphenyl-4-yl)-1-(R)-(3-methyl-[1,2,4]oxadiazol-5-yl)-ethyl]-amide 4-Hydroxy-4'-trifluoromethyl-biphenyl-3-carboxylic acid [2-(4'-fluoro-biphenyl-4-yl)-1-(R)-(3-methyl-[1,2,4]oxadiazol-5-yl)-ethyl]-amide (0.018) was prepared from 4-Methoxy-4'-trifluoromethyl-biphenyl-3-carboxylic acid [2-(4'-fluoro-biphenyl-4-yl)-1-(R)-(3-methyl [1,2,4]oxadiazol-5-yl)-ethyl]-amide (0.03 g, 0.052 mmol) using the general procedure P.

$^1$HNMR (400 MHz, $CDCl_3$): 2.41 (s, 3H), 3.46 (d, 2H), 5.82 (dd, 1H), 6.82 (br d, 1H), 7.08-7.19 (m, 2H), 7.42 (s, 1H), 7.46-7.68 (m, 9H), 11.80 (s, 1H)

Example 85

5-Fluoro-4-hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide To a solution of 5-Bromo-3-fluoro-2-hydroxy-benzaldehyde (2.0 g, 9.13 mmol), in DMF (10 mL) was added $Cs_2CO_3$ (3.56 g, 10.95 mmol) and iodomethane (2.59 g, 18.26 mmol) and heated at 70° C. for 6 h. Reaction mixture was diluted with EtOAc (25 mL) and filtered, filtrate was washed with water, brine and dried over $Na_2SO_4$. Solvent was removed under reduced pressure and silicagel column chromatography (EtOAc:Hex, 1:3) gave pure 5-Bromo-3-fluoro-2-methoxy-benzaldehyde (2.0 g).

4-Trifluorophenylboronic acid (1.05 g, 5.57 mmol) was added to a solution of 5-Bromo-3-fluoro-2-methoxy-benzaldehyde (1.0 g, 4.29 mmol), $Pd(PPh_3)_4$ (0.24 g, 0.21 mmol) and CsF (1.3 g, 8.58 mmol) in DME (10 mL ) and heated at 85° C. for 10 h. The reaction was diluted with EtOAc (20 mL) and filtered, filtrate was washed water, brine and dried over Na2SO4. Solvent was removed under reduced pressure and the silicagel column chromatography gave pure 5-Fluoro-4-methoxy-4'-trifluoromethyl-biphenyl-3-carboxaldehyde (0.91 g).

Pyridinium dichromate (0.25 g, 0.67 mmol ) was added to a solution of 5-Fluoro-4-methoxy-4'-trifluoromethyl-biphenyl-3-carbaldehyde (0.2 g, 0.67 mmol) DMF (2 mL) and stirred for 12 h, to complete the reaction more pyridinium dichromate (0.2 g , 0.53 mmol) was added and stirred for 12 h. The reaction mixture was diluted with water (5 mL) and extracted with EtOAc(10 mL). Solvent was removed under reduced pressure to get 5-Fluoro-4-methoxy-4'-trifluoromethyl-biphenyl-3-carboxylic acid (0.12 g).

5-Fluoro-4-methoxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide was prepared from 5-Fluoro-4-methoxy-4'-trifluoromethyl-biphenyl-3-carboxylic acid (0.06 g, 0.19 mmol) and 2-(3'-chloro-4'-fluoro-biphenyl-4-yl)-1-(R)-(3-methyl-[1,2,4]oxadiazol-5-yl)-ethylamine (0.063 g, 0.19 mmol) following general procedure A.

LC/MS (m/z): 628.0 $(M+1)^+$.

5-Fluoro-4-hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide was prepared from 5-Fluoro-4-methoxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide following general procedure P.

$^1$HNMR (400 MHz, $CDCl_3$): 2.41 (s, 3H), 3.46 (m, 2H), 5.83 (dd, 1H), 7.00 (br d, 1H), 7.12-7.23 (3H), 7.30 (s, 1H), 7.38 (m, 1H), 7.43-7.60 (m, 6H), 7.66 (d, 2H).

Example 86

4-Hydroxy-4'-trifluoromethyl-biphenyl-3-carboxylic acid [2-[4-(3-chloro-4-fluoro-phenoxy)-phenyl]-1-(R)-(3-methyl 1,2,4]oxadiazol-5-yl)-ethyl]-amide 2-(R)-tert-Butoxycarbonylamino-3-[4-(3-chloro-4-fluoro-phenoxy)-phenyl]-propionic acid (0.87 g) was prepared from Boc-D-tyrosine methyl ester (1.0 g, 3.38 mmol) 3-chloro-4-fluorophenylboronic acid (1.76 g, 10.15 mmol) as described in the general procedure F.

[2-[4-(3-Chloro-4-fluoro-phenoxy)-phenyl]-1-(R)-(3-methyl-[1,2,4]oxadiazol-5-yl)-ethyl]-carbamic acid tert-butyl ester (0.57 g ) was prepared from 2-(R)-tert-Butoxycarbonylamino-3-[4-(3-chloro-4-fluoro-phenoxy)-phenyl]-propionic acid [0.73 g, 1.78 mmol, which was prepared from 2-(R)-tert-Butoxycarbonylamino-3-[4-(3-chloro-4-fluoro-phenoxy)-phenyl]-propionic acid methyl ester using the general procedure C] following the general procedure O.

4-Methoxy-4'-trifluoromethyl-biphenyl-3-carboxylic acid [2-[4-(3-chloro-4-fluoro-phenoxy)-phenyl]-1-(R)-(3-methyl-[1,2,4]oxadiazol-5-yl)-ethyl]-amide (0.07 g) was prepared from 2-[4-(3-Chloro-4-fluoro-phenoxy)-phenyl]-1-(R)-(3-methyl-[1,2,4]oxadiazol-5-yl)-ethylamine hydrochloride [0.07 g, 0.182 mmol, which was prepared from [2-[4-(3-Chloro-4-fluoro-phenoxy)-phenyl]-1-(R)-(3-methyl-[1,2,4]oxadiazol-5-yl)-ethyl]-carbamic acid tert-butyl ester following general procedure N] and 4-methoxy-4'-trifluoromethyl-biphenyl-3-carboxylic acid (0.053 g, 0.18 mmol) following general procedure A.

4-Hydroxy-4'-trifluoromethyl-biphenyl-3-carboxylic acid [2-[4-(3-chloro-4-fluoro-phenoxy)-phenyl]-1-(R)-(3-methyl-[1,2,4]oxadiazol-5-yl)-ethyl]-amide (0.022 g) was prepared from 4-methoxy-4'-trifluoromethyl-biphenyl-3-carboxylic acid [2-[4-(3-chloro-4-fluoro-phenoxy)-phenyl]-1-(R)-(3-methyl-[1,2,4]oxadiazol-5-yl)-ethyl]-amide (0.04 g, 0.063 mmol) following general procedure P. $^1$HNMR (400 MHz, $CDCl_3$): 2.40 (s, 3H), 3.39 (m, 2H), 5.78 (dd, 1H), 6.80-6.94 (m, 4H), 6.90-7.14 (m, 5H), 7.47 (s, 1H), 7.54-7.74 (m, 5H), 11.85 (s, 1H); LC/MS (m/z): $(M+1)^+$.

Example 87

4-Hydroxy-4'-trifluoromethyl-biphenyl-3-carboxylic acid [2-(3'-chloro-4'-fluoro-biphenyl-3-yl)-1-(R)-(3-methyl-[1,2,4]oxadiazol-5-yl)-ethyl]-amide 2-(R)-tert-Butoxycarbonylamino-3-(3'-chloro-4'-fluoro-biphenyl-3-yl)-propionic acid (0.93 g) was prepared from (R)-N-Boc-3-bromophenylalanine (1.0 g, 2.9 mmol) and 3-chloro-4-fluorophenylboronic acid (1.0 g, 5.8 mmol) following general procedure D.

[2-(3'-Chloro-4'-fluoro-biphenyl-3-yl)-1-(R)-(3-methyl-[1,2,4]oxadiazol-5-yl)-ethyl]-carbamic acid tert-butylester (0.7 g) was prepared from 2-(R)-tert-Butoxycarbonylamino-3-(3'-chloro-4'-fluoro-biphenyl-3-yl)-propionic acid (0.9 g, 2.2 mmol) following general procedure O.

4-Methoxy-4'-trifluoromethyl-biphenyl-3-carboxylic acid [2-(3'-chloro-4'-fluoro-biphenyl-3-yl)-1-(R)-(3-methyl-[1,2,4]oxadiazol-5-yl)-ethyl]-amide (0.073 g) was prepared from 2-(3'-Chloro-4'-fluoro-biphenyl-3-yl)-1-(R)-(3-methyl-[1,2,4]oxadiazol-5-yl)-ethylamine hydrochloride salt [0.07 g, 0.19 mmol, prepared from [2-(3'-Chloro-4'-fluoro-biphenyl-3-yl)-1-(R)-(3-methyl-[1,2,4]oxadiazol-5-yl)-ethyl]-carbamic acid tert-butylester following general procedure N] and 4-Methoxy-4'-trifluoromethyl-biphenyl-3-carboxylic acid (0.056 g, 0.19 mmol) following general procedure A.

4-Hydroxy-4'-trifluoromethyl-biphenyl-3-carboxylic acid [2-(3'-chloro-4'-fluoro-biphenyl-3-yl)-1-(R)-(3-methyl-[1,2,4]oxadiazol-5-yl)-ethyl]-amide (0.022 g) was prepared from 4-Methoxy-4'-trifluoromethyl-biphenyl-3-carboxylic acid [2-(3'-chloro-4'-fluoro-biphenyl-3-yl)-1-(R)-(3-methyl-[1,2,4]oxadiazol-5-yl)-ethyl]-amide(0.04 g, 0.065 mmol) following general procedure P.

$^1$HNMR (400 MHz, $CDCl_3$): 2.41 (s, 3H), 3.47 (m, 1H), 4.86 (m, 1H), 6.90 (d, 1H), 7.07-7.15 (m, 4H), 7.20 (m, 1H), 7.29 (m, 1H), 7.37 (t, 1H), 7.42-7.46 (m, 3H), 7.52 (d, 2H), 7.66 (d, 3H)11.81 (s, 1H)

Example 88

4-Hydroxy-4'-trifluoromethyl-biphenyl-3-carboxylic acid [2-(3'-chloro-4'-fluoro-biphenyl-2-yl)-1-(R)-(3-methyl-[1,2,4]oxadiazol-5-yl)-ethyl]-amide

[2-(3'-Chloro-4'-fluoro-biphenyl-2-yl)-1-(R)-(3-methyl-[1,2,4]oxadiazol-5-yl)-ethyl]-carbamic acid tert-butylester (0.72 g) was prepared following general procedure O from 2-(R)-tert-Butoxycarbonylamino-2-(3'-chloro-4'-fluoro-biphenyl-2-yl)-propionic acid (1.0 g, 2.54 mmol) which was prepared from (D)-N-Boc-2-bromophenylalanine and 3-chloro-4-fluoro boronic acid, following general procedure D.

4-Methoxy-4'-trifluoromethyl-biphenyl-3-carboxylic acid [2-(3'-chloro-4'-fluoro-biphenyl-2-yl)-1-(R)-(3-methyl-[1,2,4]oxadiazol-5-yl)-ethyl]-amide (0.081 g) was prepared from 2-(3'-Chloro-4'-fluoro-biphenyl-2-yl)-1-(R)-(3-methyl-[1,2,4]oxadiazol-5-yl)-ethylamine hydrochloride salt (0.075 g, 0.2 mmol) which was prepared from 2-(R)-tert-Butoxycarbonylamino-2-(3'-chloro-4'-fluoro-biphenyl-2-yl)-propionic acid following general procedure N and 4-methoxy-4'-trifluoromethyl-biphenyl-3-carboxylic acid (0.06 g, 0.2 mmol) following general procedure A.

4-Hydroxy-4'-trifluoromethyl-biphenyl-3-carboxylic acid [2-(3'-chloro-4'-fluoro-biphenyl-2-yl)-1-(R)-(3-methyl-[1,2,4]oxadiazol-5-yl)-ethyl]-amide (0.024) was prepared from 4-Methoxy-4'-trifluoromethyl-biphenyl-3-carboxylic acid [2-(3'-chloro-4'-fluoro-biphenyl-2-yl)-1-(R)-(3-methyl-[1,2,4]oxadiazol-5-yl)-ethyl]-amide (0.04 g, 0.065 mmol) following general procedure P.

$^1$HNMR (400MHz, $CDCl_3$): 2.36 (s, 3H), 3.38 (dd, 1H), 3.47 (dd, 1H), 5.56 (dd, 1H), 6.74 (d, 1H), 7.04 (m, 3H), 7.14-7.37 (m, 5H), 7.40 (d, 1H), 7.60 (d, 2H), 7.66 (dd, 1H), 7.72 (d, 2H), 11.89 (s, 1H)

Example 89

5-Bromo-N-[2-(3'-chloro4'-fluoro-biphenyl-4-yl)-1-(R)-(3-methyl-[1,2,4]oxadiazol-5-yl ethyl]-2-hydroxy-benzamide The title compound (39 mg) was prepared from 2-(3'-Chloro-4'-fluoro-biphenyl-4-yl)-1-(R)-(3-methyl-[1,2,4]oxadiazol-5-yl)-ethylamine (33 mg, 0.1 mmol) and 5-bromo-2-hydroxy-benzoic acid (21 mg, 0.1 mmol) following the general procedure A.

LC-MS (m/z): 532 $(M+2)^+$; $^1$H NMR (400 MHz, $CDCl_3$): δ 2.41 (s, 3H), 3.42 (t, 2H), 5.79 (q, 1H), 6.82 (d, 1H), 6.90 (dd, 1H), 7.14 (d, 2H), 7.19 (t, 2H), 7.40 (m, 1H), 7.48 (m, 2H), 7.52 (dd, 1H), 7.58 (dd, 1H), and 11.82 (br, 1H).

Example 90

4-Hydroxy-3',5'-bis-trifluoromethyl-biphenyl-3-carboxylic acid [2-biphenyl-4-yl-1-(R)-(3-methyl-[1,2,4]oxadiazol-5-yl)-ethyl]-amide 4-Hydroxy-3',5'-bis-trifluoromethyl-biphenyl-3-carboxylic acid [2-biphenyl-4-yl-1-(R)-(3-methyl-[1,2,4]oxadiazol-5-yl)-ethyl]-amide (53 mg) was prepared from 4-benzyloxy-3',5'-bis-trifluoromethyl-biphenyl-3-carboxylic acid [2-biphenyl-4-yl-1-(R)-(3-methyl-[1,2,4]oxadiazol-5-yl)-ethyl]-amide (70 mg, 0.1 mmol) and boron tribromide (0.25 mL, 0.25 mmol, 1.0 M solution in DCM) following the general procedure P.

LC-MS (m/z): 613 $(M+2)^+$; $^1$H NMR (400 MHz, $CDCl_3$): δ 2.39 (s, 3H), 3.45 (d, 2H), 5.85 (q, 1H), 7.11 (dd, 1H), 7.17 (d, 2H), 7.34 (d, 1H), 7.38 (s, 1H), 7.41 (m, 2H), 7.49-7.53 (m, 3H), 7.56 (d, 1H), 7.63 (t, 1H), 7.67 (t, 1H), 7.83 (s, 1H), 7.91 (m, 2H), and 11.94 (br, 1H).

Example 91

Acetic acid 3-[2-(6-methoxy-4'-nitro-biphenyl-3-yl)-ethylcarbamoyl]-naphthalen-2-yl ester 3-Acetoxy-naphthalene-2-carboxylic acid (232 mg) was prepared from 3-hydroxy-naphthalene-2-carboxylic acid (188 mg, 1.0 mmol) following the general procedure K.

Acetic acid 3-[2-(6-methoxy-4'-nitro-biphenyl-3-yl)-ethylcarbamoyl]-naphthalen-2-yl ester (108 mg) was prepared from 3-Acetoxy-naphthalene-2-carboxylic acid (58 mg, 0.25 mmol) and 2-(6-Methoxy-4'-nitro-biphenyl-3-yl)-ethylamine (68 mg, 0.25 mmol following the general procedure A.

LC-MS (m/z): 485 $(M+1)^+$; $^1$H NMR (400 MHz, $CDCl_3$): δ 2.25 (s, 3H), 2.95 (t, 2H), 3.74 (q, 2H), 3.82 (s, 3H), 6.36 (br, 1H), 6.98 (d, 1H), 7.22-7.32 (m, 2H), 7.46-7.58 (m, 4H), 7.66 (d, 2H), 7.82 (d, 2H), 8.14 (s, 1H), and 8.24 (d, 1H).

Example 92

3-Biphenyl-4-yl-2-(S)-[(3-hydroxy-naphthalene-2-carbonyl)-amino]-propionic acid methyl ester The title compound (26 mg) was prepared from 0.05 g (0.1 mmol) of resin-bound 3-(4-bromophenyl)ethyl-(2 g)-[3-(hydroxy-napthalene-2-carbonyl)-amino]-propionic acid methyl ester and 36.0 mg (0.3 mmol) of phenyl boronic acid as described in the general procedure D followed by the cleavage described in example 28. LC/MS (m/z): 426 $(M+1)^+$.

Example 93

3-(3'-Chloro-4'-fluoro-biphenyl-4-yl)-2-(S)-[(3-hydroxy-naphthalene-2-carbonyl)-amino]-propionic acid methyl ester To 1.0 g (2.5 mmol) of resin-bound naphthoic acid obtained using the procedure described in example 1, was added 1.95 g (7.5 mmol) of (S)-4-bromophenylalanine methyl ester, 7.5 mL (7.5 mmol) of 1.0 M DIC in DMF, 7.5 mL (7.5 mmol) of 1.0 M HOBt in DMF, and a catalytic amount of DMAP. The resulting mixture was left on a shaker overnight. The resin was washed with DMF, MeOH, DCM three times of each to give resin-bound 3-(4-bromophenyl) ethyl-2-(S)-[3-(hydroxy-napthalene-2-carbonyl)amino]-propionic acid methyl ester.

To 0.05 g (0.1 mmol) of the above resin-bound 3-(4-bromophenyl)ethyl-(2S)-[3-(hydroxy-napthalene-2-carbonyl)-amino]-propionic acid methyl ester in 2.0 mL of DME were added 52.0 mg (0.3 mmol) of 3-chloro-4-fluorophenylboronic acid, 30 mg (0.03 mmol) of $Pd(PPh_3)_4$, and 0.3 mL (0.6 mmol) of 2N $Na_2CO_3$ solution. The mixture was heated to 80° C. for 12 h. The resin was washed with $H_20$, DMF, MeOH, DCM three times of each and cleaved with TMSBr/TFA/DCM (1:1:5) at rt for 4 h. The residue obtained after removing the solvent was purified by chromatography (DCM) to give the title compound (30 mg). LC/MS (m/z) 478 $(M+1)^+$.

By analogous methods to those described above the following compounds were synthesized.

| EX. | NAME | LC/MS (m/z) |
|---|---|---|
| 94 | 3-(4'-Fluoro-biphenyl-4-yl)-2-(S)-[(3-hydroxy-naphthalene-2-carbonyl)-amino]-propionic acid methyl ester | 444 |
| 95 | 3-(3',4'-Difluoro-biphenyl-4-yl)-2-(S)-[(3-hydroxy-naphthalene-2-carbonyl)-amino]-propionic acid methyl ester | 462 |
| 96 | 3-(4'-Chloro-biphenyl-4-yl)-2-(S)-[(3-hydroxy-naphthalene-2-carbonyl)-amino]-propionic acid methyl ester | 460 |
| 97 | 2-(S)-[(3-Hydroxy-naphthalene-2-carbonyl)-amino]-3-(4'-trifluoromethoxy-biphenyl-4-yl)-propionic acid methyl ester | 510 |
| 98 | 2-(S)-[(3-Hydroxy-naphthalene-2-carbonyl)-amino]-3-(4'-trifluoromethyl-biphenyl-4-yl)-propionic acid methyl ester | 493 |
| 99 | 3-(3',5'-Bis-trifluoromethyl-biphenyl-4-yl)-2-(S)-[(3-hydroxy-naphthalene-2-carbonyl)-amino]-propionic acid methyl ester | 562 |
| 100 | 3-(3',5'-Difluoro-biphenyl-4-yl)-2-(S)-[(3-hydroxy-naphthalene-2-carbonyl)-amino]-propionic acid methyl ester | 462 |
| 101 | 2-(S)-[(3-Hydroxy-naphthalene-2-carbonyl)-amino]-3-[1,1';4',1"]terphenyl-4-yl-propionic acid methyl ester | 502 |
| 102 | 3-(2'-Fluoro-[1,1';4',1"]terphenyl-4"-yl)-2-(S)-[(3-hydroxy-naphthalene-2-carbonyl)-amino]-propionic acid methyl ester | 507 |
| 103 | 3-(4'-tert-Butyl-biphenyl-4-yl)-2-[(3-hydroxy-naphthalene-2-(S)-carbonyl)-amino]-propionic acid methyl ester | 482 |
| 104 | 2-(S)-[(3-Hydroxy-naphthalene-2-carbonyl)-amino]-3-(4-naphthalen-2-yl-phenyl)-propionic acid methyl ester | 476 |

Example 105

2-(S)-[(3-Hydroxy-naphthalene-2-carbonyl)-amino]-3-(4-naphthalen-2-ylphenyl)-propionic acid methyl ester To 1.0 g (2.5 mmol) of resin-bound naphthoic acid obtained using the procedure described in example 1, was added 1.95 g (7.5 mmol) of (S)-4-hydroxyphenylalanine methyl ester, 7.5 mL (7.5 mmol) of 1.0 M DIC in DMF, 7.5 mL (7.5 mmol) of 1.0 M HOBt in DMF, and a catalytic amount of DMAP. The resulting mixture was left on a shaker overnight. The resin was washed with DMF, MeOH, DCM three times of each to give resin-bound 2-(3-Hydroxy-naphthalene-2-carbonyl)-amino-3-(4-hydroxy-phenyl)-propionic acid methyl ester.

To 0.05 g (0.1 mmol) of resin-bound 2-(S)-(3-Hydroxy-naphthalene-2-carbonyl)-amino-3-(4-hydroxy-phenyl)-propionic acid methyl ester was reacted with 2-(4-chloro-phenyl)-ethanol (156 mg, 1.0 mmol), DIAD (1.0 mmol), $Ph_3P$ (1.0 mmol) in THF at rt overnight.

The resin was washed and cleaved as described in Example 28 to give the title compound (25 mg). LC/MS (m/z) 504 $(M+1)^+$.

Example 106

3-{4-[2-(4-Chloro-phenyl)-ethoxy]-phenyl}-2-(S)-[(3-hydroxy-naphthalene-2-carbonyl)-amino]-propionic acid methyl ester 0.05 g (0.1 mmol) of resin-bound 2-(S)-(3-Hydroxy-naphthalene-2-carbonyl)-amino-3-(4-hydroxy-phenyl)-propionic acid methyl ester obtained in Example 105 was reacted with 2-(4-chloro-phenyl)-ethanol (156 mg, 1.0 mmol), DIAD (1.0 mmol), $Ph_3P$ (1.0 mmol) in THF at rt overnight. The resulting resin was hydrolyzed according to general procedure C. The resin was then washed and cleaved as described in Example 28 to give the title compound (20 mg). LC/MS (m/z) 490 $(M+1)^+$.

Example 107

2-(S)-[(3-Hydroxy-naphthalene-2-carbonyl)-amino]-3-[4-(4-nitro-phenoxy)-phenyl]propionic acid methyl ester To 0.05 g (0.1 mmol) of the above resin-bound 2-(S)-(3-Hydroxy-naphthalene-2-carbonyl)-amino-3-phenyl-propionic acid methyl ester as obtained in Example 105 was reacted with 4-nitro-fluorobenzene (42 mg, 0.30 mmol) as described in general procedure B.

The resin was washed with $H_2O$, DMF, MeOH, DCM three times of each and cleaved with TMSBr/TFA/DCM (1:1:5) at rt for 4 h. The residue obtained after removing the solvent was purified by chromatography (DCM) to give the title compound (28 mg). LC/MS (m/z) 487 $(M+1)^+$.

Example 108

2-(S)-[(3-Hydroxy-naphthalene-2-carbonyl)-amino]-3-[4-(3-phenyl-propylamino)-phenyl]-propionic acid methyl ester 400 mg (1.0 mmol) of resin-bound naphthoic acid was reacted with 560 mg (2.5 mmol) of (2S)-Amino-3-(4-nitro-phenyl)-propionic acid methyl ester as described in Example 105 to give resin-bound 2-(S)-(3-Hydroxy-naphthalene-2-carbonyl)-amino-3-(4-nitro-phenyl)-propionic acid methyl ester.

To 0.10 g (0.2 mmol) of the above resin was reduced by excess $SnCl_2$ hydrate in NMP at RT for 6 h, then reacted with 3-phenyl-propionaldehyde (134 mg, 1.0 mmol) as described in general procedure R. The resin was then washed and cleaved as described in Example 28 to give the title compound (48 mg). LC/MS (m/z) 483 $(M+1)^+$.

Example 109

[2-(S)-[(3-Hydroxy-naphthalene-2-carbonyl)-amino]-3-(4'-trifluoromethyl-biphenyl-4-yl)-propionylamino]-acetic acid methyl ester The resin-bound (2S)-[(3-Hydroxy-napthalene-2-carbonyl)-amino]-3-[(4'-trifluoromethyl)-biphenyl-4-yl]-propionylamino]-acetic acid methyl ester (29 mg) was prepared from 0.05 g (0.1 mmol) of resin-bound 3-(4-bromophenyl) ethyl-(2S)-[3-(hydroxy-napthalene-2-carbonyl)-amino]-propionic acid methyl ester and 58.0 mg (0.3 mmol) of 4-(trifluoromethyl)phenylboronic acid as described in general procedure D LC/MS (m/z): 494 $(M+1)^+$.

The above methyl ester (100 mg, 0.1 mmol) was hydrolyzed according to general procedure C to afford the resin-bound (2S)-[(3-Hydroxy-napthalene-2-carbonyl)-amino]-3-[(4'-trifluoromethyl)-biphenyl-4-yl]-propionylamino]-acetic acid, which was reacted with glycine methyl ester (46 mg, 0.5 mmol) as described in general procedure A. The resin was cleaved with TMSBr/TFA/DCM (1:1:5) at rt for 4 h. The residue obtained after removing the solvent was purified by chromatography (DCM) to give the title compound (20 mg). LC/MS (m/z) 551 $(M+1)^+$.

Example 110

3-Hydroxy-naphthalene-2-carboxylic acid [2-(4-methoxy-4'-nitro-biphenyl-3-yl)-ethyl]-amide To 1.0 g (2.5 mmol) of resin-bound 3-hydroxy-2-naphthoic acid obtained using the procedure described in example 1, was added a mixture of 1.5 g (7.5 mmol) of 3-Bromo-6-methoxyphenethylamine, 7.5 mL (7.5 mmol) of 1.0 M DIC in DMF, 7.5 mL (7.5 mmol) of 1.0 M HOBt in DMF, and a catalytic amount of DMAP. The resulting mixture was left on a shaker overnight. The resin was washed with DMF, MeOH, DCM three times of each to give resin-bound N-2-(3-bromo-6-methoxyphenyl)ethyl-3-hydroxyl-2-naphthamide.

To 0.05 g (0.1 mmol) of above resin-bound N-2-(3-bromo-6-methoxyphenyl)ethyl-3-hydroxyl-2-naphthamide in 2.0 mL of DME were added 36.6 mg (0.3 mmol) of 4-nitrophenylboronic acid, 30 mg (0.03 mmol) of $Pd(PPh_3)_4$, and 0.3 mL (0.6 mmol) of 2N $Na_2CO_3$ solution. The mixture was heated to 80° C. for 12 h. The resin was washed with $H_2O$, DMF, MeOH, DCM three times of each and cleaved with TMSBr/TFA/DCM (1:1:5) at rt for 4 h. The residue obtained after removing the solvent was purified by chromatography (100% methylene chloride) to give 22 mg of the title compound.

$^1H$ NMR (400 MHz, $CDCl_3$): 2.99 (t, 2H), 3.77 (dd, 2H), 3.83 (s, 3H), 6.62 (broad, 1H), 6.99 (d, 1H), 7.21 (s, 1H), 7.31-7.27 (m, 3H), 7.48 (t, 1H), 7.69-7.61 (m, 4H), 7.81 (s, 1H), 8.20 (d, 2H); LC/MS (m/z): 443$(M+1)^+$.

Example 111

3-Hydroxy-naphthalene-2-carboxylic acid [2-(6-methoxy-4'-nitro-biphenyl-3-yl)-ethyl]-amide The title compound (27 mg) was prepared from 0.05 g (0.1 mmol) of resin-bound N-2-(3-bromo-4-methoxyphenyl) ethyl-3-hydroxyl-2-naphthamide and 50.0 mg (0.3 mmol) of 4-nitro-phenyl boronic acid as described in Example 110.

$^1H$ NMR (400 MHz, $CDCl_3$): 3.11 (t, 2H), 3.78 (dd, 2H), 3.98 (s, 3H), 6.95 (broad, 1H), 7.03 (d, 1H), 7.29 (d, 2H), 7.49-7.44 (m, 2H), 7.54 (dd, 1H), 7.69-7.61 (m, 4H), 7.81 (s, 1H), 8.22 (d, 2H); LC/MS (m/z): 443 $(M+1)^+$.

Examples 112 and 113

3-Hydroxy-naphthalene-2-carboxylic acid [2-(4'-methanesulfonyl-4-methoxy-biphenyl-3-yl)-ethyl]-amide and 3-Hydroxy-naphthalene-2-carboxylic acid [2-(4-hydroxy-4'-methanesulfonyl-biphenyl-3-yl)-ethyl]-amide 3-Methoxy-2-naphthoic acid 1 g, (4.95 mmol) and 2-Methoxy-5-bromo-1-phenethylamine were coupled using the general procedure A, to obtain 450 mg of the coupled product.

The bromo derivative (414 mg, 1 mmol) was subjected to Sujuki coupling using 4-Methylsulfonyl-1 phenylboronic acid 300 mg(1.5 mmol) using the general procedure D which afforded 300 mg of the 3-Methoxy-naphthalene-2-carboxylic acid [2-(4'-methanesulfonyl-4-methoxy-biphenyl-3-yl)-ethyl]-amide.

The above methyl ether (250 mg) was then hydrolyzed with $BBr_3$ following the general procedure P which was purified on silica gel column to afford the 3-Hydroxy-naphthalene-2-carboxylic acid [2-(4'-methanesulfonyl-4-methoxy-biphenyl-3-yl)-ethyl]-amide 10 mg as well as the 3-Hydroxy-naphthalene-2-carboxylic acid [2-(4-hydroxy-4'-methanesulfonyl-biphenyl-3-yl)-ethyl]-amide (25 mg).

LC/MS 476 (M+1); $^1H$ NMR (400 MHz, $CDCl_3$): δ 3.05 (s, 3H), 3.1(m, 2H), 3.75 (m, 2H), 3.85 (s, 3H), 7.0 (d, 1H), 7.25 (s, 1H), 7.5 (m, 3H), 7.62 (d, 1H), 7.7 (m, 2H), 7.8 (m, 3H), 7.86 (d, 2H), 8.1 (d, 1H).

3-Hydroxy-naphthalene-2-carboxylic acid [2-(4-hydroxy-4'-methanesulfonyl-biphenyl-3-yl)-ethyl]-amide (Example 113)

LC/MS 462 (M+1); $^1H$ NMR (400 MHz, $CDCl_3$): δ 3.1 (s, 3H), 3.15(m, 2H), 3.7 (m, 2H), 7.0 (d, 1H), 7.2 (m, 1H), 7.3 (s, 1H), 7.5 (m, 5H), 7.7 (m, 4H), 7.86 (d, 2H).

Example 114

(3-{2-[(3-Hydroxy-naphthalene-2-carbonyl)-amino]-ethyl}-4'-methanesulfonyl-biphenyl-4-yloxy)-acetic acid methyl ester To a solution of the 3-Hydroxy-naphthalene-2-carboxylic acid [2-(4-hydroxy-4'-methanesulfonyl-biphenyl-3-yl)- ethyl]-amide (18 mg, 0.039 mmol) was in DMF were added ethylbromoacetate (0.039 mmol) and $Cs_2CO_3$ (0.039 mmol, 13 mg). The reaction mixture was for 12 hr and the reaction mixture was diluted with ethylacetate and washed with water. The organic layer was separated, dried and the crude obtained after removal of the solvent was purified on a silicagel column to afford the desired product 5 mg, and 5 mg of bis ester.

LC/MS 548 (M+1); $^1$H NMR (400 MHz, $CDCl_3$): δ 1.37(t, 3H), 3.05(s, 3H), 3.1(m, 2H), 3.65(m, 2H), 4.38(q, 2H), 4.82 (s, 2H), 7.05(d, 1H), 7.15(s, 1H), 7.35 (s, 1H), 7.45 (m, 2H), 7.55 (m, 1H), 7.7 (m, 3H), 7.95(m, 3H), 8.9(s, 1H), 9.45(s, 1H), 9.5 (t, 1H).

Example 115

3-Hydroxy-naphthalene-2-carboxylic acid [2-(3'-chloro-4'-fluoro-biphenyl-4-yl)-1-(R)-(3-methyl-[1,2,4]oxadiazol-5-yl)-ethyl]-amide 3-Methoxy-2-naphthoic acid 86 mg (0.43 mmol) and the 2-(3'-Chloro-4'-fluoro-biphenyl-4-yl)-1-(R)-(3-methyl-[1,2,4]oxadiazol-5-yl)-ethylamine 100 mg (0.35 mmol) were coupled using the general procedure A. to afford the 3-Methoxy-naphthalene-2-carboxylic acid [2-(3'-chloro-4'-fluoro-biphenyl-4-yl)-1-(R)-(3-methyl-[1,2,4]oxadiazol-5-yl)-ethyl]-amide 60 mg.

The resulting methyl ether was hydrolysed using $BBr_3$ following the general procedure P and provided the title compound (15 mg).

$^1$H NMR (400 MHz, $CDCl_3$): δ 2.4(s, 3H), 3.45(d, 2H), 5.9(m, 1H), 7.05(d, 1H), 7.2(m, 3H), 7.3(m, 2H), 7.4(m, 2H), 7.5(m, 2H), 7.6(d, 1H), 7.7 (d, 1 H), 7.75(d, 1H), 7.95(s, 1H), 11.15(s, 1H).

Example 116

2-(S)-[5-Bromo-2-(2-morpholin-4-yl-ethoxy)-benzoylamino]-3-(2'-phenoxy-biphenyl-4-yl)-propionic acid methyl ester A solution of (2S)-(5-bromo-2-hydroxy-benzoylamino)-3-(2'-phenoxy-biphenyl-4-yl)-propionic acid methyl ester (25 mg, 46 μmol, obtained by following similar procedure described for example 34), 2-morpholin-4-yl-ethanol (1.5 eq., 8.3 μL, 69 μmol) and triphenylphosphine (1.5 eq., 18 mg, 69 μmol) in anhydrous THF (1 mL) was treated with DIAD (1.5 eq., 13.5 μl, 69 μmol) as described in Procedure I. Flash column chromatography (4:1 hexanes:EtOAc) provided 13 mg of the title compound. LCMS for $C_{35}H_{35}BrN_2O_6$: 659, 661.

By analogous methods to those described above, the following compounds were synthesized.

| EX. | NAME | LC/MS $M^+$, and M + 2 (m/z) |
|---|---|---|
| 117 | 2-(S)-[5-Bromo-2-(3-pyridin-4-yl-propoxy)-benzoylamino]-3-(2'-phenoxy-biphenyl-4-yl)-propionic acid methyl ester | 665, 667 |
| 118 | 2-(S)-{5-Bromo-2-[2-(2-oxo-pyrrolidin-1-yl)-ethoxy]-benzoylamino}-3-(2'-phenoxy-biphenyl-4-yl)-propionic acid methyl ester | 657, 659 |
| 119 | 2-(S)-[5-Bromo-2-(2-morpholin-4-yl-ethoxy)-benzoylamino]-3-(2'-phenoxy-biphenyl-4-yl)-propionic acid methyl ester | 642 644 |

-continued

| EX. | NAME | LC/MS $M^+$, and M + 2 (m/z) |
|---|---|---|
| 120 | 2-(S)-[5-Bromo-2-(4,4,4-trifluoro-butoxy)-benzoylamino]-3-(2'-phenoxy-biphenyl-4-yl)-propionic acid | 643, 645 |
| 121 | 2-(S)-[5-Bromo-2-(2-pyrrolidin-1-yl-ethoxy)-benzoylamino]-3-(2'-phenoxy-biphenyl-4-yl)-propionic acid methyl ester | 657, 659 |

Example 122

2-(S)-[(4-Butoxy-3'-chloro-4'-fluoro-biphenyl-3-carbonyl)-amino]-3-(3'-tri fluoromethyl-biphenyl-4-yl)-propionic acid A mixture of 5-bromo-2-hydroxy-benzoic acid (2.21 g, 10 mmol), butyl bromide (3.46 g, 25 mmol), potassium carbonate (2.76 g, 20 mmol) and DMF (20 mL) was heated at 100° C. for 1 h. The reaction mixture was partitioned between ether (120 mL) and brine (100 mL). Ether layer was separated and washed again with brine (100 mL), dried over $MgSO_4$. Purification by flash chromatography (ethyl acetate/hexanes 1:99, 1:19, 1:9) gave 5-Bromo-2-butoxy-benzoic acid butyl ester as yellow oil (1.648 g, 5.01 mmol).

The 4-Butoxy-3'-chloro-4'-fluoro-biphenyl-3-carboxylic acid butyl ester was prepared following General Procedure D using 5-bromo-2-butoxy-benzoic acid butyl ester (1.648 g, 5.01 mmol), 3-chloro-4-fluoro-benzene boronic acid (1.31 g, 7.5 mmol), palladium tetrakis-triphenylphosphine (0.289 g, 0.25 mmol), and $Na_2CO_3$(aq) (2.0 N, 10 mL, 20 mmol) in DME (20 mL). The mixture was heated at 80° C. for 14 h. Purification by flash chromatography (ethyl acetate/hexanes 1:19, 1:9) gave the desired compound as yellow oil (0.966 g, 2.55 mmol).

Hydrolysis of the ester using General Procedure C (LiOH (1.87 g, 25 mmol), THF (8 mL) and $H_2O$ (2 mL). heated to 50° C. for 12 h furnished the acid as yellow solid which was used in the next step without purification.

The 3-(4-Bromo-phenyl)-2-(S)-[(4-Butoxy-3'-chloro-4'-fluoro-biphenyl-3-carbonyl)-amino]-propionic acid methyl ester was prepared following General Procedure A using 4-butoxy-3'-chloro-4'-fluoro-biphenyl-3-carboxylic acid from previous step, 2-(S)-amino-3-(4-bromo-phenyl)-propionic acid methyl ester hydrochloride salt (0.811 g, 2.75 mmol), HBTU (1.39 g,3.6 mmol) and DIEA (1.32 mL,7.5 mmol) in DMF (15 mL). Purification by flash chromatography (ethyl acetate/hexanes 1:7, 1:4) gave the title compound as colorless solid (0.677 g, 1.19 mmol).

2-(S)-[(4-Butoxy-3'-chloro-4'-fluoro-biphenyl-3-carbonyl)-amino]-3-(3'-trifluoromethyl-biphenyl-4-yl)-propionic acid methyl ester was prepared following General Procedure D using 3-(4-bromo-phenyl)-2-(S)-[(4-Butoxy-3'-chloro-4'-fluoro-biphenyl-3-carbonyl)-amino]-propionic acid methyl ester ((0.677 g, 1.19 mmol), 3-trifluoromethyl-benzene boronic acid (0.349 g, 1.8 mmol), palladium tetrakis-triphenylphosphine (69 mg, 0.06 mmol), and $Na_2CO_3$(aq) (2.0 N, 5 mL, 10 mmol) in DME (10 mL). The mixture was heated at 76° C. for 19 h. Purification by flash chromatography (ethyl acetate/hexanes 1:5, 1:4) gave the methyl ester of the title compound (177 mg, 0.28 mmol).

The title compound was obtained as a white solid (70 mg, 0.114 mmol) from -2-(S)-[(4-butoxy-3'-chloro-4'-fluoro-biphenyl-3-carbonyl)-amino]-3-(3'-trifluoromethyl-biphenyl-4-yl)-propionic acid methyl ester (92 mg, 0.146 mmol), LiOH (aq) (2.0 N, 0.25 mL, 0.50 mmol), THF (1 mL) and MeOH (0.25 mL) following the general Procedure C.

$^1$H-NMR (400 MHz, DMSO-$d_6$): 13.15(b, 1H), 8.59(d, 1H), 8.12(d, 1H), 7.81-7.97(m, 4H), 7.63-7.73(m, 5H), 7.49 (t, 1H), 7.24-7.31(m, 3H), 4.89(m, 1 H), 4.09(m, 2H), 3.30 (dd, 1H), 3.18(dd, 1H), 1.53(quin, 2H), 1.19(m, 2H), 0.71(t, 3H); LC-MS m/z: 614 $(M+1)^+$.

Example 123

2-(S)-(5-Chloro-2-heptyloxy-benzoylamino)-3-(4'-trifluoromethoxy-biphenyl-4-yl)-propionic acid 5-Chloro-2-hydroxy-benzoic acid (2.5 g, 28.97 mmol) was coupled with 2-Amino-3-(4-bromo-phenyl)-propionic acid methyl ester hydrochloride (4.26 g, 28.96 mmol) with HBTU (6.59 gms, 34.76 mmol) and diisopropylethylamine (8 ml, 86.91 mmol) as per general procedure A to yield the 3-(4-Bromo-phenyl)-(2S)-(5-chloro-2-hydroxy-benzoylamino)-propionic acid methyl ester. The above hydroxy compound (0.500 g, 1.21 g) was then alkylated with heptyliodide (0.410 g, 1.815 mmol) and potassium carbonate (0.050 g, 3.025 mmol) as per general procedure G to yield the 3-(4-Bromo-phenyl)-(2S)-(5-chloro-2-heptyloxy-benzoylamino)-propionic acid methyl ester (0.500 g).

The title compound was then prepared from 3-(4-Bromo-phenyl)-(2S)-(5-chloro-2-heptyloxy-benzoylamino)-propionic acid methyl ester (0.090 g, 0.176 mmol) and 4-trifluoromethoxy boronic acid (0.067 g, 0.352 mmol) with Pd $(PPh_3)$ (0.020 g, 0.0176 mmol) and 2N $Na_2CO_3$ (0.528 ml, 0.528 mmol) as per general procedure D to yield the (2S)-(5-Chloro-2-heptyloxy-benzoylamino)-3-(4'-trifluoromethoxy-biphenyl-4-yl)-propionic acid methyl ester which was further hydrolyzed as per general procedure C to give the title compound (0.050g). $^1$H-NMR(400 MHz, $CDCl_3$): 1.11 (t, 3H), 1.44(m, 8H), 1.87(m, 2H). 3.65(dddd, 2H), 4.27(m, 2H), 5.50(m, 1H), 7.18(m, 2H), 7.4(d, 1H), 7.57(m, 4H), 7.68-7.85 (m, 4H), 8.52 (S, 1H), 8.98 (bs, 1H). LC/MS (m/z): 578.2(M+2).

Example 124

2-(S)-(5-Bromo-2-heptyloxy-benzoylamino)-3-[2'-(4-trifluoromethyl-phenoxy)-biphenyl-4-yl]-propionic acid 5-Bromo-2-heptyloxy-benzoic acid was prepared by reacting 5-Bromo-2-hydroxy-benzoic acid methyl ester (1.0 g, 4.32 mmol) with Iodoheptane (1.46 g, 6.49 mmol) as per general procedure G with potassium carbonate (1.5 g, 10.8 mmol) added to it. The ester thus obtained was subjected to hydrolysis as per general procedure C to yield the 5-Bromo-2-heptyloxy-benzoic acid (0.950 g).

Also the (2S)-Amino-3-(2'-hydroxy-biphenyl-4-yl)-propionic acid was prepared from (S)-4-bromophenylalanine (5.0 g, 20.48 mmol), 2-hydroxyphenylboronic acid (4.23 g, 30.72 mmol) and Pd $(PPh_3)$ 4 (2.36 g, 2.038 mmol) as per procedure D to yield the corresponding amino acid which was further esterified with methanolic solution containing 2-3 ml of HCl to yield the corresponding HCl salt of the (2S)-Amino-3-(2'-hydroxy-biphenyl-4-yl)-propionic acid methyl ester (5.0 g).

5-Bromo-2-heptyloxy-benzoic acid (0.231 g, 0.738 mmol) and the (2S)-Amino-3-(2'-hydroxy-biphenyl-4-yl)-propionic acid methyl ester (0.200 g, 0.738 mmol) were then combined as per general procedure A with HBTU (0.335 g, 0.885 mmol) and diisopropylethylamine (0.285 g, 2.21 mmol) to yield the (2S)-(5-Bromo-2-heptyloxy-benzoylamino)-3-(2'-hydroxy-biphenyl-4-yl)-propionic acid methyl ester (0.200 g). The methyl ester of the title compound was the prepared from (2S)-(5-Bromo-2-heptyloxy-benzoylamino)-3-(2'-hydroxy-biphenyl-4-yl)-propionic acid methyl ester (0.080 g, 0.140 mmol) and the trifluoromethylboronic acid (0.050 g, 0.281 mmol) as per general procedure F, which was further hydrolyzed as per general procedure C to give the title compound (0.020 g). $^1$H-NMR(400 MHz, $CDCl_3$): 1.14(t, 3H), 1.53 (m, 8H), 1.92(m, 2H), 3.6(m, 2H), 4.21(m, 2H), 5.21(m, 1H), 7.12(d, 1H), 7.22(m, 2H), 7.36(d, 1H), 7.5(d, 2H), 7.58(m, 2H), 7.66(m, 1H), 7.78 (m, 6H), 8.62 (S, 1H), 8.9 (bs, 1H).

LC/MS (m/z): 700.2(M+2).

By analogous methods to those described above, the following compounds were synthesized

| EX. | NAME | LC/MS (m/z) |
|---|---|---|
| 125 | 2-(S)-(5-Chloro-2-heptyloxy-benzoylamino)-3-(4'-dimethylamino-biphenyl-4-yl)-propionic acid | 537 |
| 126 | 2-S)-(5-Chloro-2-heptyloxy-benzoylamino)-3-(3',4'-dichloro-biphenyl-4-yl)-propionic acid | 562 |
| 127 | 2-(S)-(5-Bromo-2-heptyloxy-benzoylamino)-3-[2'-(4-tert-butyl-phenoxy)-biphenyl-4-yl]-propionic acid | 687 |
| 128 | 3-(3'-Chloro-4'-fluoro-biphenyl-4-yl)-2-(S)-(5-chloro-2-heptyloxy-benzoylamino)-propionic acid | 546 |
| 129 | 2-(S)-(5-Chloro-2-heptyloxy-benzoylamino)-3-(4'-trifluoromethyl-biphenyl-4-yl)-propionic acid | 562 |

Example 130

2-(S)-(5-Bromo-2-cyclohexyloxy-benzoylamino)-3-(2'-phenoxy-biphenyl-4-yl)-propionic acid methyl ester 5-Bromo-salicylic acid (2.16 g, 10 mmol) was first transformed into 2-acetyl-5-bromo-salicylic acid (252 g) with acetyl chloride (2.34 g, 30 mmol) and pyridine (3.95 g, 50 mmol) in DCM, following the general procedure K. The above acid (1.29 g, 5.0 mmol) was converted into acid chloride by using oxalyl chloride (1.97 g, 15 mmol) and catalytic amount of DMF in DCM following the general procedure L, then 2-(S)-phenoxy-biphenyl alanine (1.45 g, 5.0 mmol) and DIEA (0.77 g, 6.0 mmol) were added to the acid chloride to form the coupled product (using the general procedure M), which upon hydrolysis with aq. $NaHCO_3$ gave (2S)-[5-Bromo-2-hydroxybenzoylamine]-3-(2'-phenoxybiphenyl-4-yl)-propionic acid methyl ester (1.92 g). The methyl ester (25 mg, 0.046 mmol) was then reacted with iodocyclohexane (19 mg, 0.092 mmol) as described in general procedure G to provide (2S)-(5-Bromo-2-cyclohexyloxy-benzoylamino)-3-(2'-phenoxy-biphenyl-4-yl)-propionic acid methyl ester (26 mg).

$^1$H NMR (400 MHz, $CDCl_3$): 1.15-1.45 (m, 7H), 1.75 (m, 1H), 1.95 (m, 1H), 3.24 (d, 2H), 3.75 (s, 3H), 4.30 (m, 1H), 5.05 (m, 2H), 6.90 (m, 2H), 7.01 (m, 2H), 7.10 (dd, 2H), 7.26 (m, 4H), 7.45 (m, 6H); LC/MS (m/z): 629 $(M+1)^+$.

Example 131

2-S)-(5-Bromo-2-cyclohexyloxy-benzoylamino)-3-(2'-phenoxy-biphenyl-4-yl)-propionic acid (2S)-[5-Bromo-2-(4-trifluoromethylbenzyloxy)-benzoylamine]-3-(2'-phenoxybiphenyl-4-yl)-propionic acid methyl ester in Example 130 was hydrolyzed following general procedure C to give the title compound (22 mg).

$^1H$ NMR (400 MHz, $CDCl_3$): 1.11-1.25 (m, 7H), 1.70 (m, 1H), 1.90(m, 1H), 0.328 (m, 2H), 4.28 (m, 1H), 5.06 (m, 2H), 6.89 (m, 2H), 6.99 (m, 2H), 7.17-7.51 (m, 12H); LC/MS (m/z): 615 $(M+1)^+$.

By analogous methods to those described above the following compounds were synthesized.

| EX. | NAME | LC/MS (m/z) |
|---|---|---|
| 132 | 3-Biphenyl-4-yl-2-(5-bromo-2-heptyloxy-benzoylamino)-propionic acid | 539 |
| 133 | 3-Biphenyl-4-yl-2-(S)-[2-(4-tert-butyl-benzyloxy)-5-chlorobenzoyl amino]-propionic acid | 542 |
| 134 | 2-(S)-[5-Bromo-2-(4-[1,2,4]triazol-1-yl-benzyloxy)-benzoylamino]-3-(2'-phenoxy-biphenyl-4-yl)-propionic acid | 690 |
| 135 | 2-(S)-[5-Bromo-2-(4-tert-butyl-benzyloxy)-benzoylamino]-3-(2'-phenoxy-biphenyl-4-yl)-propionic acid | 679 |

Example 136

2-S)-(2-Benzyloxy-5-bromo-benzoylamino)-3-biphenyl-4-yl-propionic acid

3-Biphenyl-4-yl-2-(S)-(5-bromo-2-hydroxy-benzoylamino)-propionic acid methyl ester (425 mg) was prepared from 2-(S)-amino-3-biphenyl-4-yl-propionic acid methyl ester-hydrochloride (1.0 g, 3.4 mmol), and 5-bromo-2-hydroxy-benzoic acid (744 mg, 3.4 mmol) as described in general procedure A except for an adapted work-up. After reaction completion, the reaction mixture was poured onto 150 mL of 1N HCl and 150 mL of EtOAc. The organic layer was washed with 1N HCl, saturated sodium bicarbonate, dried over sodium sulfate and evaporated. The crude material was purified over silica gel (8:2, DCM-hexanes).

2-(S)-(2-Benzyloxy-5-bromo-benzoylamino)-3-biphenyl-4-yl-propionic acid methyl ester (82 mg) was prepared from 3-biphenyl-4-yl-2-(S)-(5-bromo-2-hydroxy-benzoylamino)-propionic acid methyl ester (150 mg, 0.33 mmol) and benzyl bromide (0.047 mL, 0.40 mmol) as described in general procedure G and purified over silica gel (7:3, DCM-hexanes).

2-(S)-(2-Benzyloxy-5-bromo-benzoylamino)-3-biphenyl-4-yl-propionic acid methyl ester (50 mg, 0.092 mmol) was dissolved in 5 mL of THF-MeOH (4-1), cooled to 0° C. and 1.1 equiv of 2 N LiOH added. After 30 minutes, 3.3 additional equiv of 2N LiOH was added and the reaction stirred for 60 minutes. The reaction was worked up according to general procedure C to give 2-(S)-(2-benzyloxy-5-bromo-benzoylamino)-3-biphenyl-4-yl-propionic acid (34 mg)

$^1H$-NMR(400 MHz, DMSO-$d_6$): 2.92 (m, 1H), 3.17 (m, 1H), 4.71 (m, 1H), 5.25 (m, 2H), 7.18 (m, 3H), 7.28-7.42 (m, 8H), 7.52-7.64 (m, 5H), 7.81 (m, 1H), 7.52 (d, 1H); LC/MS (m/z): 532.0 $(M+1)^+$.

Example 137

3-Biphenyl-4-yl-2-(S)-[2-(3,4-bis-benzyloxy-benzyloxy)-5-bromo-benzoylamino]-propionic acid 3-Biphenyl-4-yl-2-S)-[2-(3,4-bis-benzyloxy-benzyloxy)-5-bromo-benzoylamino]-propionic acid methyl ester (340 mg) was prepared from 3-biphenyl-4-yl-2-(S)-(5-bromo-2-hydroxy-benzoylamino)-propionic acid methyl ester (400 mg, 0.92 mmol) (See example 136) and 1,2-bis-benzyloxy-4-chloromethyl-benzene (374 mg, 1.1 mmol) as described in general procedure G and purified over silica gel (8:2, DCM-hexanes).

3-Biphenyl-4-yl-2-(S)-[2-(3,4-bis-benzyloxy-benzyloxy)-5-bromo-benzoylamino]-propionic acid methyl ester (60 mg, 0.079 mmol) was dissolved in 5 mL of THF-MeOH (4-1), cooled to 0° C. and 1.1 equiv of 2 N LiOH added. After 30 minutes, 2.2 additional equiv of 2N LiOH was added and the reaction stirred for 30 minutes. The reaction was worked up according to general procedure C to give 3-biphenyl-4-yl-2-(S)-[2-(3,4-bis-benzyloxy-benzyloxy)-5-bromo-benzoylamino]-propionic acid (47 mg). $^1H$-NMR(400 MHz, DMSO-$d_6$): 2.83 (m, 1H), 3.13 (m, 1H), 4.67 (m, 1H), 5.02 (s, 2H), 5.06 (s, 2H), 5.17, (m, 2H), 6.92 (m, 1H), 6.96 (m, 1H), 7.13 (d, 2H), 7.18-7.22 (m, 2H), 7.27-7.41 (m, 13H), 7.44 (d, 2H), 7.56 (m, 2H), 7.61 (m, 1H), 7.83 (m, 1H), 8.50 (d, 1H); LC/MS (m/z): 742 $(M+1)^+$.

Example 138

3-Biphenyl-4-yl-2-(S)-([4-(4-tert-butyl-benzyloxy)-4'-trifluoromethyl-biphenyl-3-carbonyl]-amino}-propionic acid The chloro compound (Example 133,100 mg, 0.15 mmol) was reacted with 4-trifluoromethyl-phenyboronic acid (87.5 mg, 4.5 mmol) as described in general procedure D yielding the title compound (85 mg) as white solid. LC/MS (m/z): 651 $(M+1)^+$.

Example 139

3-Biphenyl-4-yl-2-(S)-{[4-(4-tert-butyl-benzoylamino)-3'-trifluoromethyl biphenyl-3-carbonyl]-amino}-propionic acid (2S)-(2-Amino-5-iodo-benzoyl-amino)-3-biphenyl-4-yl-propionic acid methyl ester (1.53 g) was prepared from (2S)-amino-3-biphenyl-4-yl-propionic acid methyl ester (1.0 g, 4.1 mmol), 5-iodo-2-amino-benzoic acid (1.23 g, 4.9 mmol) as described in general procedure A.

To a stirring solution of (2S)-(2-amino-5-iodo-benzoyl-amino)-3-biphenyl-4-yl-propionic acid methyl ester (1.0 g, 2 mmol) prepared above dissolved in DCM containing pyridine (1.58 g, 4 mmol ), was added t-butyl-benzoyl chloride (1.20 g, 2.5 mmol) at 0° C. The reaction mixture was stirred at rt for 3 h, extracted with DCM, washed with 1M HCl and brine evaporation followed by column chromatography purification (silica, $CH_2Cl_2$) giving 3-biphenyl-4-yl-(2S)-[2-(4-tert-butyl-benzoylamino)-5-iodo-benzoyl-amino]-propionic acid methyl ester (1.25 g) as a white solid which was hydrolyzed according to general procedure C yielding the title compound (1.23 g, 100%) as a white solid. $^1H$-NMR(400 MHz, DMSO-$d_6$): 1.26 (s, 9H), 3.09-3.19 (m, 1H), 3.21-3.29 (m, 1H), 4.74-4.76 (m, 1H), 7.27-7.29 (m, 1H ), 7.42-7.39 (m, 4H), 7.44-7.57 (m, 7H), 7.67-7.77 (m, 3H), 7.99 (s, 1H), 8.54 (d, 1H, J=8.0 Hz), 9.32 (d, 1H, J=8.0 Hz), 11.98 (s, 1H);

LC/MS (m/z): 647 $(M+1)^+$.

The iodo derivative (100 mg, 0.15 mmol) was reacted with 3-trifluoromethyl phenyl boronic acid (87.5 mg, 4.5 mmol) as described in general procedure D yielding the title compound (92 mg) as white solid. LC/MS (m/z): 665 $(M+1)^+$.

Example 140

3-Biphenyl-4-yl-2-(S)-[(5-chloro-2,4-dimethoxy-4'-trifluoromethyl-biphenyl-3-carbonyl)-amino]-propionic acid 2-(S)-amino-3-biphenyl-4-yl-propionic acid methyl ester (128 mg, 0.5 mmol) was reacted with 3-bromo-5-chloro-2,6-dimethoxybenzoic acid (148 mg, 0.5 mmol) as described in general procedure A. The resulting crude compound was reacted with 195 mg (1.0 mmol) of 4-(trifluoromethyl)phenylboronic acid as described in general procedure D. The product thus obtained was hydrolyzed according to general procedure C to afford the title product (180 mg) as a pure white solid.

LC/MS (m/z): 584 $(M+1)^+$.

Example 141

3-Biphenyl-4-yl-2-(S)-(3-bromo-5-chloro-2,6-dimethoxy-benzoylamino)-propionic acid 2-(S)-amino-3-biphenyl-4-yl-propionic acid methyl ester (128 mg, 0.5 mmol) was reacted with 3-bromo-5-chloro-2,6-dimethoxybenzoic acid (148 mg, 0.5 mmol) as described in general procedure A. The resulting compound was hydrolyzed according to general procedure C to afford the title product (209 mg) as a pure white solid.

LC/MS (m/z): 519 $(M+1)^+$.

Example 142

3-(3'-Chloro-4'-fluoro-biphenyl-4-yl)-2-(S)-[(4-methoxy-4'-trifluoromethyl-biphenyl-3-carbonyl)-amino]-propionic acid methyl ester 3-(3'-Chloro-4'-fluoro-biphenyl-4-yl)-2-(S)-[(4-methoxy-4'-trifluoromethyl-biphenyl-3-carbonyl)-amino]-propionic acid methyl ester (223 mg, ) was prepared from 4-Methoxy-4'-trifluoromethyl-biphenyl-3-carboxylic acid (141 mg, 0.5 mmol) and S-2-amino-3-(3'-chloro-4'-fluoro-biphenyl-4-yl)-propionic acid methyl ester (155 mg, 0.5 mmol) following the general procedure A.

LC-MS (m/z): 586 $(M+1)^+$; $^1$H NMR (400 MHz, $CDCl_3$): 63.24-3.38 (m, 2H), 3.76 (m, 1H), 3.80 (s, 3H), 3.90 (s, 3H), 5.14 (q, 1H), 6.68 (d, 1H), 7.06 (q, 1H), 7.18 (q, 1H), 7.24 (m, 3H), 7.44 (m, 2H), 7.52-7.60 (m, 2H), 7.68-7.72 (m, 3H) and 8.16 (dd, 1H).

Example 143

2-(S)-[(4-Acetoxy-4'-trifluoromethyl-biphenyl-3-carbonyl)-amino]-3-(3'-chloro-4'-fluoro-biphenyl-4-yl)-propionic acid methyl ester Acetic acid 3-chlorocarbonyl-4'-trifluoromethyl-biphenyl-4-yl ester (334 mg) was prepared from 4-acetoxy-4'-trifluoromethyl-biphenyl-3-carboxylic acid (324 mg, 1.0 mmol) following the general procedure L.

2-(S)-[(4-Acetoxy-4'-trifluoromethyl-biphenyl-3-carbonyl)-amino]-3-(3'-chloro-4'-fluoro-biphenyl-4-yl)-propionic acid methyl ester (278 mg) was prepared from acetic acid 3-chlorocarbonyl-4'-trifluoromethyl-biphenyl-4-yl ester (171 mg, 0.5 mmol) and 2-(S)-amino-3-(3'-chloro-4'-fluoro-biphenyl-4-yl)-propionic acid methyl ester (155 mg, 0.5 mmol) following the general procedure M.

LC-MS (m/z): 614 $(M+1)^+$; $^1$H NMR (400 MHz, $CDCl_3$): δ 2.05 (s, 3H), 3.24 (dd, 1H), 3.46 (dd, 1H), 3.70 (m, 1H), 3.84 (s, 3H), 5.13 (q, 1H), 7.16 (d, 2H), 7.18 (d, 1H), 7.22 (d, 1H), 7.38 (m, 1H), 7.43 (d, 2H), 7.49 (d, 1H), 7.60 (dd, 1H), 7.70 (s, 2H), 7.72 (d, 1H), 7.74 (d, 1H), and 8.26 (d, 1H).

Example 144

N-[4-(2,4-Dichloro-6-methyl-phenoxy)-2-hydroxy-phenyl]-2-(3'-trifluoromethyl-biphenyl-4-yl)-acetamide The resin-bound 2-(4-bromo-phenyl)-N-[2-Hydroxy-4-(3,4-dichloro-6-methyl-phenoxy)-phenyl]-acetamide (120 mg, 0.1 mmol, obtained from coupling reaction between the resin bound 2-Amino-5-(2,4-dichloro-6-methyl-phenoxy)-phenol and 4-bromophenyl acetic acid following the general procedure A) was reacted with 3-trifluormethyl-phenyl boronic acid (56.7 mg, 0.3 mmol) as described in the general procedure D followed by cleavage as described in example 1, to afford (27.5 mg) of title compound.

$^1$H NMR (400 MHz, $CDCl_3$): 2.13 (s, 1H), 3.86 (s, 2H), 6.33 (dd, 1H, J=8.8, 2.4 Hz), 6.37 (d, 1H, J=2.4 Hz), 6.69 (d, 1H, J=8.8 Hz), 7.15 (m, 1H), 7.30 (d, 1H, J=0.8 Hz), 7.45 (dd, 2H, J=6.4, 2.0 Hz), 7.59-7.65 (m, 4H), 7.78 (m, 1H), 7.84 (s, 1H), 8.84 (s, 1 H); LC/MS (m/z): 546 $(M+1)^+$.

Example 145

2-(4-tert-Butyl-benzoylamino)-benzoic acid methyl-amide

The 2-aminobenzoic acid (137 mg, 1.0 mmol) was reacted with 4-tert-butyl benzoyl chloride (196 mg, 1.0 mmol) as described in general procedure M. The resulting compound was coupled with methylamine (62 mg, 2.0 mmol) as described in general procedure A to afford the title product (186 mg) as a pure white solid.

LC/MS (m/z): 311 $(M+1)^+$.

Example 146

2-(S)-[(3-Hydroxy-naphthalene-2-carbonyl)-(4-pyridin-3-yl-benzyl)-amino]-3-(4-pyridin-3-yl-phenyl)-propionic acid 1.0 g (2.5 mmol) of resin-bound naphthoic acid obtained in Example 1 was reacted with 1.95 g (7.5 mmol) of (2S)-Amino-3-(4-bromophenyl)-propionic acid methyl ester as described in the general procedure A to give resin-bound 2-(S)-(3-Hydroxy-naphthalene-2-carbonyl)-amino-3-(4-bromophenyl)-propionic acid methyl ester.

0.05 g (0.1 mmol) of the above resin was treated with 4-bromobenzyl bromide (75 mg, 0.30 mmol), and Lithium tert-butoxide (0.6 mmol) in THF at RT for 6h, followed by 3-pyridyl boronic acid (123 mg, 1.0 mmol) as demonstrated in the general procedure D followed by the cleavage of the resin to afford 18 mg of the title compound. LC/MS (m/z) 594 $(M+1)^+$.

Example 147

3-Biphenyl-4-yl-2-(S)-{[5-(3-trifluoromethoxy-phenoxymethyl)-pyrazine-2-carbonyl]-amino}-propionic acid To a solution of 5-methyl-pyrazine-2-carboxylic acid methyl ester (2.0 g, 13.146 mmol) in CCl4 (25 mL0 was added NBS (2.57 g, 14.461 mmol) and benzoyl peroxide (0.318 g, 1.314 mmol) and the solution was heated at 70 C. for 1 h. Upon cooling to RT, the organic layer was washed with $NaHCO_3$, water, dried ($Na_2SO_4$), and concentrated under reduced pressure to give 0.900 g 5-Bromomethyl-pyrazine-2-carboxylic acid methyl ester.

A solution of 5-bromomethyl-pyrazine-2-carboxylic acid methyl ester (0.305 g, 1.314 mmol) in DMF (6 mL) was treated with 3-trifluoromethoxyphenol (0.280 g, 1.577 mmol) and potassium carbonate (0.400 g, 2.89 mmol) by the general procedure G. The crude product was purified by flash column chromatography on silica gel to give 0.380 g of pure 5-(3-Trifluoromethoxy-phenoxymethyl)-pyrazine-2-carboxylic acid methyl ester. LCMS: 330 $(M+2)^+$ A solution of 5-(3-trifluoromethoxy-phenoxymethyl)-pyrazine-2-carboxylic acid methyl ester (0.234 g, 0.712 mmol) in THF:MeOH (4:1, 5 mL) was treated with LiOH (0.150 g, 3.564 mmol) in 1.5 mL of water by the general procedure C to give 0.182 g of 5-(3-trifluoromethoxy-phenoxymethyl)-pyrazine-2-carboxylic acid. LCMS: 316 $(M+2)^+$ A solution of 5-(3-trifluoromethoxy-phenoxymethyl)-pyrazine-2-carboxylic acid (0.182 g, 0.579 mmol) was treated with 2(S)-amino-3-biphenyl-4-yl-propionic acid methyl ester hydrochloride (0.162 g, 0.637 mmol), HBTU (0.440 g, 1.158 mmol), and DIEA (0.310 g, 1.737 mmol) by the general procedure A. The crude crude product was purified by flash column chromatography on silica gel to give 0.170 g of 3-biphenyl-4-yl-2(S)-{[5-(3-trifluoromethoxy-phenoxymethyl)-pyrazine-2-carbonyl]-amino}-propionic acid methyl ester. LCMS: 553 $(M+2)^+$ A solution of biphenyl-4-yl-2(S)-{[5-(3-trifluoromethoxy-phenoxymethyl)-pyrazine-2-carbonyl]-amino}-propionic acid methyl ester (0.170 g, 0.308 mmol) in THF: MeOH (4:1, 5 mL) was treated with LiOH (0.064 g, 1.54 mmol) in 1.5 mL of water by the general procedure C to give 0.140 g of pure 3-biphenyl-4-yl-2(S)-{[5-(3-trifluoromethoxy-phenoxymethyl)-pyrazine-2-carbonyl]-amino}-propionic acid as a white solid. LCMS: 539 $(M+2)^+$

Example 148

4-Hydroxy-4'-trifluoromethyl-biphenyl-3-carboxylic acid [2-(3'-chloro-4'-fluoro-biphenyl-4-yl)-1-(R)-methoxymethyl-ethyl]-amide 2-(R)-tert-Butoxycarbonylamino-3-(3'-chloro-4'-fluoro-biphenyl-4-yl)-propionic acid (2.0 g, 5.07 mmol) was dissolved in 15 mL anhydrous THF and $BH_3$:THF (11 mL, 11.0 mmol, 1M solution in THF) was added drop wise at 0° C. and stirred for 10 h at room temperature. Excess $BH_3$:THF was quenched by adding methanol (~1 mL) at 0° C. Solvent was removed under vacuum and residue was dissolved in EtOAc (20 mL) and washed with water, brine and dried over $Na_2SO_4$. Solvent was removed under vacuum and silica gel column chromatography ($CH_2Cl_2$:MeOH) gave pure [1-(3'-Chloro-4'-fluoro-biphenyl-4-ylmethyl)-2-(R)-hydroxy-ethyl]-carbamic acid tert-butyl ester as white solid (1.6 g)

NaH (55 mg, 1.31 mmol, 60% by wt suspension in mineral oil) was added at 0° C. to a solution of [1-(3'-Chloro-4'-fluoro-biphenyl-4-ylmethyl)-2-(R)-hydroxy-ethyl]-carbamic acid tert-butyl ester (0.5 g, 1.31 mmol) in 5 mL anhydrous THF and stirred for 20 min at 0° C. MeI (0.37 g, 2.63 mmol) was added to the reaction mixture and stirred for 6 h at room temperature. Reaction mixture was diluted with 5 mL EtOAc, and washed with water, brine and dried over $Na_2SO_4$. Solvent was removed under vacuum and silica gel chromatography (EtOAc:Hexanes) gave pure [1-(3'-Chloro4'-fluoro-biphenyl-4-ylmethyl)-2-(R)-methoxy-ethyl]-carbamic acid tert-butyl ester (0.38 g).

[1-(3'-Chloro-4'-fluoro-biphenyl-4-ylmethyl)-2-(R)-methoxy-ethyl]-carbamic acid tert-butyl ester was converted to corresponding 1-(3'-Chloro-4'-fluoro-biphenyl-4-ylmethyl)-2-methoxy-ethylamine hydrochloride salt according to the general procedure N.

4-Methoxy-4'-trifluoromethyl-biphenyl-3-carboxylic acid [2-(3'-chloro-4'-fluoro-biphenyl-4-yl)-1-(R)-methoxymethyl-ethyl]-amide (45 mg) was prepared from 1-(3'-Chloro-4'-fluoro-biphenyl-4-ylmethyl)-2-methoxy-ethylamine hydrochloride salt (35 mg, 0.1 mmol) and 4-Methoxy-4'-trifluoromethyl-biphenyl-3-carbonyl chloride (32 mg, 0.1 mmol) in presence of triethyl amine (41 mg, 0.41 mmol) according to the general procedure M.

$^1$HNMR (400 MHz, $CDCl_3$): 3.00 (dd, 1H), 3.10 (dd, 1H), 3.37-3.50 (m, 5H), 3.99 (s, 3H), 4.50-4.61 (m, 1H), 7.07(d, 1H), 7.19 (t, 1H), 7.34-7.51 (m, 5H), 7.60 (dd, 1H), 7.74-7.76 (m, 5H), 8.25 (d, 1H), 8.50 (d, 1H),

LC/MS (m/z): 572.2 $(M+1)^+$.

$BBr_3$:DMS (13 mg, 0.04 mmol) was added to a solution of 4-Methoxy-4'-trifluoromethyl-biphenyl-3-carboxylic acid [2-(3'-chloro-4'-fluoro-biphenyl-4-yl)-1-(R)-methoxymethyl-ethyl]-amide (24 mg, 0.04 mmol) in 3 mL of anhydrous $CH_2Cl_2$, at −78° C. and slowly allowed to come to room temperature and stirred for 2 h. After completion of the reaction, reaction was cooled to −78° C. and 0.5 mL of MeOH was added, solvent was removed under vacuum and the residue was taken in ethyl acetate (4 mL) and washed with aq $NaHCO_3$ solution, water, brine and dried over $Na_2SO_4$. Solvent was removed under vacuum and silica gel column chromatography (Ethyl acetate: Hexanes) gave pure 4-Hydroxy-4'-trifluoromethyl-biphenyl-3-carboxylic acid [2-(3'-chloro-4'-fluoro-biphenyl-4-yl)-1-(R)-methoxymethyl-ethyl]-amide (14 mg).

$^1$HNMR (400 MHz, $CDCl_3$): 3.00 (dd, 1H), 3.10 (dd, 1H), 3.38-3.60 (m, 5H), 4.44-4.60 (m, 1H), 6.75 (d, 1H), 7.09 (d, 1H), 7.16-7.23 (m, 1H), 7.30-7.75 (m, 12H), 12.4 (s, 1H).

LC/MS (m/z): 558.1 $(M+1)^+$.

Example 149

3-[4-(4-Cyano-phenoxy)-phenyl]-(2S)-[(4'-trifluoromethyl-biphenyl-4-carbonyl)-amino]-propionic acid methyl ester 3-(4-Hydroxy-phenyl)-(2S)-[4'-trifluoromethyl-biphenyl-4-carbonyl)-amino]-propionic acid methyl ester (664 mg) was prepared starting from 4'-trifluoromethyl-biphenyl-4-carboxylic acid (532 mg, 2.0 mmol) and tyrosine methyl ester (462 mg, 2.0 mmol) according to general procedure A. The above compound (443 mg, 1.0 mmol) was treated with 1-fluoro-4-cyanobenzene (181 mg, 1.5 mmol) following general procedure B to give 3-[4-(4-cyano-phenoxy)-phenyl]-(2S)-[(4'-trifluoromethyl-biphenyl-4-carbonyl)-amino]-propionic acid methyl ester (360 mg). The ester was hydrolyzed following general procedure C to give the title compound (345 mg)

$^1$H NMR (400 MHz, $CDCl_3$): 3.28, 3.44 (ABX, 2H), 5.12 (dd, 1H), 6.65 (d, 1H), 6.99 (m, 4H), 7.28 (m, 2H), 7.58 (d, 2H), 7.69 (m, 6H), 7.84 (d, 2H); LC/MS (m/z): 530 $(M+1)^+$; LC/MS:545.

Example 150

3-(4'-Trifluoromethyl-biphenyl-4-yl)-2-[4-(5-trifluoromethyl-pyridin-2-yloxy)-benzoylamino]-propionic acid methyl ester 4-(5-Trifluoromethyl-pyridin-2-yloxy)-benzaldehyde was prepared from 4-fluorobenzaldehyde (2.48 g, 20 mmol) and 2-hydroxy-5-trifluoromethylpyridine (3.29 g, 20 mmol) following general procedure B. (4.62 g)

To aq. NaOH (3.2 g, 80 mmol) was added silver nitrate (3.4 g, 40 mmol) and stirred for 10 min., then the mixture was cooled to 0° C. and the above aldehyde (4.62 g, 17 mmol) was added. The mixture was stirred overnight, then filtrate through celite. The filtrate was collected and acidified with conc. HCl. The solid was collected by filtration and dried under vacuum to give 4-(5-trifluoromethyl-pyridin-2-yloxy)-benzoic acid. (3.5 g)

The title compound was prepared from 4-(5-trifluoromethyl-pyridin-2-yloxy)-benzoic acid (283 mg, 1.0 mmol) and 2-amino-3-(4'-trifluoromethyl-biphenyl-4-yl)-propionic acid methyl ester (360 mg, 1.0 mmol) following general procedure A. (580 mg) $^1$H-NMR(400 MHz, $CD_3COCD_3$): 3.24 (dd, 1H), 3.39 (dd, 1H), 3.74 (s, 3H), 4.98 (m, 1H), 6.64 (d, 1H), 7.50 (m, 2H), 7.60 (m, 2H), 7.69 (m, 3H), 7.78 (d, 2H), 7.88 (d, 2H), 7.98(m, 2H), 8.15 (m, 2H); LC/MS (m/z): 589 $(M+1)^+$.

By analogous methods to those described above, the following compound was synthesized

| EX. | NAME | LC/MS (m/z) |
|---|---|---|
| 151 | 3-(4'-Trifluoromethoxy-biphenyl-4-yl)-2-(S)-[4-(5-trifluoromethyl-pyridin-2-yloxy)-benzoylamino]-propionic acid methyl ester | 604.5 |

Biological Assay

The following assay methods may be used to identify compounds of Formula (I) that are effective in showing antiviral activity against vaccinia virus.

General Assay Procedures

Cytopathic effect was measured on the BSC40 african green monkey kidney cells using 100 μM concentrations of the compounds of Formula (I). In this assay, 96-well black Packard viewplates were seeded with BSC40 cells ($2.25\times10^4$ cells/well) in Minimum Essential Media supplemented with 5% FCS, 2 mM L-glutamine and 10 μg/mL gentamycin sulfate. When the cells became confluent (24 hrs) they were treated with 100 μM compound diluted in media. The cells were place in an incubator at 37° C. (5% $CO_2$) for 24 hours, and checked for toxicity via direct observation under the microscope and also with alamar blue which assesses cell viability and proliferation (healthy cells produce a visible color change from blue to red). The cells were scored on a scale of 0-3 where 0 corresponds to normal healthy cells, 1 corresponds to sick cells but not rounding up, 2 corresponds to cells that are rounding up, and 3 corresponds to cells that have rounded up and pulled off the plate. Compounds at concentrations that scored 1 or greater were diluted and the above assay was repeated to find the concentration at which the compound scored 0.

A vaccinia virus green fluorescent protein (vvGFP) assay was performed to test the ability of compounds of Formula (I) to inhibit viral growth as measured by a reduction in fluorescence from vaccinia virus expressing the green fluorescent protein. In this assay, 96-well black Packard viewplates were seeded with BSC40 cells in Minimum Essential Media supplemented with 5% FCS, 2 mM L-glutamine and 10 μg/mL gentamycin sulfate. When the cells became confluent, they were washed with PBS and then infected with vaccinia virus at a multiplicity of infection (moi) of 0.1 for 30 min in PBS. At 30 minutes, the cells were overlaid with 100 μl of infection media supplemented with 100 μM test compound. As controls infected cells are treated with rifampicin (blocks assembly of DNA and protein into mature virus particles), with no compound, or mock infected. Cells were placed in an incubator at 37° C. (5% $CO_2$) for 24 hrs. At 24 hours post infection (hpi), the plates were removed from the incubator, washed with PBS and fluorescence measure on a Wallac plate reader (excite at 485 nm and read at 535 nm). Wells that showed reduced fluorescence were checked visually under the microscope to verify a reduction in viral infection versus a loss of cells due to cytopathic effect from virus infection. Compounds that are found to inhibit viral replication were then checked for inhibitory effect at various concentrations to determine the $IC_{50}$ and the therapeutic index.

The compounds of Formula (I) listed in Table 1 have an $IC_{50}$ of less than or equal to about 100 μM.

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness of the mammal being treated for orthopox -mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:

1. The compound of Formula (I):

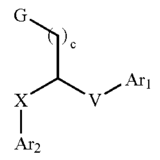

(I)

wherein c is equal to 0, 1, or 2; wherein $—CH_2—$, and $—CH_2—CH_2—$, optionally substituted 1 to 4 times with substituent(s) independently selected from the group consisting of: -alkyl, -aryl, -alkylene-aryl, -arylene-alkyl, -alkylene-arylene-alkyl, —O-alkyl, —O-aryl, and -hydroxyl;

G is: a substituted oxadiazole:

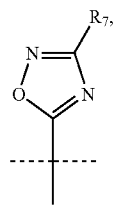

wherein $R_7$ is alkyl, aryl, alkylene-sulfonyl-alkyl or alkylene-sulfonyl-aryl;

wherein

V is: $—(CH_2)_b—O—(CH_2)_a—$, $—(CH_2)_b—N(R_8)—(CH_2)_a—$, $—(CH_2)_b—O—$, $—(CH_2)_b—N(R_8)$, $—(CH_2)_a—$, $—CH{=}CH—(R_8)—$ or a direct bond; in which a is equal to 0,1, or 2, b is equal to 1 or 2, and $R_8$ is: -hydrogen, -alkyl, -aryl, -arylene-alkyl, -alkylene-aryl, or -alkylene-arylene-alkyl; wherein the $—CH_2—$ groups may be optionally substituted 1 to 4 times with a substituent selected from the group consisting of: -alkyl, -aryl, -alkylene-aryl, -arylene-alkyl, -alkylene-arylene-alkyl, —O-alkyl, —O-aryl, -hydroxyl, —S-alkyl, and —S-aryl;

X is: —$N(R_9)$—, -$CON(R_9)$—, —$N(R_9)CO$—, —$N(R_9)CON(R_{10})$—, —$OC(O)N(R_8)$—, —$SO_2N(R_9)$—, —$N(R_9)SO_2$—, or —$N(R_9)SO_2N(R_{10})$—; wherein $R_9$ and $R_{10}$ are independently selected from the group consisting of: -hydrogen, -alkyl, -aryl, -arylene-alkyl, -alkylene-aryl, -alkylene-arylene-alkyl, and —$(CH_2)_dY$—, wherein d is equal to 0, 1, or 2, wherein Y is: -hydrogen, —$CO_2R_{11}$, —$CH_2OR_{11}$, —C(O)—$R_{11}$, —$C(O)NR_{11}R_{12}$, —$C(R_{11})$=N—O—$R_{12}$, —$NR_{11}R_{12}$, or an acid isostere;

wherein $R_{11}$ and $R_{12}$ independently selected from the group consisting of: -hydrogen, -alkyl, -aryl, -arylene-alkyl, -alkylene-aryl, -alkylene-arylene-alkyl, -heterocyclyl, or -heteroaryl;

$Ar_1$ is an aryl, or fused cycloalkylaryl, wherein $Ar_1$ is optionally substituted 1 to 7 times with substituent(s) independently selected from the group consisting of:

a) -fluoro;
b) -chloro;
c) -bromo;
d) -iodo;
e) -cyano;
f) -nitro;
g) -perfluoroalkyl;
h) -D-$R_{12}$;
i) -alkyl;
j) -aryl;
k) -cycloalkyl;
l) -alkylene-aryl;
m) -alkylene-arylene-aryl;
n) -alkylene-arylene-alkyl;
o) -arylene-alkyl;
p) -arylene-arylene-alkyl;
q) -D-alkyl;
r) -D-aryl;
s) -D-alkylene-aryl;
t) -D-arylene-alkyl;
u) -D-alkylene-arylene-aryl;
v) -D-arylene-arylene-aryl;
w) -D-alkylene-arylene-alkyl;
x) -alkylene-D-alkylene-aryl;
y) -arylene-D-alkyl;
z) -alkylene-D-aryl;
aa) -alkylene-D-cycloalkyl;
bb) -alkylene-D-arylene-alkyl;
cc) -alkylene-D-alkylene-arylene-alkyl;
dd) -alkylene-D-alkyl;
ee) -alkylene-D-$R_{13}$;
ff) -arylene-D-$R_{13}$; and
gg) -hydrogen;

wherein D is —$CH_2$—, —O—, —$N(R_{14})$—, —C(O)—, —$CON(R_{14})$—, —$N(R_{14})C(O)$—, —$N(R_{14})CON(R_{15})$—, —$N(R_{14})C(O)O$—, —$OC(O)N(R_{14})$—, —$N(R_{14})SO_2$—, —$SO_2N(R_{14})$—, —C(O)—O—, —O—C(O)—, —S—, —S(O)—, —$S(O_2)$—, —$N(R_{14})SO_2N(R_{15})$—,

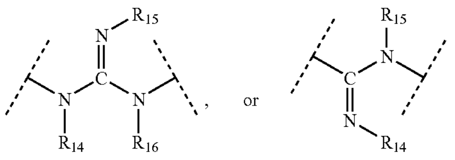

, or , and wherein $R_{13}$, $R_{14}$, $R_{15}$, and $R_{16}$ are independently selected from the group consisting of: -hydrogen, hydroxyl, -cyano, nitro, -alkyl, -aryl, -arylene-alkyl, -alkylene-aryl, and -alkylene-arylene-alkyl; and $Ar_2$ is an aryl group, wherein $Ar_2$ is optionally substituted 1 to 7 times with substituent(s) independently selected from the group consisting of:

a) -fluoro;
b) -chloro;
c) -bromo;
d) -iodo;
e) -cyano;
f) -nitro;
g) -perfluoroalkyl;
h) -T-$R_{17}$;
i) -alkyl;
j) -aryl;
k) -cycloalkyl;
l) -alkylene-aryl;
m) -alkylene-arylene-aryl;
n) -alkylene-arylene-alkyl;
o) -arylene-alkyl;
p) -arylene-arylene-alkyl;
q) -T-alkyl;
r) -T-aryl;
s) -T-alkylene-aryl;
t) -T-arylene-alkyl;
u) -T-alkylene-arylene-aryl;
v) -T-arylene-arylene-aryl;
w) -T-alkylene-arylene-alkyl;
x) -alkylene-T-alkylene-aryl;
y) -arylene-T-alkyl;
z) -alkylene-T-aryl;
aa) -alkylene-T-cycloalkyl;
bb) -alkylene-T-arylene-alkyl;
cc) -alkylene-T-alkylene-arylene-alkyl;
dd) -alkylene-T-alkyl;
ee) -alkylene-T-$R_{17;}$
ff) -arylene-T-$R_{17;}$ or
gg) -T-fused cycloalkylaryl; and
hh) -T-fused arylcycloalkyl;

wherein

T is a direct bond, —$CH_2$—, —O—, —$N(R_{18})$—, —C(O)—, —$CON(R_{18})$—, —$N(R_{18})C(O)$—, —$N(R_{18})CON(R_{19})$—, —$N(R_{18})C(O)O$—, —$OC(O)N(R_{18})$—, —$N(R_{18})SO_2$—, —$SO_2N(R_{18})$—, —C(O)—O—, —O—C(O)—, —S—, —S(O)—, —$S(O_2)$—, —$N(R_{18})SO_2N(R_{19})$—,

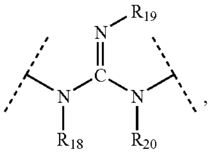, or 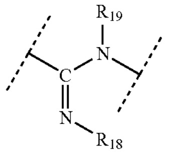 and wherein $R_{17}$, $R_{18}$, $R_{19}$ and $R_{20}$, are independently selected from the group consisting of: -hydrogen, -alkyl, -aryl, -arylene-alkyl, -alkylene-aryl, and -alkylene-arylene-alkyl;

and wherein the alkyl, aryl, alkylene, and arylene groups in $Ar_1$, $Ar_2$, G, $R_1$-$R_{21}$, may be optionally substituted 1 to 4 times with substituent(s) independently selected from the group consisting of:

a) -hydrogen;
b) -fluoro;
c) -chloro;
d) -bromo;
e) -iodo;
f) -cyano;
g) -nitro;
h) -perfluoroalkyl;
i) -Q-$R_{22}$;
j) -Q-alkyl;
k) -Q-aryl;
l) -Q-alkylene-aryl;
m) -Q-alkylene-$NR_{23}R_{24}$; and
n) -Q-alkyl-W-$R_{25}$;

wherein

Q and W are independently selected from the group consisting of: —$CH_2$—, —O—, —N($R_{26}$)—, —C(O)—, —CON($R_{26}$)—, —N($R_{26}$)C(O)—, —N($R_{26}$)CON($R_{27}$)—, —N($R_{26}$)C(O)O—, —OC(O)N($R_{26}$)—, —N($R_{26}$)$SO_2$—, —$SO_2$N($R_{26}$)—, —C(O)—O—, —O—C(O)—, and —N($R_{26}$)$SO_2$N($R_{27}$)—, wherein $R_{22}$, $R_{23}$, $R_{24}$, $R_{25}$, $R_{26}$ and $R_{27}$, are independently selected from the group consisting of: -hydrogen, -alkyl, -aryl, -arylene-alkyl, -alkylene-aryl, and -alkylene-arylene-alkyl, or a pharmaceutically acceptable salt thereof.

2. The compound of Formula (I) in claim 1 or a pharmaceutically acceptable salt thereof, wherein c is equal to 0 or 1.

3. The compound of Formula (I) in claim 1 or a pharmaceutically acceptable salt thereof, wherein c is equal to 0.

4. The compound of Formula (I) in claim 1 or a pharmaceutically acceptable salt thereof, wherein $R_7$ is an alkyl group.

5. The compound of Formula (I) in claim 1 or a pharmaceutically acceptable salt thereof, wherein V is: —$(CH_2)_a$—, —$(CH_2)_b$—O—$(CH_2)_a$—, or a direct bond, wherein a is equal to 1 or 2, and b is equal to 1.

6. The compound of Formula (I) in claim 1 or a pharmaceutically acceptable salt thereof, wherein V is: —$(CH_2)_a$— or a direct bond, wherein a is equal to 1.

7. The compound of Formula (I) in claim 1 or a pharmaceutically acceptable salt thereof, wherein X is: —N($R_9$)—, —CON($R_9$)—, —N($R_9$)CO—, or —N($R_9$)CON($R_{10}$)—, wherein $R_9$ and $R_{10}$ are independently selected from the group consisting of: -hydrogen, -alkyl, -aryl, -arylene-alkyl, -alkylene-aryl, and -alkylene-arylene-alkyl.

8. The compound of Formula (I) in claim 1 or a pharmaceutically acceptable salt thereof, wherein X is: —N($R_9$)—, —CON($R_9$)—, or —N($R_9$)CO—, wherein $R_9$ is: -hydrogen, -alkyl, -aryl, -arylene-alkyl, -alkylene-aryl, or -alkylene-arylene-alkyl.

9. The compound of Formula (I) in claim 1 or a pharmaceutically acceptable salt thereof, wherein X is —CON($R_9$)—, wherein $R_9$ is: -hydrogen.

10. The compound of Formula (I) in claim 1 or a pharmaceutically acceptable salt thereof, wherein $Ar_1$ is a mono- or bicyclic aryl group optionally substituted 1 to 7 times.

11. The compound of Formula (I) in claim 1 or a pharmaceutically acceptable salt thereof, wherein $Ar_1$ is a phenyl group having 1 to 5 substituents, wherein the substituents are independently selected from the group consisting of:

a) -fluoro;
b) -chloro
c) -bromo
d) -iodo;
e) -cyano;
f) -nitro;
g) -perfluoroalkyl;
h) -D-$R_{12}$;
i) -alkyl;
j) -aryl;
k) -cycloalkyl;
l) -alkylene-aryl;
m) -alkylene-arylene-aryl;
n) -alkylene-arylene-alkyl;
o) -arylene-alkyl;
p) -arylene-arylene-alkyl;
q) -D-alkyl;
r) -D-aryl;
s) -D-alkylene-aryl;
t) -D-arylene-alkyl;
u) -D-alkylene-arylene-aryl;
v) -D-arylene-arylene-aryl;
w) -D-alkylene-arylene-alkyl;
x) -alkylene-D-alkylene-aryl;
y) -arylene-D-alkyl;
z) -alkylene-D-aryl;
aa) -alkylene-D-cycloalkyl;
bb) -alkylene-D-arylene-alkyl;
cc) -alkylene-D-alkylene-arylene-alkyl;
dd) -alkylene-D-alkyl;
ee) -alkylene-D-$R_{13}$;
ff) -arylene-D-$R_{13}$; and
gg) -hydrogen;

wherein

D is —$CH_2$—, —O—, —N($R_{14}$)—, —C(O)—, —CON($R_{14}$)—, —N($R_{14}$)C(O)—, —N($R_{14}$)CON($R_{15}$)—, —N($R_{14}$)C(O)O—, —OC(O)N($R_{14}$)—, —N($R_{14}$)$SO_2$—, —$SO_2$N($R_{14}$)—, —C(O)—O—, —O—C(O)—, —S—, —S(O)—, —S($O_2$)—, —N($R_{14}$)$SO_2$N($R_{15}$)—,

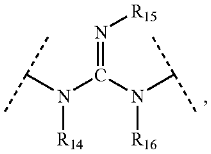, or 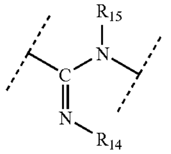, wherein $R_{13}$, $R_{14}$, $R_{15}$, and $R_{16}$ independently selected from the group consisting of: -hydrogen, hydroxyl, -cyano, nitro, -alkyl, -aryl, -arylene-alkyl, -alkylene-aryl, and -alkylene-arylene-alkyl.

12. The compound of Formula (I) in claim 1 or a pharmaceutically acceptable salt thereof, wherein $Ar_1$ is a mono-substituted phenyl group wherein the substituent is selected from the group consisting of : -aryl, -arylene-alkyl, -D-aryl, -D-alkylene-arylene-alkyl, or -arylene-D-alkyl; wherein D comprises —O—, —N($R_{14}$)—, —CON($R_{14}$)—, or —N($R_{14}$)C(O)—, wherein $R_{14}$ is: -hydrogen; -alkyl; or -aryl.

13. The compound of Formula (I) in claim 1 or a pharmaceutically acceptable salt thereof, wherein $Ar_1$ is:

2'-(4-tert-butyl-phenoxy)-biphenyl-4-yl,
2'-(4-trifluoromethyl-phenoxy)-biphenyl-4-yl,
2'-phenoxy-biphenyl-4-yl,
2'-trifluoromethyl-biphenyl-4-yl,
3',4'-dichloro-biphenyl-4-yl,
3',4'-difluoro-biphenyl-4-yl,
3',5'-bis-trifluoromethyl-biphenyl-4-yl,
3',5'-difluoro-biphenyl-4-yl,
3'-chloro-4'-fluoro-6-methoxy-biphenyl-3-yl,
3'-chloro-4'-fluoro-biphenyl-2-yl,
3'-chloro-4'-fluoro-biphenyl-3-yl,
3'-chloro-4'-fluoro-biphenyl-4-yl,
3'-chloro-biphenyl-4-yl,
3'-nitro-biphenyl-4-yl,
3'-trifluoromethoxy-biphenyl-4-yl,
3'-trifluoromethyl-biphenyl-4-yl,
4'-benzyloxy-3'-fluoro-biphenyl-4-yl,
4-benzyloxy-phenyl,
4'-chloro-biphenyl-4-yl,
4'-fluoro-biphenyl-4-yl,
4'-methanesulfonyl-biphenyl-4-yl,
4-naphthalen-2-yl-phenyl,
4'-nitro-biphenyl-4-yl,
4'-phenoxy-biphenyl-4-yl,
4-pyridin-3-yl-phenyl,
4'-tert-butyl-biphenyl-4-yl,
4'-trifluoromethyl-biphenyl-4-yl,
6-methoxy-4'-nitro-biphenyl-3-yl,
biphenyl,
biphenyl-4-yl,
chlorofluorophenoxy-phenyl, or
(cyano-phenoxy)-phenyl.

14. The compound of Formula (I) in claim 1 or a pharmaceutically acceptable salt thereof, wherein $Ar_1$ is:

[2-(4-Chloro-phenyl)-ethoxy]-phenyl,
(4-nitro-phenoxy)-phenyl,
(3-phenyl-propylamino)-phenyl,
4-methoxy-4'-nitro-biphenyl-3-yl,
(4'-methanesulfonyl-4-methoxy-biphenyl-3-yl), or
(4'-methanesulfonyl-4-hydroxy-biphenyl-3-yl).

15. The compound of Formula (I) in claim 1 or a pharmaceutically acceptable salt thereof, wherein $Ar_1$ is an unsubstituted biphenyl group.

16. The compound of Formula (I) in claim 1 or a pharmaceutically acceptable salt thereof, wherein $Ar_1$ is a biphenyl group substituted with at least one of the following groups: fluoro, chloro, trifluoroalkyl, trifluoroalkoxy, nitro, benzyloxy, phenoxy, and alkylsulfonyl.

17. The compound of Formula (I) in claim 1 or a pharmaceutically acceptable salt thereof, wherein $Ar_2$ is a phenyl or 2-naphthyl, group , wherein $Ar_2$ is substituted 1 to 5 times with substituents independently selected from the group consisting of:

a) -fluoro;
b) -chloro;
c) -bromo;
d) -iodo;
e) -cyano;
f) -nitro;
g) -perfluoroalkyl;
h) -T-$R_{17}$;
i) -alkyl;
j) -aryl;
k) -arylene-alkyl;
l) -T-alkyl;
m) -T-alkylene-aryl;
n) -T-alkylene-arylene-aryl;
o) -T-alkylene-arylene-alkyl; and
p) -arylene-T-alkyl;

wherein

T is —$CH_2$—, —O—, —N($R_{18}$)—, —CON($R_{18}$)—, or —N($R_{18}$)C(O)—; wherein $R_{17}$, and $R_{18}$, are independently selected from a group consisting of: -hydrogen, -alkyl, and -aryl.

18. The compound of Formula (I) in claim 1 or a pharmaceutically acceptable salt thereof, wherein $Ar_2$ is:

3'-chloro-4'-fluoro-4-hydroxy-biphenyl,
2-hydroxy-5-[2-(4'-trifluoromethyl-biphenyl-3-yl)-acetylamino]-phenyl,
3',5'-difluoro-4-hydroxy-biphenyl,
3'-chloro-4'-fluoro-4-hydroxy-biphenyl,
3'-fluoro-4-hydroxy-biphenyl,
3'-trifluoromethyl-biphenyl-4-yl,
4'-amino-4-hydroxy-biphenyl,
4'-fluoro-4-hydroxy-biphenyl,
4-hydroxy-2'-trifluoromethyl-biphenyl,
4-hydroxy-3',5'-bis-trifluoromethyl-biphenyl,
4-hydroxy-3'-nitro-biphenyl,
4-hydroxy-4'-trifluoromethoxy-biphenyl,
4-hydroxy-4'-trifluoromethyl-biphenyl,
4-hydroxy-biphenyl,
5-bromo-2-hydroxy-phenyl,
5-chloro-4-hydroxy-4'-trifluoromethyl-biphenyl,
5-fluoro-4-hydroxy-4'-trifluoromethyl-biphenyl, or
6-benzyloxy-4-hydroxy-4'-trifluoromethyl-biphenyl.

19. The compound of Formula (I) in claim 1 or a pharmaceutically acceptable salt thereof, wherein $Ar_2$ is: 3'-chloro-4'-fluoro-4-hydroxy-biphenyl, or 4-hydroxy-4'-trifluoromethyl-biphenyl.

20. The compound of Formula (I) in claim 1 or a pharmaceutically acceptable salt thereof, wherein $Ar_2$ is:

[2-(3,4-bis-benzyloxy-benzyloxy)-benzyloxy]-5-bromo-phenyl,
2-(4-tert-butyl-benzyloxy)-5-chlorophenyl,
3-bromo-5-chloro-2,6-dimethoxy-phenyl,
4-(4-tert-butyl-benzyloxy)-4'-trifluoromethyl-biphenyl,
4-acetoxy-2-phenyl-4'-trifluoromethyl-biphenyl,
4-acetoxy-4'-trifluoromethyl-biphenyl,
4-amino-4'-trifluoromethyl-biphenyl,
4-butoxy-3'-chloro-4'-fluoro-biphenyl,
4-methanesulfonylamino-4'-trifluoromethyl-biphenyl,
4-methoxy-4'-trifluoromethyl-biphenyl,
5-bromo-2-(4-tert-butyl-benzyloxy)-phenyl,
5-bromo-2-cyclohexyloxy-phenyl,
5-bromo-2-heptyloxy-phenyl,
5-chloro-2,4-dimethoxy-4'-trifluoromethyl-biphenyl, or
5-chloro-2-heptyloxy-phenyl.

21. The compound of Formula (I) in claim 1 or a pharmaceutically acceptable salt thereof, wherein $Ar_2$ is:

5-bromo-2-(4,4,4-trifluoro-butoxy)-phenyl.

22. The compound of Formula (I) in claim 1 or a pharmaceutically acceptable salt thereof, wherein $Ar_2$ is: 3-hydroxy-naphthalene.

23. The compound of Formula (I) in claim 1 or a pharmaceutically acceptable salt thereof, wherein $Ar_2$ is: a phenyl or biphenyl group containing a hydroxy, alkyloxy, or acetoxy group ortho to the $Ar_2$ group's point of attachment to X.

24. The compound of Formula (I) in claim 1 or a pharmaceutically acceptable salt thereof, wherein $Ar_2$ is: a phenyl or biphenyl group containing a hydroxy, alkyloxy, or acetoxy group ortho to the $Ar_2$ group's point of attachment to X and further substituted with at least one of the following groups fluoro, chloro, trifluoroalkyl, trifluoroalkoxy, nitro, benzyloxy, phenoxy, phenyl, and alkylsulfonyl.

25. The compound of Formula (I) in claim 1 selected from the group consisting of:

4-Hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide, 4-Hydroxy-4'-trifluoromethyl-biphenyl-3-carboxylic acid [2-(4'-benzyloxy-3'-fluoro-biphenyl-4-yl)-1-(R)-(3-methyl-[1,2,4]oxadiazol-5-yl)-ethyl]-amide, 4-Hydroxy-4'-nitro-biphenyl-3-carboxylic acid [2-(3'-chloro-4'-fluoro -biphenyl-4-yl)-1-(R)-(3-methyl-[1,2,4]oxadiazol-5-yl)-ethyl]-amide, 4-Hydroxy-3',5'-bis-trifluoromethyl-biphenyl-3-carboxylic acid [2-(3'-chloro -4'-fluoro-biphenyl-4-yl)-1-(R)-(3-methyl-[1,2,4]oxadiazol-5-yl)-ethyl]-amide, 4-Hydroxy-4'-trifluoromethyl-biphenyl-3-carboxylic acid [2-(4'-methanesulfonyl-biphenyl-4-yl)-1-(R)-(3-methyl-[1,2,4]oxadiazol-5-yl)-ethyl]-amide, Acetic acid 3-[2-(3'-chloro-4'-fluoro-biphenyl-4-yl)-1-(R)-(3-methyl -[1,2,4]oxadiazol-5-yl)-ethylcarbamoyl]-4'-trifluoromethyl-biphenyl-4-yl ester, 6-Benzyloxy-4-hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide, 5-Bromo-N-[2-(3'-chloro-4'-fluoro-biphenyl-4-yl)-1-(R)-(3-methyl-[1,2,4]oxadiazol-5-yl)-ethyl]-2-hydroxy-benzamide, 4-Hydroxy-3';5'-bis-trifluoromethyl-biphenyl-3-carboxylic acid [2-biphenyl-4-yl-1-(R)-(3-methyl-[1,2,4]oxadiazol-5-yl)-ethyl]-amide, 4-Hydroxy-3',5'-bis-trifluoromethyl-biphenyl-3-carboxylic acid [2-(4'-methanesulfonyl-biphenyl-4-yl)-1-(R)-(-methyl-[1,2,4]oxadiazol-5-yl)-ethyl]-amide, Acetic acid 5'-[2-(3'-chloro-4'-fluoro-biphenyl-4-yl)-1-(R)-(3-methyl-[1,2,4]oxadiazol-5-yl) ethylcarbamoyl]-4-trifluoromethyl[1,1';3',1"]terphenyl-4'-yl ester 5-Chloro-4-hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide, 4-Hydroxy-4'-trifluoromethyl-biphenyl-3-carboxylic acid [2-(4-benzyloxy-phenyl)-1-(R)-(3-methyl-[1,2,4]oxadiazol-5-yl)-ethyl]-amide, 5-Fluoro-4-hydroxy-4'-trifluoromethyl-biphenyl-3-carboxylic acid [2-(3'-chloro-4'-fluoro-biphenyl-4-yl)-1-(R)-(3-methyl-[1,2,4]oxadiazol-5-yl)-ethyl]-amide, 4-Hydroxy-4'-trifluoromethyl-biphenyl-3-carboxylic acid [2-[4-(3-chloro-4-fluoro-phenoxy)-phenyl]-1-(R)-(3-methyl-[1,2,4]oxadiazol-5-yl)-ethyl]-amide, 3-Hydroxy-naphthalene-2-carboxylic acid [2-(3'-chloro-4'-fluoro-biphenyl -4-yl)-1-(R)-(3-methyl-[1,2,4]oxadiazol-5-yl)-ethyl]-amide, and 4-Hydroxy-4'-trifluoromethyl-biphenyl-3-carboxylic acid [1(R)-(3-tert-butyl-[1,2,4]oxadiazol-5-y)-2-(3'-chloro-4'-fluoro-biphenyl-4-yl)-ethyl]-amide.

and pharmaceutically acceptable salts thereof.

26. A pharmaceutical composition comprising a compound of Formula (I)

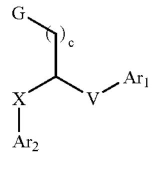

(I)

wherein c is equal to 0, 1, or 2; wherein $—CH_2—$, and $—CH_2—CH_2—$, are optionally substituted 1 to 4 times with substituent(s) independently selected from the group consisting of: -alkyl, -aryl, -alkylene-aryl, -arylene-alkyl, -alkylene-arylene-alkyl, —O-alkyl, —O-aryl, or -hydroxyl;

G -is a substituted oxadiazole:

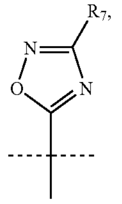

wherein $R_7$ is alkyl, aryl, alkylene-sulfonyl-alkyl or alkylene-sulfonyl-aryl.

wherein

V is: $—(CH_2)_b—O—(CH_2)_a—$, $—(CH_2)_b—N(R_8)—(CH_2)_a—$, $—(CH_2)_b—O—$, $—(CH_2)_b—N(R_8)$, $—(CH_2)_a—$, $-CH{=}CH—(CR_8)—$or a direct bond; in which a is equal to 0,1, or 2, b is equal to 1 or 2, and $R_8$ is: -hydrogen, -alkyl, -aryl, -arylene-alkyl, -alkylene-aryl, or -alkylene-arylene-alkyl; wherein the $—CH_2—$ groups may be optionally substituted 1 to 4 times with a substituent selected from the group consisting of: -alkyl, -aryl, -alkylene-aryl, -arylene-alkyl, -alkylene-arylene-alkyl, —O-alkyl, —O-aryl, and -hydroxyl;

X is: $—N(R_9)—$, $—CON(R_9)—$, $—N(R_9)CO—$, $—N(R_9)CON(R_{10})—$, $—OC(O)N(R_8)—$, $—SO_2N(R_9)—$, $—N(R_9)SO_2—$, or $—N(R_9)SO_2N(R_{10})—$; wherein $R_9$ and $R_{10}$ are independently selected from the group consisting of: -hydrogen, -alkyl, -aryl, arylene-alkyl, -alkylene-aryl, -alkylene-arylene-alkyl, and $—(CH_2)_dY—$, wherein d is equal to 0, 1, or 2, wherein Y is: -hydrogen, $—CO_2R_{11}$, $—CH_2OR_{11}$, $—C(O)—R_{11}$, $—C(O)NR_{11}R_{12}$, $—C(R_{11}){=}N—O—R_{12}$, $—NR_{11}R_{12}$, or an acid isostere;

wherein $R_{11}$ and $R_{12}$ independently selected from the group consisting of: -hydrogen, -alkyl, -aryl, -arylene-alkyl, -alkylene-aryl, or -alkylene-arylene-alkyl, $Ar_1$ is an aryl, or fused cycloalkylaryl, wherein $Ar_1$ is optionally substituted 1 to 7 times with substituent(s) independently selected from the group consisting of:
a) -fluoro;
b) -chloro;
c) -bromo;
d) -iodo;
e) -cyano;
f) -nitro;
g) -perfluoroalkyl;
h) -D-$R_{12}$;
i) -alkyl;
j) -aryl;
k) -cycloalkyl;
l) -alkylene-aryl;
m) -alkylene-arylene-aryl;
n) -alkylene-arylene-alkyl;
o) -arylene-alkyl;
p) -arylene-arylene-alkyl;
q) -D-alkyl;
r) -D-aryl;
s) -D-alkylene-aryl;
t) -D-arylene-alkyl;
u) -D-alkylene-arylene-aryl;
v) -D-arylene-arylene-aryl;
w) -D-alkylene-arylene-alkyl;
x) -alkylene-D-alkylene-aryl;
y) -arylene-D-alkyl;
z)-alkylene-D-aryl;
aa) -alkylene-D-cycloalkyl;
bb) -alkylene-D-arylene-alkyl;
cc) -alkylene-D-alkylene-arylene-alkyl;
dd) -alkylene-D-alkyl;
ee) -alkylene-D-$R_{13}$; and
ff) -arylene-D-$R_{13}$;

wherein D is —$CH_2$—, —O—, —N($R_{14}$)—, —C(O)—, —CON($R_{14}$)—, —N($R_{14}$)C(O)—, —N($R_{14}$)CON($R_{15}$)—, —N($R_{14}$)C(O)O—, —OC(O)N($R_{14}$)—, —N($R_{14}$)$SO_2$—, —$SO_2$N($R_{14}$)—, —C(O)—O—, —O—C(O)—, —S—, —S(O)—, —S($O_2$)—, —N($R_{14}$)$SO_2$N($R_{15}$)—,

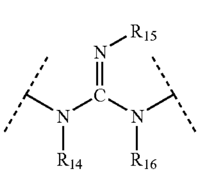
, or
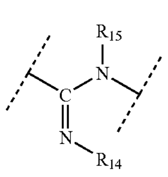
, and wherein
$R_{13}$, $R_{14}$, $R_{15}$, and $R_{16}$ independently selected from the group consisting of: -hydrogen, hydroxyl, -cyano, nitro, -alkyl, -aryl, -arylene-alkyl, -alkylene-aryl, and -alkylene-arylene-alkyl; and $Ar_2$ is an aryl group, wherein $Ar_2$ is optionally substituted 1 to 7 times with substitutent(s) independently selected from the group consisting of:
a) -fluoro;
b) -chloro;
c) -bromo;
d) -iodo;
e) -cyano;
f) -nitro;
g) -perfluoroalkyl;
h) -T-$R_{17}$;

i) -alkyl;
j) -aryl;
k) -cycloalkyl;
l) -alkylene-aryl;
m) -alkylene-arylene-aryl;
n) -alkylene-arylene-alkyl;
o) -arylene-alkyl;
p) -arylene-arylene-alkyl;
q) -T-alkyl;
r) -T-aryl;
s) -T-alkylene-aryl;
t) -T-arylene-alkyl;
u) -T-alkylene-arylene-aryl;
v) -T-arylene-arylene-aryl;
w) -T-alkylene-arylene-alkyl;
x) -alkylene-T-alkylene-aryl;
y) -arylene-T-alkyl;
z) -alkylene-T-aryl;
aa) -alkylene-T-cycloalkyl;
bb) -alkylene-T-arylene-alkyl;
cc) -alkylene-T-alkylene-arylene-alkyl;
dd) -alkylene-T-alkyl;
ee) -alkylene-T-$R_{17}$;
ff) -arylene-T-$R_{17}$; or
gg) -T-fused cycloalkylaryl; and
hh) -T-fused arylcycloalkyl;

wherein
T is a direct bond, —$CH_2$—, —O—, —N($R_{18}$)—, —CON($R_{18}$)—, —N($R_{18}$)C(O)—, —N($R_{18}$)CON($R_{19}$)—, —N($R_{18}$)C(O)O—, —OC(O)N($R_{18}$)—, —N($R_{18}$)$SO_2$—, —$SO_2$N($R_{18}$)—, —C(O)—O—, —O—C(O)—, —S—, —S(O)—, —S($O_2$)—, —N($R_{18}$)$SO_2$N($R_{19}$)—,

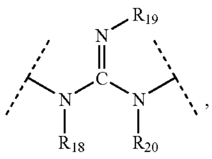
, or
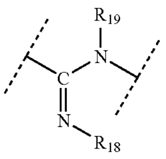
and wherein $R_{17}$, $R_{18}$, $R_{19}$ and $R_{20}$, are independently selected from the group consisting of: -hydrogen, -alkyl, -aryl, -arylene-alkyl, -alkylene-aryl, and -alkylene-arylene-alkyl;

and wherein
the alkyl, aryl, alkylene, and arylene groups in $Ar_1$, $Ar_2$, G, $R_1$-$R_{21}$, may be optionally substituted 1 to 4 times with substituent(s) independently selected from the group consisting of:
a) -hydrogen;
b) -fluoro;
c) -chloro;
d) -bromo;
e) -iodo;
f) -cyano;
g) -nitro;
h) -perfluoroalkyl;
i) -Q-$R_{22}$;
j) -Q-alkyl;
k) -Q-aryl;
l) -Q-alkylene-aryl;
m) -Q-alkylene-$NR_{23}R_{24}$; and
n) -Q-alkyl-W-$R_{25}$;

wherein

Q and W are independently selected from the group consisting of: —$CH_2$—, —O—, —$N(R_{26})$—, —C(O)—, —$CON(R_{26})$—, —$N(R_{26})C(O)$—, —$N(R_{26})CON(R_{27})$—, —$N(R_{26})C(O)O$—, —$OC(O)N(R_{26})$—, —$N(R_{26})SO_2$—, —$SO_2N(R_{26})$—, —C(O)—O—, —O—C(O)—, and —$N(R_{26})SO_2N(R_{27})$—, wherein $R_{22}$, $R_{23}$, $R_{24}$, $R_{25}$, $R_{26}$ and $R_{27}$, are independently selected from the group consisting of: -hydrogen, -alkyl, -aryl, -arylene-alkyl, -alkylene-aryl, and -alkylene-arylene-alkyl, or a pharmaceutically acceptable salt thereof.

27. The pharmaceutical composition of claim 26, comprising a therapeutically effective amount of the compound of Formula (I) or a pharmaceutically acceptable salt thereof.

28. The pharmaceutical composition of claim 26, further comprising one or more pharmaceutically acceptable carriers, excipients, or diluents.

29. The pharmaceutical composition of claim 26, wherein the compound of Formula (I) or a pharmaceutically acceptable salt thereof.

30. The pharmaceutical composition of claim 26, further comprising one or more additional therapeutic agents selected from the group consisting of antibiotics, hormones, biologic response modifiers, analgesics, nonsteroidal anti-inflammatory drugs, disease-modifying antirheumatic drugs, glucocorticoids, immunosuppressants, immunomodulators, thrombolytic agents, antidepressants, gyrase inhibitors, beta lactam antibiotics, antifungal agents, and antiviral agents.

31. The pharmaceutical composition of claim 26 in the form of an oral dosage.

32. The pharmaceutical composition of claim 26 in the form of a parenteral dosage unit.

33. The pharmaceutical composition of claim 26, wherein said compound of Formula (I) or a pharmaceutically acceptable salt thereof comprises a dose in a range from about 0.01 to 1,000 mg/kg of body weight per day.

34. The pharmaceutical composition of claim 26, wherein said compound of Formula (I) or a pharmaceutically acceptable salt thereof comprises a dose in a range from about 0.1 to 100 mg/kg of body weight per day.

35. The pharmaceutical composition of claim 26 wherein said compound of Formula (I) or a pharmaceutically acceptable salt thereof comprises a dose in a range from about 0.5 to 10 mg/kg of body weight per day.

* * * * *